US011945847B2

(12) United States Patent
Donnelly et al.

(10) Patent No.: US 11,945,847 B2
(45) Date of Patent: Apr. 2, 2024

(54) OPTOGENETIC INDUCTION OF NEURODEGENERATIVE DISEASE PATHOLOGIES

(71) Applicant: UNIVERSITY OF PITTSBURGH—OF THE COMMONWEALTH SYSTEM OF HIGHER EDUCATION, Pittsburgh, PA (US)

(72) Inventors: Christopher James Donnelly, Pittsburgh, PA (US); Jacob R. Mann, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 183 days.

(21) Appl. No.: 16/491,758

(22) PCT Filed: Mar. 7, 2018

(86) PCT No.: PCT/US2018/021335
§ 371 (c)(1),
(2) Date: Sep. 6, 2019

(87) PCT Pub. No.: WO2018/165293
PCT Pub. Date: Sep. 13, 2018

(65) Prior Publication Data
US 2021/0139547 A1    May 13, 2021

Related U.S. Application Data

(60) Provisional application No. 62/468,065, filed on Mar. 7, 2017.

(51) Int. Cl.
| | | |
|---|---|---|
| C07K 14/47 | (2006.01) | |
| C12N 15/62 | (2006.01) | |
| C12N 15/79 | (2006.01) | |
| C12Q 1/00 | (2006.01) | |
| G01N 33/50 | (2006.01) | |

(52) U.S. Cl.
CPC .............. C07K 14/47 (2013.01); C12N 15/62 (2013.01); C12N 15/79 (2013.01); G01N 33/5008 (2013.01); G01N 2800/28 (2013.01)

(58) Field of Classification Search
None
See application file for complete search history.

(56) References Cited

U.S. PATENT DOCUMENTS

| | | | |
|---|---|---|---|
| 9,097,703 B2 | 8/2015 | Dolmetsch et al. | |
| 2011/0053857 A1* | 3/2011 | Lindquist | C12N 15/1079 435/254.2 |
| 2012/0237966 A1 | 9/2012 | Dolmetsch et al. | |
| 2012/0291146 A1 | 11/2012 | Klein et al. | |
| 2013/0345294 A1 | 12/2013 | Yang et al. | |
| 2016/0040173 A1 | 2/2016 | Yang et al. | |
| 2016/0326219 A1 | 11/2016 | Riedler et al. | |

FOREIGN PATENT DOCUMENTS

| | | |
|---|---|---|
| EP | 2781601 | 9/2014 |
| WO | 2011130540 | 10/2011 |

OTHER PUBLICATIONS

Calabretta, S., et al. 2015 Trends in Biochemical Sciences 40(11): 662-672. (Year: 2015).*
Zhang, Y-J., et al. 2009 PNAS 106(18): 7607-7612. (Year: 2009).*
International Search Report and Written Opinion dated Jun. 11, 2018, from International Application No. PCT/ US2018/021335, 15 pages.
Grusch, M. et al. "Spatio-temporally precise activation of engineered receptor tyrosine kinases by light", The EMBO Journal, vol. 33, No. 15, pp. 1713-1726 (2014).
Taslimi, A. et al. "An optimized optogenetic clustering tool for probing protein interaction and function", Nat. Commun. 5: 4925, 2015.
Bugaj, L. et al. "Optogenetic protein clustering and signaling activation in mammalian cells", Nature Methods, vol. 10, No. 3, Mar. 1, 2013, pp. 249-252.
Extended EP Search Report dated Aug. 11, 2020, from related EP application No. 18764959, 7 pages.
Altschul, Stephen F., et al. "Basic local alignment search tool." Journal of molecular biology 215.3 (1990): 403-410.
Altschul, Stephen F., et al. "Gapped BLAST and PSI-BLAST: a new generation of protein database search programs." Nucleic acids research 25.17 (1997): 3389-3402.
Beaucage, S. L., and Marvin H. Caruthers. "Deoxynucleoside phosphoramidites—a new class of key intermediates for deoxypolynucleotide synthesis." Tetrahedron Letters 22.20 (1981): 1859-1862.

(Continued)

Primary Examiner — Marsha Tsay
(74) Attorney, Agent, or Firm — Meunier Carlin & Curfman LLC

(57) ABSTRACT

The present disclosure relates to compounds, compositions, and methods for the inducing neurodegenerative disease pathologies. In one aspect, disclosed herein is a nucleotide sequence encoding a chimeric polypeptide, comprising: a first nucleotide sequence encoding a light-induced oligomerization domain and a second nucleotide sequence encoding a neurodegenerative disease in target protein. Disclosed herein is a method of inducing a neurodegenerative disease pathology in a cell, comprising the steps: introducing into the cell an expression vector encoding a chimeric polypeptide, comprising: a first nucleotide sequence encoding a light-induced oligomerization domain and a second nucleotide sequence encoding a low complexity domain from a neurodegenerative disease target protein, wherein the first nucleotide sequence is operably linked to a promoter; expressing the chimeric polypeptide; and inducing oligomerization of the chimeric polypeptide by stimulation with blue light.

14 Claims, 22 Drawing Sheets

Specification includes a Sequence Listing.

(56) References Cited

OTHER PUBLICATIONS

Boshart, Michael, et al. "A very strong enhancer is located upstream of an immediate early gene of human cytomegalovirus." cell 41.2 (1985): 521-530.
Henikoff, Steven, and Jorja G. Henikoff. "Amino acid substitution matrices from protein blocks." Proceedings of the National Academy of Sciences 89.22 (1992): 10915-10919.
Karlin, Samuel, and Stephen F. Altschul. "Applications and statistics for multiple high-scoring segments in molecular sequences." Proceedings of the National Academy of Sciences 90.12 (1993): 5873-5877.
Kennedy, Matthew J., et al. "Rapid blue-light-mediated induction of protein interactions in living cells." Nature methods 7.12 (2010): 973.
Matteucci, Mark Douglas, and M. Ho Caruthers. "Synthesis of deoxyoligonucleotides on a polymer support." Journal of the American Chemical Society 103.11 (1981): 3185-3191.
O'hare, K., C. Benoist, and R. Breathnach. "Transformation of mouse fibroblasts to methotrexate resistance by a recombinant plasmid expressing a prokaryotic dihydrofolate reductase." Proceedings of the National Academy of Sciences 78.3 (1981): 1527-1531.
Shin, Yongdae, et al. "Spatiotemporal control of intracellular phase transitions using light-activated optoDroplets." Cell 168.1-2 (2017): 159-171.
Takebe, Yutaka, et al. "SR alpha promoter: an efficient and versatile mammalian cDNA expression system composed of the simian virus 40 early promoter and the R-U5 segment of human T-cell leukemia virus type 1 long terminal repeat." Molecular and cellular biology 8.1 (1988): 466-472.
Taslimi, Amir, et al. "An optimized optogenetic clustering tool for probing protein interaction and function." Nature communications 5 (2014): 4925.
Wang, Xue, Xianjun Chen, and Yi Yang. "Spatiotemporal control of gene expression by a light-switchable transgene system." Nature methods 9.3 (2012): 266.
Zoltowski, Brian D., and Brian R. Crane. "Light activation of the LOV protein vivid generates a rapidly exchanging dimer." Biochemistry 47.27 (2008): 7012-7019.
International Preliminary Report on Patentability issued for Application No. PCT/US2018/021335, dated Sep. 19, 2019.
Otte, Charlton G. et al. "Optogenetic TDP-43 nucleation induces persistent insoluble species and progressive motor dysfunction in vivo," 2020, Neurobiology of Disease146, 1-10.
Mann, Jacob R. et al. "RNA Binding Antagonizes Neurotoxic Phase Transitions of TDP-43," 2019, Neuron 102, 321-338.

* cited by examiner

| | AT8 | PHF1 | MC1 |
|---|---|---|---|
| VFAU-TAU(WT)-MCH | + | + | + |
| CRY-TAU(WT)-MCH | + | + | + |
| MCH-VVD-TAU(WT) | + | + | + |

OPTOGENETIC INDUCTION OF NEURODEGENERATIVE DISEASE PATHOLOGIES

CROSS REFERENCE TO RELATED APPLICATIONS

This application claims the benefit of U.S. Provisional Patent Application Ser. No. 62/468,065 filed Mar. 7, 2017, the disclosure of which is expressly incorporated herein by reference.

FIELD

The present disclosure relates to compounds, compositions, and methods for the inducing neurodegenerative disease pathologies.

BACKGROUND

The world is aging. By the year 2050, the proportion of individuals over the age of 60 will have doubled to 2 billion from 605 million in 2000. Unfortunately, aging is the single greatest risk factor for developing a fatal neurodegenerative disease. In turn, the number of individuals with dementias such as Alzheimer's disease (AD), Lewy Body Dementia (LBD), Frontotemporal Dementia (FTD), and movement disorders such as Parkinson's Disease (PD) and Amyotrophic Lateral Sclerosis (ALS) will significantly increase. Nearly 6.5 million individuals within the United States are currently living with one of these diseases and the associated costs are unsustainable.

In the United States, the current economic burden of AD, PD, and ALS is an estimated $241 billion dollars per year. AD and ALS/FTD patients can incur personal medical costs upwards of $100,000-$250,000 per year. For AD, it is estimated that 13.8 million individuals in the United States will have been diagnosed by 2050, up from 4.7 million in 2010, while the worldwide number of ALS cases will rise ~31% by 2040 and no effective treatment currently exists for these disorders. Despite a variety of genetic mutations that contribute to these neurodegenerative disorders, there is no known single cause. However, despite this diversity, nearly all patients within each disease exhibit a common neuropathological hallmark in the form of intracellular protein aggregates. Animal models to recapitulate these neuropathologies currently require using either genetic mutations or grossly overexpressing proteins and these often do not mimic patient pathology. What is needed are new and improved methods for inducing neurodegenerative disease pathologies in cell lines and animal models.

The compounds, compositions, and methods disclosed herein address these and other needs.

SUMMARY

Disclosed herein are compounds, compositions, and methods for inducing neurodegenerative disease pathologies in a cell or animal. The inventors have developed new methods for inducing neurodegenerative disease pathologies in cells and animals without the need for genetic mutations or grossly overexpressing neurodegenerative disease proteins.

In one aspect, disclosed herein is a nucleotide sequence encoding a chimeric polypeptide, comprising: a first nucleotide sequence encoding a light-induced oligomerization domain and a second nucleotide sequence encoding a low complexity domain from a neurodegenerative disease target protein.

In one aspect, disclosed herein is an expression vector encoding a chimeric polypeptide, comprising: a first nucleotide sequence encoding a light-induced oligomerization domain and a second nucleotide sequence encoding a low complexity domain from a neurodegenerative disease target protein, wherein the first nucleotide sequence is operably linked to a promoter.

In one aspect, disclosed herein is a cell comprising a nucleotide sequence encoding a chimeric polypeptide, comprising: a first nucleotide sequence encoding a light-induced oligomerization domain and a second nucleotide sequence encoding a neurodegenerative disease target protein.

In one aspect, disclosed herein is a chimeric polypeptide comprising: a light-induced oligomerization domain; and a low complexity domain from a neurodegenerative disease target protein.

In one aspect, disclosed herein is a method of inducing a neurodegenerative disease pathology in a cell, comprising the steps:
introducing into the cell an expression vector encoding a chimeric polypeptide, comprising:
  a first nucleotide sequence encoding a light-induced oligomerization domain and a second nucleotide sequence encoding a low complexity domain from a neurodegenerative disease target protein, wherein the first nucleotide sequence is operably linked to a promoter;
expressing the chimeric polypeptide; and
inducing oligomerization of the chimeric polypeptide by stimulation with blue light.

In another aspect, disclosed herein is a method of screening for an agent that modulates protein aggregation, comprising the steps:
introducing into a cell an expression vector encoding a chimeric polypeptide, comprising:
  a first nucleotide sequence encoding a light-induced oligomerization domain and a second nucleotide sequence encoding a low complexity domain from a neurodegenerative disease target protein, wherein the first nucleotide sequence is operably linked to a promoter;
expressing the chimeric polypeptide;
introducing the agent into a culture media comprising the cell;
inducing oligomerization of the chimeric polypeptide by stimulation with blue light; and
determining modulation of protein aggregation by the agent.

In one embodiment, the light-induced oligomerization domain is selected from the group consisting of CRYPHR, CRY2OLIG, NcVVD, NcVVDY50W, NcLOV, VfAU1, YtvA, EL222, RsLOV, and AsLOV2. In one embodiment, the light-induced oligomerization domain is selected from the list of domains in Table 2. In one embodiment, the light-induced oligomerization domain is NcVVDY50W. In one embodiment, the light-induced oligomerization domain is CRY2OLIG. In one embodiment, the light-induced oligomerization domain is CRYPHR.

In one embodiment, the light-induced oligomerization domain is selected from the group consisting of a CRY2 PHR domain (for example, CRY2 PHR, CRY2OLIG) or a light-oxygen-voltage-sensing (LOV) domain (for example, NcVVD, NcVVDY50W, VfAU1, YtvA, EL222, RsLOV, AsLOV2).

In one embodiment, the low complexity domain from a neurodegenerative disease target protein is selected from the group consisting of TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15. In one embodiment, the low complexity domain from a neurodegenerative disease target protein is selected from Table 3. In one embodiment, the low complexity domain from a neurodegenerative disease target protein is TDP-43. In one embodiment, the low complexity domain from a neurodegenerative disease target protein is Alpha synuclein. In one embodiment, the low complexity domain from a neurodegenerative disease target protein is Tau.

In one embodiment, the cell is a mammalian cell. In one embodiment, the cell is a human cell.

In one embodiment, the blue light has a wavelength between 405 nm and 499 nm. In one embodiment, the blue light has a wavelength of about 465 nm.

BRIEF DESCRIPTION OF THE DRAWINGS

The accompanying figures, which are incorporated in and constitute a part of this specification, illustrate several aspects described below.

FIG. 1, panel A shows that ALS exhibits extreme genetic heterogeneity, especially since these mutations are found in only ~10% of ALS cases. As described in Table 1, despite these genetic causes of ALS, nearly all patients show the same neuropathology in the motor cortex and spinal cord. The right panel shows an example of ALS neuropathology by H and E staining of paraffin tissue sections from an ALS patient motor cortex. Shown are cytoplasmic aggregates of TDP-43. TDP-43 is predominantly nuclear in normal cells as represented by *. In ALS, TDP-43 is absent from the nucleus and aggregates in the cytoplasm as shown by the arrow. Although ALS is used as an example, cytoplasmic aggregate neuropathology is a common feature of many neurodegenerative diseases, see Table 1.

FIG. 2A shows examples of the CRY2OLIG-TDP-43 arrangements and truncated CRY2OLIG-274 arrangements used in this work. FIG. 2B shows a model of the described technology.

(FIGS. 4A-4B) C-terminal fragments of TDP-43 (optoRRM2+LCD/optoLCD) rapidly oligomerize after a brief pulse (8 sec, 10% laser power, 488 nm) of blue light when monitored by live confocal microscopy. These oligomers persist much longer than the Cry2 photoreceptor alone (~10 min disassembly). (FIGS. 4C-4D) Optogenetic LCD fragments also continue to aggregate following brief light pulses, growing in size over time. (FIG. 4E) Persistent blue light stimulation of the TDP-43 LCD forms intracellular aggregates in the cells. Fluorescent recovery after photobleaching (FRAP) experiments show that persistent light LCD inclusions do not recover from FRAP indicating that these are insoluble.

(FIG. 5A-5C) Representative images showing optoTDP43 that (FIG. 5B) first experiences gradual cytoplasmic mislocalization, (FIG. 5C) which was confirmed by nuclear/cytoplasmic fractionation. (FIG. 5D) Mislocalization is followed by optoTDP43 aggregation, as measured by simultaneous chronic blue light exposure and high-throughput automated confocal microscopy, that increases in propensity with increasing light exposure. (FIG. 5E) Fluorescence recovery after photobleaching (FRAP) imaging was performed to assess dynamicity of optoTDP43 structures. Lack of fluorescence recovery shows that light-induced optoTDP43 aggregates are non-dynamic, immobile granules reminiscent of aggregated structures. (FIG. 5F) Detergent-solubility of optoTDP43 structures was assessed by subcellular fractionation to confirm aggregated state of light-induced optoTDP43 granules. (Left lanes) Non-optogenetic TDP-43 (TDP43-mCh) shows no changes in solubility with and without light treatment, while optoTDP43 (right lanes) displays a drastic shift to the insoluble fraction with chronic blue light stimulation. In addition to increased insolubility of exogenous, full-length optoTDP43 (top band), chronic blue light exposure also results in recruitment of aberrant optoTDP43 cleavage products (middle bands), as well as endogenous full-length TDP-43 and disease-relevant cleavage products (bottom bands), to the detergent-insoluble, urea-soluble fraction of cell lysates as is observed in patient tissue. (FIG. 5G) To confirm direct recruitment of non-optogenetic TDP-43 species to exogenous light-induced optoTDP43 inclusions, EGFP-tagged TDP-43 was co-expressed with optoTDP43 or the Cry2 photoreceptor-only control. In cells exposed to chronic blue light stimulation, strong co-localization is observed between optoTDP43 inclusions and EGFP-TDP43, confirming the ability of optoTDP43 inclusions to directly recruit other TDP-43 species. This recruitment appears to be dependent on TDP43:TDP43 interactions, as no co-localization is observed with Cry2-mCh puncta following blue light exposure. (FIG. 5H-5J) Immunofluorescence analysis was performed on light-induced optoTDP43 aggregates to confirm pathological hallmarks seen in patient tissue. optoTDP43 inclusions appear to be (FIG. 5H) ubiquitinated, (FIG. 5I) hyperphosphorylated, and (FIG. 5J) p62-positive, all of which have been observed with TDP-43 inclusions in patient CNS. (FIG. 5K) Automated high-throughput confocal microscopy was performed to assess the neurotoxicity of light-induced optoTDP43 inclusions. Human ReN neurons expressing TDP43-mCh or optoTDP43 were exposed to chronic blue light stimulation and viability was simultaneously monitored by longitudinal imaging. Neurons expressing non-optogenetic TDP43-mCh showed no significant decrease in survival with or without blue light exposure. However, neurons expressing optoTDP43 that were exposed to blue light stimulation display significantly decreased viability over time, suggesting optoTDP43 inclusions are neurotoxic. *=p<0.05, **=p<0.01

FIG. 6A shows the chronic stimulation paradigm and FIG. 6B shows representative images of α-synuclein clustering with light over time along with quantification of clustering in FIG. 6C. These data indicate that this optogenetic system can be employed to induce the clustering and aggregation of multiple neurodegenerative disease proteins that are prone to aggregation, that is, contain prion-like domains/LCD/IDDs. FIG. 6D shows that α-synuclein fused to the LOV (dimerizing photoreceptor) forms intracellular clusters of alpha synuclein. FIG. 6E shows that light induced α-synuclein LOV aggregates exhibit pathological hallmarks of synucleinopathies including phosphorylation at serine 129 and p62 positivity.

(FIGS. 7A-7C) HEK293 cells expressing Cry2 photoreceptor-alone or Cry2-Tau fusion proteins were exposed to chronic blue light stimulation (16 hours, 488 nm, 10 mW). Cry2-Tau-expressing cells show fibril-like aggregates that co-stain with phospho-Tau antibodies AT8 (FIG. 7A) and PHF1 (FIG. 7B), as well as the pathological conformation-dependent Tau antibody MC1 (FIG. 7C). (FIG. 7D) Summary showing the various optogenetic Tau constructs that co-localize with pathological Tau antibodies after light-induction of neurofibrillary tangle formation.

(FIG. 8A-FIG. 8B) HEK293 cells expressing VVD-Tau or VfAU-Tau fusion proteins were exposed to chronic blue light stimulation (16 hours, 488 nm, 10 mW). Both fusion proteins co-stain with phospho-Tau antibodies AT8 and PHF1, and the pathological conformation-dependent Tau antibody MC1. (FIG. 8C) Differentiated MAP2+ human ReN neurons expressing VVD-Tau also shows neurofibrillary tangle formation following chronic light treatment that co-localizes with AT8. (FIG. 8D) Fluorescence recovery after photobleaching analysis was performed on light-induced tangles and shows a lack of fluorescence recovery, indicating a non-dynamic, immobile structure. (FIG. 8E) Urea extraction was next performed to confirm insoluble tau species with light treatment in HEK293 cells expressing VVD-Tau. Cells exposed to chronic light show increased levels of soluble and insoluble 150 kDa tau species which is present in Alzheimer's Disease and Frontotemporal Dementia patient tissue.

FIG. 9A shows that a TDP-43-CRY2OLIG-mCh protein mislocalizes but does not exhibit the ability to aggregate as the CRY2OLIG-TDP-43-mCh arrangement does. Similarly, FIG. 9B shows that the mCh-aSyn-NvVVDY50W does not have the ability to aggregate. This data shows that the protein arrangement and light stimulation paradigms are important for inducing neuropathological protein aggregates as observed in the CNS tissue of patients with neurodegenerative disease.

FIG. 10A shows that acute stimulation of HEK cells expressing CRY2OLIG-TDP274-mCh can induce the formation of pathological aggregates within 1 hour. These aggregates can grow in size and become toxic over time. FIG. 10B is a schematic of a screening pipeline to use the induction of neurodegenerative disease pathology to identify therapeutic compounds that rescue toxicity and prevent or remove the formation of the induced neurodegenerative disease pathology.

DETAILED DESCRIPTION

Figure 1:
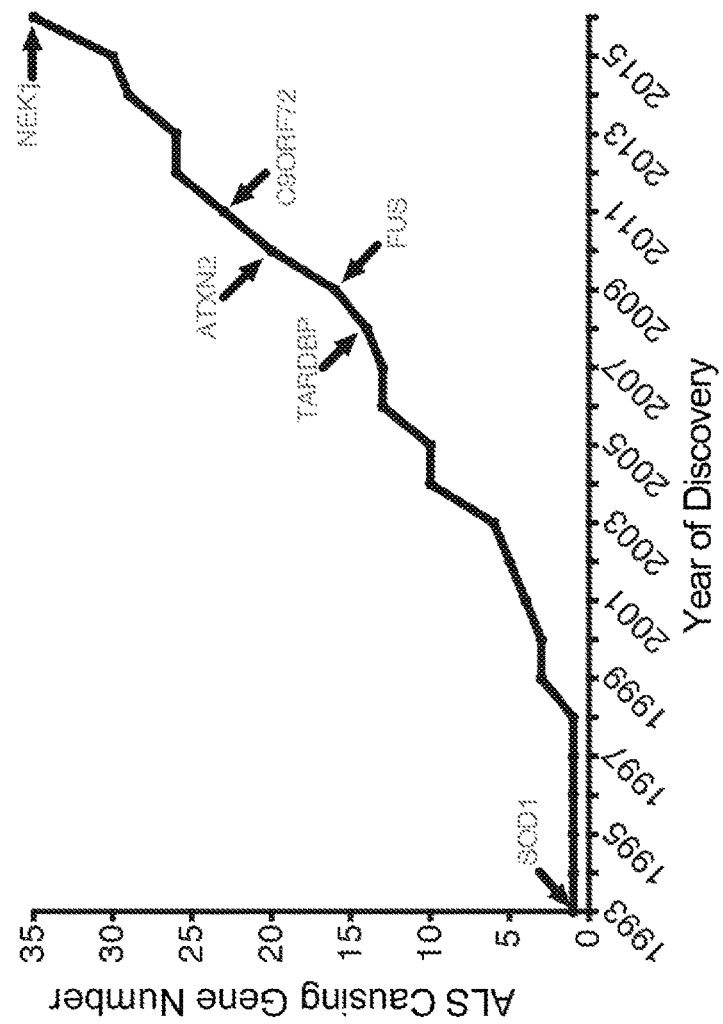
FIG. 1 shows the examples of genetic causes of ALS and the common neuropathology. The left panel shows a graph of the number of ALS-causing genes on the Y axis, and the X axis indicates the year each mutation was discovered.
Figure 1:
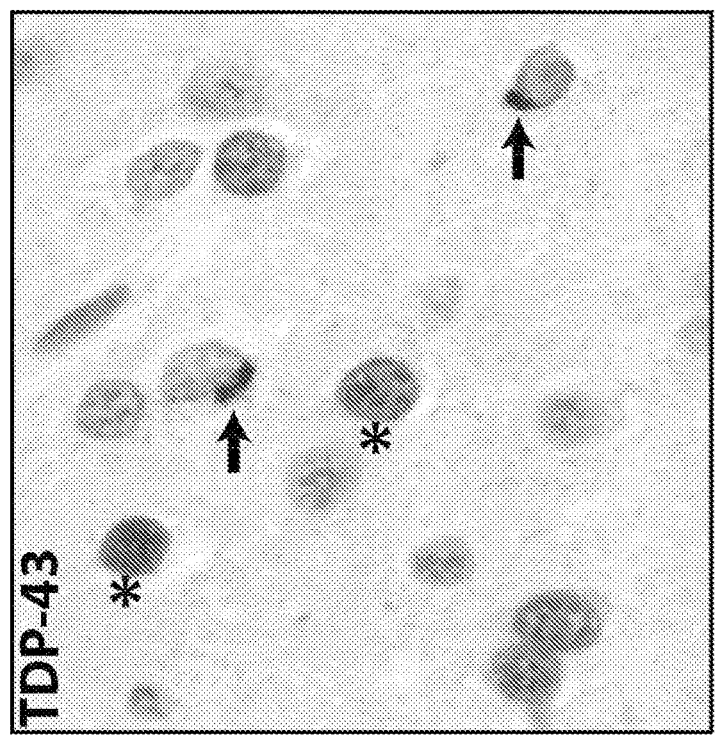
Figure 2A:
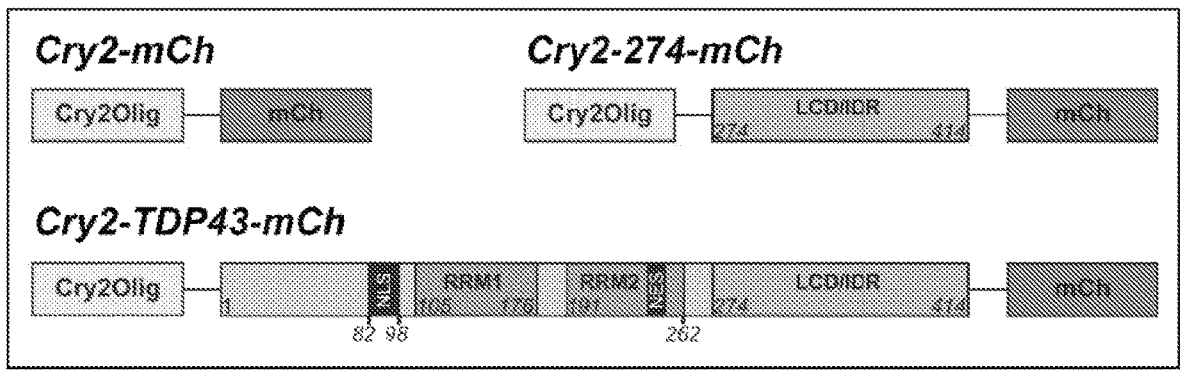
FIGS. 2A-2B describe methods to generate neuropathological aggregate proteins containing an LCD/IDR/Prion-like domain with light using TDP-43 and CRY2OLIG as an example. Various protein arrangements and blue light exposure paradigms were developed to induce protein aggregation of proteins and protein fragments containing LCD/IDR/prion-like domains, promote the mislocalization of nuclear proteins and recapitulate the neuropathology of neurodegenerative diseases. TDP-43 is a predominantly nuclear protein that contains an IDR/IDD/prion-like domain, and is mislocalized and aggregated in ALS, FTD, and some AD patients, as an example. DNA sequences were engineered to generate amino acid sequences that encode for a the CRY2OLIG protein that clusters when exposed to blue light generated a fusion protein either the entire TDP-43 protein (cry2-TDP43-mCh) or just the low complexity domain (LCD/IDD/prion-like domain), which makes TDP-43 aggregation prone (Cry2-274-mCh). As a control, CRY2OLIG alone was used. All constructs were fused to a fluorescent protein called mCherry (mCh) to visualize the proteins in live cells. CRY2OLIG-mCh reversibly clusters with blue light stimulation but the CRY2OLIG-TDP-43-mCh or the truncated CRY2OLIG-274-mCh forms irreversible aggregates with specific blue light stimulation paradigms.
Figure 2B:
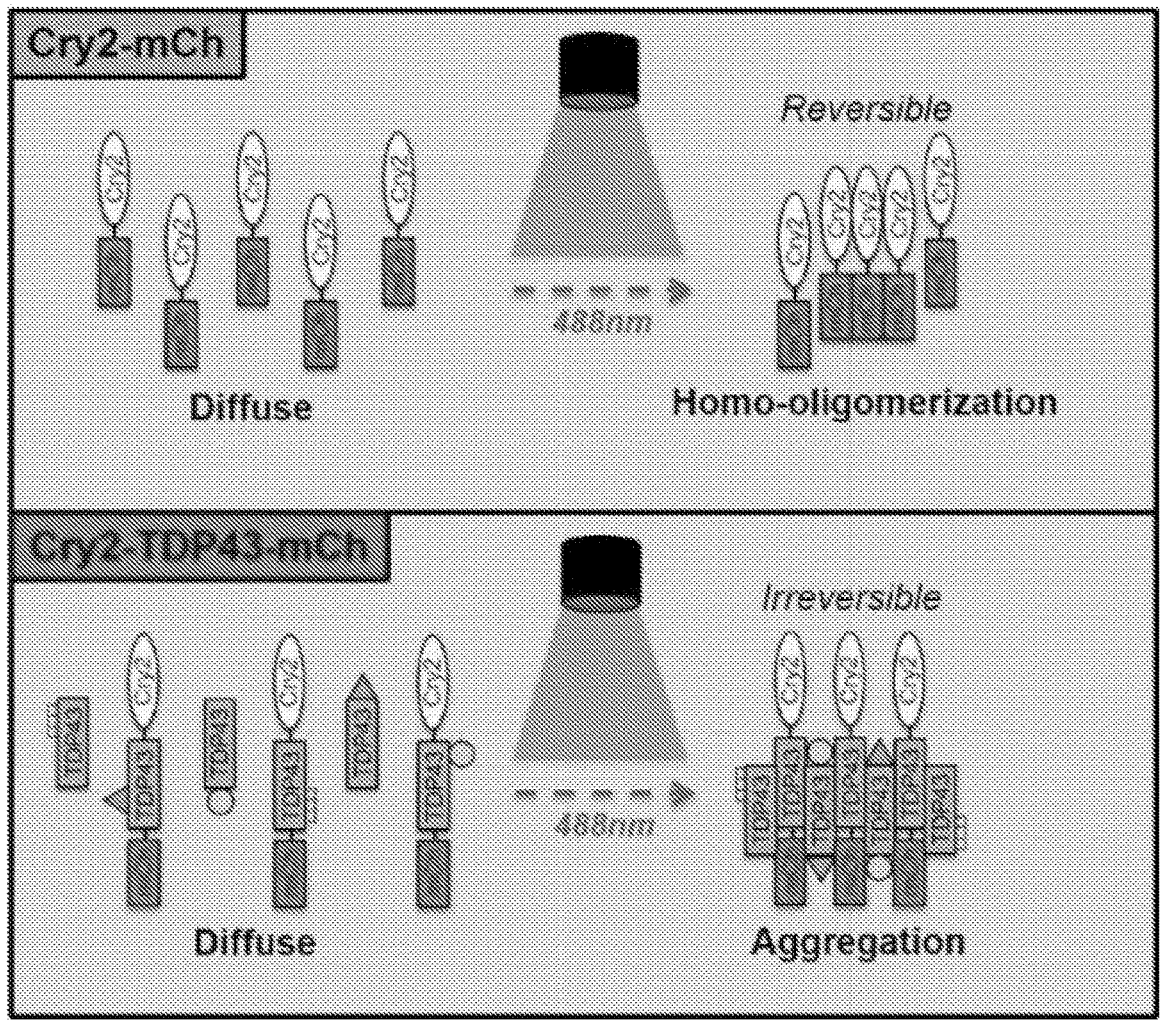
Figure 3:
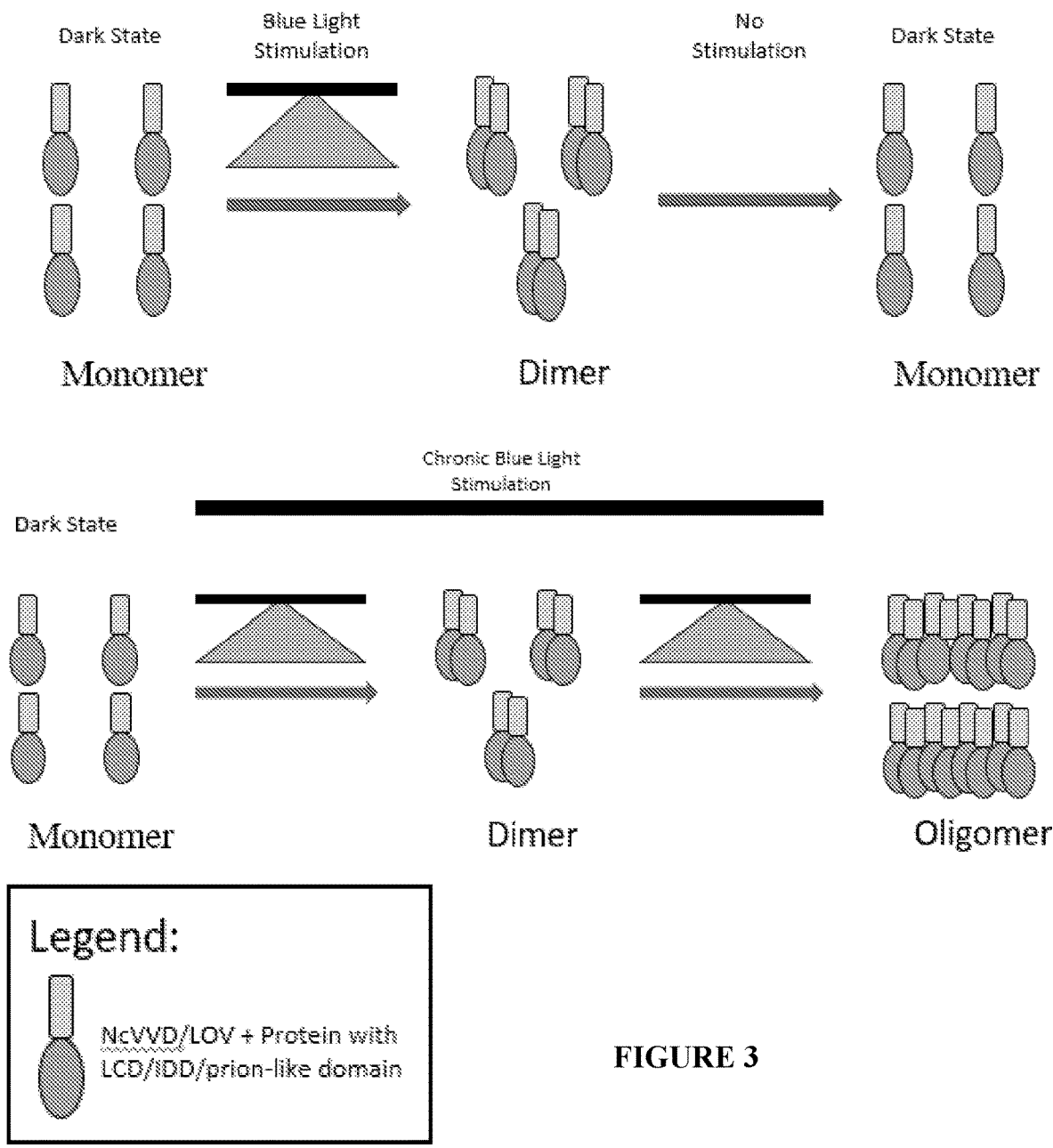
FIG. 3 shows a schematic describing blue light induced oligomerization and aggregation of proteins employing the NcVVD, NcVVDY50W or NcLOV photoreceptor. The NcVVD or LOV domain have only been shown to homodimerize with blue light stimulation. A light exposure paradigm to induce oligomerization and aggregation was developed. The top panel shows a schematic of how a single acute stimulation with blue light (405-499 nm) induces the homodimerization of the LOV protein when fused to a protein of interest. The bottom panel shows that chronic stimulation with blue light promotes the homooligomerization of NcVVD or LOV fusion proteins that contain a prion-like domain/LCD/IDD.
Figure 4A:
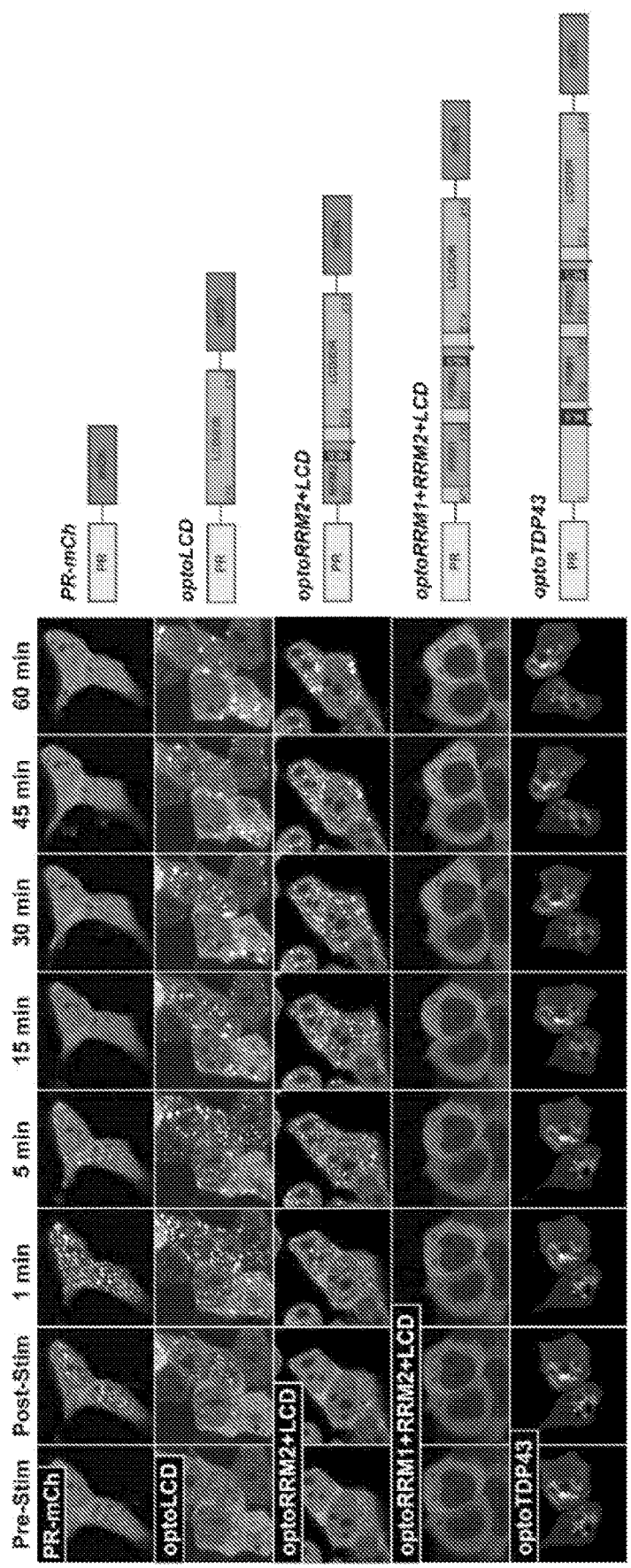
FIGS. 4A-4E show light-induced aggregation of low-complexity domain proteins. Optogenetic TDP-43 fragments containing the low-complexity domain (LCD) undergo progressive aggregation with light stimulation.
Figure 4B:
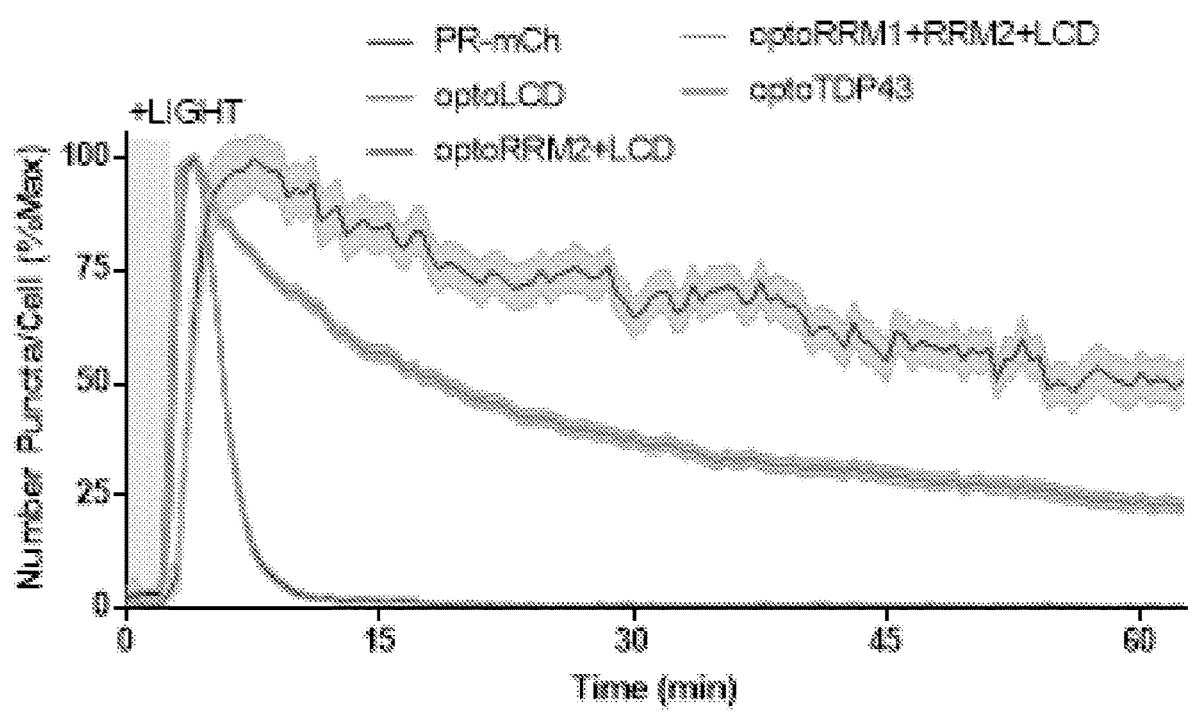
Figure 4C:
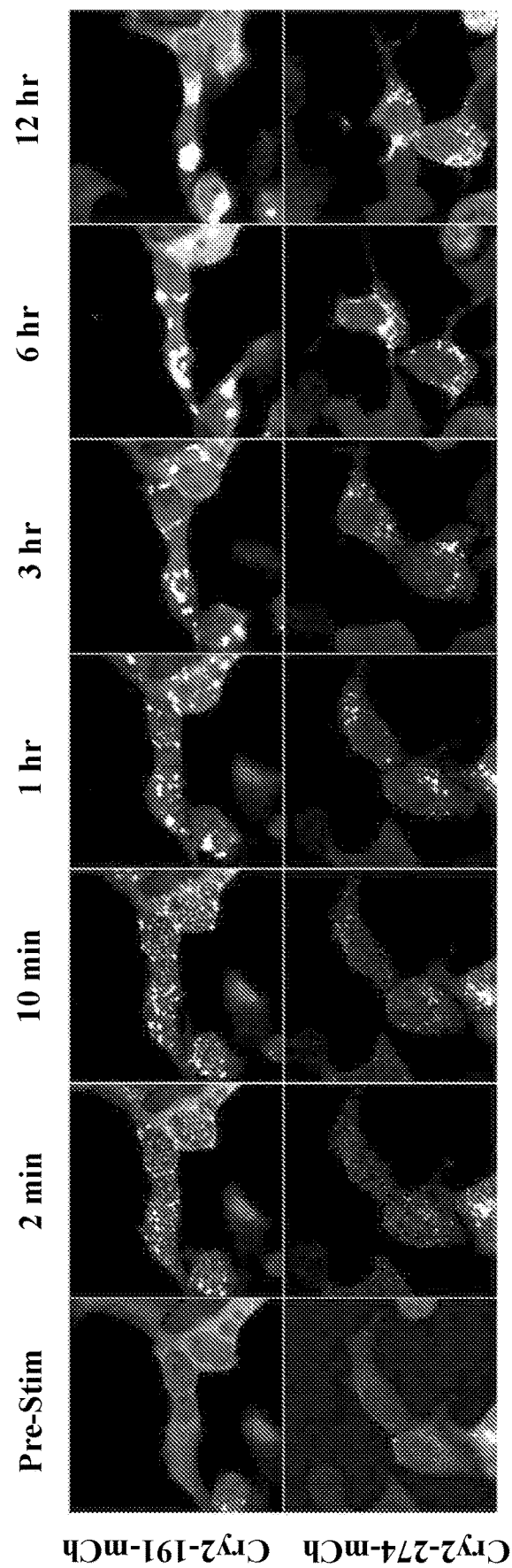
Figure 4D:
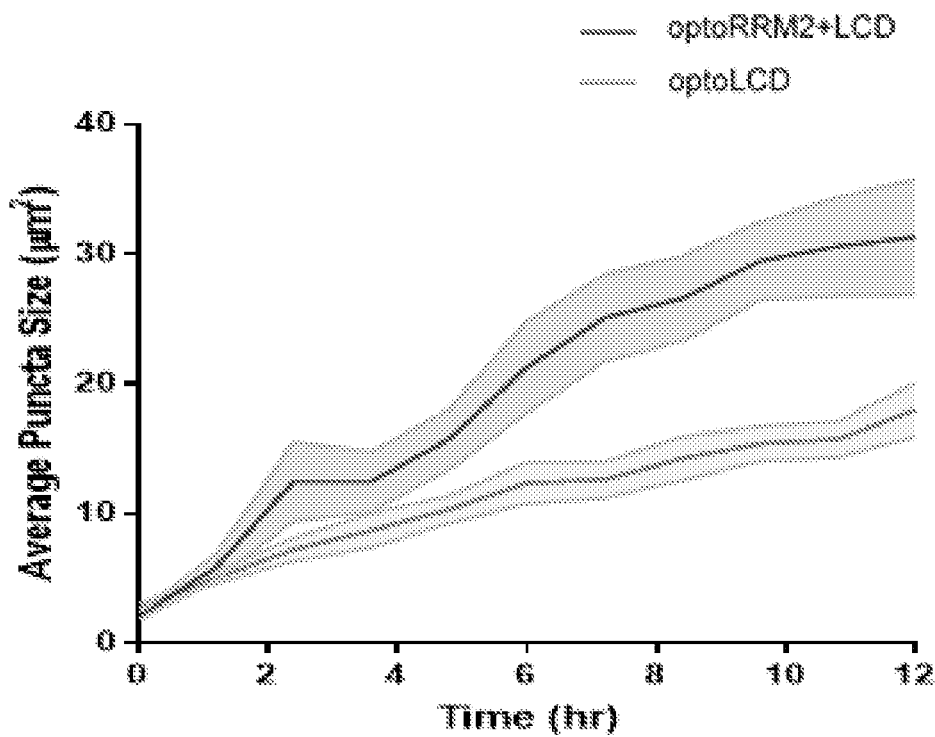
Figure 4E:
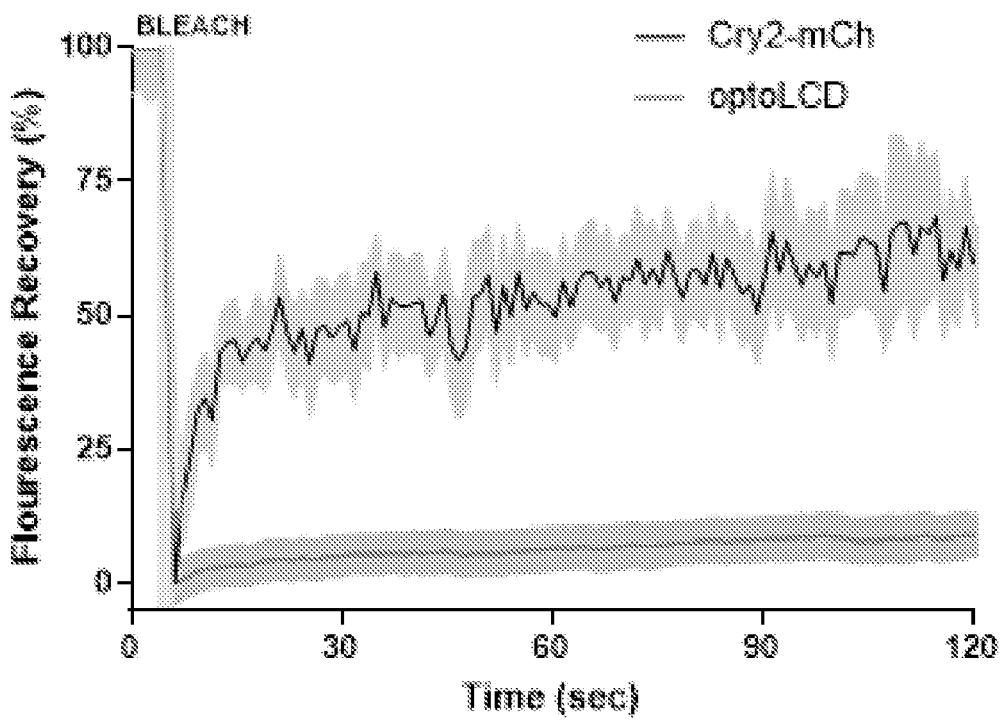

Disclosed herein are compounds, compositions, and methods for inducing neurodegenerative disease pathologies in a cell or animal. The inventors have developed new methods for inducing neurodegenerative disease pathologies in cells and animals without the need for genetic mutations or grossly overexpressing neurodegenerative disease proteins.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The following definitions are provided for the full understanding of terms used in this specification.

Terminology

As used herein, the article "a," "an," and "the" means "at least one," unless the context in which the article is used clearly indicates otherwise.

The term "about" as used herein when referring to a measurable value such as an amount, a percentage, and the like, is meant to encompass variations of ±20%, ±10%, ±5%, or ±1% from the measurable value.

As used herein, the terms "may," "optionally," and "may optionally" are used interchangeably and are meant to include cases in which the condition occurs as well as cases in which the condition does not occur.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The terms "polynucleotide", "nucleotide sequence", and "nucleic acid sequence" are used interchangeably herein and refer to a single or double stranded polymer composed of nucleotide monomers.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "variant" or "derivative" as used herein refers to an amino acid sequence derived from the amino acid sequence of the parent protein having one or more amino acid substitutions, insertions, and/or deletions.

Chimeric Constructs

In one aspect, disclosed herein is a nucleotide sequence encoding a chimeric polypeptide, comprising: a first nucleotide sequence encoding a light-induced oligomerization domain and a second nucleotide sequence encoding a low complexity domain from a neurodegenerative disease target protein.

In one aspect, disclosed herein is an expression vector encoding a chimeric polypeptide, comprising: a first nucleotide sequence encoding a light-induced oligomerization domain and a second nucleotide sequence encoding a low complexity domain from a neurodegenerative disease target protein, wherein the first nucleotide sequence is operably linked to a promoter.

In some embodiments, the expression vector encoding a chimeric polypeptide is comprised in a plasmid or in a virus or viral vector. A plasmid or a viral vector can be capable of extrachromosomal replication or, optionally, can integrate into the host genome. As used herein, the term "integrated" used in reference to an expression vector (e.g., a plasmid or viral vector) means the expression vector, or a portion thereof, is incorporated (physically inserted or ligated) into the chromosomal DNA of a host cell. As used herein, a "viral vector" refers to a virus-like particle containing genetic material which can be introduced into a eukaryotic cell without causing substantial pathogenic effects to the eukaryotic cell. A wide range of viruses or viral vectors can be used for transduction, but should be compatible with the cell type the virus or viral vector are transduced into (e.g., low toxicity, capability to enter cells). Suitable viruses and viral vectors include adenovirus, lentivirus, retrovirus, among others. In some embodiments, the expression vector encoding a chimeric polypeptide is a naked DNA or is comprised in a nanoparticle (e.g., liposomal vesicle, porous silicon nanoparticle, gold-DNA conjugate particle, polyethylenimine polymer particle, cationic peptides, etc.).

The expression vectors disclosed herein are, in some embodiments, capable of inducing a neurodegenerative disease pathology in a cell (e.g., inducing aggregation of a protein) without substantially altering the expression level of a protein involved in the neurodegenerative disease pathology. For example and without limitation, the expression vector can induce aggregation of a protein having a low complexity domain from a neurodegenerative disease target protein without substantially increasing or decreasing the expression level of an endogenous target protein which comprises the same low complexity domain. As such, a cell comprising a herein disclosed nucleotide sequence encoding a chimeric polypeptide can have substantially unchanged expression levels of an endogenous neurodegenerative disease target protein comprising a low complexity domain, as compared to a cell of the same cell type which does not comprise the nucleotide sequence encoding a chimeric polypeptide. The term "substantially unchanged expression levels," as used herein, refers to a change in expression level, if any, to a degree not known or not suspected to cause or be associated with inducing a neurodegenerative disease pathology in a cell.

The expression vectors disclosed herein are, in some embodiments, are capable of inducing a neurodegenerative disease pathology in a cell (e.g., inducing aggregation of a protein) using a wild-type form of a low complexity domain from a neurodegenerative disease target protein. Thus, in some embodiments, the low complexity domain from a neurodegenerative disease target protein does not include a mutation which differs from the wild-type sequence and which is known or suspected to cause or be associated with inducing a neurodegenerative disease pathology in a cell. For example and without limitation, the expression vector can comprise a low complexity domain from a wild-type TDP-43 protein which does not contain a mutation such as Q331K, known to cause or be associated with ALS.

In one aspect, disclosed herein is a cell comprising a nucleotide sequence encoding a chimeric polypeptide, comprising: a first nucleotide sequence encoding a light-induced oligomerization domain and a second nucleotide sequence encoding a neurodegenerative disease target protein.

In some embodiments, the cell is a cell which can be affected by a neurodegenerative disease. For example, the cell can be a glial cell or a neuronal cell.

In one aspect, disclosed herein is a chimeric polypeptide comprising: a light-induced oligomerization domain; and a low complexity domain from a neurodegenerative disease target protein.

In one embodiment, the light-induced oligomerization domain is selected from the group consisting of CRYPHR, CRY2OLIG, NcVVD, NcVVDY50W, and NcLOV. In one embodiment, the light-induced oligomerization domain is selected from the group consisting of CRYPHR, CRY2OLIG, NcVVD, NcVVDY50W, NcLOV, VfAU1, YtvA, EL222, RsLOV, and AsLOV2. In one embodiment, the light-induced oligomerization domain is selected from the list of domains in Table 2. In one embodiment, the light-induced oligomerization domain is selected from a variant of CRYPHR, CRY2OLIG, NcVVD, NcVVDY50W, NcLOV, VfAU1, YtvA, EL222, RsLOV, or AsLOV2. In one embodiment, the light-induced oligomerization domain is selected from a fragment of CRYPHR, CRY2OLIG, NcVVD, NcVVDY50W, NcLOV, VfAU1, YtvA, EL222, RsLOV, or AsLOV2.

In one embodiment, the light-induced oligomerization domain is NcVVDY50W. In one embodiment, the light-induced oligomerization domain is CRY2OLIG. In one embodiment, the light-induced oligomerization domain is CRYPHR. In one embodiment, the light-induced oligomerization domain comprises a LOV domain from the VVD protein. In one embodiment, the light-induced oligomerization domain comprises a LOV domain from the LOV protein. In one embodiment, the light-induced oligomerization domain comprises a PHR domain. In one embodiment, the light-induced oligomerization domain comprises a PHR domain, from the CRY2 protein. In one embodiment, the light-induced oligomerization domain is VfAU1. In one embodiment, the light-induced oligomerization domain is YtvA. In one embodiment, the light-induced oligomerization domain is EL222. In one embodiment, the light-induced oligomerization domain is RsLOV. In one embodiment, the light-induced oligomerization domain is AsLOV2.

In one embodiment, the light-induced oligomerization domain is at least 90% identical to CRYPHR. In one embodiment, the light-induced oligomerization domain is at least 90% identical to NcVVD. In one embodiment, the light-induced oligomerization domain is at least 90% identical to NcVVDY50W. In one embodiment, the light-induced oligomerization domain is at least 90% identical to NcLOV. In one embodiment, the light-induced oligomerization domain is at least 90% identical to CRY2OLIG. In one embodiment, the light-induced oligomerization domain is at least 90% identical to VfAU1. In one embodiment, the light-induced oligomerization domain is at least 90% identical to YtvA. In one embodiment, the light-induced oligomerization domain is at least 90% identical to EL222. In one embodiment, the light-induced oligomerization domain is at least 90% identical to RsLOV. In one embodiment, the light-induced oligomerization domain is at least 90% identical to AsLOV2.

In some embodiments, the first nucleotide sequence can comprise a nucleotide sequence which encodes a light-induced oligomerization domain selected from the group consisting of CRYPHR, CRY2OLIG, NcVVD, NcVVDY50W, NcLOV, and VfAU1LOV.

In some embodiments, the first nucleotide sequence can comprise a nucleotide sequence which encodes an amino acid sequence that is at least 70% identical to SEQ ID NO:1, SEQ ID NO:2, SEQ ID NO:3, SEQ ID NO:4, SEQ ID NO:5, SEQ ID NO:92, SEQ ID NO:93, SEQ ID NO:99, SEQ ID NO:100, SEQ ID NO:101, or SEQ ID NO:102. In some embodiments, the first nucleotide sequence can encode an amino acid sequence which is at least 75% identical, at least 80% identical, at least 85% identical, at least 90% identical, at least 95% identical, or at least 99% identical to SEQ ID NO:1, SEQ ID NO:2, SEQ ID NO:3, SEQ ID NO:4, SEQ ID NO:5, SEQ ID NO:92, SEQ ID NO:93, SEQ ID NO:99, SEQ ID NO:100, SEQ ID NO:101, or SEQ ID NO:102. In some embodiments, the first nucleotide sequence can comprise SEQ ID NO:1, SEQ ID NO:2, SEQ ID NO:3, SEQ ID NO:4, SEQ ID NO:5, SEQ ID NO:92, SEQ ID NO:93, SEQ ID NO:99, SEQ ID NO:100, SEQ ID NO:101, or SEQ ID NO:102. In some embodiments, the first nucleotide sequence can comprise SEQ ID NO:94. The nucleotide sequence can be that of the wild type nucleic acid sequence encoding an amino acid sequence disclosed herein. In some embodiments, the nucleotide sequence is modified from the wild type sequence, but due to the degeneracy of the genetic code, can still encode for the same amino acid sequence. In some embodiments, the nucleotide sequence is a variant of one of the sequences disclosed herein (or encodes of variant protein sequence). In some embodiments, the nucleotide sequence is a fragment of one of the nucleic acids herein, or encodes a fragment of one of the amino acids disclosed herein. In some embodiments, the nucleotide sequence is codon optimized (for example, to improve expression).

In one embodiment, the light-induced oligomerization domain is selected from the group consisting of a CRY2 PHR domain (for example, CRY2 PHR, CRY2OLIG) or a light-oxygen-voltage-sensing (LOV) domain (for example, NcVVD, NcVVDY50W, VfAU1, YtvA, EL222, RsLOV, AsLOV2).

In one embodiment, the low complexity domain from a neurodegenerative disease target protein is selected from the group consisting of TDP-43, Alpha synuclein, Tau, Fus, TIA1, SOD1, Huntingtin, Ataxin 2, and hnRNPA2B1. In one embodiment, the low complexity domain from a neurodegenerative disease target protein is selected from the group consisting of TDP-43, Alpha synuclein, Tau, Fus, TIA1, SOD1, Huntingtin, Ataxin 2, hnRNPA1, and hnRNPA2B1. In one embodiment, the low complexity domain from a neurodegenerative disease target protein is selected from the group consisting of TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15. In one embodiment, the low complexity domain from a neurodegenerative disease target protein is selected from a variant of TDP-43, Alpha synuclein, Tau, TIA1, SOD1, Huntingtin, Ataxin 2, hnRNPA1, hnRNPA2B1, EWS RNA Binding Protein 1, or TATA box binding protein factor 15. In one embodiment, the low complexity domain from a neurodegenerative disease target protein is selected from a fragment of TDP-43, Alpha synuclein, Tau, TIA1, SOD1, Huntingtin, Ataxin 2, hnRNPA1, hnRNPA2B1, EWS RNA Binding Protein 1, or TATA box binding protein factor 15. In one embodiment, the fragment of TDP-43, Alpha synuclein, Tau, TIA1, SOD1, Huntingtin, Ataxin 2, hnRNPA1, hnRNPA2B1, EWS RNA Binding Protein 1, or TATA box binding protein factor 15 comprises a low complexity domain (or fragment thereof) within each neurodegenerative disease target protein.

In one embodiment, the low complexity domain from a neurodegenerative disease target protein is selected from Table 3. In one embodiment, the low complexity domain is from any neurodegenerative disease target protein that aggregates in neurodegenerative diseases.

In one embodiment, the low complexity domain from a neurodegenerative disease target protein is selected from the group consisting of an amino acid sequence with at least 90% identity to TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15. In one embodiment, the low complexity domain from a neurodegenerative disease target protein is selected from the group consisting of an amino acid sequence with at least 90% identity to a low complexity domain from a neurodegenerative disease target protein is selected from Table 3. In one embodiment, the low complexity domain from a neurodegenerative disease target protein is selected from an orthologue of the group consisting of TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15.

In one embodiment, the low complexity domain from a neurodegenerative disease target protein is selected from the group consisting of an amino acid sequence with at least 60% (for example, at least 60%, at least 70%, at least 80%, at least 90%, at least 95%) identity to TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15 (or a fragment thereof).

In one embodiment, the low complexity domain from a neurodegenerative disease target protein is TDP-43. In one embodiment, the low complexity domain from a neurodegenerative disease target protein is Alpha synuclein. In one embodiment, the low complexity domain from a neurodegenerative disease target protein is Tau. In one embodiment, the low complexity domain from a neurodegenerative disease target protein is Fus. In one embodiment, the low complexity domain from a neurodegenerative disease target protein is TIA1. In one embodiment, the low complexity domain from a neurodegenerative disease target protein is SOD1. In one embodiment, the low complexity domain from a neurodegenerative disease target protein is Huntingtin. In one embodiment, the low complexity domain from a neurodegenerative disease target protein is Ataxin 2. In one embodiment, the low complexity domain from a neurodegenerative disease target protein is hnRNPA1. In one embodiment, the low complexity domain from a neurodegenerative disease target protein is hnRNPA2B1. In one embodiment, the low complexity domain from a neurodegenerative disease target protein is EWS RNA Binding Protein 1. In one embodiment, the low complexity domain from a neurodegenerative disease target protein is TATA box binding protein factor 15.

In one embodiment, a VVD light-induced oligomerization domain is fused to a low complexity domain of TDP-43. In one embodiment, a VVD light-induced oligomerization is fused to full length TDP-43 (comprising a low complexity domain). In one embodiment, a light-induced oligomerization domain is fused to a low complexity domain from any neurodegenerative disease target protein that aggregates in neurodegenerative diseases.

In one embodiment, a light-induced oligomerization domain is fused to a low complexity domain of TDP-43, wherein the sequence of the low complexity domain of TDP-43 comprises SEQ ID NO:95, SEQ ID NO:96, SEQ ID NO:97, or SEQ ID NO:98 (or a fragment thereof).

In one embodiment, the nucleotide sequence encoding the chimeric polypeptide may further comprise a third nucleotide sequence encoding a reporter protein such as a fluorescent protein (to allow visualization of the protein aggregates by fluorescence). In one embodiment, the fluorescent protein is mCherry (mCh). In some embodiments, the fluorescent protein is GFP or YFP. In some embodiments, the first nucleotide sequence can encode a light-induced oligomerization domain comprising a PHR domain of the *Arabidopsis* Cryptochrome 2 protein (e.g., CRYPHR). In some embodiments, the light-induced oligomerization domain can comprise a wild-type CRYPHR amino acid sequence as disclosed, for example, in SEQ ID NO:1, or optionally, can comprise a mutated CRYPHR amino acid sequence as disclosed, for example, in SEQ ID NO:2. In some embodiments, a mutated CRYPHR amino acid sequence can comprise a E490G mutation, which can increase efficiency of clustering upon blue light stimulation as compared to a wild-type CRYPHR amino acid sequence. In some embodiments, the first nucleotide sequence can encode a light-induced oligomerization domain, wherein the light-induced oligomerization domain comprises a polypeptide sequence which is at least 70% identical to SEQ ID NO:1 or SEQ ID NO:2. In some embodiments, the first nucleotide sequence can encode a light-induced oligomerization domain, wherein the light-induced oligomerization domain comprises a polypeptide sequence which is at least 75% identical, at least 80% identical, at least 85% identical, at least 90% identical, at least 95% identical, or at least 99% identical to SEQ ID NO:1 or SEQ ID NO:2. In some embodiments, the first nucleotide sequence can encode a light-induced oligomerization domain comprising the polypeptide sequence of SEQ ID NO:1 or SEQ ID NO:2.

In some embodiments, the first nucleotide sequence can encode a light-induced oligomerization domain comprising Light-Oxygen-Voltage-Sensing Domain (LOV) from *Neurospora* Vivid protein (e.g., LOV, NcVVD, NcVVDY50W, NcLOV, VfAU1, YtvA, EL222, RsLOV, and/or AsLOV2). In some embodiments, the light-induced oligomerization domain can comprise a wild-type LOV amino acid sequence as disclosed, for example, in SEQ ID NO:3, SEQ ID NO:4, SEQ ID NO:92, SEQ ID NO:93, SEQ ID NO:99, SEQ ID NO:100, SEQ ID NO:101, or SEQ ID NO:102, or optionally, can comprise a mutated LOV amino acid sequence as disclosed, for example, in SEQ ID NO:5. In some embodiments, a mutated LOV amino acid sequence can comprise a Y50W mutation, which can reduce the rate of dissipation from a dimerized state as compared to a wild-type LOV amino acid sequence. In some embodiments, the first nucleotide sequence can encode a light-induced oligomerization domain, wherein the light-induced oligomerization domain comprises a polypeptide sequence which is at least 70% identical to SEQ ID NO:3, SEQ ID NO:4, SEQ ID NO:5, SEQ ID NO:92, SEQ ID NO:93, SEQ ID NO:99, SEQ ID NO:100, SEQ ID NO:101, or SEQ ID NO:102. In some embodiments, the first nucleotide sequence can encode a light-induced oligomerization domain, wherein the light-induced oligomerization domain comprises a polypeptide sequence which is at least 75% identical, at least 80% identical, at least 85% identical, at least 90% identical, at least 95% identical, or at least 99% identical to SEQ ID NO:3, SEQ ID NO:4, SEQ ID NO:5, SEQ ID NO:92, SEQ ID NO:93, SEQ ID NO:99, SEQ ID NO:100, SEQ ID NO:101, or SEQ ID NO:102. In some embodiments, the first nucleotide sequence can encode a light-induced oligomerization domain comprising the polypeptide sequence of SEQ ID NO:3, SEQ ID NO:4, SEQ ID NO:5, SEQ ID NO:92, SEQ ID NO:93, SEQ ID NO:99, SEQ ID NO:100, SEQ ID NO:101, or SEQ ID NO:102.

In some embodiments, the first nucleotide sequence can encode a light-induced oligomerization domain comprising a PHR domain of the *Arabidopsis* Cryptochrome 2 protein (e.g., CRYPHR), and the second nucleotide sequence can encode a low complexity domain from a neurodegenerative disease target protein. In some embodiments, the first nucleotide sequence can encode a light-induced oligomerization domain comprising a PHR domain of the *Arabidopsis Cryptochrome* 2 protein (e.g., CRYPHR), and the second nucleotide sequence can encode a low complexity domain from a neurodegenerative disease target protein comprising TDP-43. In some embodiments, the second nucleotide sequence can encode a low complexity domain from a neurodegenerative disease target protein comprising full-length TDP-43 (e.g., SEQ ID NO:6 or SEQ ID NO:7). In some embodiments, the second nucleotide sequence can encode a low complexity domain from a neurodegenerative disease target protein comprising truncated TDP-43 (e.g., SEQ ID NO:8, SEQ ID NO:9, SEQ ID NO:10, SEQ ID NO:11, SEQ ID NO:12, or SEQ ID NO:13). In some embodiments, a truncated TDP-43 comprises or consists of amino acids 105-414, 191-414, or 274-414 of the full-length TDP-43 amino acid sequence. Thus, in some embodiments, the first nucleotide sequence can encode a light-induced oligomerization domain comprising CRYPHR, and the second nucleotide sequence can encode a low complexity domain from a neurodegenerative disease target protein comprising full-length or truncated TDP-43, wherein the first nucleotide sequence and the second nucleotide sequence encode a chimeric polypeptide sequence which is at least 75% identical, at least 80% identical, at least 85% identical, at least 90% identical, at least 95% identical, or at least 99% identical to SEQ ID NO:6, SEQ ID NO:7, SEQ ID NO:8, SEQ ID NO:9, SEQ ID NO:10, SEQ ID NO:11, SEQ ID NO:12, or SEQ ID NO:13. In some embodiments, the first nucleotide sequence and the second nucleotide sequence encode a chimeric polypeptide sequence according to SEQ ID NO:6, SEQ ID NO:7, SEQ ID NO:8, SEQ ID NO:9, SEQ ID NO:10, SEQ ID NO:11, SEQ ID NO:12, or SEQ ID NO:13. In some embodiments, SEQ ID NO:6 is selected. In some embodiments, SEQ ID NO:11 is selected.

In some embodiments, a nucleotide sequence encoding a chimeric polypeptide comprising a first nucleotide sequence and a second nucleotide sequence can further contain a third nucleotide sequence encoding a reporter protein or fragment thereof (e.g., a fluorescent protein such as mCherry, also referred to as mCH). Thus, in some embodiments, a first nucleotide sequence can encode a light-induced oligomerization domain comprising CRYPHR, a second nucleotide sequence can encode a low complexity domain from a neurodegenerative disease target protein comprising full-length or truncated TDP-43, and a third nucleotide sequence can encode a mCherry protein, wherein the first, second, and third nucleotide sequences encode a chimeric polypeptide sequence which is at least 75% identical, at least 80% identical, at least 85% identical, at least 90% identical, at least 95% identical, or at least 99% identical to SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25. In some embodiments, the first, second, and third nucleotide sequences encode a chimeric polypeptide sequence according to SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25. In some embodiments, SEQ ID NO:14 is selected. In some embodiments, SEQ ID NO:23 is selected.

In some embodiments, the first nucleotide sequence can encode a light-induced oligomerization domain comprising a LOV photoreceptor domain (e.g., NcVVD, NcVVDY50W, NcLOV, VfAU1, YtvA, EL222, RsLOV, and AsLOV2), and the second nucleotide sequence can encode a low complexity domain from a neurodegenerative disease target protein. In some embodiments, the first nucleotide sequence can encode a light-induced oligomerization domain comprising a LOV photoreceptor domain (e.g., NcVVD, NcVVDY50W, NcLOV, VfAU1, YtvA, EL222, RsLOV, and AsLOV2), and the second nucleotide sequence can encode a low complexity domain from a neurodegenerative disease target protein comprising TDP-43. In some embodiments, the second nucleotide sequence can encode a low complexity domain from a neurodegenerative disease target protein comprising full-length TDP-43 (e.g., SEQ ID NO:26 or SEQ ID NO:27). In some embodiments, the second nucleotide sequence can encode a low complexity domain from a neurodegenerative disease target protein comprising truncated TDP-43 (e.g., SEQ ID NO:28, SEQ ID NO:29, SEQ ID NO:30, SEQ ID NO:31, SEQ ID NO:32, or SEQ ID NO:33). In some embodiments, a truncated TDP-43 consists of amino acids 105-414, 191-414, or 274-414 of the full-length TDP-43 amino acid sequence. Thus, in some embodiments, the first nucleotide sequence can encode a light-induced oligomerization domain comprising NcVVDY50W, and the second nucleotide sequence can encode a low complexity domain from a neurodegenerative disease target protein comprising full-length or truncated TDP-43, wherein the first nucleotide sequence and the second nucleotide sequence encode a chimeric polypeptide sequence which is at least 75% identical, at least 80% identical, at least 85% identical, at least 90% identical, at least 95% identical, or at least 99% identical to SEQ ID NO:26, SEQ ID NO:27, SEQ ID NO:28, SEQ ID NO:29, SEQ ID NO:30, SEQ ID NO:31, SEQ ID NO:32, or SEQ ID NO:33. In some embodiments, the first nucleotide sequence and the second nucleotide sequence encode a chimeric polypeptide sequence according to SEQ ID NO:26, SEQ ID NO:27, SEQ ID NO:28, SEQ ID NO:29, SEQ ID NO:30, SEQ ID NO:31, SEQ ID NO:32, or SEQ ID NO:33.

In some embodiments, a nucleotide sequence encoding a chimeric polypeptide comprising a first nucleotide sequence and a second nucleotide sequence can further contain a third nucleotide sequence encoding a reporter protein or fragment thereof (e.g., a fluorescent protein such as mCherry). Thus, in some embodiments, a first nucleotide sequence can encode a light-induced oligomerization domain comprising NcVVDY50W, a second nucleotide sequence can encode a low complexity domain from a neurodegenerative disease target protein comprising full-length or truncated TDP-43, and a third nucleotide sequence can encode a mCherry protein, wherein the first, second, and third nucleotide sequences encode a chimeric polypeptide sequence which is at least 75% identical, at least 80% identical, at least 85% identical, at least 90% identical, at least 95% identical, or at least 99% identical to SEQ ID NO:34, SEQ ID NO:35, SEQ ID NO:36, SEQ ID NO:37, SEQ ID NO:38, SEQ ID NO:39, SEQ ID NO:40, or SEQ ID NO:41. In some embodiments, the first, second, and third nucleotide sequences encode a chimeric polypeptide sequence according to SEQ ID NO:34, SEQ ID NO:35, SEQ ID NO:36, SEQ ID NO:37, SEQ ID NO:38, SEQ ID NO:39, SEQ ID NO:40, or SEQ ID NO:41. In some embodiments, SEQ ID NO:34 is selected. In some embodiments, SEQ ID NO:41 is selected.

In some embodiments, the first nucleotide sequence can encode a light-induced oligomerization domain comprising a PHR domain of the *Arabidopsis* Cryptochrome 2 protein (e.g., CRY2OLIG), and the second nucleotide sequence can encode a low complexity domain from a neurodegenerative disease target protein comprising α-synuclein. Thus, in some embodiments, the first nucleotide sequence can encode a light-induced oligomerization domain comprising CRY2OLIG, and the second nucleotide sequence can encode a low complexity domain from a neurodegenerative disease target protein comprising α-synuclein, wherein the first nucleotide sequence and the second nucleotide sequence encode a chimeric polypeptide sequence which is at least 75% identical, at least 80% identical, at least 85% identical, at least 90% identical, at least 95% identical, or at least 99% identical to SEQ ID NO:42 or SEQ ID NO:43. In some embodiments, the first nucleotide sequence and the second nucleotide sequence encode a chimeric polypeptide sequence according to SEQ ID NO:42 or SEQ ID NO:43.

In some embodiments, a nucleotide sequence encoding a chimeric polypeptide comprising a first nucleotide sequence and a second nucleotide sequence can further contain a third nucleotide sequence encoding a reporter protein or fragment thereof (e.g., a fluorescent protein such as mCherry). Thus, in some embodiments, a first nucleotide sequence can encode a light-induced oligomerization domain comprising CRY2OLIG, a second nucleotide sequence can encode a low complexity domain from a neurodegenerative disease target protein comprising α-synuclein, and a third nucleotide sequence can encode a mCherry protein, wherein the first, second, and third nucleotide sequences encode a chimeric polypeptide sequence which is at least 75% identical, at least 80% identical, at least 85% identical, at least 90% identical, at least 95% identical, or at least 99% identical to SEQ ID NO:44, SEQ ID NO:45, or SEQ ID NO:46. In some embodiments, the first, second, and third nucleotide sequences encode a chimeric polypeptide sequence according to SEQ ID NO:44, SEQ ID NO:45, or SEQ ID NO:46. In some embodiments, SEQ ID NO:44 is selected.

In some embodiments, the first nucleotide sequence can encode a light-induced oligomerization domain comprising a LOV photoreceptor domain (e.g., NcVVD, NcVVDY50W, NcLOV, VfAU1, YtvA, EL222, RsLOV, and AsLOV2), and the second nucleotide sequence can encode a low complexity domain from a neurodegenerative disease target protein comprising α-synuclein. Thus, in some embodiments, the first nucleotide sequence can encode a light-induced oligomerization domain comprising NcVVDY50W, and the second nucleotide sequence can encode a low complexity domain from a neurodegenerative disease target protein comprising α-synuclein, wherein the first nucleotide sequence and the second nucleotide sequence encode a chimeric polypeptide sequence which is at least 75% identical, at least 80% identical, at least 85% identical, at least 90% identical, at least 95% identical, or at least 99% identical to SEQ ID NO:47 or SEQ ID NO:48. In some embodiments, the first nucleotide sequence and the second nucleotide sequence encode a chimeric polypeptide sequence according to SEQ ID NO:47 or SEQ ID NO:48.

In some embodiments, a nucleotide sequence encoding a chimeric polypeptide comprising a first nucleotide sequence and a second nucleotide sequence can further contain a third nucleotide sequence encoding a reporter protein or fragment thereof (e.g., a fluorescent protein such as mCherry). Thus, in some embodiments, a first nucleotide sequence can encode a light-induced oligomerization domain comprising NcVVDY50W, a second nucleotide sequence can encode a low complexity domain from a neurodegenerative disease target protein comprising α-synuclein, and a third nucleotide sequence can encode a mCherry protein, wherein the first, second, and third nucleotide sequences encode a chimeric polypeptide sequence which is at least 75% identical, at least 80% identical, at least 85% identical, at least 90% identical, at least 95% identical, or at least 99% identical to SEQ ID NO:49, SEQ ID NO:50, or SEQ ID NO:51. In some embodiments, the first, second, and third nucleotide sequences encode a chimeric polypeptide sequence according to SEQ ID NO:49, SEQ ID NO:50, or SEQ ID NO:51. In some embodiments, SEQ ID NO:51 is selected.

In some embodiments, the first nucleotide sequence is positioned upstream of the second nucleotide sequence. In some embodiments, the first nucleotide sequence is positioned downstream of the second nucleotide sequence.

In some embodiments, where the sequences disclosed herein contain a methionine at the start of the protein, the protein without the methionine is also disclosed. In some embodiments, where the sequences disclosed herein do not contain a methionine at the start of the protein, the protein with the methionine at the start of the protein is also disclosed.

In some embodiments, the nucleotide sequence encoding a chimeric polypeptide comprises a sequence selected from SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO: 66, SEQ ID NO:67, SEQ ID NO:68, SEQ ID NO:69, SEQ ID NO:70, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, or SEQ ID NO:91.

Methods

In one aspect, disclosed herein is a method of inducing a neurodegenerative disease pathology in a cell, comprising the steps:

introducing into the cell an expression vector encoding a chimeric polypeptide, comprising:
    a first nucleotide sequence encoding a light-induced oligomerization domain and a second nucleotide sequence encoding a low complexity domain from a neurodegenerative disease target protein, wherein the first nucleotide sequence is operably linked to a promoter;
expressing the chimeric polypeptide; and
inducing oligomerization of the chimeric polypeptide by stimulation with blue light.

In another aspect, disclosed herein is a method of screening for an agent that modulates protein aggregation, comprising the steps:

introducing into a cell an expression vector encoding a chimeric polypeptide, comprising:
    a first nucleotide sequence encoding a light-induced oligomerization domain and a second nucleotide sequence encoding a low complexity domain from a neurodegenerative disease target protein, wherein the first nucleotide sequence is operably linked to a promoter;
expressing the chimeric polypeptide;
introducing the agent into a culture media comprising the cell;
inducing oligomerization of the chimeric polypeptide by stimulation with blue light; and
determining modulation of protein aggregation by the agent.

In one embodiment, the light-induced oligomerization domain is selected from the group consisting of a CRY2 PHR domain (for example, CRY2 PHR, CRY2OLIG) or a light-oxygen-voltage-sensing (LOV) domain (for example, NcVVD, NcVVDY50W, VfAU1, YtvA, EL222, RsLOV, AsLOV2).

In one embodiment, the light-induced oligomerization domain is selected from the group consisting of CRYPHR, CRY2OLIG, NcVVD, NcVVDY50W, and NcLOV. In one embodiment, the light-induced oligomerization domain is selected from the group consisting of CRYPHR, CRY2OLIG, NcVVD, NcVVDY50W, NcLOV, VfAU1, YtvA, EL222, RsLOV, and AsLOV2. In one embodiment, the light-induced oligomerization domain is selected from the list of domains in Table 2. In one embodiment, the light-induced oligomerization domain is selected from a variant of CRYPHR, CRY2OLIG, NcVVD, NcVVDY50W, NcLOV, VfAU1, YtvA, EL222, RsLOV, or AsLOV2. In one embodiment, the light-induced oligomerization domain is selected from a fragment of CRYPHR, CRY2OLIG, NcVVD, NcVVDY50W, NcLOV, VfAU1, YtvA, EL222, RsLOV, or AsLOV2.

In one embodiment, the light-induced oligomerization domain is NcVVDY50W. In one embodiment, the light-induced oligomerization domain is CRY2OLIG. In one embodiment, the light-induced oligomerization domain is CRYPHR. In one embodiment, the light-induced oligomerization domain comprises a LOV domain from the VVD protein. In one embodiment, the light-induced oligomerization domain comprises a LOV domain from the LOV protein. In one embodiment, the light-induced oligomerization domain comprises a PHR domain. In one embodiment, the light-induced oligomerization domain comprises a PHR domain, from the CRY2 protein. In one embodiment, the light-induced oligomerization domain is VfAU1. In one embodiment, the light-induced oligomerization domain is YtvA. In one embodiment, the light-induced oligomerization domain is EL222. In one embodiment, the light-induced oligomerization domain is RsLOV. In one embodiment, the light-induced oligomerization domain is AsLOV2.

In one embodiment, the low complexity domain from a neurodegenerative disease target protein is selected from the group consisting of TDP-43, Alpha synuclein, Tau, Fus, TIA1, SOD1, Huntingtin, Ataxin 2, hnRNPA1, and hnRNPA2B1. In one embodiment, the low complexity domain from a neurodegenerative disease target protein is selected from the group consisting of TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15. In one embodiment, the low complexity domain from a neurodegenerative disease target protein is selected from a variant of TDP-43, Alpha synuclein, Tau, TIA1, SOD1, Huntingtin, Ataxin 2, hnRNPA1, hnRNPA2B1, EWS RNA Binding Protein 1, or TATA box binding protein factor 15. In one embodiment, the low complexity domain from a neurodegenerative disease target protein is selected from a fragment of TDP-43, Alpha synuclein, Tau, TIA1, SOD1, Huntingtin, Ataxin 2, hnRNPA1, hnRNPA2B1, EWS RNA Binding Protein 1, or TATA box binding protein factor 15. In one embodiment, the fragment of TDP-43, Alpha synuclein, Tau, TIA1, SOD1, Huntingtin, Ataxin 2, hnRNPA1, hnRNPA2B1, EWS RNA Binding Protein 1, or TATA box binding protein factor 15 comprises the low complexity domain within each neurodegenerative disease target protein.

In one embodiment, the low complexity domain from a neurodegenerative disease target protein is selected from Table 3. In one embodiment, the low complexity domain is from any neurodegenerative disease target protein that aggregates in neurodegenerative diseases.

In one embodiment, the low complexity domain from a neurodegenerative disease target protein is selected from the group consisting of an amino acid sequence with at least 90% identity to TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15. In one embodiment, the low complexity domain from a neurodegenerative disease target protein is selected from the group consisting of an amino acid sequence with at least 90% identity to a low complexity domain from a neurodegenerative disease target protein is selected from Table 3. In one embodiment, the low complexity domain from a neurodegenerative disease target protein is selected from an orthologue of the group consisting of TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15.

In one embodiment, the low complexity domain from a neurodegenerative disease target protein is selected from the group consisting of an amino acid sequence with at least 60% (for example, at least 60%, at least 70%, at least 80%, at least 90%, at least 95%) identity to TDP-43, Alpha synuclein, Tau, Fus, TIA1, SOD1, Huntingtin, Ataxin 2, hnRNPA1, hnRNPA2B1, EWS RNA Binding Protein 1, and TATA box binding protein factor 15 (or a fragment thereof).

In one embodiment, the low complexity domain from a neurodegenerative disease target protein is TDP-43. In one embodiment, the low complexity domain from a neurodegenerative disease target protein is Alpha synuclein. In one embodiment, the low complexity domain from a neurodegenerative disease target protein is Tau. In one embodiment, the low complexity domain from a neurodegenerative disease target protein is Fus. In one embodiment, the low complexity domain from a neurodegenerative disease target protein is TIA1. In one embodiment, the low complexity domain from a neurodegenerative disease target protein is SOD1. In one embodiment, the low complexity domain from a neurodegenerative disease target protein is Huntingtin. In one embodiment, the low complexity domain from a neurodegenerative disease target protein is Ataxin 2. In one embodiment, the low complexity domain from a neurodegenerative disease target protein is hnRNPA1. In one embodiment, the low complexity domain from a neurodegenerative disease target protein is hnRNPA2B1. In one embodiment, the low complexity domain from a neurodegenerative disease target protein is EWS RNA Binding Protein 1. In one embodiment, the low complexity domain from a neurodegenerative disease target protein is TATA box binding protein factor 15.

In one embodiment, the cell is a mammalian cell. In one embodiment, the cell is a human cell. In one embodiment, the cell is selected from the group consisting of yeast, insect, avian, fish, worm, amphibian, *Xenopus*, bacteria, algae and mammalian cells. In one embodiment, disclosed herein is a non-human transgenic organism, wherein the organism is an insect, fish, bird, worm, amphibian, *Xenopus*, or non-human mammal.

To induce a neurodegenerative disease pathology refers to the action of bringing about the neurodegenerative disease pathology, or increasing the phenotype, symptoms, or severity of the neurodegenerative disease pathology, as compared to refraining from performing the selected action.

The neurodegenerative disease pathology can include an array of pathologies known to be or suspected to be associated with any one or more neurodegenerative diseases. Examples of such pathologies include, but are not limited to, protein aggregation in the cytoplasm of a cell, mislocalization of nuclear proteins to, for example, the cytoplasm, increased expression of ubiquitin, cell degeneration and/or death, extracellular Amyloid Beta (Aβ) aggregation, and/or intracellular and/or cytoplasmic aggregation of Tau protein. Protein aggregates can, in some embodiments, be colocalized with p62 protein, can be hyper-phosphorylated, can include endogenous protein comprising the low complexity domain from a neurodegenerative disease target protein (e.g., endogenous TDP-43), or combinations thereof.

Increased ubiquitination or increased expression of ubiquitin can be a phenotypic feature of neurodegenerative diseases. Ubiquitin has numerous cellular roles, including "tagging" proteins (e.g., by covalent linkage) for degradation in a proteasome. Increased ubiquitin expression in a cell is typically compared to a control. In some embodiments, a cell having increased ubiquitin has at least 50% increased ubiquitin expression compared to a control. In some embodiments, a cell having increased ubiquitin has at least 60%, at least 70%, at least 80%, at least 90%, at least 95%, at least 98%, or at least 99% increased ubiquitin expression compared to a control.

Ubiquitin expression in a cell can be determined at the transcriptional level, the translational level, or combinations thereof, and can be measured via a wide array of methods used to measure gene or polypeptide expression levels. In some embodiments, ubiquitin expression can be measured at the gene transcription level. For example and without limitation, levels of ubiquitin mRNA transcripts can be determined by radiation absorbance (e.g., ultraviolet light absorption at 260, 280, or 230 nm), quantification of fluorescent dye or tag emission (e.g., ethidium bromide intercalation), quantitative polymerase chain reaction (qPCR) of cDNA produced from mRNA transcripts, southern blot analysis, gene expression microarray, or other suitable methods. Increased levels of mRNA transcripts can be used to infer or estimate increased levels of polypeptide expression. In some embodiments, ubiquitin expression can be measured at the post-translational level. For example and without limitation, levels of ubiquitin polypeptide can be determined by radiation absorbance (e.g., ultraviolet light), bicinchoninic acid (BCA) assay, Bradford assay, biuret test, Lowry method, Coomassie-blue staining, functional or enzymatic assay, immunodetection methods and/or Western blot analysis, or other suitable methods.

As used herein, the term "introducing," "introduce," and grammatical variations thereof, as it relates to introducing an expression vector into a cell, refers to any method suitable for transferring the expression vector into the cell. The term includes as examples, but is not limited to, conjugation, transformation/transfection (e.g., divalent cation exposure, heat shock, electroporation), nuclear microinjection, incubation with calcium phosphate polynucleotide precipitate, high velocity bombardment with polynucleotide-coated microprojectiles (e.g., via gene gun), lipofection, cationic polymer complexation (e.g., DEAE-dextran, polyethylenimine), dendrimer complexation, mechanical deformation of cell membranes (e.g., cell-squeezing), sonoporation, optical transfection, impalefection, hydrodynamic polynucleotide delivery, Agrobacterium-mediated transformation, transduction (e.g., transduction with a virus or viral vector), natural or artificial competence, protoplast fusion, magnetofection, nucleofection, or combinations thereof. An introduced expression vector, or a polynucleotide therefrom, can be genetically integrated or exist extrachromosomally.

A range of blue light wavelengths can be used in the disclosed methods. In one embodiment, the blue light has a wavelength from about 400 nm to about 500 nm. In one embodiment, the blue light has a wavelength from about 405 nm to about 499 nm. In one embodiment, the blue light has a wavelength from about 420 nm to about 490 nm. In one embodiment, the blue light has a wavelength from about 450 nm to about 490 nm. In one embodiment, the blue light has a wavelength from about 460 nm to about 495 nm. In one embodiment, the blue light has a wavelength of about 488 nm. In one embodiment, the blue light has a wavelength of about 475 nm. In one embodiment, the blue light has a wavelength of about 465 nm.

In one embodiment, the blue light has a wavelength of about 405 nm, about 410 nm, about 415 nm, about 420 nm, about 425 nm, about 430 nm, about 435 nm, about 440 nm, about 445 nm, about 450 nm, about 455 nm, about 460 nm, about 465 nm, about 470 nm, about 475 nm, about 480 nm, about 485 nm, about 490 nm, about 495 nm, or about 500 nm.

The methods can include various degrees of blue light stimulation. In some embodiments, the stimulation is acute or, optionally, chronic. Acute stimulation refers stimulation with pulses of blue light from about 0.2 to about 60 seconds, wherein the wavelength of the blue light can be any herein disclosed blue light wavelength. In some embodiments, the acute stimulation includes pulses of blue light from about 0.5 second to about 30 seconds, from about 1 second to about 20 seconds, or about 5 seconds. The blue light can be provided by a blue light source or a broad-spectrum light source filtered for the disclosed wavelengths.

In some embodiments, acute stimulation can result in temporary aggregation of a light-induced oligomerization domain (e.g., cytoplasmic prion-like domains/LCD/IDD protein fragments). Temporary aggregation, in some embodiments, includes protein aggregation observable by the herein disclosed methods for less than about twenty minutes or, optionally, less than about fifteen minutes, less than about ten minutes, or about five minutes or less. In some embodiments, acute stimulation does not result in aggregation of cytoplasmic prion-like domains/LCD/IDD protein fragments for twenty minutes or more.

In some embodiments, acute stimulation can result in aggregation of a light-induced oligomerization domain which is shorter in duration than aggregation of a light-induced oligomerization domain fused with a low complexity domain from a neurodegenerative disease target protein. In some embodiments, acute stimulation can result in aggregation of a light-induced oligomerization domain fused with a low complexity domain from a neurodegenerative disease target protein which is shorter in duration than aggregation of the same protein having an amino acid mutation known to cause or be associated with a neurodegenerative disease (e.g., TDP-43 Q331K).

Chronic stimulation is defined by exposure to blue light having a wavelength from about 400 nm to about 500 nm for a duration of about 1 minute or longer (for example, at least 1 minute, at least 5 minutes, at least 10 minutes, at least 30 minutes, at least 60 minutes, at least 2 hours, at least 4 hours, at least 8 hours, at least 12 hours, at least 24 hours, at least 36 hours, or more) from about 0.1 mW/cm$^2$ to 8 mW/cm$^2$ (within 400 nm-500 nm wavelength).

The methods disclosed herein can, in some embodiments, induce a neurodegenerative disease pathology in a cell (e.g., aggregation of a protein) without substantially altering the expression level of a protein involved in the neurodegenerative disease pathology. For example and without limitation, the methods can induce aggregation of a chimeric polypeptide comprising TDP-43 (which can include aggregation of endogenous TDP-43) without substantially increasing or decreasing the expression level of endogenous TDP-43. In some or further embodiments, the methods can induce a neurodegenerative disease pathology in a cell using a wild-type form of a low complexity domain from a neurodegenerative disease target protein. Thus, in some embodiments, the low complexity domain from a neurodegenerative disease target protein does not include a mutation which differs from the wild-type sequence and which is known or suspected to cause or be associated with inducing a neurodegenerative disease pathology in a cell. For example and without limitation, the methods can induce aggregation of a chimeric polypeptide comprising wild-type TDP-43 protein, or fragment thereof, which does not contain a mutation such as Q331K, known to cause or be associated with ALS.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Optogenetic Induction of Neurodegenerative Disease Pathologies

The world is aging. By the year 2050, the proportion of individuals over the age of 60 will have doubled to 2 billion from 605 million in 2000. Unfortunately, aging is the single greatest risk factor for developing a fatal neurodegenerative disease. In turn, the number of individuals with dementias such as Alzheimer's disease (AD), Lewy Body Dementia (LBD), Frontotemporal Dementia (FTD), and movement disorders such as Parkinson's Disease (PD) and Amyotrophic Lateral Sclerosis (ALS) will significantly increase. Nearly 6.5 million individuals within the United States are currently living with one of these diseases and the associated costs are unsustainable. In the United States, the current economic burden of AD, PD, and ALS is an estimated $241 billion dollars per year. AD and ALS/FTD patients can incur personal medical costs upwards of $100,000-$250,000 per year. For AD, it is estimated that 13.8 million individuals in the United States will have been diagnosed by 2050, up from 4.7 million in 2010, while the worldwide number of ALS cases will rise ~31% by 2040. Moreover, no effective treatment currently exists for these disorders.

Two decades of genetic analysis has uncovered a number of neurodegenerative disease-associated mutations. However, these are found in only a fraction of AD, LBD, FTD, PD, and ALS patients (Table 1).

80-75% of patients have no family history. However, all patients exhibit some form of cytoplasmic protein aggregation that are comprised of either TDP-43 (45% of cases), Tau (45% of cases), or FUS (5% of cases) proteins. Parkinson's Disease (PD), is characterized by the progressive degeneration of dopaminergic neurons in the substantia nigra and while only 10% of patients have a known genetic cause, nearly all patients (99%) show cytoplasmic aggregation of the α-synuclein protein. Amyotrophic Lateral Sclerosis (ALS) is characterized by the rapid degeneration of the motor neurons in the motor cortex in the spinal cord leading patient paralysis and death. Only 10% of ALS patients have a family history of the disease while nearly 90% of cases occur sporadically. To date, nearly 35 causative genetic mutations have been identified in various genes (see FIG. 1), however despite this genetic diversity, nearly all ALS patients exhibit the same neuropathology. Nearly 97% of ALS patients show the cytoplasmic mislocalization of the predominantly nuclear TDP-43 protein in the affected regions. Patients with mutations in the SOD1 or FUS gene also show cytoplasmic aggregations of these proteins but this occurs in only 2% and 1% of all ALS cases, respectively.

Together, this table highlights that the principal unifying factor of many neurodegenerative diseases are the neuropathological hallmarks. These neuropathologies primarily occur in the form of intracellular protein aggregates and in the vast majority of cases these intracellular protein aggregations form regardless of any known genetic cause. Moreover, these neuropathologies predominantly form in the region and cell types most affected in each disease.

Interestingly, despite the lack of a common known genetic or environmental cause, these are universal neuropathological features among patients for each disease. Thus, the vast

TABLE 1

List of common neurodegenerative diseases, pathology and contribution of genetic components.

| Disease | Symptoms | Affected CNS Regions | Life Expectancy (years) | Primary Aggregate Pathology | Genetic Cause |
|---|---|---|---|---|---|
| AD | Memory loss, confusion | Entorhinal cortex, Hippocampus | 8-10 | Tau (100%), Aβ (100%) | 2-3% |
| FTD | Personality change, compulsivity, aphasia | Frontal lobe, Temporal lobe | 7-10 | TDP-43 (45%), Tau (45%), Fus (5%) | 20-25% |
| PD | Stiffness, muscle rigidity, slowing of movement | Substantia nigra | 15-20+ | α-synuclein (99%) | 10% |
| ALS | Muscle weakness, paralysis | Motor cortex, Spinal cord | 3-5 | TDP-43 (97%), SOD1(2%), Fus (1%), | 10% |

Table 1 describes a selection of neurodegenerative diseases, the primary symptoms, the affected region of the central nervous system (CNS), the aggregate neuropathology observed in patient CNS, percent of patients exhibiting this pathology and the percent of patients that harbor some genetic component of the disease (known or unknown mutation within the family). Alzheimer's disease (AD) is characterized by memory loss and confusion due to degeneration of the hippocampus and entorhinal cortex. Only 1-3% of patients harbor a causal genetic mutation; however all patients show a common aggregate pathology in the affected tissue. This is characterized by the extracellular Amyloid Beta (Aβ) aggregates and intracellular and cytoplasmic aggregations of the Tau protein. Frontotemporal Dementia (FTD) is characterized by the progressive degeneration of the frontal and temporal lobes and while 20-25% of patients can harbor a genetic cause of the disease, the majority of patients (90-100% of all patients depending on the disease) exhibit the same pathology in the central nervous system despite no known genetic cause. These pathological hallmarks manifest in the form of insoluble protein clumps or aggregates in the central nervous system (Table 1, FIG. 1).

To date, it is not possible to accurately model neurodegenerative disease aggregation that mimics human neuropathology. For each neurodegenerative disease, there is a primary component of the intracellular protein aggregate which harbor protein domains which make these proteins aggregation prone when in a high local concentration (also known as: prion-like domain, low complexity domain, intrinsically disordered domain, intrinsically disordered region). Therefore, current methods to model these neurodegenerative disease aggregates rely on overexpressing these aggregate-prone proteins in vitro or in vivo that comprise the neurodegenerative disease aggregates as the high cellular concentration can, in some models, form aggregates. In addition to, or alternatively, another method of modeling these diseases is to express mutated forms of proteins that comprise neurodegenerative disease aggregates. These mutations are found in a very small subset of patients and typically enhance the ability of the protein to aggregate. Unfortunately, none of these methods recapitulate the cellular environment of patients because the vast majority of patients do not harbor any disease-causing mutation, nor do they grossly overexpress the components of the aggregates. In fact, despite gross overexpression of these proteins, many models still do not exhibit the human neuropathology. This disconnect between the patient biology and model systems has significantly contributed to the lack of translatability of current neurodegenerative disease models.

Described in this example are novel methods to spatially and temporally induce protein aggregates without simple overexpressing of aggregate prone genes or expressing mutant forms of these genes. Thus, this method better recapitulates the human disease condition. Here, an innovative approach has been undertaken to address this challenging biological problem by harnessing the power of optogenetics (controlling protein function with light). A series of novel DNA arrangements have been constructed that can induce neurodegenerative disease pathology as observed in patients only when the cells are exposed to specific light stimuli. This method is used to create in vitro and in vivo model systems to mimic the neuropathology observed in patients and induce this pathology only after the cells are exposed to specific light wavelengths. This novel approach can transform neurodegenerative disease modeling and, unlike the expression of mutant transgenes, can be used to generate various disease models that are applicable to the vast majority of patients and are temporally and spatially inducible.

A series of DNA arrangements have been developed comprising the PHR domain (CRY2OLIG or CRY2 PHR) or light-oxygen-voltage-sensing (LOV) domain (NcVVD, NcVVDY50W, Vfau1, YtvA, EL222, RsLOV, AsLOV2) which cluster or homodimerize, respectively, in response to blue light exposure (Table 2) and the DNA sequence of genes that encode for proteins that contain low complexity domains (LCDs) and comprise neurodegenerative disease protein aggregates (Table 3).

TABLE 2

List of photoreceptors/light-induced oligomerization domains to optogenetically induce neurodegenerative pathologies in cells with blue light exposure.

| Nomenclature | Protein Domain | Organism | Light Stimuli (nm) | Light Response | Features |
|---|---|---|---|---|---|
| CRYPHR | Photolyase homology region (PHR) | *Arabidopsis* | 405-499 | Homo-oligomerization | Endogenous protein domain |
| CRY2OLIG | Photolyase homology region (PHR) with E490A mutation | *Arabidopsis* | 405-499 | Homo-oligomerization | E490G Mutation to enhance clustering |
| NcVVD | Light-oxygen-voltage-sensing (LOV) domain | *Neurospora* | 405-499 | Homo-dimerization | LOV domain of VVD gene |
| NcVVDY50W | Light-oxygen-voltage-sensing (LOV) domain | *Neurospora* | 405-499 | Homo-dimerization | VVD Y50G Mutation to enhance clustering |
| NcLOV | Light-oxygen-voltage-sensing (LOV) domain | *Neurospora* | 405-499 | Homo-dimerization | Clustering LOV domain from NcVVD with no linker |
| Vfau1 | Light-oxygen-voltage-sensing (LOV) domain | *Vucheria frigida* | 405-499 | Homo-dimerization | |
| YtvA | Light-oxygen-voltage-sensing (LOV) domain | *Bacillus subtillis* | 405-499 | Homo-dimerization | |
| EL222 | Light-oxygen-voltage-sensing (LOV) domain | *Erythrobacter litoralis* | 405-499 | Homo-dimerization | |
| RsLOV | Light-oxygen-voltage-sensing (LOV) domain | *Rhodobacter sphaeroides* | 405-499 | Homo-dimerization | |
| AsLOV2 | Light-oxygen-voltage-sensing (LOV) domain | *Avena sativa* | 405-499 | Intramolecular conformational change | |

Table 2 shows a list of photoreceptors to be employed to optogenetically induce neurodegenerative pathologies in cells upon blue light exposure. Variations of the PHR domain of the Cryptochrome 2 protein found in the *Arabidopsis* plant will be one family of photoreceptors employed (named CRY2 PHR and CRY2OLIG in this document). The PHR domain of the CRY2 protein and its variants have the ability to cluster/homo-oligomerize for ~5 minutes when exposed to a single pulse of blue light (within the 405-499 nm range). The CRY2 PHR is an endogenous protein sequence found in *Arabidopsis*. While the CRY2OLIG is the endogenous amino acid sequence but has a E490G mutation and has been shown to exhibit a slightly increased efficiency of clustering upon blue light stimulation. The self-binding of CRY2 PHR and CRY2OLIG act through the same mechanism and requires intracellular FAD+. Various arrangements of CRY2OLIG and target proteins that comprise neuropathological protein aggregates have been generated to show modulation of the light-induced clustering properties of CRY2OLIG to induce neurodegenerative disease pathology of both predominantly cytoplasmic and predominantly nuclear proteins. This includes inducing the cytoplasmic mislocalization of nuclear proteins as observed in patient neuropathology. In addition, these protein domains have been used to induce the aggregation of intrinsically disordered domains/prion-like domains/low complexity domains of truncated versions of these neurodegenerative proteins.

Vivid (VVD) is a protein generated in the *Neurospora* organism and is a photoreceptor that homodimerizes in response to blue light (within the 405-499 nm range). The Light-Oxygen-Voltage-Sensing (LOV) domain is common throughout many organisms but this domain is very small in this organism. NcLOV is only the LOV domain of the VVD protein but is conserved throughout other species. NcVVD comprises a small fragment of the N-term VVD protein and the VVD LOV domain. NcVVDY50W from the NcVVD protein sequence however is altered by a Y50W change that promotes a slower ability to dissipate from the dimerized state. It was shown here that persistent dimerization of LOV domains induces oligomerization with chronic light and when fused to an LCD containing protein (FIGS. 6, 8). Although LOV domains are not reported to form oligomers, a light stimulation paradigm to induce protein clustering of specific protein arrangements of these photoreceptors and specific target neurodegenerative disease proteins has been developed herein. Additional LOV domains used herein also include VfAU1, YtvA, EL222, RsLOV, and AsLOV2.

TABLE 3

Target neurodegenerative disease proteins.

| Gene Symbol | Encoded Protein | Associated Disease | Human RefSeqGene | Predominant Cellular Localization |
|---|---|---|---|---|
| TARDBP | TDP-43 | ALS, FTD, AD, CTE | NG_008734.1 | Nuclear |
| SNCA | Alpha Synuclein | PD, LBD, AD, MSA | NG_011851.1 | Cytoplasmic |
| MAPT | Tau | AD, FTD, CTE, PD | NG_007398.1 | Cytoplasmic |
| FUS | FUS | FTD, ALS | NG_012889.2 | Nuclear |
| SOD1 | SOD1 | ALS | NG_008689.1 | Cytoplasmic |
| TIA1 | TIA1 | ALS | NG_029967.1 | Cytoplasmic & Nuclear |
| ATXN2 | Ataxin 2 | ALS | NG_011572.2 | Cytoplasmic |
| HNRNPA1 | hnRNPA1 | ALS | NG_033830 1 | Nuclear |
| HNRNPA2B1 | hnRNPA2B1 | ALS | NG_029680.1 | Nuclear |
| EWSR1 | EWS RNA Binding Protein 1 | ALS | NG_023240.1 | Nuclear |
| TAF15 | TATA box binding protein factor 15 | ALS | NG_023279.1 | Nuclear |

Abbreviations:
ALS, Amyotrophic Lateral Sclerosis;
FTD, Frontotemporal Dementia;
PD, Parkinsons Disease;
AD, Alzheimer's Disease;
CTE, Chronic Traumatic Encephalopathy;
LBD, Lewy Body Dementia Table 3 describes a list of target neurodegenerative disease proteins to generate protein arrangements that recapitulate neurodegenerative disease pathology. Novel arrangements of the photoreceptors in Table 2 fused to neurodegenerative disease proteins such as those listed in Table 3 that respond to these various blue light exposure paradigms to recapitulate neurodegenerative disease pathologies are disclosed herein. This technology is also used to aggregate the prion-like domains/LCD/IDDs of truncated versions of these components that comprise neuropathological aggregates in patients. In this example, studies have been performed with CRY2OLIG and LOV fused to TDP-43, α-synuclein, and Tau proteins. In another example, the target neurodegenerative disease protein can be Huntingtin gene/protein (Accession Ref. NM_002111; NP_002102.4). However, a method was developed that can be applied to any photoreceptor with dimerizing or oligomerization capabilities due to the light treatment paradigms created. The primary purpose of this method is to control the local concentration of neurodegenerative disease proteins for specific periods of time forcing intramolecular crowding of proteins that contain LCDs and aggregate in neurodegenerative diseases. Each neurodegenerative disease protein and photoreceptor arrangement can require specific light stimulation parameters due to the nature of the protein. For example, cytoplasmic proteins or truncated versions of nuclear proteins to localize them to the cytoplasm typically (but not always) require short stimulation paradigms while predominantly nuclear proteins chronic stimulation since the protein will need to be trapped in the cytoplasm during translation (e.g. TDP-43, FUS). Details of the stimulation paradigms are discussed below.

Light exposure then forces these unique fusion protein arrangements into close proximity and employing chronic or repeated light stimulation, neurodegenerative disease aggregate pathologies of full length proteins or the LCDs alone can be obtained. This temporal and spatial control of neurodegenerative disease aggregates is novel since it does not require overexpression or mutation that are only relevant to a small subset of patients for each disease (Table 1). These proteins are forced to interact and form the disease pathology as occurs in human patients rather than filling the cell with these aggregate prone proteins.

Figure 5A:
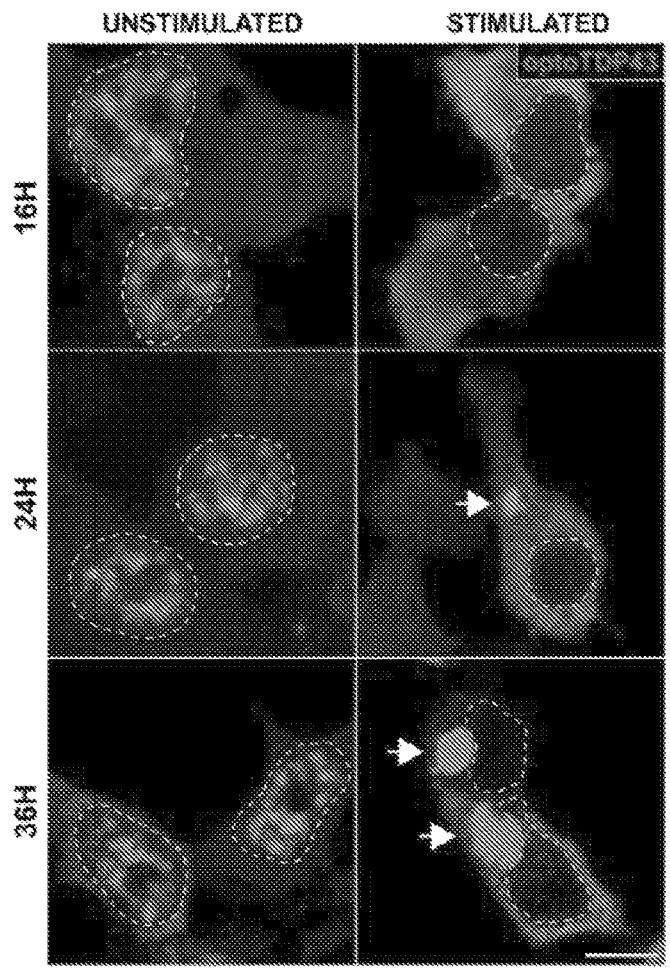
FIGS. 5A-5K show chronic blue light stimulation induces optoTDP43 mislocalization and aggregation that recapitulates pathological hallmarks seen in patient CNS tissue. HEK293 cells expressing optoTDP43-mCh were exposed to 488 nm LED stimulation or darkness for up to 36 hours.
Figure 5B:
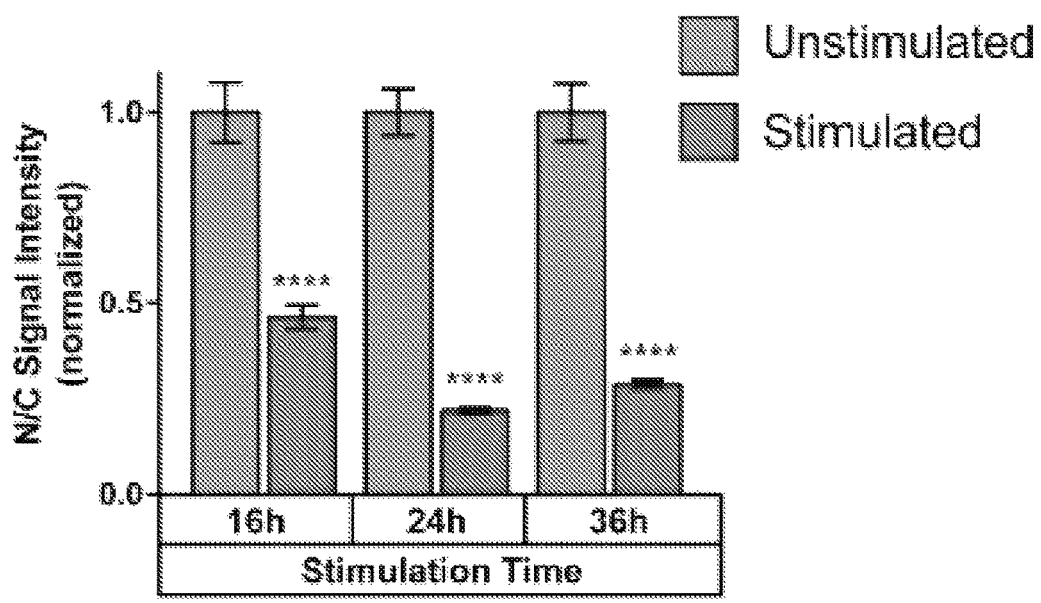
Figure 5C:
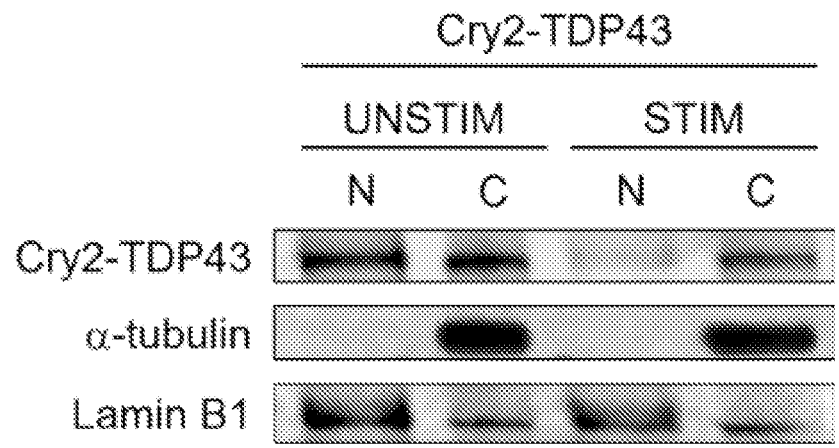
Figure 5D:
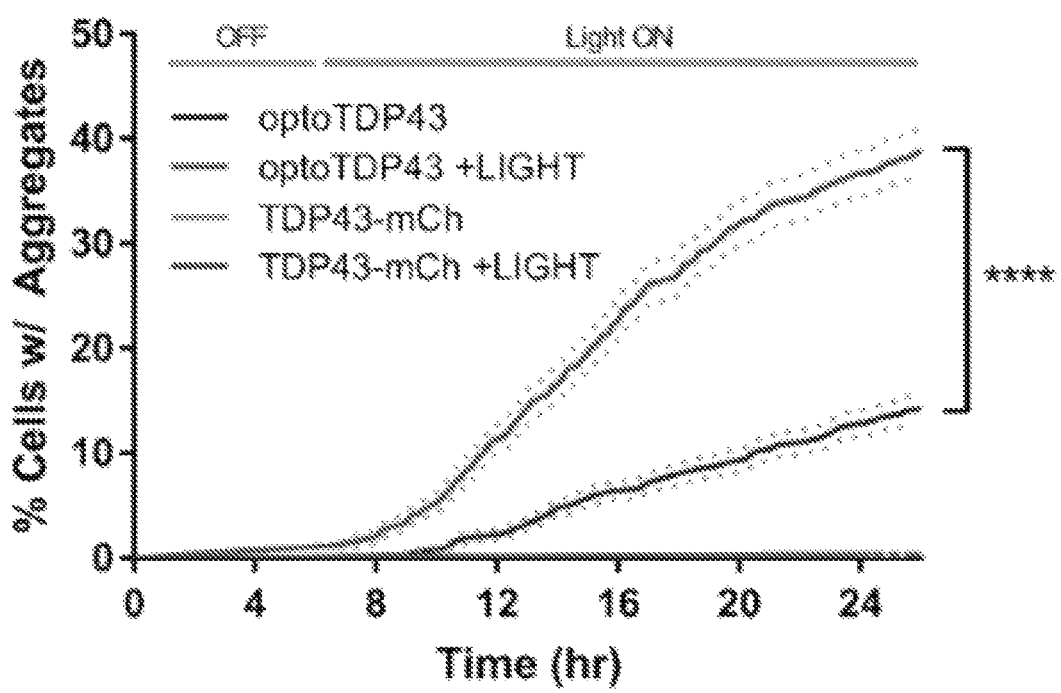
Figure 5E:
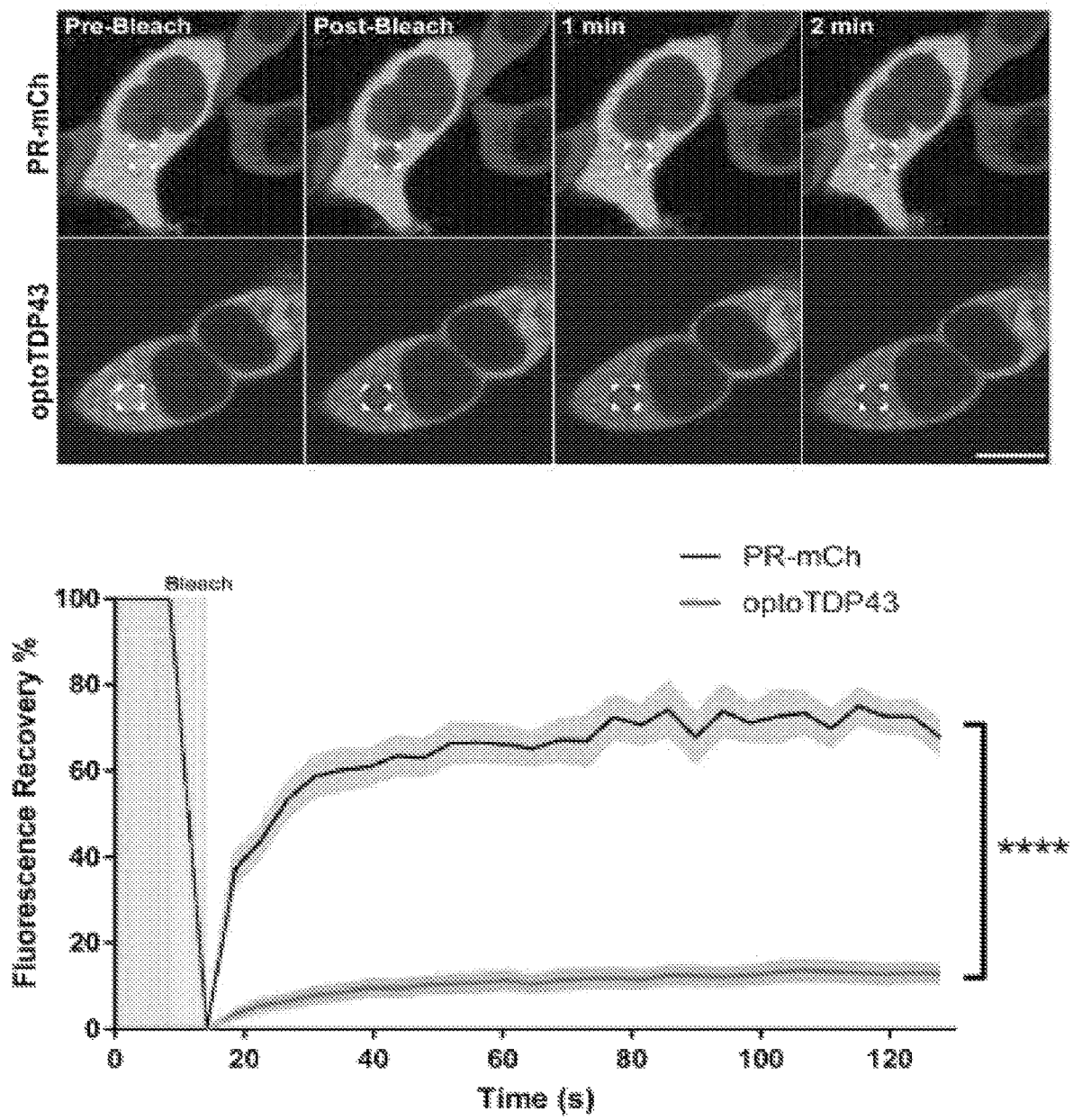
Figure 5F:
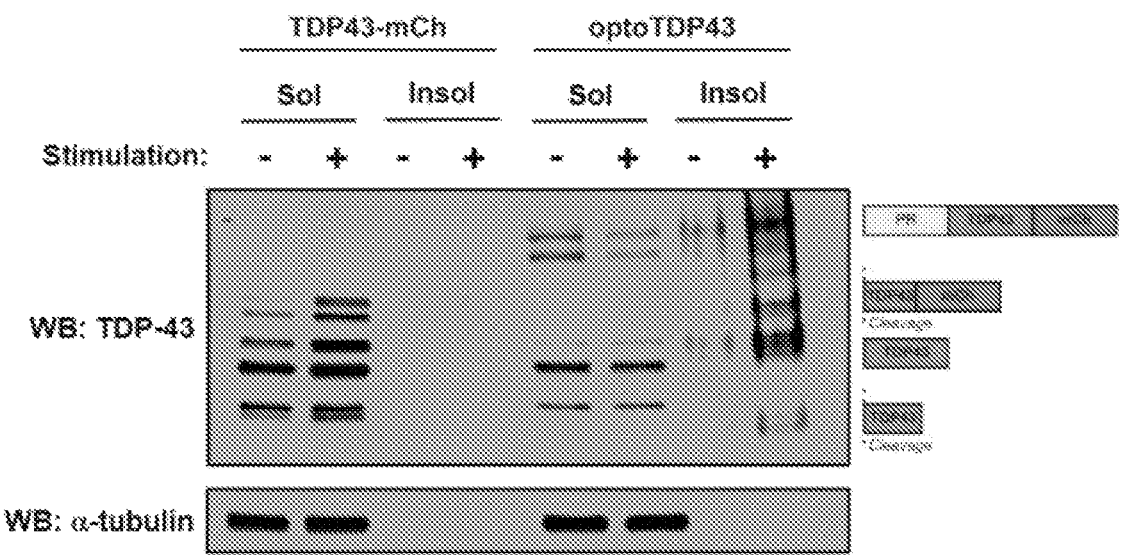
Figure 5G:
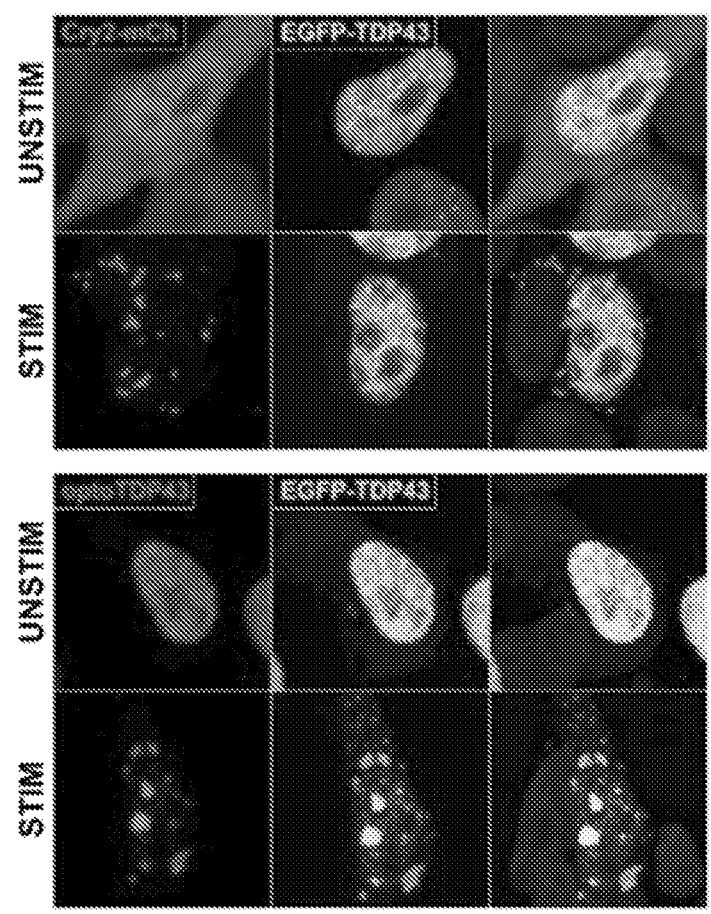
Figure 5H:
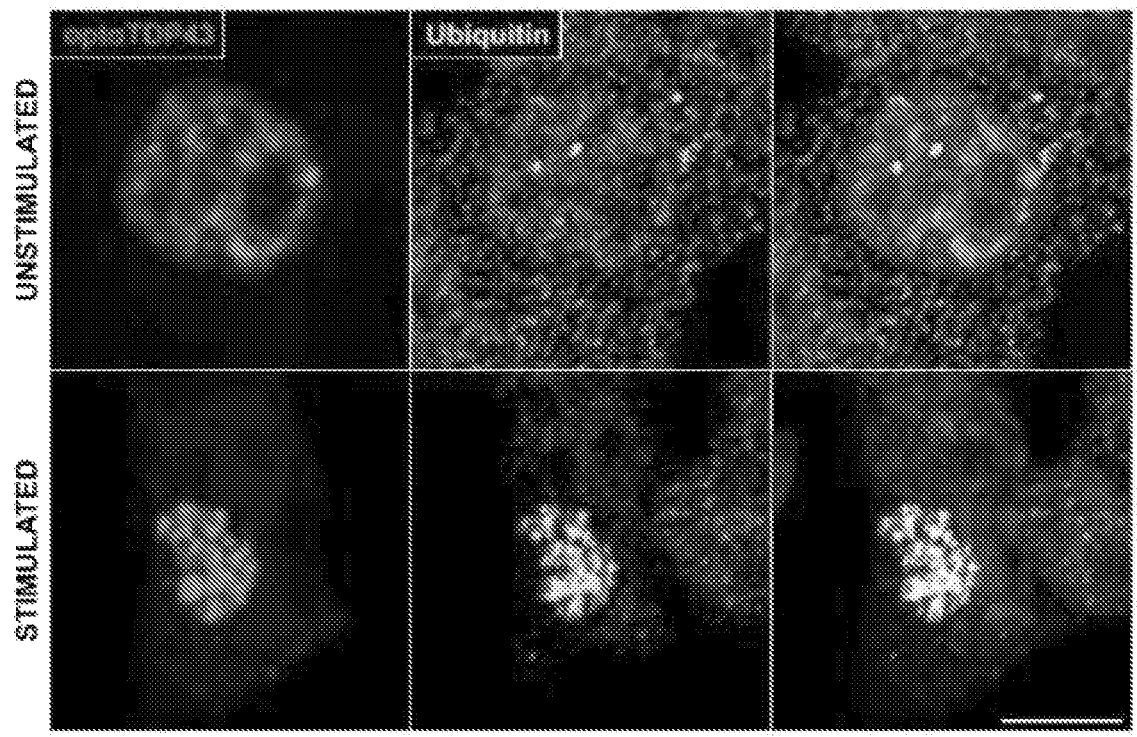
Figure 5I:
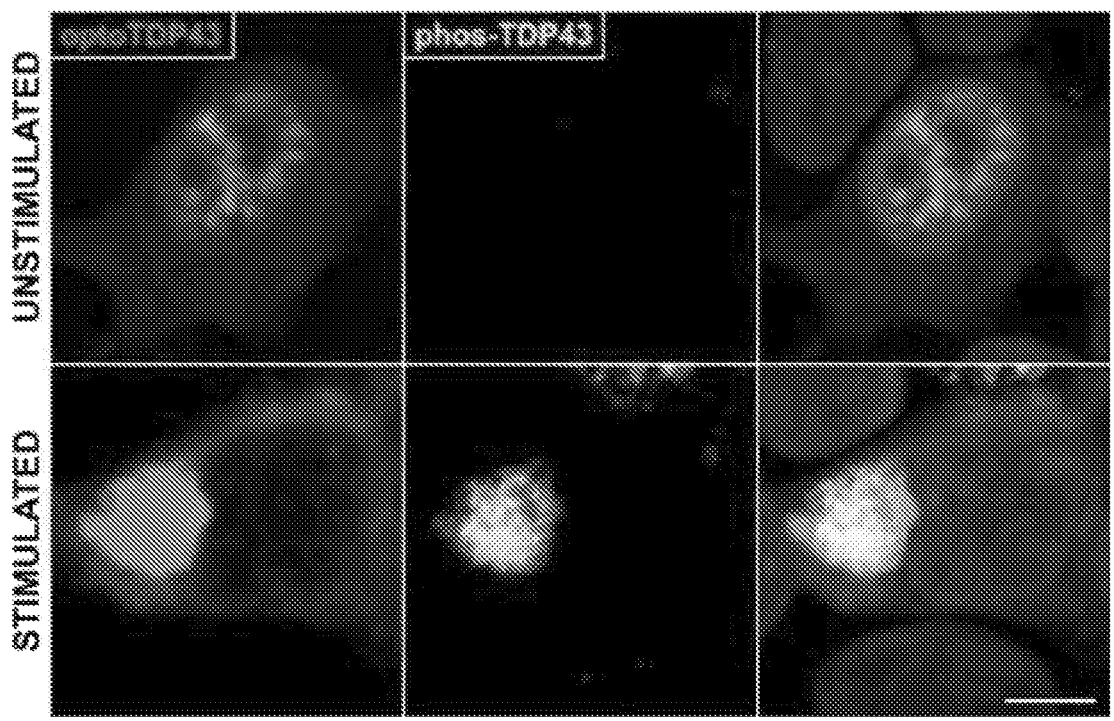
Figure 5J:
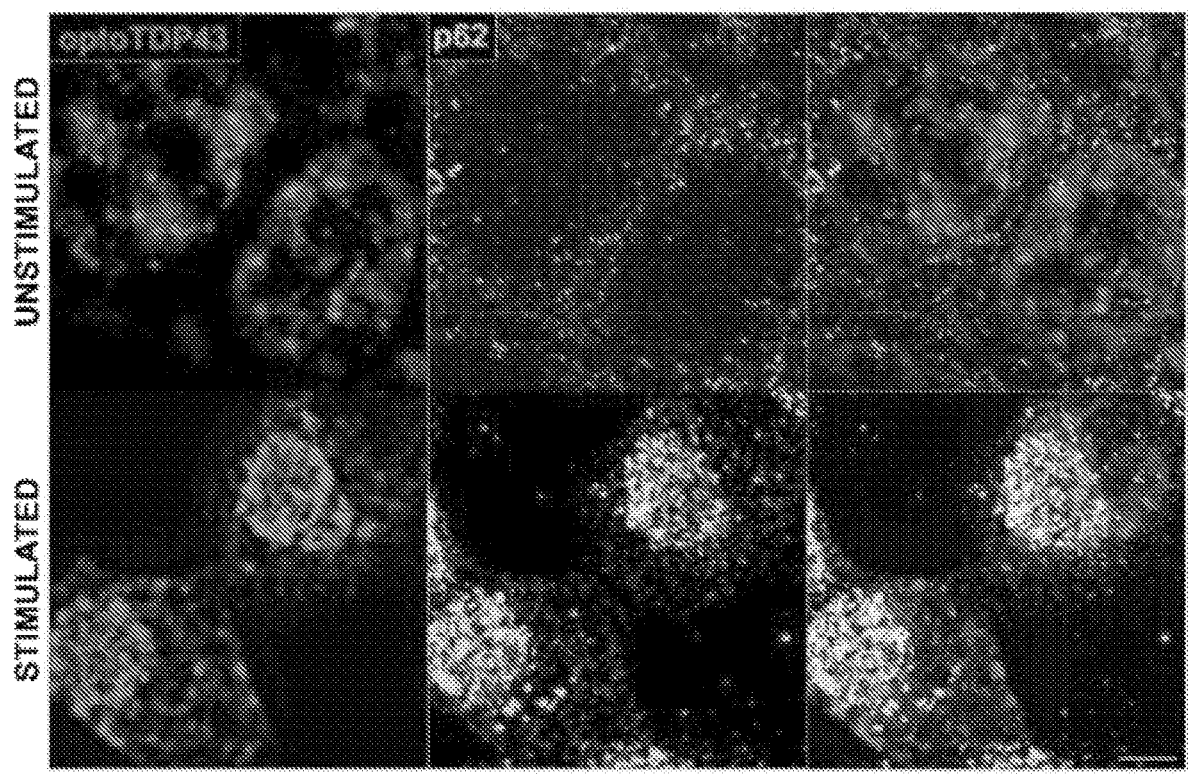
Figure 5K:
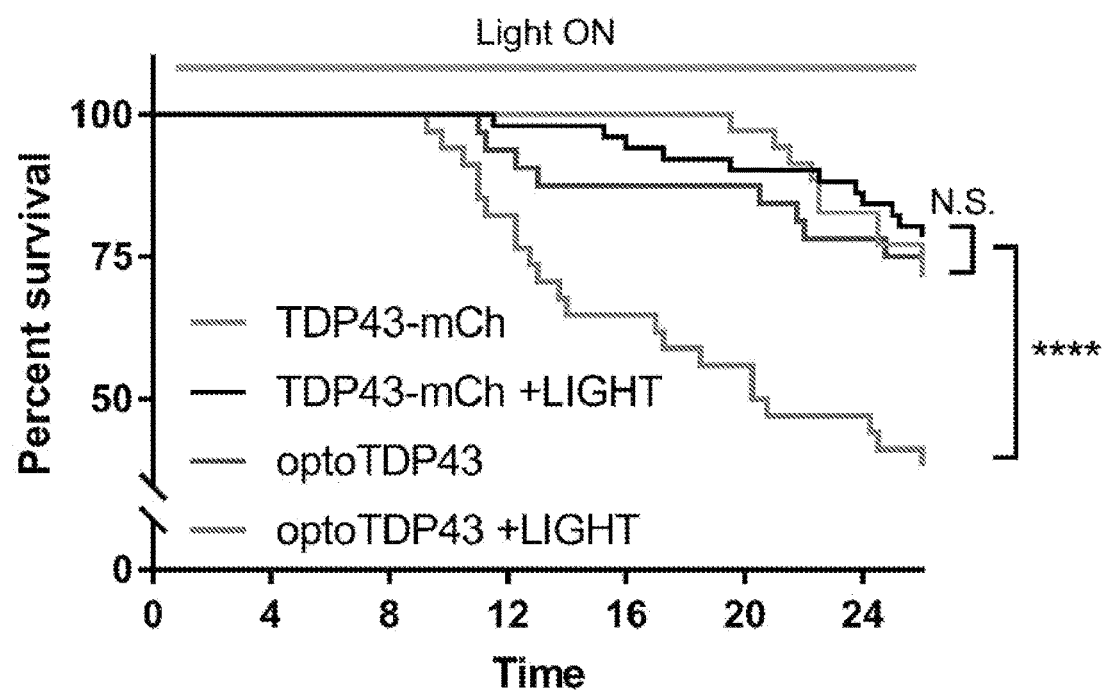
Figure 6A:
FIGS. 6A-6E show chronic stimulation of CRY2OLIG α-synuclein or α-synuclein LOV induces clustering and aggregation. Chronic stimulation of a CRY2-asyn-mCh was tested to induce clustering or the α-synuclein protein.
Figure 6B:
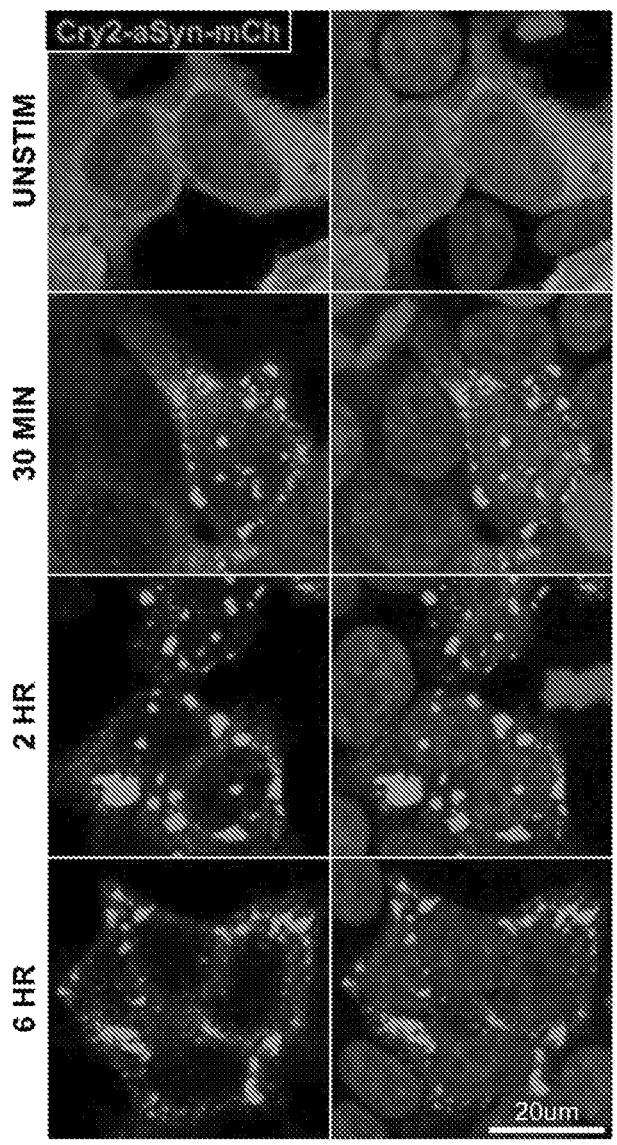
Figure 6C:
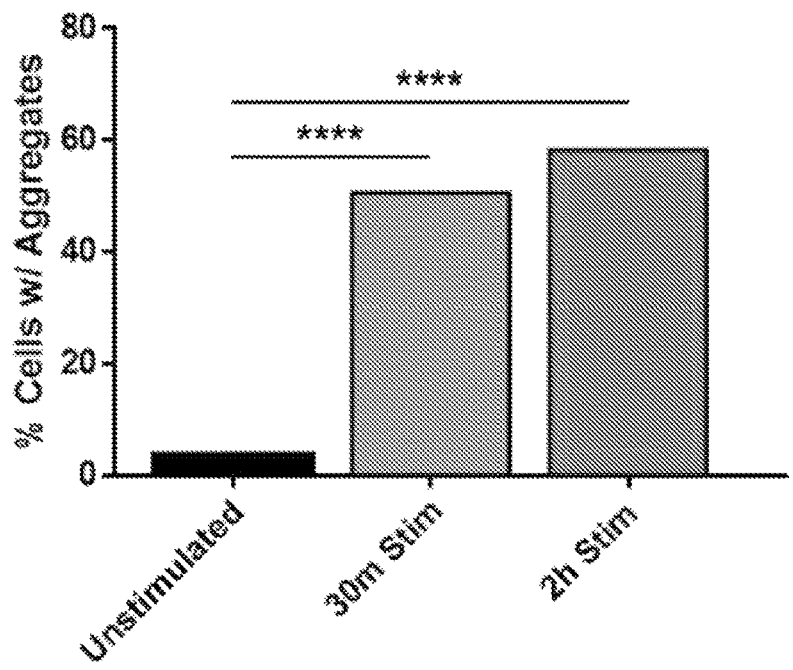
Figure 6D:
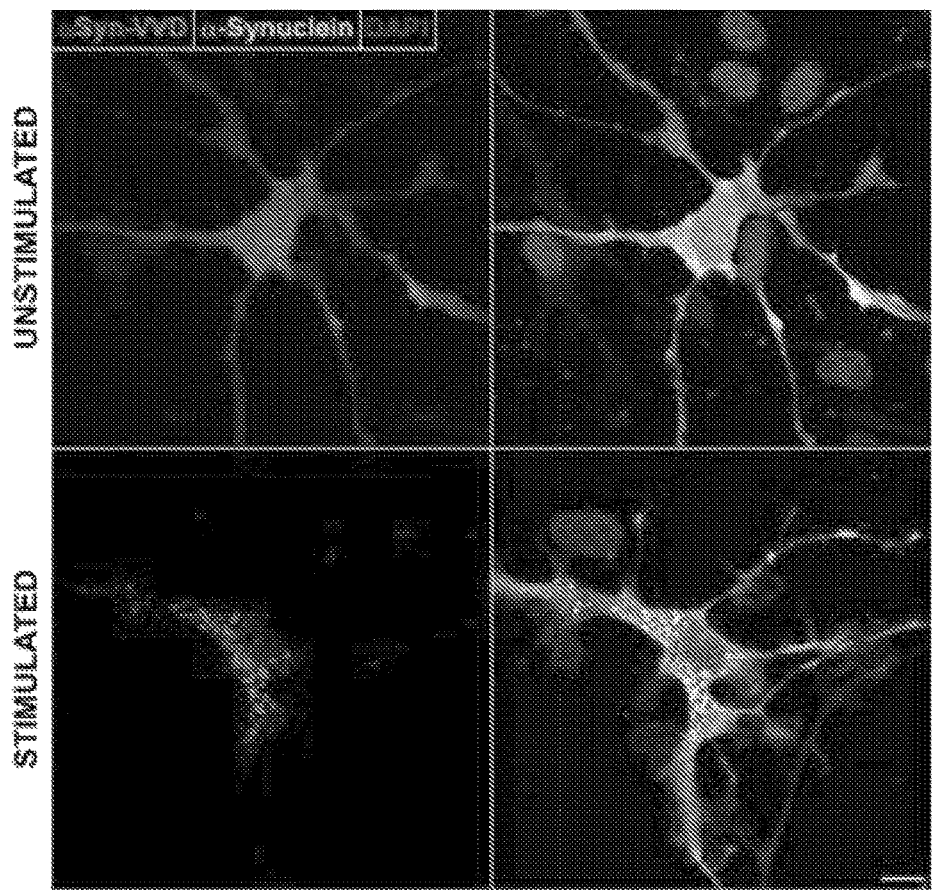
Figure 6E:
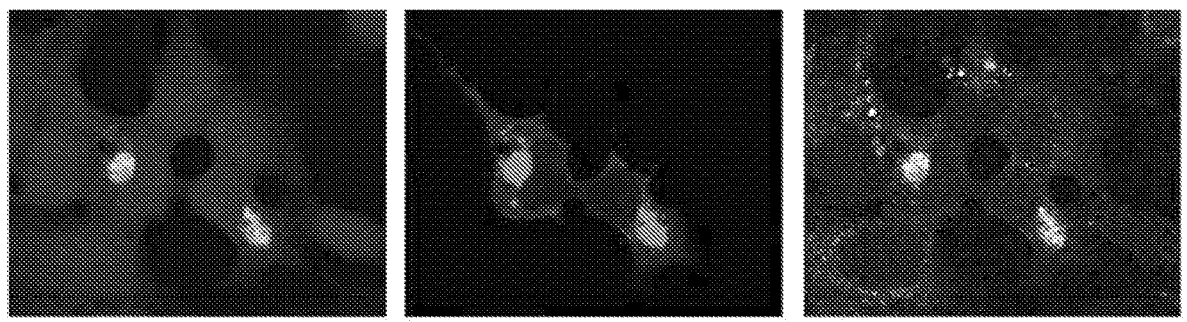
Figure 7A:
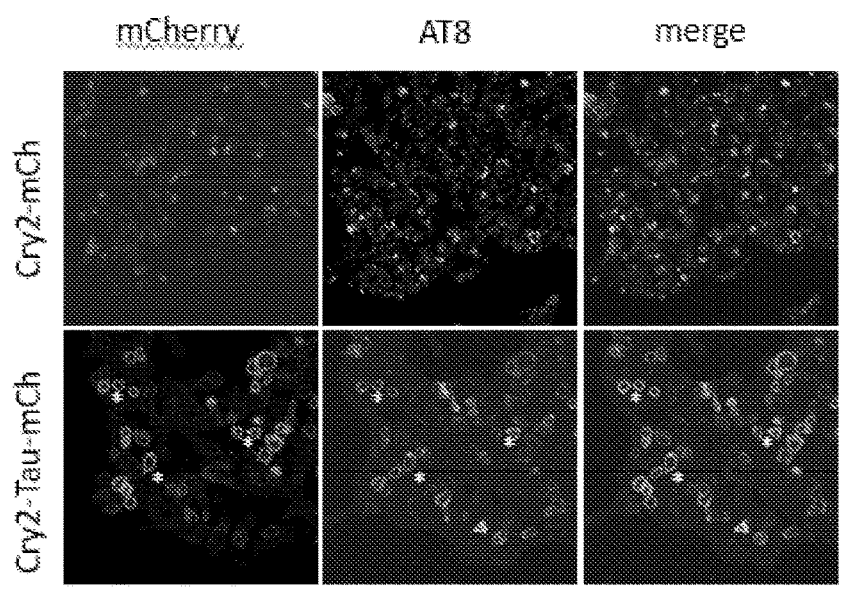
FIGS. 7A-7D show Cry2-Tau fusion protein shows pathological markers for various tauopathies.
Figure 7B:
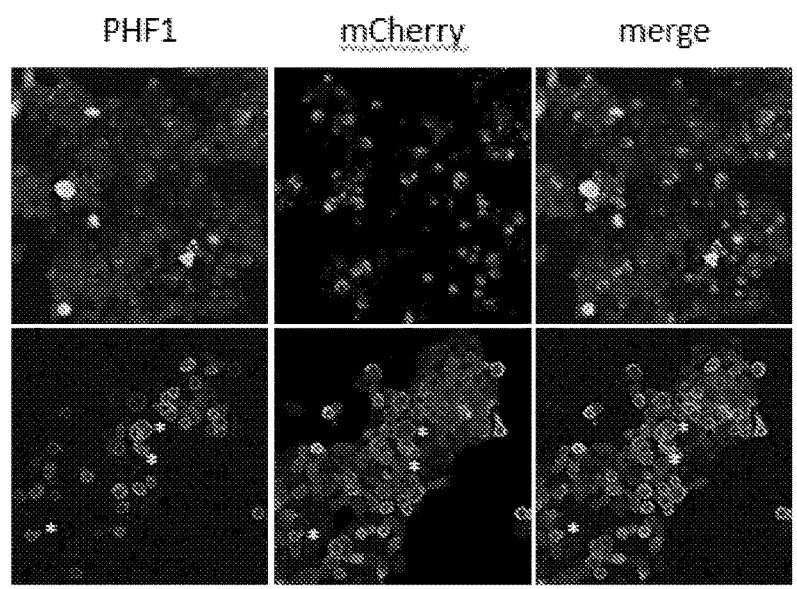
Figures 7C, 7D:
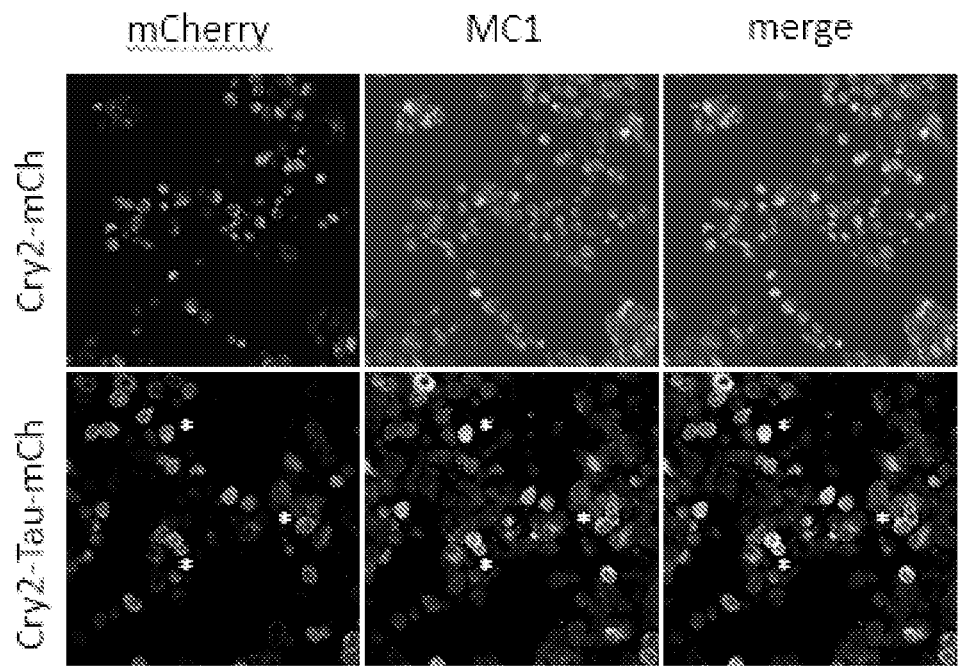
Figure 8A:
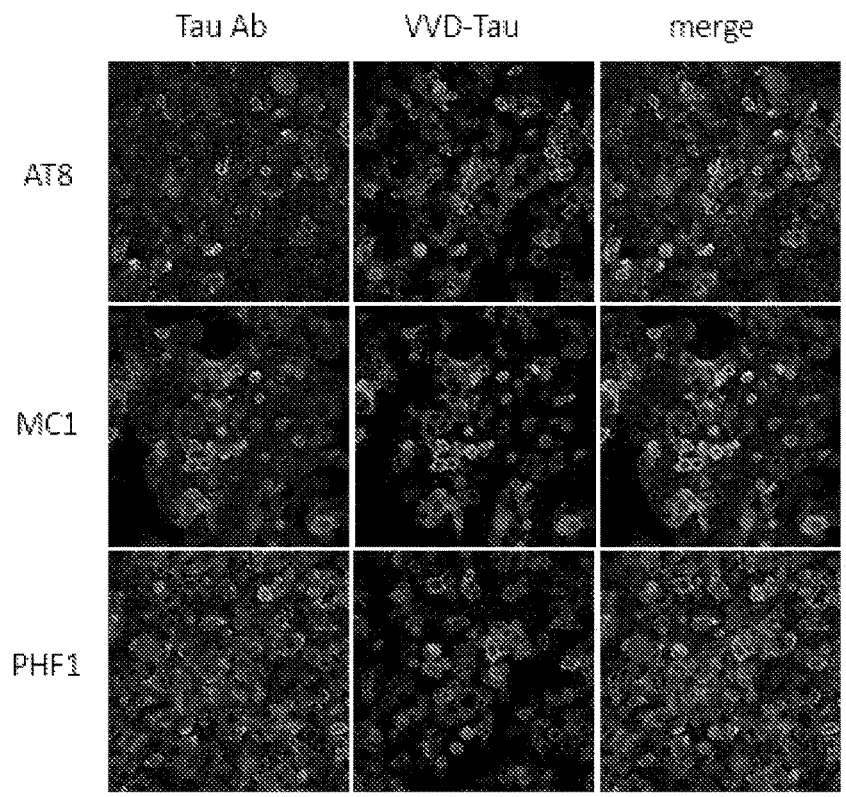
FIGS. 8A-8E show LOV-Tau fusion proteins also show pathological markers for various tauopathies and are insoluble.
Figure 8B:
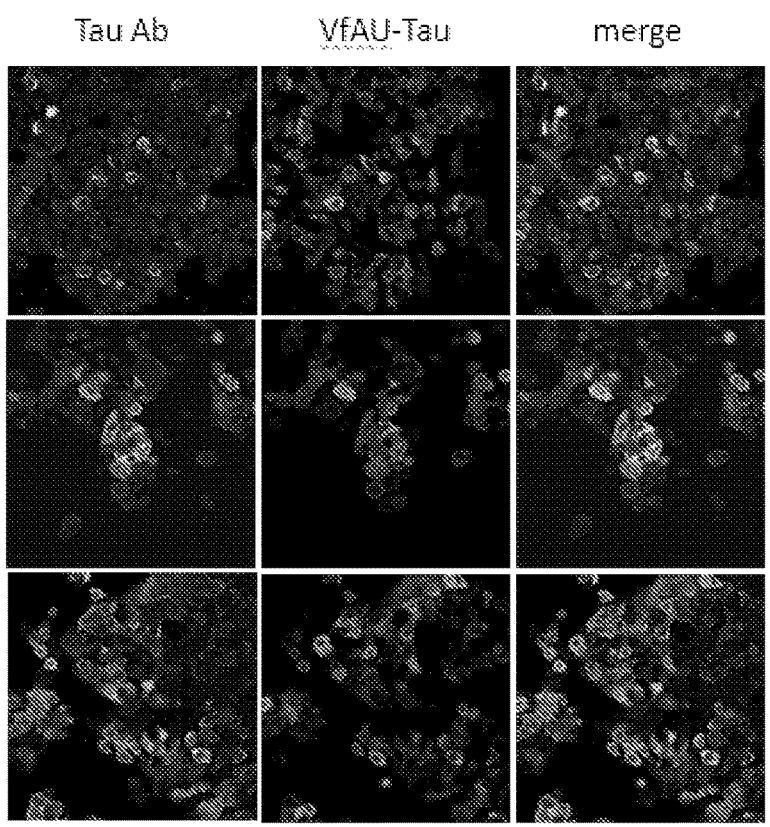
Figure 8C:
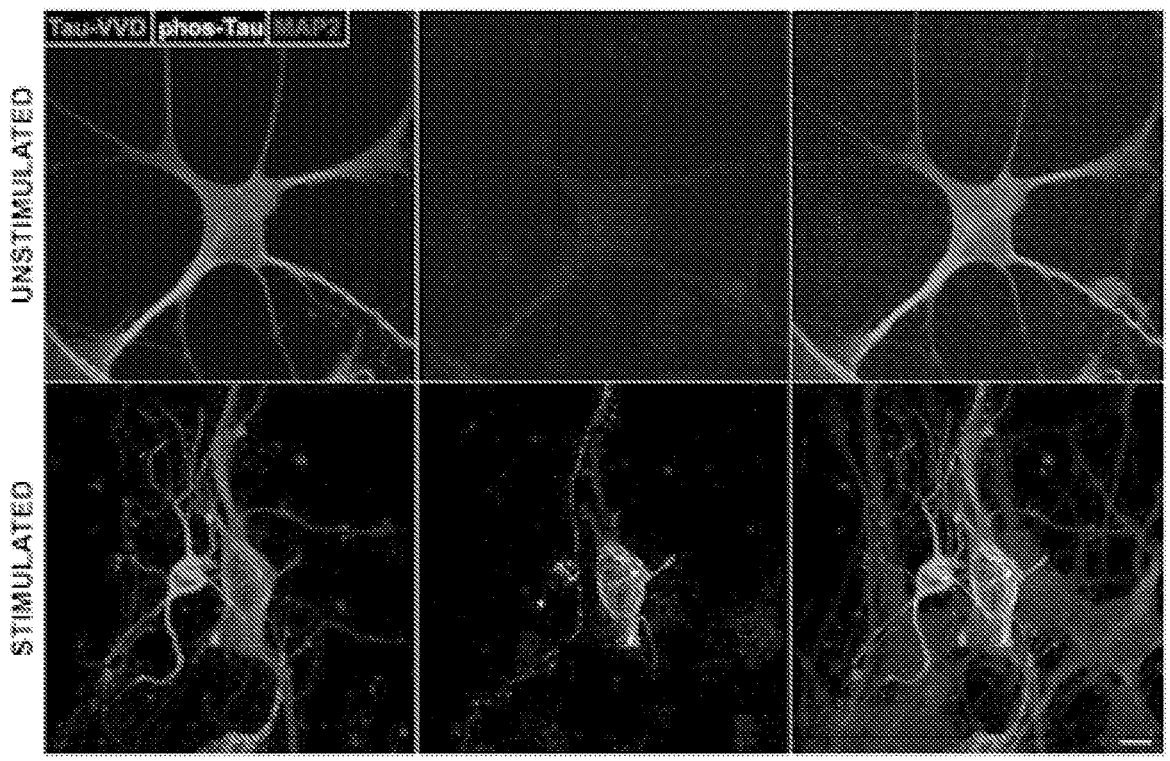
Figure 8D:
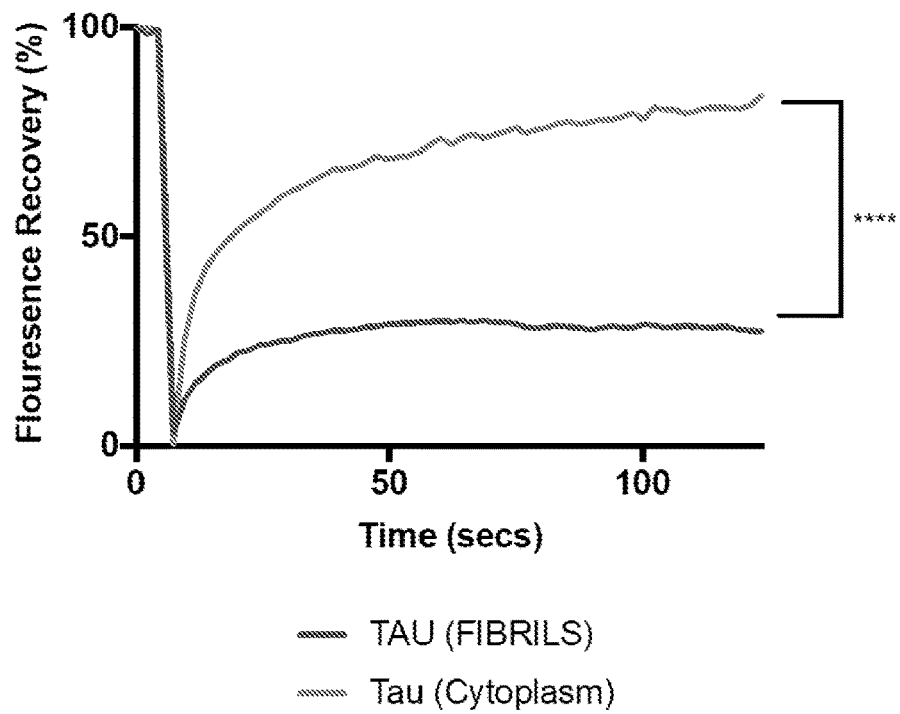
Figure 8E:
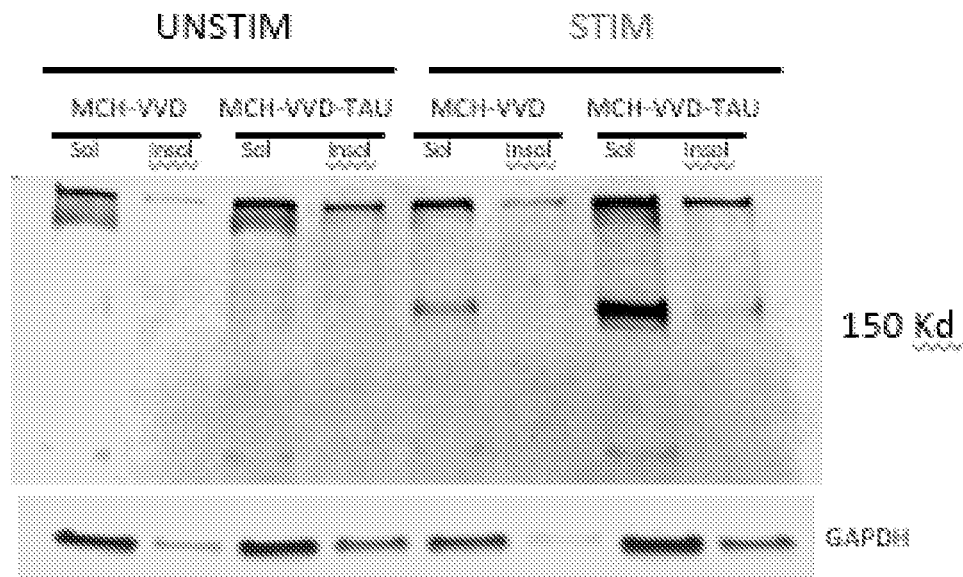
Figure 9A:
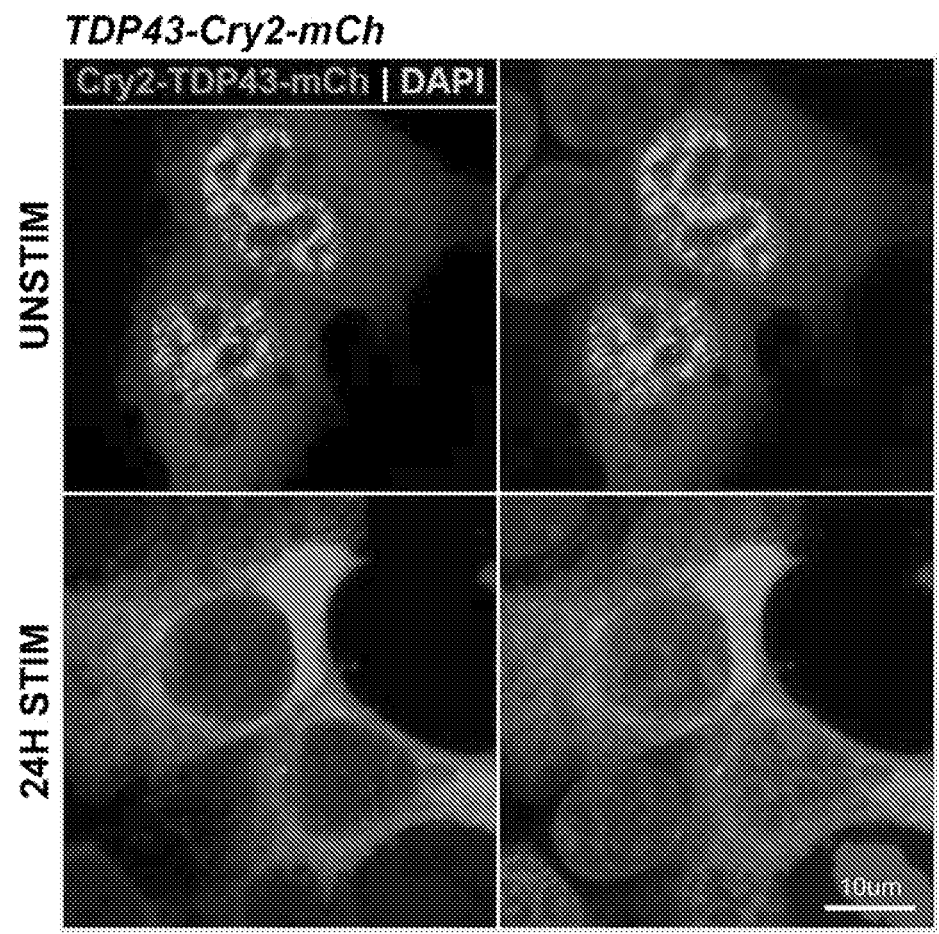
FIGS. 9A-9B show the aggregation potential of CRY2 or VVD fusion proteins based on the protein arrangement and light stimulation paradigm combination. Studies indicate that the ability of Cry2 or VVD photoreceptor to stimulate clustering and activation are dependent on the protein arrangement as well as the light stimulation paradigm.
Figure 9B:
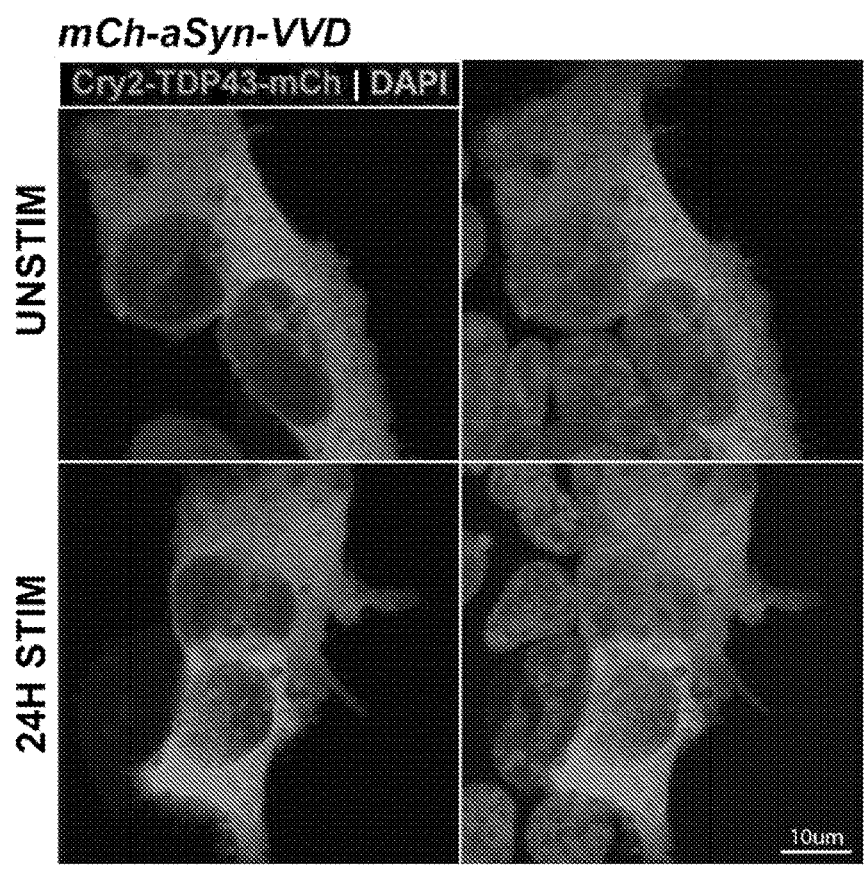

Beyond protein aggregation, this system creates light-induced pathologies that mimic key pathological features found in patients making it unique compared to overexpression systems. The TDP-43 protein, which contains an LCD, was combined with the CRY2OLIG photoreceptor domain which clusters when exposed to blue light and becomes insoluble and aggregated with persistent light treatment. Fusion proteins of the full length and partial LCD sequence were generated to recapitulate human neurodegenerative disease pathology, including the cytoplasmic mislocalization of nuclear proteins that occurs in patients with ALS and FTD. This system could induce neurodegenerative disease protein aggregates in live HEK cells by exposing them to various blue light stimuli paradigms (FIGS. 4-5). In addition, biochemical hallmarks of ALS, FTD, and AD (FIG. 7) were produced showing that the cell is responding to the light-induced aggregates as observed in patient CNS despite the addition of these tags. Notably, TDP-43 neuropathology is one of the more complex neuropathologies to mimic since it is a predominantly nuclear protein but is found to be mislocalized to the cytoplasm in patients. Employing this DNA arrangement and light stimulation system as an example, cytoplasmic TDP-43 aggregates were obtained that are also ubiquitinylated, cleaved, and hyperphosphorylated as observed in ALS, FTD, and AD patients. TDP-43 pathology is also found in AD as well as Chronic Traumatic Encephalopathy (CTE) thus highlighting the potential disease relevance of this work. In addition, a protein arrangement and light stimulation paradigm was developed to induce the aggregation of α-synuclein (FIG. 6), which is found in the CNS of patients diagnosed with Parkinson's Disease and Lewy Body Dementia. Methods were also developed to induce intracellular aggregation of Tau protein using both the Cry-PHR and LOV photoreceptors (FIG. 7) and persistent blue light stimulation. These tau tangles are pathological hallmarks of AD, FTD and CTE in HEK cells. These also exhibit pathological hallmarks of Tauopathy observed in patients including hyperphosphorylation using specific antibodies developed against pathological tau inclusions (FIGS. 7-8). Finally, it was shown that this method can be utilized to seed aggregations, as aggregates of TDP-43 formed using this method recruit endogenous TDP-43 to seed the pathogenic neuropathology (FIGS. 5F, 5G).

A novel methodology to force oligomerization and aggregation of LOV domain proteins fused to proteins that contain LCDs was also developed. The LOV domains, including NcVVDY50W has only been shown to dimerize with blue light stimulation. Using a chronic blue light stimulation paradigm (described in FIGS. 3 and 6-8), oligomerization and eventual aggregation of a LCD containing protein fused to the LOV sequence is induced. This amino acid sequence is significantly smaller than the PHR domain of CRY2 and may act as an alternative to CRY2 PHR since it is less likely to interfere with the endogenous target protein function.

Figure 10A:
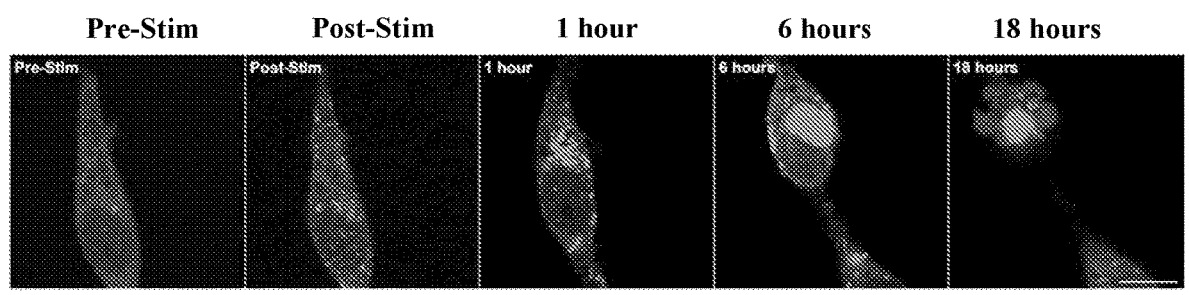
FIGS. 10A-10B show that blue light induced TDP-43 aggregates or truncated LCD/IDR/prion-like domain aggregates are toxic to cells.
Figure 10B:
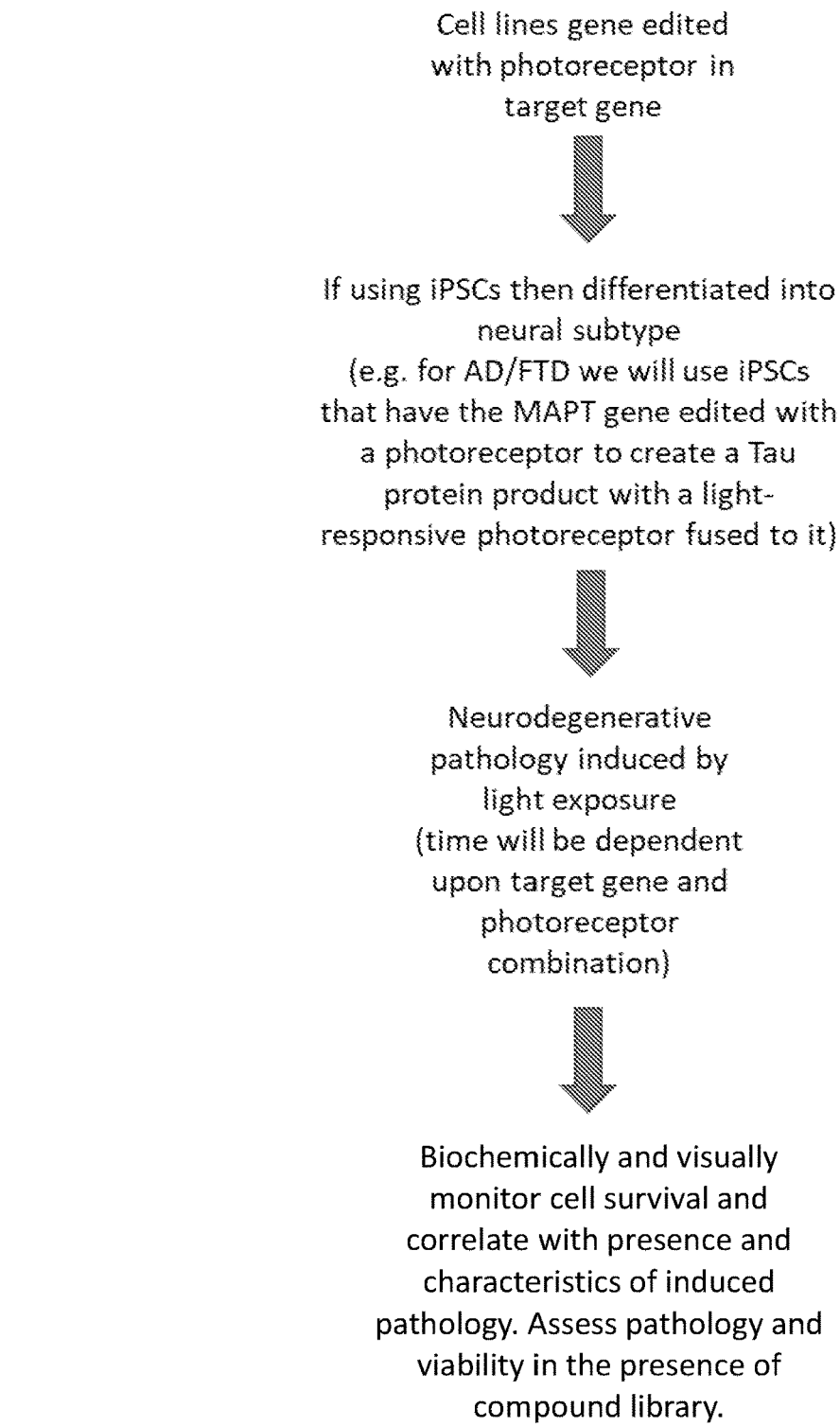

In some embodiments, DNA arrangements are constructed that encode for the PHR domains (CRY2 PHR or CRY2OLIG) or LOV photoreceptor proteins (NcVVD, NcVVDY50W, Vfau1, YtvA, EL222, RsLOV, AsLOV2) (or 90% similarity) fused to either the LCD fragment or full length neurodegenerative disease proteins listed in Table 3 (or 90% similarity). In some embodiments, disclosed herein are methods of employing blue light exposure treatment paradigms to induce these neurodegenerative disease pathologies. In other embodiments, the resulting protein aggregates and cell viability are used as a readout for neurodegenerative disease drug screening (FIG. 10). This system is used by pharmacologically or genetically mitigating neurodegenerative disease pathology formation or resident time can identify novel compounds for the treatment of specific neurodegenerative diseases. The following embodiments are also disclosed:

1. Generation of Novel Model Systems: These photoreceptor sequences are inserted into the genome of various in vitro and in vivo systems which can act as a new model to study neurodegenerative diseases. Some examples of in vitro uses include human and rodent cell lines, induced pluripotent stem cells (iPSCs), or yeast. Some examples of in vivo uses include invertebrates: *Drosophila melanogaster* (fruit fly), *Caenorhabditis elegans* (round worm), or *Danio rerio* (zebrafish). Other examples of in vivo uses include vertebrates: mouse, rat, or non-human primate.

2. These compounds, methods, and systems (such as iPSC) with edited genomes are used in high throughput drug screening systems. To achieve this, neurodegenerative disease pathologies are induced by stimulating cells with light. Cell viability and formation and residence time of protein aggregate/pathology in the presence of compound libraries are then examined. In addition, assays also involve employing survival and neuropathology of in vivo models following induction with light.

```
SEQUENCES
Amino Acid Sequences of Photoreceptor Tools:
Amino Acid Sequences of the Photolyase-Homologous Region (PHR) domain of the
Arabidopsis Cryptochrome 2 protein:
SEQ ID NO: 1. Cryptochrome 2 PHR Domain; Cry2PHR:
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTREAQIMIGAA
```

SEQ ID NO: 2. Cryptochrome 2 PHR Domain with E490G substitution; Cry2Olig:
(E490G in bold)
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAA

Amino Acid Sequences containing the Light-Oxygen-Voltage-Sensing Domain (LOV) from *Neurospora* Vivid protein:
SEQ ID NO: 3. VVD LOV Domain only:
MTSCALILCDLKQKDTPIVYASEAFLYMTGYSNAEVLGRNCRFLQSPDGMVKPKSTRKYVDSNTINTMRKAIDRNAEVQ

VEVVNFKKNGQRFVNFLTMIPVRDETGEYRYSMGFQCETE

SEQ ID NO: 4. NcVivid (NcVVD):
HTLYAPGGYDIMGYLIQIMNRPNPQVELGPVDTSCALILCDLKQKDTPIVYASEAFLYMTGYSNAEVLGRNCRFLQSPD

GMVKPKSTRKYVDSNTINTMRKAIDRNAEVQVEVVNFKKNGQRFVNFLTMIPVRDETGEYRYSMGFQCETE

SEQ ID NO: 5. NcVivid Y50W substitution; NcVVDY50W: (Y50W in bold)
HTLYAPGGYDIMGWLIQIMNRPNPQVELGPVDTSCALILCDLKQKDTPIVYASEAFLYMTGYSNAEVLGRNCRFLQSPD

GMVKPKSTRKYVDSNTINTMRKAIDRNAEVQVEVVNFKKNGQRFVNFLTMIPVRDETGEYRYSMGFQCETE

TDP-43 Protein Arrangements Generated:
1. Cry2olig Fusion Proteins Amino Acid Sequences:
A) Full Length TDP-43 Protein No Reporter
SEQ ID NO: 6. Cry2olig-TDP-43:
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARGMSEYIRVTEDENDEPIEIPSEDDGTVLLSTVTAQFPGACGLRYRNPVSQC

MRGVRLVEGILHAPDAGWGNLVYVVNYPKDNKRKMDETDASSAVKVKRAVQKTSDLIVLGLPWKTTEQDLKEYFSTF

GEVLMVQVKKDLKTGHSKGFGFVRFTEYETQVKVMSQRHMIDGRWCDCKLPNSKQSQDEPLRSRKVFVGRCTEDMT

EDELREFFSQYGDVMDVFIPKPFRAFAFVTFADDQIAQSLCGEDLIIKGISVHISNAEPKHNSNRQLERSGRFGGNPGGF

GNQGGFGNSRGGAGLGNNQGSNMGGGMNFGAFSINPAMMAAAQAALQSSWGMMGMLASQQNQSGPSGN

NQNQGNMQREPNQAFGSGNNSYSGSNSGAAIGWGSASNAGSGSGFNGGFGSSMDSKSSGWGM

SEQ ID NO: 7. TDP-43-Cry2olig:
MSEYIRVTEDENDEPIEIPSEDDGTVLLSTVTAQFPGACGLRYRNPVSQCMRGVRLVEGILHAPDAGWGNLVYVVNYP

KDNKRKMDETDASSAVKVKRAVQKTSDLIVLGLPWKTTEQDLKEYFSTFGEVLMVQVKKDLKTGHSKGFGFVRFTEYE

TQVKVMSQRHMIDGRWCDCKLPNSKQSQDEPLRSRKVFVGRCTEDMTEDELREFFSQYGDVMDVFIPKPFRAFAFVT

FADDQIAQSLCGEDLIIKGISVHISNAEPKHNSNRQLERSGRFGGNPGGFGNQGGFGNSRGGAGLGNNQGSNMGG

GMNFGAFSINPAMMAAAQAALQSSWGMMGMLASQQNQSGPSGNNQNQGNMQREPNQAFGSGNNSYSGSNS

GAAIGWGSASNAGSGSGFNGGFGSSMDSKSSGWGM LEAT

MKMDKKTIVWFRRDLRIEDNPALAAAAHEGSVFPVFIWCPEEEGQFYPGRASRWWMKQSLAHLSQSLKALGSDLTLI

KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

-continued

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAA

B) Truncated TDP-43 Proteins No Reporter
SEQ ID NO: 8. TDP-43$^{(AA274-414)}$-Cry2olig:
MGRFGGNPGGFGNQGGFGNSRGGGAGLGNNQGSNMGGGMNFGAFSINPAMMAAAQAALQSSWGMMGMLA

SQQNQSGPSGNNQNQGNMQREPNQAFGSGNNSYSGSNSGAAIGWGSASNAGSGSGFNGGFGSSMDSKSSGWG

MLEATMKMDKKTIVWFRRDLRIEDNPALAAAAHEGSVFPVFIWCPEEEGQFYPGRASRWWMKQSLAHLSQSLKALG

SDLTLIKTHNTISAILDCIRVTGATKVVFNHLYDPVSLVRDHTVKEKLVERGISVQSYNGDLLYEPWEIYCEKGKPFTSFNSY

WKKCLDMSIESVMLPPPWRLMPITAAAEAIWACSIEELGLENEAEKPSNALLTRAWSPGWSNADKLLNEFIEKQLIDYA

KNSKKVVGNSTSLLSPYLHFGEISVRHVFQCARMKQIIWARDKNSEGEESADLFLRGIGLREYSRYICFNFPFTHEQSLLSH

LRFFPWDADVDKFKAWRQGRTGYPLVDAGMRELWATGWMHNRIRVIVSSFAVKFLLLPWKWGMKYFWDTLLDAD

LECDILGWQYISGSIPDGHELDRLDNPALQGAKYDPEGEYIRQWLPELARLPTEWIHHPWDAPLTVLKASGVELGTNYA

KPIVDIDTARELLAKAISRTRGAQIMIGAA

SEQ ID NO: 9. TDP-43$^{(AA191-414)}$-Cry2olig:
MRKVFVGRCTEDMTEDELREFFSQYGDVMDVFIPKPFRAFAFVTFADDQIAQSLCGEDLIIKGISVHISNAEPKHNSNR

QLERSGRFGGNPGGFGNQGGFGNSRGGGAGLGNNQGSNMGGGMNFGAFSINPAMMAAAQAALQSSWGMMG

MLASQQNQSGPSGNNQNQGNMQREPNQAFGSGNNSYSGSNSGAAIGWGSASNAGSGSGFNGGFGSSMDSKSSG

WGMLEATMKMDKKTIVWFRRDLRIEDNPALAAAAHEGSVFPVFIWCPEEEGQFYPGRASRWWMKQSLAHLSQSLK

ALGSDLTLIKTHNTISAILDCIRVTGATKVVFNHLYDPVSLVRDHTVKEKLVERGISVQSYNGDLLYEPWEIYCEKGKPFTSF

NSYWKKCLDMSIESVMLPPPWRLMPITAAAEAIWACSIEELGLENEAEKPSNALLTRAWSPGWSNADKLLNEFIEKQLI

DYAKNSKKVVGNSTSLLSPYLHFGEISVRHVFQCARMKQIIWARDKNSEGEESADLFLRGIGLREYSRYICFNFPFTHEQS

LLSHLRFFPWDADVDKFKAWRQGRTGYPLVDAGMRELWATGWMHNRIRVIVSSFAVKFLLLPWKWGMKYFWDTLL

DADLECDILGWQYISGSIPDGHELDRLDNPALQGAKYDPEGEYIRQWLPELARLPTEWIHHPWDAPLTVLKASGVELGT

NYAKPIVDIDTARELLAKAISRTRGAQIMIGAA

SEQ ID NO: 10. TDP-43$^{(AA105-414)}$-Cry2olig:
MDLIVLGLPWKTTEQDLKEYFSTFGEVLMVQVKKDLKTGHSKGFGFVRFTEYETQVKVMSQRHMIDGRWCDCKLPNS KQSQDEPLRSRKVFVGRCTEDMTEDELREFFSQYGDVMDVFIPKPFRAFAFVTFADDQIAQSLCGEDLIIKGISVHISNAE

PKHNSNRQLERSGRFGGNPGGFGNQGGFGNSRGGGAGLGNNQGSNMGGGMNFGAFSINPAMMAAAQAALQSS

WGMMGMLASQQNQSGPSGNNQNQGNMQREPNQAFGSGNNSYSGSNSGAAIGWGSASNAGSGSGFNGGFGSS

MDSKSSGWGM

LEATMKMDKKTIVWFRRDLRIEDNPALAAAAHEGSVFPVFIWCPEEEGQFYPGRASRWWMKQSLAHLSQSLKALGSD

LTLIKTHNTISAILDCIRVTGATKVVFNHLYDPVSLVRDHTVKEKLVERGISVQSYNGDLLYEPWEIYCEKGKPFTSFNSYW

KKCLDMSIESVMLPPPWRLMPITAAAEAIWACSIEELGLENEAEKPSNALLTRAWSPGWSNADKLLNEFIEKQLIDYAK

NSKKVVGNSTSLLSPYLHFGEISVRHVFQCARMKQIIWARDKNSEGEESADLFLRGIGLREYSRYICFNFPFTHEQSLLSHL

RFFPWDADVDKFKAWRQGRTGYPLVDAGMRELWATGWMHNRIRVIVSSFAVKFLLLPWKWGMKYFWDTLLDADL

ECDILGWQYISGSIPDGHELDRLDNPALQGAKYDPEGEYIRQWLPELARLPTEWIHHPWDAPLTVLKASGVELGTNYAK

PIVDIDTARELLAKAISRTRGAQIMIGAA

SEQ ID NO: 11. Cry2olig-TDP-43$^{(AA274-414)}$:
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

-continued

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARGGRFGGNPGGFGNQGGFGNSRGGGAGLGNNQGSNMGGGMNFGAFSI

NPAMMAAAQAALQSSWGMMGMLASQQNQSGPSGNNQNQGNMQREPNQAFGSGNNSYSGSNSGAAIGWGSA

SNAGSGSGFNGGFGSSMDSKSSGWGM

SEQ ID NO: 12. Cry2olig-TDP-43$^{(\Delta A191-414)}$:
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARGRKVFVGRCTEDMTEDELREFFSQYGDVMDVFIPKPFRAFAFVTFADDQI

AQSLCGEDLIIKGISVHISNAEPKHNSNRQLERSGRFGGNPGGFGNQGGFGNSRGGGAGLGNNQGSNMGGGMNFG

AFSINPAMMAAAQAALQSSWGMMGMLASQQNQSGPSGNNQNQGNMQREPNQAFGSGNNSYSGSNSGAAIGW

GSASNAGSGSGFNGGFGSSMDSKSSGWGM

SEQ ID NO: 13. Cry2olig-TDP-43$^{(\Delta A105-414)}$:
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARGDLIVLGLPWKTTEQDLKEYFSTFGEVLMVQVKKDLKTGHSKGFGFVRFTE

YETQVKVMSQRHMIDGRWCDCKLPNSKQSQDEPLRSRKVFVGRCTEDMTEDELREFFSQYGDVMDVFIPKPFRAFAF

VTFADDQIAQSLCGEDLIIKGISVHISNAEPKHNSNRQLERSGRFGGNPGGFGNQGGFGNSRGGGAGLGNNQGSNM

GGGMNFGAFSINPAMMAAAQAALQSSWGMMGMLASQQNQSGPSGNNQNQGNMQREPNQAFGSGNNSYSGS

NSGAAIGWGSASNAGSGSGFNGGFGSSMDSKSSGWGM

C) Full Length TDP-43 Protein + mCherry Reporter
SEQ ID NO: 14. Cry2olig-TDP-43-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARG

MSEYIRVTEDENDEPIEIPSEDDGTVLLSTVTAQFPGACGLRYRNPVSQCMRGVRLVEGILHAPDAGWGNLVYVVNYP

KDNKRKMDETDASSAVKVKRAVQKTSDLIVLGLPWKTTEQDLKEYFSTFGEVLMVQVKKDLKTGHSKGFGFVRFTEYE

TQVKVMSQRHMIDGRWCDCKLPNSKQSQDEPLRSRKVFVGRCTEDMTEDELREFFSQYGDVMDVFIPKPFRAFAFVT

FADDQIAQSLCGEDLIIKGISVHISNAEPKHNSNRQLERSGRFGGNPGGFGNQGGFGNSRGGGAGLGNNQGSNMGG

GMNFGAFSINPAMMAAAQAALQSSWGMMGMLASQQNQSGPSGNNQNQGNMQREPNQAFGSGNNSYSGSNS

-continued

GAAIGWGSASNAGSGSGFNGGFGSSMDSKSSGWGMSRDPPVATMVSKGEEDNMAIIKEFMRFKVHMEGSVNGHE

FEIEGEGEGRPYEGTQTAKLKVTKGGPLPFAWDILSPQFMYGSKAYVKHPADIPDYLKLSFPEGFKWERVMNFEDGGV

VTVTQDSSLQDGEFIYKVKLRGTNFPSDGPVMQKKTMGWEASSERMYPEDGALKGEIKQRLKLKDGGHYDAEVKTTY

KAKKPVQLPGAYNVNIKLDITSHNEDYTIVEQYERAEGRHSTGGMDELYK

SEQ ID NO: 15. TDP-43-Cry2olig-mCherry:
MSEYIRVTEDENDEPIEIPSEDDGTVLLSTVTAQFPGACGLRYRNPVSQCMRGVRLVEGILHAPDAGWGNLVYVVNYP

KDNKRKMDETDASSAVKVKRAVQKTSDLIVLGLPWKTTEQDLKEYFSTFGEVLMVQVKKDLKTGHSKGFGFVRFTEYE

TQVKVMSQRHMIDGRWCDCKLPNSKQSQDEPLRSRKVFVGRCTEDMTEDELREFFSQYGDVMDVFIPKPFRAFAFVT

FADDQIAQSLCGEDLIIKGISVHISNAEPKHNSNRQLERSGRFGGNPGGFGNQGGFGNSRGGGAGLGNNQGSNMGG

GMNFGAFSINPAMMAAAQAALQSSWGMMGMLASQQNQSGPSGNNQNQGNMQREPNQAFGSGNNSYSGSNS

GAAIGWGSASNAGSGSGFNGGFGSSMDSKSSGWGMLEATMKMDKKTIVWFRRDLRIEDNPALAAAAHEGSVFPVFI

WCPEEEGQFYPGRASRWWMKQSLAHLSQSLKALGSDLTLIKTHNTISAILDCIRVTGATKVVFNHLYDPVSLVRDHTVK

EKLVERGISVQSYNGDLLYEPWEIYCEKGKPFTSFNSYWKKCLDMSIESVMLPPPWRLMPITAAAEAIWACSIEELGLEN

EAAEKPSNALLTRAWSPGWSNADKLLNEFIEKQLIDYAKNSKKVVGNSTSLLSPYLHFGEISVRHVFQCARMKQIIWARD

KNSEGEESADLFLRGIGLREYSRYICFNFPPFTHEQSLLSHLRFFPWDADVDKFKAWRQGRTGYPLVDAGMRELWATGW

MHNRIRVIVSSFAVKFLLLPWKWGMKYFWDTLLDADLECDILGWQYISGSIPDGHELDRLDNPALQGAKYDPEGEYIR

QWLPELARLPTEWIHHPWDAPLTVLKASGVELGTNYAKPIVDIDTARELLAKAISRTRGAQIMIGAAARDPPVATMVSK

GEEDNMAIIKEFMRFKVHMEGSVNGHEFEIEGEGEGRPYEGTQTAKLKVTKGGPLPFAWDILSPQFMYGSKAYVKHP

ADIPDYLKLSFPEGFKWERVMNFEDGGVVTVTQDSSLQDGEFIYKVKLRGTNFPSDGPVMQKKTMGWEASSERMYP

EDGALKGEIKQRLKLKDGGHYDAEVKTTYKAKKPVQLPGAYNVNIKLDITSHNEDYTIVEQYERAEGRHSTGGMDELYK

SEQ ID NO: 16. mCherry-TDP-43-Cry2olig:
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKMSEYIRVTEDENDEPIEIPSEDDGTVLLSTVTAQFPGACGLRYRNPVSQCMRGVRLVEGILHAPDAGWGNLVYVV

NYPKDNKRKMDETDASSAVKVKRAVQKTSDLIVLGLPWKTTEQDLKEYFSTFGEVLMVQVKKDLKTGHSKGFGFVRFT

EYETQVKVMSQRHMIDGRWCDCKLPNSKQSQDEPLRSRKVFVGRCTEDMTEDELREFFSQYGDVMDVFIPKPFRAFA

FVTFADDQIAQSLCGEDLIIKGISVHISNAEPKHNSNRQLERSGRFGGNPGGFGNQGGFGNSRGGGAGLGNNQGSNM

GGGMNFGAFSINPAMMAAAQAALQSSWGMMGMLASQQNQSGPSGNNQNQGNMQREPNQAFGSGNNSYSGS

NSGAAIGWGSASNAGSGSGFNGGFGSSMDSKSSGWGMLEATMKMDKKTIVWFRRDLRIEDNPALAAAAHEGSVFP

VFIWCPEEEGQFYPGRASRWWMKQSLAHLSQSLKALGSDLTLIKTHNTISAILDCIRVTGATKVVFNHLYDPVSLVRDHT

VKEKLVERGISVQSYNGDLLYEPWEIYCEKGKPFTSFNSYWKKCLDMSIESVMLPPPWRLMPITAAAEAIWACSIEELGL

ENEAEKPSNALLTRAWSPGWSNADKLLNEFIEKQLIDYAKNSKKVVGNSTSLLSPYLHFGEISVRHVFQCARMKQIIWA

RDKNSEGEESADLFLRGIGLREYSRYICFNFPPFTHEQSLLSHLRFFPWDADVDKFKAWRQGRTGYPLVDAGMRELWAT

GWMHNRIRVIVSSFAVKFLLLPWKWGMKYFWDTLLDADLECDILGWQYISGSIPDGHELDRLDNPALQGAKYDPEGE

YIRQWLPELARLPTEWIHHPWDAPLTVLKASGVELGTNYAKPIVDIDTARELLAKAISRTRGAQIMIGAA

D) Truncated TDP-43 Proteins + mCherry Reporter
SEQ ID NO: 17. TDP-43$^{(\Delta 274\text{-}414)}$-Cry2olig-mCherry:
MGRFGGNPGGFGNQGGFGNSRGGGAGLGNNQGSNMGGGMNFGAFSINPAMMAAAQAALQSSWGMMGMLA

SQQNQSGPSGNNQNQGNMQREPNQAFGSGNNSYSGSNSGAAIGWGSASNAGSGSGFNGGFGSSMDSKSSGWG

MLEATMKMDKKTIVWFRRDLRIEDNPALAAAAHEGSVFPVFIWCPEEEGQFYPGRASRWWMKQSLAHLSQSLKALG

SDLTLIKTHNTISAILDCIRVTGATKVVFNHLYDPVSLVRDHTVKEKLVERGISVQSYNGDLLYEPWEIYCEKGKPFTSFNSY

WKKCLDMSIESVMLPPPWRLMPITAAAEAIWACSIEELGLENEAEKPSNALLTRAWSPGWSNADKLLNEFIEKQLIDYA

KNSKKVVGNSTSLLSPYLHFGEISVRHVFQCARMKQIIWARDKNSEGEESADLFLRGIGLREYSRYICFNFPFTHEQSLLSH

LRFFPWDADVDKFKAWRQGRTGYPLVDAGMRELWATGWMHNRIRVIVSSFAVKFLLLPWKWGMKYFWDTLLDAD

LECDILGWQYISGSIPDGHELDRLDNPALQGAKYDPEGEYIRQWLPELARLPTEWIHHPWDAPLTVLKASGVELGTNYA

KPIVDIDTARELLAKAISRTRGAQIMIGAAARDPPVATMVSKGEEDNMAIIKEFMRFKVHMEGSVNGHEFEIEGEGEGR

PYEGTQTAKLKVTKGGPLPFAWDILSPQFMYGSKAYVKHPADIPDYLKLSFPEGFKWERVMNFEDGGVVTVTQDSSLQ

DGEFIYKVKLRGTNFPSDGPVMQKKTMGWEASSERMYPEDGALKGEIKQRLKLKDGGHYDAEVKTTYKAKKPVQLPG

AYNVNIKLDITSHNEDYTIVEQYERAEGRHSTGGMDELYK

SEQ ID NO: 18. TDP-43$^{(\Delta 191-414)}$-Cry2olig-mCherry:
MRKVFVGRCTEDMTEDELREFFSQYGDVMDVFIPKPFRAFAFVTFADDQIAQSLCGEDLIIKGISVHISNAEPKHNSNR

QLERSGRFGGNPGGFGNQGGFGNSRGGGAGLGNNQGSNMGGGMNFGAFSINPAMMAAAQAALQSSWGMMG

MLASQQNQSGPSGNNQNQGNMQREPNQAFGSGNNSYSGSNSGAAIGWGSASNAGSGSGFNGGFGSSMDSKSSG

WGMLEATMKMDKKTIVWFRRDLRIEDNPALAAAAHEGSVFPVFIWCPEEEGQFYPGRASRWWMKQSLAHLSQSLK

ALGSDLTLIKTHNTISAILDCIRVTGATKVVFNHLYDPVSLVRDHTVKEKLVERGISVQSYNGDLLYEPWEIYCEKGKPFTSF

NSYWKKCLDMSIESVMLPPPWRLMPITAAAEAIWACSIEELGLENEAEKPSNALLTRAWSPGWSNADKLLNEFIEKQLI

DYAKNSKKVVGNSTSLLSPYLHFGEISVRHVFQCARMKQIIWARDKNSEGEESADLFLRGIGLREYSRYICFNFPFTHEQS

LLSHLRFFPWDADVDKFKAWRQGRTGYPLVDAGMRELWATGWMHNRIRVIVSSFAVKFLLLPWKWGMKYFWDTLL

DADLECDILGWQYISGSIPDGHELDRLDNPALQGAKYDPEGEYIRQWLPELARLPTEWIHHPWDAPLTVLKASGVELGT

NYAKPIVDIDTARELLAKAISRTRGAQIMIGAAARDPPVATMVSKGEEDNMAIIKEFMRFKVHMEGSVNGHEFEIEGEG

EGRPYEGTQTAKLKVTKGGPLPFAWDILSPQFMYGSKAYVKHPADIPDYLKLSFPEGFKWERVMNFEDGGVVTVTQDS

SLQDGEFIYKVKLRGTNFPSDGPVMQKKTMGWEASSERMYPEDGALKGEIKQRLKLKDGGHYDAEVKTTYKAKKPVQ

LPGAYNVNIKLDITSHNEDYTIVEQYERAEGRHSTGGMDELYK

SEQ ID NO: 19. TDP-43$^{(\Delta 105-414)}$-Cry2olig-mCherry:
MDLIVLGLPWKTTEQDLKEYFSTFGEVLMVQVKKDLKTGHSKGFGFVRFTEYETQVKVMSQRHMIDGRWCDCKLPNS KQSQDEPLRSRKVFVGRCTEDMTEDELREFFSQYGDVMDVFIPKPFRAFAFVTFADDQIAQSLCGEDLIIKGISVHISNAE

PKHNSNRQLERSGRFGGNPGGFGNQGGFGNSRGGGAGLGNNQGSNMGGGMNFGAFSINPAMMAAAQAALQSS

WGMMGMLASQQNQSGPSGNNQNQGNMQREPNQAFGSGNNSYSGSNSGAAIGWGSASNAGSGSGFNGGFGSS

MDSKSSGWGMLEATMKMDKKTIVWFRRDLRIEDNPALAAAAHEGSVFPVFIWCPEEEGQFYPGRASRWWMKQSL

AHLSQSLKALGSDLTLIKTHNTISAILDCIRVTGATKVVFNHLYDPVSLVRDHTVKEKLVERGISVQSYNGDLLYEPWEIYC

EKGKPFTSFNSYWKKCLDMSIESVMLPPPWRLMPITAAAEAIWACSIEELGLENEAEKPSNALLTRAWSPGWSNADKL

LNEFIEKQLIDYAKNSKKVVGNSTSLLSPYLHFGEISVRHVFQCARMKQIIWARDKNSEGEESADLFLRGIGLREYSRYICF

NFPFTHEQSLLSHLRFFPWDADVDKFKAWRQGRTGYPLVDAGMRELWATGWMHNRIRVIVSSFAVKFLLLPWKWG

MKYFWDTLLDADLECDILGWQYISGSIPDGHELDRLDNPALQGAKYDPEGEYIRQWLPELARLPTEWIHHPWDAPLTV

LKASGVELGTNYAKPIVDIDTARELLAKAISRTRGAQIMIGAAARDPPVATMVSKGEEDNMAIIKEFMRFKVHMEGSVN

GHEFEIEGEGEGRPYEGTQTAKLKVTKGGPLPFAWDILSPQFMYGSKAYVKHPADIPDYLKLSFPEGFKWERVMNFED

GGVVTVTQDSSLQDGEFIYKVKLRGTNFPSDGPVMQKKTMGWEASSERMYPEDGALKGEIKQRLKLKDGGHYDAEV

KTTYKAKKPVQLPGAYNVNIKLDITSHNEDYTIVEQYERAEGRHSTGGMDELYK

SEQ ID NO: 20. mCherry-Cry2olig-TDP-43$^{(\Delta 274-414)}$:
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYK

```
MKMDKKTIVWFRRDLRIEDNPALAAAAHEGSVFPVFIWCPEEEGQFYPGRASRWWMKQSLAHLSQSLKALGSDLTLI

KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARGGRFGGNPGGFGNQGGFGNSRGGGAGLGNNQGSNMGGGMNFGAFSI

NPAMMAAAQAALQSSWGMMGMLASQQNQSGPSGNNQNQGNMQREPNQAFGSGNNSYSGSNSGAAIGWGSA

SNAGSGSGFNGGFGSSMDSKSSGWGM

SEQ ID NO: 21. mCherry-Cry2olig-TDP-43$^{(\Delta 191-414)}$:
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYK

MKMDKKTIVWFRRDLRIEDNPALAAAAHEGSVFPVFIWCPEEEGQFYPGRASRWWMKQSLAHLSQSLKALGSDLTLI

KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARGRKVFVGRCTEDMTEDELREFFSQYGDVMDVFIPKPFRAFAFVTFADDQI

AQSLCGEDLIIKGISVHISNAEPKHNSNRQLERSGRFGGNPGGFGNQGGFGNSRGGGAGLGNNQGSNMGGGMNFG

AFSINPAMMAAAQAALQSSWGMMGMLASQQNQSGPSGNNQNQGNMQREPNQAFGSGNNSYSGSNSGAAIGW

GSASNAGSGSGFNGGFGSSMDSKSSGWGM

SEQ ID NO: 22. mCherry-Cry2olig-TDP-43$^{(\Delta 105-414)}$:
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKMKMDKKTIVWFRRDLRIEDNPALAAAAHEGSVFPVFIWCPEEEGQFYPGRASRWWMKQSLAHLSQSLKALGSD

LTLIKTHNTISAILDCIRVTGATKVVFNHLYDPVSLVRDHTVKEKLVERGISVQSYNGDLLYEPWEIYCEKGKPFTSFNSYW

KKCLDMSIESVMLPPPWRLMPITAAAEAIWACSIEELGLENEAEKPSNALLTRAWSPGWSNADKLLNEFIEKQLIDYAK

NSKKVVGNSTSLLSPYLHFGEISVRHVFQCARMKQIIWARDKNSEGEESADLFLRGIGLREYSRYICFNFPFTHEQSLLSHL

RFFPWDADVDKFKAWRQGRTGYPLVDAGMRELWATGWMHNRIRVIVSSFAVKFLLLPWKWGMKYFWDTLLDADL

ECDILGWQYISGSIPDGHELDRLDNPALQGAKYDPEGEYIRQWLPELARLPTEWIHHPWDAPLTVLKASGVELGTNYAK

PIVDIDTARELLAKAISRTRGAQIMIGAAARGDLIVLGLPWKTTEQDLKEYFSTFGEVLMVQVKKDLKTGHSKGFGFVRF

TEYETQVKVMSQRHMIDGRWCDCKLPNSKQSQDEPLRSRKVFVGRCTEDMTEDELREFFSQYGDVMDVFIPKPFRAF

AFVTFADDQIAQSLCGEDLIIKGISVHISNAEPKHNSNRQLERSGRFGGNPGGFGNQGGFGNSRGGGAGLGNNQGSN

MGGGMNFGAFSINPAMMAAAQAALQSSWGMMGMLASQQNQSGPSGNNQNQGNMQREPNQAFGSGNNSYS

GSNSGAAIGWGSASNAGSGSGFNGGFGSSMDSKSSGWGM

SEQ ID NO: 23. Cry2olig-TDP-43$^{(\Delta 274-414)}$-mCherry:
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC
```

-continued

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARGGRFGGNPGGFGNQGGFGNSRGGGAGLGNNQGSNMGGGMNFGAFSI

NPAMMAAAQAALQSSWGMMGMLASQQNQSGPSGNNQNQGNMQREPNQAFGSGNNSYSGSNSGAAIGWGSA

SNAGSGSGFNGGFGSSMDSKSSGWGMSRDPPVATMVSKGEEDNMAIIKEFMRFKVHMEGSVNGHEFEIEGEGEGR

PYEGTQTAKLKVTKGGPLPFAWDILSPQFMYGSKAYVKHPADIPDYLKLSFPEGFKWERVMNFEDGGVVTVTQDSSLQ

DGEFIYKVKLRGTNFPSDGPVMQKKTMGWEASSERMYPEDGALKGEIKQRLKLKDGGHYDAEVKTTYKAKKPVQLPG

AYNVNIKLDITSHNEDYTIVEQYERAEGRHSTGGMDELYK

SEQ ID NO: 24. Cry2olig-TDP-43$^{(\Delta A191-414)}$-mCherry:
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARGRKVFVGRCTEDMTEDELREFFSQYGDVMDVFIPKPFRAFAFVTFADDQ1

AQSLCGEDLIIKGISVHISNAEPKHNSNRQLERSGRFGGNPGGFGNQGGFGNSRGGGAGLGNNQGSNMGGGMNFG

AFSINPAMMAAAQAALQSSWGMMGMLASQQNQSGPSGNNQNQGNMQREPNQAFGSGNNSYSGSNSGAAIGW

GSASNAGSGSGFNGGFGSSMDSKSSGWGMSRDPPVATMVSKGEEDNMAIIKEFMRFKVHMEGSVNGHEFEIEGEG

EGRPYEGTQTAKLKVTKGGPLPFAWDILSPQFMYGSKAYVKHPADIPDYLKLSFPEGFKWERVMNFEDGGVVTVTQDS

SLQDGEFIYKVKLRGTNFPSDGPVMQKKTMGWEASSERMYPEDGALKGEIKQRLKLKDGGHYDAEVKTTYKAKKPVQ

LPGAYNVNIKLDITSHNEDYTIVEQYERAEGRHSTGGMDELYK

SEQ ID NO: 25. Cry2olig-TDP-43$^{(\Delta A105-414)}$-mCherry:
MDLIVLGLPWKTTEQDLKEYFSTFGEVLMVQVKKDLKTGHSKGFGFVRFTEYETQVKVMSQRHMIDGRWCDCKLPNS KQSQDEPLRSRKVFVGRCTEDMTEDELREFFSQYGDVMDVFIPKPFRAFAFVTFADDQIAQSLCGEDLIIKGISVHISNAE

PKHNSNRQLERSGRFGGNPGGFGNQGGFGNSRGGGAGLGNNQGSNMGGGMNFGAFSINPAMMAAAQAALQSS

WGMMGMLASQQNQSGPSGNNQNQGNMQREPNQAFGSGNNSYSGSNSGAAIGWGSASNAGSGSGFNGGFGSS

MDSKSSGWGMLEATMKMDKKTIVWFRRDLRIEDNPALAAAAHEGSVFPVFIWCPEEEGQFYPGRASRWWMKQSL

AHLSQSLKALGSDLTLIKTHNTISAILDCIRVTGATKVVFNHLYDPVSLVRDHTVKEKLVERGISVQSYNGDLLYEPWEIYC

EKGKPFTSFNSYWKKCLDMSIESVMLPPPWRLMPITAAAEAIWACSIEELGLENEAEKPSNALLTRAWSPGWSNADKL

LNEFIEKQLIDYAKNSKKVVGNSTSLLSPYLHFGEISVRHVFQCARMKQIIWARDKNSEGEESADLFLRGIGLREYSRYICF

NFPPFTHEQSLLSHLRFFPWDADVDKFKAWRQGRTGYPLVDAGMRELWATGWMHNRIRVIVSSFAVKFLLLPWKWG

MKYFWDTLLDADLECDILGWQYISGSIPDGHELDRLDNPALQGAKYDPEGEYIRQWLPELARLPTEWIHHPWDAPLTV

LKASGVELGTNYAKPIVDIDTARELLAKAISRTRGAQIMIGAASRDPPVATMVSKGEEDNMAIIKEFMRFKVHMEGSVN

GHEFEIEGEGEGRPYEGTQTAKLKVTKGGPLPFAWDILSPQFMYGSKAYVKHPADIPDYLKLSFPEGFKWERVMNFED

GGVVTVTQDSSLQDGEFIYKVKLRGTNFPSDGPVMQKKTMGWEASSERMYPEDGALKGEIKQRLKLKDGGHYDAEV

KTTYKAKKPVQLPGAYNVNIKLDITSHNEDYTIVEQYERAEGRHSTGGMDELYK

2. NcVVDY50W Fusion Proteins Amino Acid Sequences:
A) Full length TDP-43 Protein no reporter
SEQ ID NO: 26. NcVVDY50W-TDP-43
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEAMS

EYIRVTEDENDEPIEIPSEDDGTVLLSTVTAQFPGACGLRYRNPVSQCMRGVRLVEGILHAPDAGWGNLVYVVNYPKD

NKRKMDETDASSAVKVKRAVQKTSDLIVLGLPWKTTEQDLKEYFSTFGEVLMVQVKKDLKTGHSKGFGFVRFTEYETQ

VKVMSQRHMIDGRWCDCKLPNSKQSQDEPLRSRKVFVGRCTEDMTEDELREFFSQYGDVMDVFIPKPFRAFAFVTFA

DDQIAQSLCGEDLIIKGISVHISNAEPKHNSNRQLERSGRFGGNPGGFGNQGGFGNSRGGGAGLGNNQGSNMGGG

MNFGAFSINPAMMAAAQAALQSSWGMMGMLASQQNQSGPSGNNQNQGNMQREPNQAFGSGNNSYSGSNSG

AAIGWGSASNAGSGSGFNGGFGSSMDSKSSGWGM

SEQ ID NO: 27. TDP-43-NcVVDY50W
MSEYIRVTEDENDEPIEIPSEDDGTVLLSTVTAQFPGACGLRYRNPVSQCMRGVRLVEGILHAPDAGWGNLVYVVNYP

KDNKRKMDETDASSAVKVKRAVQKTSDLIVLGLPWKTTEQDLKEYFSTFGEVLMVQVKKDLKTGHSKGFGFVRFTEYE

TQVKVMSQRHMIDGRWCDCKLPNSKQSQDEPLRSRKVFVGRCTEDMTEDELREFFSQYGDVMDVFIPKPFRAFAFVT

FADDQIAQSLCGEDLIIKGISVHISNAEPKHNSNRQLERSGRFGGNPGGFGNQGGFGNSRGGGAGLGNNQGSNMGG

GMNFGAFSINPAMMAAAQAALQSSWGMMGMLASQQNQSGPSGNNQNQGNMQREPNQAFGSGNNSYSGSNS

GAAIGWGSASNAGSGSGFNGGFGSSMDSKSSGWGMFRAQRHTLYAPGGYDIMGWLIQIMNRPNPQVELGPVDTS

CALILCDLKQKDTPIVYASEAFLYMTGYSNAEVLGRNCRFLQSPDGMVKPKSTRKYVDSNTINTMRKAIDRNAEVQVEV

VNFKKNGQRFVNFLTMIPVRDETGEYRYSMGFQCETE

B) Truncated TDP-43 protein no reporter
SEQ ID NO: 28. TDP-43$^{(AA105-414)}$-NcVVDY50W
MDLIVLGLPWKTTEQDLKEYFSTFGEVLMVQVKKDLKTGHSKGFGFVRFTEYETQVKVMSQRHMIDGRWCDCKLPNS KQSQDEPLRSRKVFVGRCTEDMTEDELREFFSQYGDVMDVFIPKPFRAFAFVTFADDQ1AQSLCGEDLIIKGISVHISNAE

PKHNSNRQLERSGRFGGNPGGFGNQGGFGNSRGGGAGLGNNQGSNMGGGMNFGAFSINPAMMAAAQAALQSS

WGMMGMLASQQNQSGPSGNNQNQGNMQREPNQAFGSGNNSYSGSNSGAAIGWGSASNAGSGSGFNGGFGSS

MDSKSSGWGMFRAQRHTLYAPGGYDIMGWLIQIMNRPNPQVELGPVDTSCALILCDLKQKDTPIVYASEAFLYMTGY

SNAEVLGRNCRFLQSPDGMVKPKSTRKYVDSNTINTMRKAIDRNAEVQVEVVNFKKNGQRFVNFLTMIPVRDETGEY

RYSMGFQCETE

SEQ ID NO: 29. TDP-43$^{(AA191-414)}$-NcVVDY50W
MRKVFVGRCTEDMTEDELREFFSQYGDVMDVFIPKPFRAFAFVTFADDQIAQSLCGEDLIIKGISVHISNAEPKHNSNR

QLERSGRFGGNPGGFGNQGGFGNSRGGGAGLGNNQGSNMGGGMNFGAFSINPAMMAAAQAALQSSWGMMG

MLASQQNQSGPSGNNQNQGNMQREPNQAFGSGNNSYSGSNSGAAIGWGSASNAGSGSGFNGGFGSSMDSKSSG

WGMFRAQRHTLYAPGGYDIMGWLIQIMNRPNPQVELGPVDTSCALILCDLKQKDTPIVYASEAFLYMTGYSNAEVLG

RNCRFLQSPDGMVKPKSTRKYVDSNTINTMRKAIDRNAEVQVEVVNFKKNGQRFVNFLTMIPVRDETGEYRYSMGFQ

CETE

SEQ ID NO: 30. TDP-43$^{(AA274-414)}$-NcVVDY50W
MGRFGGNPGGFGNQGGFGNSRGGGAGLGNNQGSNMGGGMNFGAFSINPAMMAAAQAALQSSWGMMGMLA

SQQNQSGPSGNNQNQGNMQREPNQAFGSGNNSYSGSNSGAAIGWGSASNAGSGSGFNGGFGSSMDSKSSGWG

MFRAQRHTLYAPGGYDIMGWLIQIMNRPNPQVELGPVDTSCALILCDLKQKDTPIVYASEAFLYMTGYSNAEVLGRNC

RFLQSPDGMVKPKSTRKYVDSNTINTMRKAIDRNAEVQVEVVNFKKNGQRFVNFLTMIPVRDETGEYRYSMGFQCET

E

SEQ ID NO: 31. NcVVDY50W-TDP-43$^{(AA105-414)}$
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEADLI

-continued

VLGLPWKTTEQDLKEYFSTFGEVLMVQVKKDLKTGHSKGFGFVRFTEYETQVKVMSQRHMIDGRWCDCKLPNSKQS

QDEPLRSRKVFVGRCTEDMTEDELREFFSQYGDVMDVFIPKPFRAFAFVTFADDQIAQSLCGEDLIIKGISVHISNAEPKH

NSNRQLERSGRFGGNPGGFGNQGGFGNSRGGGAGLGNNQGSNMGGGMNFGAFSINPAMMAAAQAALQSSWG

MMGMLASQQNQSGPSGNNQNQGNMQREPNQAFGSGNNSYSGSNSGAAIGWGSASNAGSGSGFNGGFGSSMD

SKSSGWGM

SEQ ID NO: 32. NcVVDY50W-TDP-43 $^{(\Delta A191-414)}$
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEARKV

FVGRCTEDMTEDELREFFSQYGDVMDVFIPKPFRAFAFVTFADDQIAQSLCGEDLIIKGISVHISNAEPKHNSNRQLERS

GRFGGNPGGFGNQGGFGNSRGGGAGLGNNQGSNMGGGMNFGAFSINPAMMAAAQAALQSSWGMMGMLAS

QQNQSGPSGNNQNQGNMQREPNQAFGSGNNSYSGSNSGAAIGWGSASNAGSGSGFNGGFGSSMDSKSSGWGM

SEQ ID NO: 33. NcVVDY50W-TDP-43 $^{(\Delta A274-414)}$
HTLYAPGGYDIMGWLIQIMNRPNPQVELGPVDTSCALILCDLKQKDTPIVYASEAFLYMTGYSNAEVLGRNCRFLQSPD

GMVKPKSTRKYVDSNTINTMRKAIDRNAEVQVEVVNFKKNGQRFVNFLTMIPVRDETGEYRYSMGFQCETEAGRFGG

NPGGFGNQGGFGNSRGGGAGLGNNQGSNMGGGMNFGAFSINPAMMAAAQAALQSSWGMMGMLASQQNQS

GPSGNNQNQGNMQREPNQAFGSGNNSYSGSNSGAAIGWGSASNAGSGSGFNGGFGSSMDSKSSGWGM

C) Full length TDP-43 Protein + mCherry Reporter
SEQ ID NO: 34. NcVVDY50W-TDP-43-mCherry
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEAMS

EYIRVTEDENDEPIEIPSEDDGTVLLSTVTAQFPGACGLRYRNPVSQCMRGVRLVEGILHAPDAGWGNLVYVVNYPKD

NKRKMDETDASSAVKVKRAVQKTSDLIVLGLPWKTTEQDLKEYFSTFGEVLMVQVKKDLKTGHSKGFGFVRFTEYETQ

VKVMSQRHMIDGRWCDCKLPNSKQSQDEPLRSRKVFVGRCTEDMTEDELREFFSQYGDVMDVFIPKPFRAFAFVTFA

DDQIAQSLCGEDLIIKGISVHISNAEPKHNSNRQLERSGRFGGNPGGFGNQGGFGNSRGGGAGLGNNQGSNMGGG

MNFGAFSINPAMMAAAQAALQSSWGMMGMLASQQNQSGPSGNNQNQGNMQREPNQAFGSGNNSYSGSNSG

AAIGWGSASNAGSGSGFNGGFGSSMDSKSSGWGMFAPVATMVSKGEEDNMAIIKEFMRFKVHMEGSVNGHEFEIE

GEGEGRPYEGTQTAKLKVTKGGPLPFAWDILSPQFMYGSKAYVKHPADIPDYLKLSFPEGFKWERVMNFEDGGVVTVT

QDSSLQDGEFIYKVKLRGTNFPSDGPVMQKKTMGWEASSERMYPEDGALKGEIKQRLKLKDGGHYDAEVKTTYKAKK

PVQLPGAYNVNIKLDITSHNEDYTIVEQYERAEGRHSTGGMDELYK

SEQ ID NO: 35. mCherry-TDP-43-NcVVDY50W
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLKMSEYIRVTEDENDEPIEIPSEDDGTVLLSTVTAQFPGACGLRYRNPVSQCMRGVRLVEGILHAPDAGWGNL

VYVVNYPKDNKRKMDETDASSAVKVKRAVQKTSDLIVLGLPWKTTEQDLKEYFSTFGEVLMVQVKKDLKTGHSKGFGF

VRFTEYETQVKVMSQRHMIDGRWCDCKLPNSKQSQDEPLRSRKVFVGRCTEDMTEDELREFFSQYGDVMDVFIPKPF

RAFAFVTFADDQIAQSLCGEDLIIKGISVHISNAEPKHNSNRQLERSGRFGGNPGGFGNQGGFGNSRGGGAGLGNNQ

GSNMGGGMNFGAFSINPAMMAAAQAALQSSWGMMGMLASQQNQSGPSGNNQNQGNMQREPNQAFGSGNN

SYSGSNSGAAIGWGSASNAGSGSGFNGGFGSSMDSKSSGWGMFRAQRHTLYAPGGYDIMGWLIQIMNRPNPQVEL

GPVDTSCALILCDLKQKDTPIVYASEAFLYMTGYSNAEVLGRNCRFLQSPDGMVKPKSTRKYVDSNTINTMRKAIDRNA

EVQVEVVNFKKNGQRFVNFLTMIPVRDETGEYRYSMGFQCETE

D) Truncated TDP-43 protein + mCherry Reporter
SEQ ID NO: 36. mCherry-TDP-43<sup>(Δ4105-414)</sup>-NcVVDY50W
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLKDLIVLGLPWKTTEQDLKEYFSTFGEVLMVQVKKDLKTGHSKGFGFVRFTEYETQVKVMSQRHMIDGRWCD

CKLPNSKQSQDEPLRSRKVFVGRCTEDMTEDELREFFSQYGDVMDVFIPKPFRAFAFVTFADDQIAQSLCGEDLIIKGIS

VHISNAEPKHNSNRQLERSGRFGGNPGGFGNQGGFGNSRGGAGLGNNQGSNMGGGMNFGAFSINPAMMAAA

QAALQSSWGMMGMLASQQNQSGPSGNNQNQGNMQREPNQAFGSGNNSYSGSNSGAAIGWGSASNAGSGSGF

NGGGFGSSMDSKSSGWGMFRAQRHTLYAPGGYDIMGWLIQIMNRPNPQVELGPVDTSCALILCDLKQKDTPIVYASEA

FLYMTGYSNAEVLGRNCRFLQSPDGMVKPKSTRKYVDSNTINTMRKAIDRNAEVQVEVVNFKKNGQRFVNFLTMIPV

RDETGEYRYSMGFQCETE

SEQ ID NO: 37. mCherry-TDP-43<sup>(Δ4191-414)</sup>-NcVVDY50W
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLKRKVFVGRCTEDMTEDELREFFSQYGDVMDVFIPKPFRAFAFVTFADDQIAQSLCGEDLIIKGISVHISNAEPK

HNSNRQLERSGRFGGNPGGFGNQGGFGNSRGGAGLGNNQGSNMGGGMNFGAFSINPAMMAAAQAALQSSW

GMMGMLASQQNQSGPSGNNQNQGNMQREPNQAEGSGNNSYSGSNSGAAIGWGSASNAGSGSGENGGEGSSM

DSKSSGWGMFRAQRHTLYAPGGYDIMGWLIQIMNRPNPQVELGPVDTSCALILCDLKQKDTPIVYASEAFLYMTGYS

NAEVLGRNCRFLQSPDGMVKPKSTRKYVDSNTINTMRKAIDRNAEVQVEVVNFKKNGQRFVNFLTMIPVRDETGEYR

YSMGFQCETE

SEQ ID NO: 38. mCherry-TDP-43<sup>(Δ4274-414)</sup>-NcVVDY50W
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLKGRFGGNPGGFGNQGGFGNSRGGAGLGNNQGSNMGGGMNFGAFSINPAMMAAAQAALQSSWGM

MGMLASQQNQSGPSGNNQNQGNMQREPNQAFGSGNNSYSGSNSGAAIGWGSASNAGSGSGFNGGFGSSMDSK

SSGWGMFRAQRHTLYAPGGYDIMGWLIQIMNRPNPQVELGPVDTSCALILCDLKQKDTPIVYASEAFLYMTGYSNAE

VLGRNCRFLQSPDGMVKPKSTRKYVDSNTINTMRKAIDRNAEVQVEVVNFKKNGQRFVNFLTMIPVRDETGEYRYSM

GFQCETE

SEQ ID NO: 39. NcVVDY50W-TDP-43<sup>(Δ4105-414)</sup>-mCherry
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEADLI

VLGLPWKTTEQDLKEYFSTFGEVLMVQVKKDLKTGHSKGFGFVRFTEYETQVKVMSQRHMIDGRWCDCKLPNSKQS

QDEPLRSRKVFVGRCTEDMTEDELREFFSQYGDVMDVFIPKPFRAFAFVTFADDQIAQSLCGEDLIIKGISVHISNAEPKH

NSNRQLERSGRFGGNPGGFGNQGGFGNSRGGAGLGNNQGSNMGGGMNFGAFSINPAMMAAAQAALQSSWG

MMGMLASQQNQSGPSGNNQNQGNMQREPNQAFGSGNNSYSGSNSGAAIGWGSASNAGSGSGFNGGFGSSMD

SKSSGWGMFAPVATMVSKGEEDNMAIIKEFMRFKVHMEGSVNGHEFEIEGEGEGRPYEGTQTAKLKVTKGGPLPFA

WDILSPQFMYGSKAYVKHPADIPDYLKLSFPEGFKWERVMNFEDGGVVTVTQDSSLQDGEFIYKVKLRGTNFPSDGPV

MQKKTMGWEASSERMYPEDGALKGEIKQRLKLKDGGHYDAEVKTTYKAKKPVQLPGAYNVNIKLDITSHNEDYTIVEQ

YERAEGRHSTGGMDELYK

SEQ ID NO: 40. NcVVDY50W-TDP-43$^{(\Delta 4191-414)}$-mCherry
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEARKV

FVGRCTEDMTEDELREFFSQYGDVMDVFIPKPFRAFAFVTFADDQIAQSLCGEDLIIKGISVHISNAEPKHNSNRQLERS

GRFGGNPGGFGNQGGFGNSRGGGAGLGNNQGSNMGGGMNFGAFSINPAMMAAAQAALQSSWGMMGMLAS

QQNQSGPSGNNQNQGNMQREPNQAFGSGNNSYSGSNSGAAIGWGSASNAGSGSGFNGGFGSSMDSKSSGWGM

FAPVATMVSKGEEDNMAIIKEFMRFKVHMEGSVNGHEFEIEGEGEGRPYEGTQTAKLKVTKGGPLPFAWDILSPQFM

YGSKAYVKHPADIPDYLKLSFPEGFKWERVMNFEDGGVVTVTQDSSLQDGEFIYKVKLRGTNFPSDGPVMQKKTMG

WEASSERMYPEDGALKGEIKQRLKLKDGGHYDAEVKTTYKAKKPVQLPGAYNVNIKLDITSHNEDYTIVEQYERAEGRH

STGGMDELYK

SEQ ID NO: 41. NcVVDY50W-TDP-43$^{(\Delta 4274-414)}$-mCherry
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEAGRF

GGNPGGFGNQGGFGNSRGGGAGLGNNQGSNMGGGMNFGAFSINPAMMAAAQAALQSSWGMMGMLASQQN

QSGPSGNNQNQGNMQREPNQAFGSGNNSYSGSNSGAAIGWGSASNAGSGSGFNGGFGSSMDSKSSGWGMFAP

VATMVSKGEEDNMAIIKEFMRFKVHMEGSVNGHEFEIEGEGEGRPYEGTQTAKLKVTKGGPLPFAWDILSPQFMYGS

KAYVKHPADIPDYLKLSFPEGFKWERVMNFEDGGVVTVTQDSSLQDGEFIYKVKLRGTNFPSDGPVMQKKTMGWEA

SSERMYPEDGALKGEIKQRLKLKDGGHYDAEVKTTYKAKKPVQLPGAYNVNIKLDITSHNEDYTIVEQYERAEGRHSTG

GMDELYK

Alpha Synuclein Protein Arrangements Generated:
1. Cry2olig Fusion Proteins Amino Acid Sequences:
A) Full Length alpha synuclein (asyn) Protein No Reporter
SEQ ID NO: 42. Cry2olig-asyn
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAMDVFMKGLSKAKEGVVAAAEKTKQGVAEAAGKTKEGVLYVGSKTKEGVVH

GVATVAEKTKEQVTNVGGAVVTGVTAVAQKTVEGAGSIAAATGFVKKDQLGKNEEGAPQEGILEDMPVDPDNEAYE

MPSEEGYQDYEPEA

SEQ ID NO: 43. Asyn-Cry2
MDVFMKGLSKAKEGVVAAAEKTKQGVAEAAGKTKEGVLYVGSKTKEGVVHGVATVAEKTKEQVTNVGGAVVTGVTA

VAQKTVEGAGSIAAATGFVKKDQLGKNEEGAPQEGILEDMPVDPDNEAYEMPSEEGYQDYEPEADPPVATMKMDKK

TIVWFRRDLRIEDNPALAAAAHEGSVFPVFIWCPEEEGQFYPGRASRWWMKQSLAHLSQSLKALGSDLTLIKTHNTISA

ILDCIRVTGATKVVFNHLYDPVSLVRDHTVKEKLVERGISVQSYNGDLLYEPWEIYCEKGKPFTSFNSYWKKCLDMSIESV

MLPPPWRLMPITAAAEAIWACSIEELGLENEAEKPSNALLTRAWSPGWSNADKLLNEF1EKQLIDYAKNSKKVVGNSTS

LLSPYLHFGEISVRHVFQCARMKQIIWARDKNSEGEESADLFLRGIGLREYSRYICFNFPFTHEQSLLSHLRFFPWDADVD

KFKAWRQGRTGYPLVDAGMRELWATGWMHNRIRVIVSSFAVKFLLLPWKWGMKYFWDTLLDADLECDILGWQYIS

GSIPDGHELDRLDNPALQGAKYDPEGEYIRQWLPELARLPTEWIHHPWDAPLTVLKASGVELGTNYAKPIVDIDTARELL

AKAISRTRGAQIMIGAA

B) Full Length alpha synuclein (asyn) Protein + mCherry Reporter
SEQ ID NO: 44. Cry2olig-asyn-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAMDVFMKGLSKAKEGVVAAAEKTKQGVAEAAGKTKEGVLYVGSKTKEGVVH

GVATVAEKTKEQVTNVGGAVVTGVTAVAQKTVEGAGSIAAATGFVKKDQLGKNEEGAPQEGILEDMPVDPDNEAYE

MPSEEGYQDYEPEADPPVATMVSKGEEDNMAIIKEFMRFKVHMEGSVNGHEFEIEGEGEGRPYEGTQTAKLKVTKGG

PLPFAWDILSPQFMYGSKAYVKHPADIPDYLKLSFPEGFKWERVMNFEDGGVVTVTQDSSLQDGEFIYKVKLRGTNFPS

DGPVMQKKTMGWEASSERMYPEDGALKGEIKQRLKLKDGGHYDAEVKTTYKAKKPVQLPGAYNVNIKLDITSHNEDY

TIVEQYERAEGRHSTGGMDELYK

SEQ ID NO: 45. Cry2olig-mCherry-Asyn
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARDPPVATMVSKGEEDNMAIIKEFMRFKVHMEGSVNGHEFEIEGEGEGRPY

EGTQTAKLKVTKGGPLPFAWDILSPQFMYGSKAYVKHPADIPDYLKLSFPEGFKWERVMNFEDGGVVTVTQDSSLQD

GEFIYKVKLRGTNFPSDGPVMQKKTMGWEASSERMYPEDGALKGEIKQRLKLKDGGHYDAEVKTTYKAKKPVQLPGA

YNVNIKLDITSHNEDYTIVEQYERAEGRHSTGGMDELYKMDVFMKGLSKAKEGVVAAAEKTKQGVAEAAGKTKEGVLY

VGSKTKEGVVHGVATVAEKTKEQVTNVGGAVVTGVTAVAQKTVEGAGSIAAATGFVKKDQLGKNEEGAPQEGILED

MPVDPDNEAYEMPSEEGYQDYEPEA

SEQ ID NO: 46. Asyn-Cry2-mCherry
MDVFMKGLSKAKEGVVAAAEKTKQGVAEAAGKTKEGVLYVGSKTKEGVVHGVATVAEKTKEQVTNVGGAVVTGVTA

VAQKTVEGAGSIAAATGFVKKDQLGKNEEGAPQEGILEDMPVDPDNEAYEMPSEEGYQDYEPEADPPVATMKMDKK

TIVWFRRDLRIEDNPALAAAAHEGSVFPVFIWCPEEEGQFYPGRASRWWMKQSLAHLSQSLKALGSDLTLIKTHNTISA

ILDCIRVTGATKVVFNHLYDPVSLVRDHTVKEKLVERGISVQSYNGDLLYEPWEIYCEKGKPFTSFNSYWKKCLDMSIESV

MLPPPWRLMPITAAAEAIWACSIEELGLENEAEKPSNALLTRAWSPGWSNADKLLNEFIEKQLIDYAKNSKKVVGNSTS

LLSPYLHFGEISVRHVFQCARMKQIIWARDKNSEGEESADLFLRGIGLREYSRYICFNFPFTHEQSLLSHLRFFPWDADVD

KFKAWRQGRTGYPLVDAGMRELWATGWMHNRIRVIVSSFAVKFLLLPWKWGMKYFWDTLLDADLECDILGWQYIS

GSIPDGHELDRLDNPALQGAKYDPEGEYIRQWLPELARLPTEWIHHPWDAPLTVLKASGVELGTNYAKPIVDIDTARELL

AKAISRTRGAQIMIGAAAMVSKGEEDNMAIIKEFMRFKVHMEGSVNGHEFEIEGEGEGRPYEGTQTAKLKVTKGGPLP

FAWDILSPQFMYGSKAYVKHPADIPDYLKLSFPEGFKWERVMNFEDGGVVTVTQDSSLQDGEFIYKVKLRGTNFPSDG

PVMQKKTMGWEASSERMYPEDGALKGEIKQRLKLKDGGHYDAEVKTTYKAKKPVQLPGAYNVNIKLDITSHNEDYTIV

EQYERAEGRHSTGGMDELYK

1. NcVVD Fusion Proteins Amino Acid Sequences:
A) Full Length alpha synuclein (asyn) Protein No Reporter
SEQ ID NO: 47. Asyn-NcVVDY50W
MDVFMKGLSKAKEGVVAAAEKTKQGVAEAAGKTKEGVLYVGSKTKEGVVHGVATVAEKTKEQVTNVGGAVVTGVTA

VAQKTVEGAGSIAAATGFVKKDQLGKNEEGAPQEGILEDMPVDPDNEAYEMPSEEGYQDYEPEAFHTLYAPGGYDIM

GWLIQIMNRPNPQVELGPVDTSCALILCDLKQKDTPIVYASEAFLYMTGYSNAEVLGRNCRFLQSPDGMVKPKSTRKYV

DSNTINTMRKAIDRNAEVQVEVVNFKKNGQRFVNFLTMIPVRDETGEYRYSMGFQCETE

SEQ ID NO: 48. NcVVDY50W-Asyn
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEAMD

VFMKGLSKAKEGVVAAAEKTKQGVAEAAGKTKEGVLYVGSKTKEGVVHGVATVAEKTKEQVTNVGGAVVTGVTAVA

QKTVEGAGSIAAATGFVKKDQLGKNEEGAPQEGILEDMPVDPDNEAYEMPSEEGYQDYEPEA

B) Full Length alpha synuclein (asyn) Protein + mCherry Reporter
SEQ ID NO: 49. mCherry-Asyn-NcVVDY50W
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYSKMDVFMKGLSKAKEGVVAAAEKTKQGVAEAAGKTKEGVLYVGSKTKEGVVHGVATVAEKTKEQVTNVGGAVV

TGVTAVAQKTVEGAGSIAAATGFVKKDQLGKNEEGAPQEGILEDMPVDPDNEAYEMPSEEGYQDYEPEAFHTLYAPG

GYDIMGWLIQIMNRPNPQVELGPVDTSCALILCDLKQKDTPIVYASEAFLYMTGYSNAEVLGRNCRFLQSPDGMVKPK

STRKYVDSNTINTMRKAIDRNAEVQVEVVNFKKNGQRFVNFLTMIPVRDETGEYRYSMGFQCETE

SEQ ID NO: 50. mCherry-NcVVDY50W-Asyn
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLRSRAQRHTLYAPGGYDIMGWLIQIMNRPNPQVELGPVDTSCALILCDLKQKDTPIVYASEAFLYMTGYSNAE

VLGRNCRFLQSPDGMVKPKSTRKYVDSNTINTMRKAIDRNAEVQVEVVNFKKNGQRFVNFLTMIPVRDETGEYRYSM

GFQCETEALEFCSRRYRGPMDVFMKGLSKAKEGVVAAAEKTKQGVAEAAGKTKEGVLYVGSKTKEGVVHGVATVAEK

TKEQVTNVGGAVVTGVTAVAQKTVEGAGSIAAATGFVKKDQLGKNEEGAPQEGILEDMPVDPDNEAYEMPSEEGYQ

DYEPEA

SEQ ID NO: 51. NcVVDY50W-Asyn-mCherry
MHTLYAPGGYDIMGWLIQIMNRPNPQVELGPVDTSCALILCDLKQKDTPIVYASEAFLYMTGYSNAEVLGRNCRFLQS

PDGMVKPKSTRKYVDSNTINTMRKAIDRNAEVQVEVVNFKKNGQRFVNFLTMIPVRDETGEYRYSMGFQCETEAMD

VFMKGLSKAKEGVVAAAEKTKQGVAEAAGKTKEGVLYVGSKTKEGVVHGVATVAEKTKEQVTNVGGAVVTGVTAVA

QKTVEGAGSIAAATGFVKKDQLGKNEEGAPQEGILEDMPVDPDNEAYEMPSEEGYQDYEPEAFAPVATMVSKGEED

NMAIIKEFMRFKVHMEGSVNGHEFEIEGEGEGRPYEGTQTAKLKVTKGGPLPFAWDILSPQFMYGSKAYVKHPADIPD

YLKLSFPEGFKWERVMNFEDGGVVTVTQDSSLQDGEFIYKVKLRGTNFPSDGPVMQKKTMGWEASSERMYPEDGAL

KGEIKQRLKLKDGGHYDAEVKTTYKAKKPVQLPGAYNVNIKLDITSHNEDYTIVEQYERAEGRHSTGGMDELYK

SEQ ID NO: 52. Alphasynuclein-mCherry-NcVVD (wildtype)
MDVFMKGLSKAKEGVVAAAEKTKQGVAEAAGKTKEGVLYVGSKTKEGVVHGVATVAEKTKEQVTNVGGAVVTGVTA

VAQKTVEGAGSIAAATGFVKKDQLGKNEEGAPQEGILEDMPVDPDNEAYEMPSEEGYQDYEPEALLPVATMVSKGEE

DNMAIIKEFMRFKVHMEGSVNGHEFEIEGEGEGRPYEGTQTAKLKVTKGGPLPFAWDILSPQFMYGSKAYVKHPADIP

DYLKLSFPEGFKWERVMNFEDGGVVTVTQDSSLQDGEFIYKVKLRGTNFPSDGPVMQKKTMGWEASSERMYPEDGA

LKGEIKQRLKLKDGGHYDAEVKTTYKAKKPVQLPGAYNVNIKLDITSHNEDYTIVEQYERAEGRHSTGGMDELYKSGLRS

RAQASNSAVDGTAGPMHTLYAPGGYDIMGYLIQIMNRPNPQVELGPVDTSCALILCDLKQKDTPIVYASEAFLYMTGY

2SNAEVLGRNCRFLQSPDGMVKPKSTRKYVDSNTINTMRKAIDRNAEVQVEVVNFKKNGQRFVNFLTMIPVRDETGE

YRYSMGFQCETEGIHRI*

SEQ ID NO: 53. mCherry-alphasynuclein-NcVVD (wildtype)
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGE1QRLKLKDGGHYDAEVKTTYKAKKPVQLPGAYNVNIKLDITSHNEDYTIVEQYERAEGRHSTGGMD

ELYKSGLRSRAQMDVFMKGLSKAKEGVVAAAEKTKQGVAEAAGKTKEGVLYVGSKTKEGVVHGVATVAEKTKEQVTN

VGGAVVTGVTAVAQKTVEGAGSIAAATGFVKKDQLGKNEEGAPQEGILEDMPVDPDNEAYEMPSEEGYQDYEPEAS

NSAVDGTAGPMHTLYAPGGYDIMGYLIQIMNRPNPQVELGPVDTSCALILCDLKQKDTPIVYASEAFLYMTGYSNAEVL

GRNCRFLQSPDGMVKPKSTRKYVDSNTINTMRKAIDRNAEVQVEVVNFKKNGQRFVNFLTMIPVRDETGEYRYSMGF

QCETEGIHRI*

SEQ ID NO: 54. mCherry-NcVVD (wildtype)-alphasynuclein
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLRSRAQASNSAVDGTAGPMHTLYAPGGYDIMGYLIQIMNRPNPQVELGPVDTSCALILCDLKQKDTPIVYASE

AFLYMTGYSNAEVLGRNCRFLQSPDGMVKPKSTRKYVDSNTINTMRKAIDRNAEVQVEVVNFKKNGQRFVNFLTMIP

VRDETGEYRYSMGFQCETEGMDVFMKGLSKAKEGVVAAAEKTKQGVAEAAGKTKEGVLYVGSKTKEGVVHGVATVA

EKTKEQVTNVGGAVVTGVTAVAQKTVEGAGSIAAATGFVKKDQLGKNEEGAPQEGILEDMPVDPDNEAYEMPSEEG

YQDYEPEAHRI*

Tau
SEQ ID NO: 55. mCherry-Tau
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLRSRAQASNSAVDGTAGPMAEPRQEFEVMEDHAGTYGLGDRKDQGGYTMHQDQEGDTDAGLKESPLQTP

TEDGSEEPGSETSDAKSTPTAEDVTAPLVDEGAPGKQAAAQPHTEIPEGTTAEEAGIGDTPSLEDEAAGHVTQARMVS

KSKDGTGSDDKKAKGADGKTKIATPRGAAPPGQKGQANATRIPAKTPPAPKTPPSSGEPPKSGDRSGYSSPGSPGTPG

SRSRTPSLPTPPTREPKKVAVVRTPPKSPSSAKSRLQTAPVPMPDLKNVKSKIGSTENLKHQPGGGKVQIINKKLDLSNV

QSKCGSKDNIKHVPGGGSVQIVYKPVDLSKVTSKCGSLGNIHHKPGGGQVEVKSEKLDFKDRVQSKIGSLDNITHVPGG

GNKKIETHKLTFRENAKAKTDHGAEIVYKSPVVSGDTSPRHLSNVSSTGSIDMVDSPQLATLADEVSASLAKQGLGIHRI*

SEQ ID NO: 56. mCherry-VfAU-Tau
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLRSRAQASNSAVDGTAGPMPDYSLVKALQMAQQNFVITDASLPDNPIVYASRGFLTLTGYSLDQILGRNCRFL

QGPETDPRAVDKIRNAITKGVDTSVCLLNYRQDGTTFWNLFFVAGLRDSKGNIVNYVGVQSKVSEDYAKLLVNEQNIEY

KGVRTSNMLRRKPGGIHRIMAEPRQEFEVMEDHAGTYGLGDRKDQGGYTMHQDQEGDTDAGLKESPLQTPTEDGS

EEPGSETSDAKSTPTAEDVTAPLVDEGAPGKQAAAQPHTEIPEGTTAEEAGIGDTPSLEDEAAGHVTQARMVSKSKDG

TGSDDKKAKGADGKTKIATPRGAAPPGQKGQANATRIPAKTPPAPKTPPSSGEPPKSGDRSGYSSPGSPGTPGSRSRTP

SLPTPPTREPKKVAVVRTPPKSPSSAKSRLQTAPVPMPDLKNVKSKIGSTENLKHQPGGGKVQIINKKLDLSNVQSKCGS

KDNIKHVPGGGSVQIVYKPVDLSKVTSKCGSLGNIHHKPGGGQVEVKSEKLDFKDRVQSKIGSLDNITHVPGGGNKKIET

HKLTFRENAKAKTDHGAEIVYKSPVVSGDTSPRHLSNVSSTGSIDMVDSPQLATLADEVSASLAKQGLITDHNQPYHICR

GFTCFKKPPTPPPEPET*

SEQ ID NO: 57. mCherry-(y50w)-Tau
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLRSRAQASNSAVDGTAGPMHTLYAPGGYDIMGWLIQIMNRPNPQVELGPVDTSCALILCDLKQKDTPIVYAS

EAFLYMTGYSNAEVLGRNCRFLQSPDGMVKPKSTRKYVDSNTINTMRKAIDRNAEVQVEVVNFKKNGQRFVNFLTMI

PVRDETGEYRYSMGFQCETEGMAEPRQEFEVMEDHAGTYGLGDRKDQGGYTMHQDEGDTDAGLKESPLQTPTED

GSEEPGSETSDAKSTPTAEDVTAPLVDEGAPGKQAAAQPHTEIPEGTTAEEAGIGDTPSLEDEAAGHVTQARMVSKSK

DGTGSDDKKAKGADGKTKIATPRGAAPPGQKGQANATRIPAKTPPAPKTPPSSGEPPKSGDRSGYSSPGSPGTPGSRS

RTPSLPTPPTREPKKVAVVRTPPKSPSSAKSRLQTAPVPMPDLKNVKSKIGSTENLKHQPGGGKVQIINKKLDLSNVQSK

CGSKDNIKHVPGGGSVQIVYKPVDLSKVTSKCGSLGNIHHKPGGGQVEVKSEKLDFKDRVQSKIGSLDNITHVPGGGNK

KIETHKLTFRENAKAKTDHGAEIVYKSPVVSGDTSPRHLSNVSSTGSIDMVDSPQLATLADEVSASLAKQGLHRI*

SEQ ID NO: 58. mCherry-Tau-NcVVD(y50w)
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLTMAEPRQEFEVMEDHAGTYGLGDRKDQGGYTMHQDEGDTDAGLKESPLQTPTEDGSEEPGSETSDAKS

TPTAEDVTAPLVDEGAPGKQAAAQPHTEIPEGTTAEEAGIGDTPSLEDEAAGHVTQARMVSKSKDGTGSDDKKAKGA

DGKTKIATPRGAAPPGQKGQANATRIPAKTPPAPKTPPSSGEPPKSGDRSGYSSPGSPGTPGSRSRTPSLPTPPTREPKK

VAVVRTPPKSPSSAKSRLQTAPVPMPDLKNVKSKIGSTENLKHQPGGGKVQIINKKLDLSNVQSKCGSKDNIKHVPGGG

SVQIVYKPVDLSKVTSKCGSLGNIHHKPGGGQVEVKSEKLDFKDRVQSKIGSLDNITHVPGGGNKKIETHKLTFRENAKA

KTDHGAEIVYKSPVVSGDTSPRHLSNVSSTGSIDMVDSPQLATLADEVSASLAKQGLRRAQRHTLYAPGGYDIMGWLI

QIMNRPNPQVELGPVDTSCALILCDLKQKDTPIVYASEAFLYMTGYSNAEVLGRNCRFLQSPDGMVKPKSTRKYVDSNT

INTMRKAIDRNAEVQVEVVNFKKNGQRFVNFLTMIPVRDETGEYRYSMGFQCETEALEFCSRRYRGPGIHRI*

SEQ ID NO: 59. mCherry-NcVVD(y50w)-Tau
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLRSRAQRHTLYAPGGYDIMGWLIQIMNRPNPQVELGPVDTSCALILCDLKQKDTPIVYASEAFLYMTGYSNAE

VLGRNCRFLQSPDGMVKPKSTRKYVDSNTINTMRKAIDRNAEVQVEVVNFKKNGQRFVNFLTMIPVRDETGEYRYSM

GFQCETEALAMAEPRQEFEVMEDHAGTYGLGDRKDQGGYTMHQDEGDTDAGLKESPLQTPTEDGSEEPGSETSDA

KSTPTAEDVTAPLVDEGAPGKQAAAQPHTEIPEGTTAEEAGIGDTPSLEDEAAGHVTQARMVSKSKDGTGSDDKKAKG

ADGKTKIATPRGAAPPGQKGQANATRIPAKTPPAPKTPPSSGEPPKSGDRSGYSSPGSPGTPGSRSRTPSLPTPPTREPK

KVAVVRTPPKSPSSAKSRLQTAPVPMPDLKNVKSKIGSTENLKHQPGGGKVQIINKKLDLSNVQSKCGSKDNIKHVPGG

GSVQIVYKPVDLSKVTSKCGSLGNIHHKPGGGQVEVKSEKLDFKDRVQSKIGSLDNITHVPGGGNKKIETHKLTFRENAK

AKTDHGAEIVYKSPVVSGDTSPRHLSNVSSTGSIDMVDSPQLATLADEVSASLAKQGLRCSRRYRGPGIHRI*

SEQ ID NO: 60. Tau-mCherry-NcVVD(y50w)
MAEPRQEFEVMEDHAGTYGLGDRKDQGGYTMHQDEGDTDAGLKESPLQTPTEDGSEEPGSETSDAKSTPTAEDVT

APLVDEGAPGKQAAAQPHTEIPEGTTAEEAGIGDTPSLEDEAAGHVTQARMVSKSKDGTGSDDKKAKGADGKTKIATP

-continued

RGAAPPGQKGQANATRIPAKTPPAPKTPPSSGEPPKSGDRSGYSSPGSPGTPGSRSRTPSLPTPPTREPKKVAVVRTPPK

SPSSAKSRLQTAPVPMPDLKNVKSKIGSTENLKHQPGGGKVQIINKKLDLSNVQSKCGSKDNIKHVPGGGSVQIVYKPV

DLSKVTSKCGSLGNIHHKPGGGQVEVKSEKLDFKDRVQSKIGSLDNITHVPGGGNKKIETHKLTFRENAKAKTDHGAEIV

YKSPVVSGDTSPRHLSNVSSTGSIDMVDSPQLATLADEVSASLAKQGLALPVATMVSKGEEDNMAIIKEFMRFKVHME

GSVNGHEFEIEGEGEGRPYEGTQTAKLKVTKGGPLPFAWDILSPQFMYGSKAYVKHPADIPDYLKLSFPEGFKWERVM

NFEDGGVVTVTQDSSLQDGEFIYKVKLRGTNFPSDGPVMQKKTMGWEASSERMYPEDGALKGEIKQRLKLKDGGHY

DAEVKTTYKAKKPVQLPGAYNVNIKLDITSHNEDYTIVEQYERAEGRHSTGGMDELYKSGLRSRAQRHTLYAPGGYDIM

GWLIQIMNRPNPQVELGPVDTSCALILCDLKQKDTPIVYASEAFLYMTGYSNAEVLGRNCRFLQSPDGMVKPKSTRKYV

DSNTINTMRKAIDRNAEVQVEVVNFKKNGQRFVNFLTMIPVRDETGEYRYSMGFQCETEALEFCSRRYRGPGIHRI*

SEQ ID NO: 61. Cry-mCherry-Tau
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARDPPVATMVSKGEEDNMAIIKEFMRFKVHMEGSVNGHEFEIEGEGEGRPY

EGTQTAKLKVTKGGPLPFAWDILSPQFMYGSKAYVKHPADIPDYLKLSFPEGFKWERVMNFEDGGVVTVTQDSSLQD

GEFIYKVKLRGTNFPSDGPVMQKKTMGWEASSERMYPEDGALKGEIKQRLKLKDGGHYDAEVKTTYKAKKPVQLPGA

YNVNIKLDITSHNEDYTIVEQYERAEGRHSTGGMDELYKSRMAEPRQEFEVMEDHAGTYGLGDRKDQGGYTMHQDQ

EGDTDAGLKESPLQTPTEDGSEEPGSETSDAKSTPTAEDVTAPLVDEGAPGKQAAAQPHTEIPEGTTAEEAGIGDTPSLE

DEAAGHVTQARMVSKSKDGTGSDDKKAKGADGKTKIATPRGAAPPGQKGQANATRIPAKTPPAPKTPPSSGEPPKSG

DRSGYSSPGSPGTPGSRSRTPSLPTPPTREPKKVAVVRTPPKSPSSAKSRLQTAPVPMPDLKNVKSKIGSTENLKHQPGG

GKVQIINKKLDLSNVQSKCGSKDNIKHVPGGGSVQIVYKPVDLSKVTSKCGSLGNIHHKPGGGQVEVKSEKLDFKDRVQ

SKIGSLDNITHVPGGGNKKIETHKLTFRENAKAKTDHGAEIVYKSPVVSGDTSPRHLSNVSSTGSIDMVDSPQLATLADE

VSASLAKQGLGDSRS*

SEQ ID NO: 62. Tau-mCherry
MAEPRQEFEVMEDHAGTYGLGDRKDQGGYTMHQDQEGDTDAGLKESPLQTPTEDGSEEPGSETSDAKSTPTAEDVT

APLVDEGAPGKQAAAQPHTEIPEGTTAEEAGIGDTPSLEDEAAGHVTQARMVSKSKDGTGSDDKKAKGADGKTKIATP

RGAAPPGQKGQANATRIPAKTPPAPKTPPSSGEPPKSGDRSGYSSPGSPGTPGSRSRTPSLPTPPTREPKKVAVVRTPPK

SPSSAKSRLQTAPVPMPDLKNVKSKIGSTENLKHQPGGGKVQIINKKLDLSNVQSKCGSKDNIKHVPGGGSVQIVYKPV

DLSKVTSKCGSLGNIHHKPGGGQVEVKSEKLDFKDRVQSKIGSLDNITHVPGGGNKKIETHKLTFRENAKAKTDHGAEIV

YKSPVVSGDTSPRHLSNVSSTGSIDMVDSPQLATLADEVSASLAKQGLFATMVSKGEEDNMAIIKEFMRFKVHMEGSV

NGHEFEIEGEGEGRPYEGTQTAKLKVTKGGPLPFAWDILSPQFMYGSKAYVKHPADIPDYLKLSFPEGFKWERVMNFE

DGGVVTVTQDSSLQDGEFIYKVKLRGTNFPSDGPVMQKKTMGWEASSERMYPEDGALKGEIKQRLKLKDGGHYDAE

VKTTYKAKKPVQLPGAYNVNIKLDITSHNEDYTIVEQYERAEGRHSTGGMDELYKSGLRSRAQASNSAVDGTAGPGSTG

SR*

SEQ ID NO: 63. Tau-Cry2olig-mCherry
MAEPRQEFEVMEDHAGTYGLGDRKDQGGYTMHQDQEGDTDAGLKESPLQTPTEDGSEEPGSETSDAKSTPTAEDVT

APLVDEGAPGKQAAAQPHTEIPEGTTAEEAGIGDTPSLEDEAAGHVTQARMVSKSKDGTGSDDKKAKGADGKTKIATP

RGAAPPGQKGQANATRIPAKTPPAPKTPPSSGEPPKSGDRSGYSSPGSPGTPGSRSRTPSLPTPPTREPKKVAVVRTPPK

SPSSAKSRLQTAPVPMPDLKNVKSKIGSTENLKHQPGGGKVQIINKKLDLSNVQSKCGSKDNIKHVPGGGSVQIVYKPV

-continued

DLSKVTSKCGSLGNIHHKPGGGQVEVKSEKLDFKDRVQSKIGSLDNITHVPGGGNKKIETHKLTFRENAKAKTDHGAEIV

YKSPVVSGDTSPRHLSNVSSTGSIDMVDSPQLATLADEVSASLAKQGLALPDSDLEATMKMDKKTIVWFRRDLRIEDNP

ALAAAAHEGSVFPVFIWCPEEEGQFYPGRASRWWMKQSLAHLSQSLKALGSDLTLIKTHNTISAILDCIRVTGATKVVF

NHLYDPVSLVRDHTVKEKLVERGISVQSYNGDLLYEPWEIYCEKGKPFTSFNSYWKKCLDMSIESVMLPPPWRLMPITA

AAEAIWACSIEELGLENEAEKPSNALLTRAWSPGWSNADKLLNEFIEKQLIDYAKNSKKVVGNSTSLLSPYLHFGEISVRH

VFQCARMKQIIWARDKNSEGEESADLFLRGIGLREYSRYICFNFPFTHEQSLLSHLRFFPWDADVDKFKAWRQGRTGYP

LVDAGMRELWATGWMHNRIRVIVSSFAVKFLLLPWKWGMKYFWDTLLDADLECDILGWQYISGSIPDGHELDRLDN

PALQGAKYDPEGEYIRQWLPELARLPTEWIHHPWDAPLTVLKASGVELGTNYAKPIVDIDTARELLAKAISRTRGAQIMI

GAAARDPPVATMVSKGEEDNMAIIKEFMRFKVHMEGSVNGHEFEIEGEGEGRPYEGTQTAKLKVTKGGPLPFAWDIL

SPQFMYGSKAYVKHPADIPDYLKLSFPEGFKWERVMNFEDGGVVTVTQDSSLQDGEFIYKVKLRGTNFPSDGPVMQK

KTMGWEASSERMYPEDGALKGEIKQRLKLKDGGHYDAEVKTTYKAKKPVQLPGAYNVNIKLDITSHNEDYTIVEQYER

AEGRHSTGGMDELYK*

SEQ ID NO: 64. Cry2Olig-Tau-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAPMAEPRQEFEVMEDHAGTYGLGDRKDQGGYTMHQDQEGDTDAGLKESP

LQTPTEDGSEEPGSETSDAKSTPTAEDVTAPLVDEGAPGKQAAAQPHTEIPEGTTAEEAGIGDTPSLEDEAAGHVTQAR

MVSKSKDGTGSDDKKAKGADGKTKIATPRGAAPPGQKGQANATRIPAKTPPAPKTPPSSGEPPKSGDRSGYSSPGSPG

TPGSRSRTPSLPTPPTREPKKVAVVRTPPKSPSSAKSRLQTAPVPMPDLKNVKSKIGSTENLKHQPGGGKVQIINKKLDLS

NVQSKCGSKDNIKHVPGGGSVQIVYKPVDLSKVTSKCGSLGNIHHKPGGGQVEVKSEKLDFKDRVQSKIGSLDNITHVP

GGGNKKIETHKLTFRENAKAKTDHGAEIVYKSPVVSGDTSPRHLSNVSSTGSIDMVDSPQLATLADEVSASLAKQGLGD

PPVATMVSKGEEDNMAIIKEFMRFKVHMEGSVNGHEFEIEGEGEGRPYEGTQTAKLKVTKGGPLPFAWDILSPQFMY

GSKAYVKHPADIPDYLKLSFPEGFKWERVMNFEDGGVVTVTQDSSLQDGEFIYKVKLRGTNFPSDGPVMQKKTMGW

EASSERMYPEDGALKGEIKQRLKLKDGGHYDAEVKTTYKAKKPVQLPGAYNVNIKLDITSHNEDYTIVEQYERAEGRHST

GGMDELYK*

SEQ ID NO: 65. Cry-mCherry-Tau
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAARDPPVATMVSKGEEDNMAIIKEFMRFKVHMEGSVNGHEFEIEGEGEGRPY

EGTQTAKLKVTKGGPLPFAWDILSPQFMYGSKAYVKHPADIPDYLKLSFPEGFKWERVMNFEDGGVVTVTQDSSLQD

GEFIYKVKLRGTNFPSDGPVMQKKTMGWEASSERMYPEDGALKGEIKQRLKLKDGGHYDAEVKTTYKAKKPVQLPGA

YNVNIKLDITSHNEDYTIVEQYERAEGRHSTGGMDELYKSRMAEPRQEFEVMEDHAGTYGLGDRKDQGGYTMHQDQ

EGDTDAGLKESPLQTPTEDGSEEPGSETSDAKSTPTAEDVTAPLVDEGAPGKQAAAQPHTEIPEGTTAEEAGIGDTPSLE

DEAAGHVTQARMVSKSKDGTGSDDKKAKGADGKTKIATPRGAAPPGQKGQANATRIPAKTPPAPKTPPSSGEPPKSG

DRSGYSSPGSPGTPGSRSRTPSLPTPPTREPKKVAVVRTPPKSPSSAKSRLQTAPVPMPDLKNVKSKIGSTENLKHQPGG

GKVQIINKKLDLSNVQSKCGSKDNIKHVPGGGSVQIVYKPVDLSKVTSKCGSLGNIHHKPGGGQVEVKSEKLDFKDRVQ

SKIGSLDNITHVPGGGNKKIETHKLTFRENAKAKTDHGAEIVYKSPVVSGDTSPRHLSNVSSTGSIDMVDSPQLATLADE

VSASLAKQGLGDSRS*

SEQ ID NO: 66. mCherry-Tau-NcVVD(y50w)
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLTMAEPRQEFEVMEDHAGTYGLGDRKDQGGYTMHQDQEGDTDAGLKESPLQTPTEDGSEEPGSETSDAKS

TPTAEDVTAPLVDEGAPGKQAAAQPHTEIPEGTTAEEAGIGDTPSLEDEAAGHVTQARMVSKSKDGTGSDDKKAKGA

DGKTKIATPRGAAPPGQKGQANATRIPAKTPPAPKTPPSSGEPPKSGDRSGYSSPGSPGTPGSRSRTPSLPTPPTREPKK

VAVVRTPPKSPSSAKSRLQTAPVPMPDLKNVKSKIGSTENLKHQPGGGKVQIINKKLDLSNVQSKCGSKDNIKHVPGGG

SVQIVYKPVDLSKVTSKCGSLGNIHHKPGGGQVEVKSEKLDFKDRVQSKIGSLDNITHVPGGGNKKIETHKLTFRENAKA

KTDHGAEIVYKSPVVSGDTSPRHLSNVSSTGSIDMVDSPQLATLADEVSASLAKQGLRRAQRHTLYAPGGYDIMGWLI

QIMNRPNPQVELGPVDTSCALILCDLKQKDTPIVYASEAFLYMTGYSNAEVLGRNCRFLQSPDGMVKPKSTRKYVDSNT

INTMRKAIDRNAEVQVEVVNFKKNGQRFVNFLTMIPVRDETGEYRYSMGFQCETEALEFCSRRYRGPGIHRI*

SEQ ID NO: 67. mCherry-NcVVD(y50w)-Tau
MVSKGEEDNMAIIKEFMRFKVHMEGSVNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVKLRGTNFPSDGPVMQKKTMGWEASSER

MYPEDGALKGEIKQRLKLKDGGHYDAEVKTTYKAKKPVQLPGAYNVNIKLDITSHNEDYTIVEQYERAEGRHSTGGMD

ELYKSGLRSRAQRHTLYAPGGYDIMGWLIQIMNRPNPQVELGPVDTSCALILCDLKQKDTPIVYASEAFLYMTGYSNAE

VLGRNCRFLQSPDGMVKPKSTRKYVDSNTINTMRKAIDRNAEVQVEVVNFKKNGQRFVNFLTMIPVRDETGEYRYSM

GFQCETEALAMAEPRQEFEVMEDHAGTYGLGDRKDQGGYTMHQDQEGDTDAGLKESPLQTPTEDGSEEPGSETSDA

KSTPTAEDVTAPLVDEGAPGKQAAAQPHTEIPEGTTAEEAGIGDTPSLEDEAAGHVTQARMVSKSKDGTGSDDKKAKG

ADGKTKIATPRGAAPPGQKGQANATRIPAKTPPAPKTPPSSGEPPKSGDRSGYSSPGSPGTPGSRSRTPSLPTPPTREPK

KVAVVRTPPKSPSSAKSRLQTAPVPMPDLKNVKSKIGSTENLKHQPGGGKVQIINKKLDLSNVQSKCGSKDNIKHVPGG

GSVQIVYKPVDLSKVTSKCGSLGNIHHKPGGGQVEVKSEKLDFKDRVQSKIGSLDNITHVPGGGNKKIETHKLTFRENAK

AKTDHGAEIVYKSPVVSGDTSPRHLSNVSSTGSIDMVDSPQLATLADEVSASLAKQGLRCSRRYRGPGIHRI*

SEQ ID NO: 68. Cry-Tau
MKMDKKTIVWFRRDLRIEDNPALAAAAHEGSVFPVFIWCPEEEGQFYPGRASRWWMKQSLAHLSQSLKALGSDLTLI

KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQMAEPRQEFEVMEDHAGTYGLGDRKDQGGYTMHQDQEGDTDAGLKESP

LQTPTEDGSEEPGSETSDAKSTPTAEDVTAPLVDEGAPGKQAAAQPHTEIPEGTTAEEAGIGDTPSLEDEAAGHVTQAR

MVSKSKDGTGSDDKKAKGADGKTKIATPRGAAPPGQKGQANATRIPAKTPPAPKTPPSSGEPPKSGDRSGYSSPGSPG

TPGSRSRTPSLPTPPTREPKKVAVVRTPPKSPSSAKSRLQTAPVPMPDLKNVKSKIGSTENLKHQPGGGKVQIINKKLDLS

NVQSKCGSKDNIKHVPGGGSVQIVYKPVDLSKVTSKCGSLGNIHHKPGGGQVEVKSEKLDFKDRVQSKIGSLDNITHVP

GGGNKKIETHKLTFRENAKAKTDHGAEIVYKSPVVSGDTSPRHLSNVSSTGSIDMVDSPQLATLADEVSASLAKQGLATL

DHNQPYHICRGFTCFKKPPTPPPEPET*

-continued

SEQ ID NO: 69. NcVVD(y50w)-Tau
MHTLYAPGGYDIMGWLIQIMNRPNPQVELGPVDTSCALILCDLKQKDTPIVYASEAFLYMTGYSNAEVLGRNCRFLQS
PDGMVKPKSTRKYVDSNTINTMRKAIDRNAEVQVEVVNFKKNGQRFVNFLTMIPVRDETGEMAEPRQEFEVMEDHA
GTYGLGDRKDQGGYTMHQDQEGDTDAGLKESPLQTPTEDGSEEPGSETSDAKSTPTAEDVTAPLVDEGAPGKQAAA
QPHTEIPEGTTAEEAGIGDTPSLEDEAAGHVTQARMVSKSKDGTGSDDKKAKGADGKTKIATPRGAAPPGQKGQANA
TRIPAKTPPAPKTPPSSGEPPKSGDRSGYSSPGSPGTPGSRSRTPSLPTPPTREPKKVAVVRTPPKSPSSAKSRLQTAPVP
MPDLKNVKSKIGSTENLKHQPGGGKVQIINKKLDLSNVQSKCGSKDNIKHVPGGGSVQIVYKPVDLSKVTSKCGSLGNI
HHKPGGGQVEVKSEKLDFKDRVQSKIGSLDNITHVPGGGNKKIETHKLTFRENAKAKTDHGAEIVYKSPVVSGDTSPRH
LSNVSSTGSIDMVDSPQLATLADEVSASLAKQGLHRI*

SEQ ID NO: 70. Tau-Cry
MAEPRQEFEVMEDHAGTYGLGDRKDQGGYTMHQDQEGDTDAGLKESPLQTPTEDGSEEPGSETSDAKSTPTAEDVT
APLVDEGAPGKQAAAQPHTEIPEGTTAEEAGIGDTPSLEDEAAGHVTQARMVSKSKDGTGSDDKKAKGADGKTKIATP
RGAAPPGQKGQANATRIPAKTPPAPKTPPSSGEPPKSGDRSGYSSPGSPGTPGSRSRTPSLPTPPTREPKKVAVVRTPPK
SPSSAKSRLQTAPVPMPDLKNVKSKIGSTENLKHQPGGGKVQIINKKLDLSNVQSKCGSKDNIKHVPGGGSVQIVYKPV
DLSKVTSKCGSLGNIHHKPGGGQVEVKSEKLDFKDRVQSKIGSLDNITHVPGGGNKKIETHKLTFRENAKAKTDHGAEIV
YKSPVVSGDTSPRHLSNVSSTGSIDMVDSPQLATLADEVSASLAKQGLMKMDKKTIVWFRRDLRIEDNPALAAAAHEG
SVFPVFIWCPEEEGQFYPGRASRWWMKQSLAHLSQSLKALGSDLTLIKTHNTISAILDCIRVTGATKVVFNHLYDPVSLV
RDHTVKEKLVERGISVQSYNGDLLYEPWEIYCEKGKPFTSFNSYWKKCLDMSIESVMLPPPWRLMPITAAAEAIWACSI
EELGLENEAEKPSNALLTRAWSPGWSNADKLLNEFIEKQLIDYAKNSKKVVGNSTSLLSPYLHFGEISVRHVFQCARMKQ
IIWARDKNSEGEESADLFLRGIGLREYSRYICFNFPFTHEQSLLSHLRFFPWDADVDKFKAWRQGRTGYPLVDAGMREL
WATGWMHNRIRVIVSSFAVKFLLLPWKWGMKYFWDTLLDADLECDILGWQYISGSIPDGHELDRLDNPALQGAKYD
PEGEYIRQWLPELARLPTEWIHHPWDAPLTVLKASGVELGTNYAKPIVDIDTARELLAKAISRTRGAQIMIGAAATLDHN
QPYHICRGFTCFKKPPTPPPEPET*

SEQ ID NO: 71. Tau-VfAU
MAEPRQEFEVMEDHAGTYGLGDRKDQGGYTMHQDQEGDTDAGLKESPLQTPTEDGSEEPGSETSDAKSTPTAEDVT
APLVDEGAPGKQAAAQPHTEIPEGTTAEEAGIGDTPSLEDEAAGHVTQARMVSKSKDGTGSDDKKAKGADGKTKIATP
RGAAPPGQKGQANATRIPAKTPPAPKTPPSSGEPPKSGDRSGYSSPGSPGTPGSRSRTPSLPTPPTREPKKVAVVRTPPK
SPSSAKSRLQTAPVPMPDLKNVKSKIGSTENLKHQPGGGKVQIINKKLDLSNVQSKCGSKDNIKHVPGGGSVQIVYKPV
DLSKVTSKCGSLGNIHHKPGGGQVEVKSEKLDFKDRVQSKIGSLDNITHVPGGGNKKIETHKLTFRENAKAKTDHGAEIV
YKSPVVSGDTSPRHLSNVSSTGSIDMVDSPQLATLADEVSASLAKQGLPDYSLVKALQMAQQNFVITDASLPDNPIVYA
SRGFLTLTGYSLDQILGRNCRFLQGPETDPRAVDKIRNAITKGVDTSVCLLNYRQDGTTFWNLFFVAGLRDSKGNIVNYV
GVQSKVSEDYAKLLVNEQNIEYKGVRTSNMLRRKPGLQSTVPRARDPPDLDN*

SEQ ID NO: 72. Tau-NcVVD(y50w)
MAEPRQEFEVMEDHAGTYGLGDRKDQGGYTMHQDQEGDTDAGLKESPLQTPTEDGSEEPGSETSDAKSTPTAEDVT

APLVDEGAPGKQAAAQPHTEIPEGTTAEEAGIGDTPSLEDEAAGHVTQARMVSKSKDGTGSDDKKAKGADGKTKIATP

RGAAPPGQKGQANATRIPAKTPPAPKTPPSSGEPPKSGDRSGYSSPGSPGTPGSRSRTPSLPTPPTREPKKVAVVRTPPK

SPSSAKSRLQTAPVPMPDLKNVKSKIGSTENLKHQPGGGKVQIINKKLDLSNVQSKCGSKDNIKHVPGGGSVQIVYKPV

DLSKVTSKCGSLGNIHHKPGGGQVEVKSEKLDFKDRVQSKIGSLDNITHVPGGGNKKIETHKLTFRENAKAKTDHGAEIV

YKSPVVSGDTSPRHLSNVSSTGSIDMVDSPQLATLADEVSASLAKQGLHTLYAPGGYDIMGWLIQIMNRPNPQVELGP

VDTSCALILCDLKQKDTPIVYASEAFLYMTGYSNAEVLGRNCRFLQSPDGMVKPKSTRKYVDSNTINTMRKAIDRNAEV

QVEVVNFKKNGQRFVNFLTMIPVRDETGEYRYSMGFQCETELQSTVPRARDPPDLDN*

-continued

SEQ ID NO: 73. Tau-NcVVD(wildtype)
MAEPRQEFEVMEDHAGTYGLGDRKDQGGYTMHQDQEGDTDAGLKESPLQTPTEDGSEEPGSETSDAKSTPTAEDVT
APLVDEGAPGKQAAAQPHTEIPEGTTAEEAGIGDTPSLEDEAAGHVTQARMVSKSKDGTGSDDKKAKGADGKTKIATP
RGAAPPGQKGQANATRIPAKTPPAPKTPPSSGEPPKSGDRSGYSSPGSPGTPGSRSRTPSLPTPPTREPKKVAVVRTPPK
SPSSAKSRLQTAPVPMPDLKNVKSKIGSTENLKHQPGGGKVQIINKKLDLSNVQSKCGSKDNIKHVPGGGSVQIVYKPV
DLSKVTSKCGSLGNIHHKPGGGQVEVKSEKLDFKDRVQSKIGSLDNITHVPGGGNKKIETHKLTFRENAKAKTDHGAEIV
YKSPVVSGDTSPRHLSNVSSTGSIDMVDSPQLATLADEVSASLAKQGLHTLYAPGGYDIMGWLIQIMNRPNPQVELGP
VDTSCALILCDLKQKDTPIVYASEAFLYMTGYSNAEVLGRNCRFLQSPDGMVKPKSTRKYVDSNTINTMRKAIDRNAEV
QVEVVNFKKNGQRFVNFLTMIPVRDETGEYRYSMGFQCETELQSTVPRARDPPDLDN*

SEQ ID NO: 74. VfAU-Tau
MPDYSLVKALQMAQQNFVITDASLPDNPIVYASRGFLTLTGYSLDQILGRNCRFLQGPETDPRAVDKIRNAITKGVDTS
VCLLNYRQDGTTFWNLFFVAGLRDSKGNIVNYVGVQSKVSEDYAKLLVNEQNIEYKGVRTSNMLRRKPGSLMAEPRQ
EFEVMEDHAGTYGLGDRKDQGGYTMHQDQEGDTDAGLKESPLQTPTEDGSEEPGSETSDAKSTPTAEDVTAPLVDE
GAPGKQAAAQPHTEIPEGTTAEEAGIGDTPSLEDEAAGHVTQARMVSKSKDGTGSDDKKAKGADGKTKIATPRGAAP
PGQKGQANATRIPAKTPPAPKTPPSSGEPPKSGDRSGYSSPGSPGTPGSRSRTPSLPTPPTREPKKVAVVRTPPKSPSSA
KSRLQTAPVPMPDLKNVKSKIGSTENLKHQPGGGKVQIINKKLDLSNVQSKCGSKDNIKHVPGGGSVQIVYKPVDLSKV
TSKCGSLGNIHHKPGGGQVEVKSEKLDFKDRVQSKIGSLDNITHVPGGGNKKIETHKLTFRENAKAKTDHGAEIVYKSPV
VSGDTSPRHLSNVSSTGSIDMVDSPQLATLADEVSASLAKQGLSNSAVDGTAGPGSTGSR*

SEQ ID NO: 75. Cry-TDP(F147L)-mCherry
MKMDKKTIVWFRRDLRIEDNPALAAAAHEGSVFPVFIWCPEEEGQFYPGRASRWWMKQSLAHLSQSLKALGSDLTLI
KTHNTISAILDCIRVTGATKVVFNHLYDPVSLVRDHTVKEKLVERGISVQSYNGDLLYEPWEIYCEKGKPFTSFNSYWKKC
LDMSIESVMLPPPWRLMPITAAAEAIWACSIEELGLENEAEKPSNALLTRAWSPGWSNADKLLNEFIEKQLIDYAKNSK
KVVGNSTSLLSPYLHFGEISVRHVFQCARMKQIIWARDKNSEGEESADLFLRGIGLREYSRYICFNFPFTHEQSLLSHLRFF
PWDADVDKFKAWRQGRTGYPLVDAGMRELWATGWMHNRIRVIVSSFAVKFLLLPWKWGMKYFWDTLLDADLEC
DILGWQYISGSIPDGHELDRLDNPALQGAKYDPEGEYIRQWLPELARLPTEWIHHPWDAPLTVLKASGVELGTNYAKPI
VDIDTARELLAKAISRTRGAQIMIGAAARGMSEYIRVTEDENDEPIEIPSEDDGTVLLSTVTAQFPGACGLRYRNPVSQC
MRGVRLVEGILHAPDAGWGNLVYVVNYPKDNKRKMDETDASSAVKVKRAVQKTSDLIVLGLPWKTTEQDLKEYFSTF
GEVLMVQVKKDLKTGHSKGLGFVRFTEYETQVKVMSQRHMIDGRWCDCKLPNSKQSQDEPLRSRKVFVGRCTEDMT
EDELREFFSQYGDVMDVFIPKPFRAFAFVTFADDQIAQSLCGEDLIIKGISVHISNAEPKHNSNRQLERSGRFGGNPGGF
GNQGGFGNSRGGAGLGNNQGSNMGGGMNFGAFSINPAMMAAAQAALQSSWGMMGMLASQQNQSGPSGN
NQNQGNMQREPNQAFGSGNNSYSGSNSGAAIGWGSASNAGSGSGFNGGFGSSMDSKSSGWGMSRDPPVATMV
SKGEEDNMAIIKEFMRFKVHMEGSVNGHEFEIEGEGEGRPYEGTQTAKLKVTKGGPLPFAWDILSPQFMYGSKAYVKH
PADIPDYLKLSFPEGFKWERVMNFEDGGVVTVTQDSSLQDGEFIYKVKLRGTNFPSDGPVMQKKTMGWEASSERMY
PEDGALKGEIKQRLKLKDGGHYDAEVKTTYKAKKPVQLPGAYNVNIKLDITSHNEDYTIVEQYERAEGRHSTGGMDELY
K*

SEQ ID NO: 76. Cry-TDP(F229L)-mCherry
MKMDKKTIVWFRRDLRIEDNPALAAAAHEGSVFPVFIWCPEEEGQFYPGRASRWWMKQSLAHLSQSLKALGSDLTLI
KTHNTISAILDCIRVTGATKVVFNHLYDPVSLVRDHTVKEKLVERGISVQSYNGDLLYEPWEIYCEKGKPFTSFNSYWKKC
LDMSIESVMLPPPWRLMPITAAAEAIWACSIEELGLENEAEKPSNALLTRAWSPGWSNADKLLNEFIEKQLIDYAKNSK
KVVGNSTSLLSPYLHFGEISVRHVFQCARMKQIIWARDKNSEGEESADLFLRGIGLREYSRYICFNFPFTHEQSLLSHLRFF
PWDADVDKFKAWRQGRTGYPLVDAGMRELWATGWMHNRIRVIVSSFAVKFLLLPWKWGMKYFWDTLLDADLEC
DILGWQYISGSIPDGHELDRLDNPALQGAKYDPEGEYIRQWLPELARLPTEWIHHPWDAPLTVLKASGVELGTNYAKPI -continued

VDIDTARELLAKAISRTRGAQIMIGAAARGMSEYIRVTEDENDEPIEIPSEDDGTVLLSTVTAQFPGACGLRYRNPVSQC

MRGVRLVEGILHAPDAGWGNLVYVVNYPKDNRKMDETDASSAVKVKRAVQKTSDLIVLGLPWKTTEQDLKEYFSTF

GEVLMVQVKKDLKTGHSKGFGFVRFTEYETQVKVMSQRHMIDGRWCDCKLPNSKQSQDEPLRSRKVFVGRCTEDMT

EDELREFFSQYGDVMDVFIPKPFRALAFVTFADDQIAQSLCGEDLIIKGISVHISNAEPKHNSNRQLERSGRFGGNPGGF

GNQGGFGNSRGGGAGLGNNQGSNMGGGMNFGAFSINPAMMAAAQAALQSSWGMMGMLASQQNQSGPSGN

NQNQGNMQREPNQAFGSGNNSYSGSNSGAAIGWGSASNAGSGSGFNGGFGSSMDSKSSGWGMSRDPPVATMV

SKGEEDNMAIIKEFMRFKVHMEGSVNGHEFEIEGEGEGRPYEGTQTAKLKVTKGGPLPFAWDILSPQFMYGSKAYVKH

PADIPDYLKLSFPEGFKWERVMNFEDGGVVTVTQDSSLQDGEFIYKVKLRGTNFPSDGPVMQKKTMGWEASSERMY

PEDGALKGEIKQRLKLKDGGHYDAEVKTTYKAKKPVQLPGAYNVNIKLDITSHNEDYTIVEQYERAEGRHSTGGMDELY

K*

SEQ ID NO: 77. Cry-TDP(S409,410A)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQMSEYIRVTEDENDEPIEIPSEDDGTVLLSTVTAQFPGACGLRYRNPVSQCM

RGVRLVEGILHAPDAGWGNLVYVVNYPKDNRKMDETDASSAVKVKRAVQKTSDLIVLGLPWKTTEQDLKEYFSTFGE

VLMVQVKKDLKTGHSKGFGFVRFTEYETQVKVMSQRHMIDGRWCDCKLPNSKQSQDEPLRSRKVFVGRCTEDMTED

ELREFFSQYGDVMDVFIPKPFRAFAFVTFADDQIAQSLCGEDLIIKGISVHISNAEPKHNSNRQLERSGRFGGNPGGFGN

QGGFGNSRGGGAGLGNNQGSNMGGGMNFGAFSINPAMMAAAQAALQSSWGMMGMLASQQNQSGPSGNNQ

NQGNMQREPNQAFGSGNNSYSGSNSGAAIGWGSASNAGSGSGFNGGFGSSMDSKAAGWGMWDPPVATMVSK

GEEDNMAIIKEFMRFKVHMEGSVNGHEFEIEGEGEGRPYEGTQTAKLKVTKGGPLPFAWDILSPQFMYGSKAYVKHP

ADIPDYLKLSFPEGFKWERVMNFEDGGVVTVTQDSSLQDGEFIYKVKLRGTNFPSDGPVMQKKTMGWEASSERMYP

EDGALKGEIKQRLKLKDGGHYDAEVKTTYKAKKPVQLPGAYNVNIKLDITSHNEDYTIVEQYERAEGRHSTGGMDELYK*

SEQ ID NO: 78. Cry-TDP(S409,410D)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQMSEYIRVTEDENDEPIEIPSEDDGTVLLSTVTAQFPGACGLRYRNPVSQCM

RGVRLVEGILHAPDAGWGNLVYVVNYPKDNRKMDETDASSAVKVKRAVQKTSDLIVLGLPWKTTEQDLKEYFSTFGE

VLMVQVKKDLKTGHSKGFGFVRFTEYETQVKVMSQRHMIDGRWCDCKLPNSKQSQDEPLRSRKVFVGRCTEDMTED

ELREFFSQYGDVMDVFIPKPFRAFAFVTFADDQIAQSLCGEDLIIKGISVHISNAEPKHNSNRQLERSGRFGGNPGGFGN

QGGFGNSRGGGAGLGNNQGSNMGGGMNFGAFSINPAMMAAAQAALQSSWGMMGMLASQQNQSGPSGNNQ

NQGNMQREPNQAFGSGNNSYSGSNSGAAIGWGSASNAGSGSGFNGGFGSSMDSKDDGWGMWDPPVATMVSK

GEEDNMAIIKEFMRFKVHMEGSVNGHEFEIEGEGEGRPYEGTQTAKLKVTKGGPLPFAWDILSPQFMYGSKAYVKHP

ADIPDYLKLSFPEGFKWERVMNFEDGGVVTVTQDSSLQDGEFIYKVKLRGTNFPSDGPVMQKKTMGWEASSERMYP

EDGALKGEIKQRLKLKDGGHYDAEVKTTYKAKKPVQLPGAYNVNIKLDITSHNEDYTIVEQYERAEGRHSTGGMDELYK*

SEQ ID NO: 79. Cry-TDP(A321V)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQMSEYIRVTEDENDEPIEIPSEDDGTVLLSTVTAQFPGACGLRYRNPVSQCM

RGVRLVEGILHAPDAGWGNLVYVVNYPKDNRKMDETDASSAVKVKRAVQKTSDLIVLGLPWKTTEQDLKEYFSTFGE

VLMVQVKKDLKTGHSKGFGFVRFTEYETQVKVMSQRHMIDGRWCDCKLPNSKQSQDEPLRSRKVFVGRCTEDMTED

ELREFFSQYGDVMDVFIPKPFRAFAFVTFADDQ1AQSLCGEDLIIKGISVHISNAEPKHNSNRQLERSGRFGGNPGGFGN

QGGFGNSRGGGAGLGNNQGSNMGGGMNFGAFSINPVMMAAAQAALQSSWGMMGMLASQQNQSGPSGNNQ

NQGNMQREPNQAFGSGNNSYSGSNSGAAIGWGSASNAGSGSGFNGGFGSSMDSKSSGWGWDPPVATMVSKGEE

DNMAIIKEFMRFKVHMEGSVNGHEFEIEGEGEGRPYEGTQTAKLKVTKGGPLPFAWDILSPQFMYGSKAYVKHPADIP

DYLKLSFPEGFKWERVMNFEDGGVVTVTQDSSLQDGEFIYKVKLRGTNFPSDGPVMQKKTMGWEASSERMYPEDGA

LKGEIKQRLKLKDGGHYDAEVKTTYKAKKPVQLPGAYNVNIKLDITSHNEDYTIVEQYERAEGRHSTGGMDELYK*

SEQ ID NO: 80. Cry-TDP(m337V)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQMSEYIRVTEDENDEPIEIPSEDDGTVLLSTVTAQFPGACGLRYRNPVSQCM

RGVRLVEGILHAPDAGWGNLVYVVNYPKDNRKMDETDASSAVKVKRAVQKTSDLIVLGLPWKTTEQDLKEYFSTFGE

VLMVQVKKDLKTGHSKGFGFVRFTEYETQVKVMSQRHMIDGRWCDCKLPNSKQSQDEPLRSRKVFVGRCTEDMTED

ELREFFSQYGDVMDVFIPKPFRAFAFVTFADDQIAQSLCGEDLIIKGISVHISNAEPKHNSNRQLERSGRFGGNPGGFGN

QGGFGNSRGGGAGLGNNQGSNMGGGMNFGAFSINPAMMAAAQAALQSSWGMVGMLASQQNQSGPSGNNQN

QGNMQREPNQAFGSGNNSYSGSNSGAAIGWGSASNAGSGSGFNGGFGSSMDSKSSGWGWDPPVATMVSKGEED

NMAIIKEFMRFKVHMEGSVNGHEFEIEGEGEGRPYEGTQTAKLKVTKGGPLPFAWDILSPQFMYGSKAYVKHPADIPD

YLKLSFPEGFKWERVMNFEDGGVVTVTQDSSLQDGEFIYKVKLRGTNFPSDGPVMQKKTMGWEASSERMYPEDGAL

KGE1KQRLKLKDGGHYDAEVKTTYKAKKPVQLPGAYNVNIKLDITSHNEDYTIVEQYERAEGRHSTGGMDELYK*

SEQ ID NO: 81. Cry-TDP(LCD, A321V)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQGRFGGNPGGFGNQGGFGNSRGGGAGLGNNQGSNMGGGMNFGAFSI

NPVMMAAAQAALQSSWGMMGMLASQQNQSGPSGNNQNQGNMQREPNQAFGSGNNSYSGSNSGAAIGWGSA

SNAGSGSGFNGGFGSSMDSKSSGWGMRDPPVATMVSKGEEDNMAIIKEFMRFKVHMEGSVNGHEFEIEGEGEGRP

-continued

YEGTQTAKLKVTKGGPLPFAWDILSPQFMYGSKAYVKHPADIPDYLKLSFPEGFKWERVMNFEDGGVVTVTQDSSLQD

GEFIYKVKLRGTNFPSDGPVMQKKTMGWEASSERMYPEDGALKGEIKQRLKLKDGGHYDAEVKTTYKAKKPVQLPGA

YNVNIKLDITSHNEDYTIVEQYERAEGRHSTGGMDELYK*

SEQ ID NO: 82. Cry-TDP(LCD, M337V)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQGRFGGNPGGFGNQGGFGNSRGGGAGLGNNQGSNMGGGMNFGAFSI

NPAMMAAAQAALQSSWGMVGMLASQQNQSGPSGNNQNQGNMQREPNQAFGSGNNSYSGSNSGAAIGWGSA

SNAGSGSGFNGGFGSSMDSKSSGWGMRDPPVATMVSKGEEDNMAIIKEFMRFKVHMEGSVNGHEFEIEGEGERP

YEGTQTAKLKVTKGGPLPFAWDILSPQFMYGSKAYVKHPADIPDYLKLSFPEGFKWERVMNFEDGGVVTVTQDSSLQD

GEFIYKVKLRGTNFPSDGPVMQKKTMGWEASSERMYPEDGALKGEIKQRLKLKDGGHYDAEVKTTYKAKKPVQLPGA

YNVNIKLDITSHNEDYTIVEQYERAEGRHSTGGMDELYK*

SEQ ID NO: 83. Cry-TDP(LCD, S409, 410A)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQGRFGGNPGGFGNQGGFGNSRGGGAGLGNNQGSNMGGGMNFGAFSI

NPAMMAAAQAALQSSWGMMGMLASQQNQSGPSGNNQNQGNMQREPNQAFGSGNNSYSGSNSGAAIGWGSA

SNAGSGSGFNGGFGSSMDSKAAGWGMRDPPVATMVSKGEEDNMAIIKEFMRFKVHMEGSVNGHEFEIEGEGER

PYEGTQTAKLKVTKGGPLPFAWDILSPQFMYGSKAYVKHPADIPDYLKLSFPEGFKWERVMNFEDGGVVTVTQDSSLQ

DGEFIYKVKLRGTNFPSDGPVMQKKTMGWEASSERMYPEDGALKGEIKQRLKLKDGGHYDAEVKTTYKAKKPVQLPG

AYNVNIKLDITSHNEDYTIVEQYERAEGRHSTGGMDELYK*

SEQ ID NO: 84. Cry-TDP(LCD, S409, 410D)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAPGRFGGNPGGFGNQGGFGNSRGGGAGLGNNQGSNMGGGMNFGAFSIN

PAMMAAAQAALQSSWGMMGMLASQQNQSGPSGNNQNQGNMQREPNQAFGSGNNSYSGSNSGAAIGWGSAS

NAGSGSGFNGGFGSSMDSKDDGWGMTRDPPVATMVSKGEEDNMAIIKEFMRFKVHMEGSVNGHEFEIEGEGER

PYEGTQTAKLKVTKGGPLPFAWDILSPQFMYGSKAYVKHPADIPDYLKLSFPEGFKWERVMNFEDGGVVTVTQDSSLQ

DGEFIYKVKLRGTNFPSDGPVMQKKTMGWEASSERMYPEDGALKGEIKQRLKLKDGGHYDAEVKTTYKAKKPVQLPG

AYNVNIKLDITSHNEDYTIVEQYERAEGRHSTGGMDELYK*

SEQ ID NO: 85. Cry-TDP(5FL)-mcherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQMSEYIRVTEDENDEPIEIPSEDDGTVLLSTVTAQFPGACGLRYRNPVSQCM

RGVRLVEGILHAPDAGWGNLVYVVNYPKDNKRKMDETDASSAVKVKRAVQKTSDLIVLGLPWKTTEQDLKEYFSTFGE

VLMVQVKKDLKTGHSKGLGLVRFTEYETQVKVMSQRHMIDGRWCDCKLPNSKQSQDEPLRSRKVLVGRCTEDMTED

ELREFFSQYGDVMDVFIPKPFRALALVTFADDQ1AQSLCGEDLIIKGISVHISNAEPKHNSNRQLERSGRFGGNPGGFGN

QGGFGNSRGGGAGLGNNQGSNMGGGMNFGAFSINPAMMAAAQAALQSSWGMMGMLASQQNQSGPSGNNQ

NQGNMQREPNQAFGSGNNSYSGSNSGAAIGWGSASNAGSGSGFNGGFGSSMDSKSSGWGMWDPPVATMVSKG

EEDNMAIIKEFMRFKVHMEGSVNGHEFEIEGEGEGRPYEGTQTAKLKVTKGGPLPFAWDILSPQFMYGSKAYVKHPA

DIPDYLKLSFPEGFKWERVMNFEDGGVVTVTQDSSLQDGEFIYKVKLRGTNFPSDGPVMQKKTMGWEASSERMYPE

DGALKGEIKQRLKLKDGGHYDAEVKTTYKAKKPVQLPGAYNVNIKLDITSHNEDYTIVEQYERAEGRHSTGGMDELYK*

SEQ ID NO: 86. Cry-TDP(RRM1)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQDLIVLGLPWKTTEQDLKEYFSTFGEVLMVQVKKDLKTGHSKGFGFVRFTEY

ETQVKVMSQRHMIDGRWCDCKLPNSKQSQDEPLRSRDPPVATMVSKGEEDNMAIIKEFMRFKVHMEGSVNGHEFEI

EGEGEGRPYEGTQTAKLKVTKGGPLPFAWDILSPQFMYGSKAYVKHPADIPDYLKLSFPEGFKWERVMNFEDGGVVTV

TQDSSLQDGEFIYKVKLRGTNFPSDGPVMQKKTMGWEASSERMYPEDGALKGEIKQRLKLKDGGHYDAEVKTTYKAK

KPVQLPGAYNVNIKLDITSHNEDYTIVEQYERAEGRHSTGGMDELYK*

SEQ ID NO: 87. Cry-TDP(RRM2)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQRKVFVGRCTEDMTEDELREFFSQYGDVMDVFIPKPFRAFAFVTFADDQIA

QSLCGEDLIIKGISVHISNAEPRDPPVATMVSKGEEDNMAIIKEFMRFKVHMEGSVNGHEFEIEGEGEGRPYEGTQTAK

LKVTKGGPLPFAWDILSPQFMYGSKAYVKHPADIPDYLKLSFPEGFKWERVMNFEDGGVVTVTQDSSLQDGEFIYKVKL

RGTNFPSDGPVMQKKTMGWEASSERMYPEDGALKGEIKQRLKLKDGGHYDAEVKTTYKAKKPVQLPGAYNVNIKLDI

TSHNEDYTIVEQYERAEGRHSTGGMDELYK*

-continued

SEQ ID NO: 88. Cry-TDP(RRM1 + 2)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQDLIVLGLPWKTTEQDLKEYFSTFGEVLMVQVKKDLKTGHSKGFGFVRFTEY

ETQVKVMSQRHMIDGRWCDCKLPNSKQSQDEPLRSRKVFVGRCTEDMTEDELREFFSQYGDVMDVFIPKPFRAFAFV

TFADDQIAQSLCGEDLIIKGISVHISNAEPRDPPVATMVSKGEEDNMAIIKEFMRFKVHMEGSVNGHEFEIEGEGEGRP

YEGTQTAKLKVTKGGPLPFAWDILSPQFMYGSKAYVKHPADIPDYLKLSFPEGFKWERVMNFEDGGVVTVTQDSSLQD

GEFIYKVKLRGTNFPSDGPVMQKKTMGWEASSERMYPEDGALKGEIKQRLKLKDGGHYDAEVKTTYKAKKPVQLPGA

YNVNIKLDITSHNEDYTIVEQYERAEGRHSTGGMDELYK*

SEQ ID NO: 89. Cry-TDP(dLCD)-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQMSEYIRVTEDENDEPIEIPSEDDGTVLLSTVTAQFPGACGLRYRNPVSQCM

RGVRLVEGILHAPDAGWGNLVYVVNYPKDNRKMDETDASSAVKVKRAVQKTSDLIVLGLPWKTTEQDLKEYFSTFGE

VLMVQVKKDLKTGHSKGFGFVRFTEYETQVKVMSQRHMIDGRWCDCKLPNSKQSQDEPLRSRKVFVGRCTEDMTED

ELREFFSQYGDVMDVFIPKPFRAFAFVTFADDQIAQSLCGEDLIIKGISVHISNAEPKHNSNRQLERSRDPPVATMVSKG

EEDNMAIIKEFMRFKVHMEGSVNGHEFEIEGEGEGRPYEGTQTAKLKVTKGGPLPFAWDILSPQFMYGSKAYVKHPA

DIPDYLKLSFPEGFKWERVMNFEDGGVVTVTQDSSLQDGEFIYKVKLRGTNFPSDGPVMQKKTMGWEASSERMYPE

DGALKGEIKQRLKLKDGGHYDAEVKTTYKAKKPVQLPGAYNVNIKLDITSHNEDYTIVEQYERAEGRHSTGGMDELYK*

FUS Protein Arrangements Generated:
1. Cry2olig Fusion Proteins Amino Acid Sequences:
A) Full Length FUS Protein No Reporter
SEQ ID NO: 90. Cry2Olig-FUS
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQCRATMYPYDVPDYAMASNDYTQQATQSYGAYPTQPGQGYSQQSSQPY

GQQSYSGYSQSTDTSGYGQSSYSSYGQSQNTGYGTQSTPQGYGSTGGYGSSQSSQSSYGQQSSYPGYGQQPAPSSTS

GSYGSSSQSSSYGQPQSGSYSQQPSYGGQQQSYGQQQSYNPPQGYGQQNQYNSSSGGGGGGGGGGNYGQDQSS

MSSGGGSGGGYGNQDQSGGGGSGGYGQQDRGGRGRGGSGGGGGGGGGGYNRSSGGYEPRGRGGGRGGRGGM

GGSDRGGFNKFGGPRDQGSRHDSEQDNSDNNTIFVQGLGENVTIESVADYFKQIGIIKTNKKTGQPMINLYTDRETGK

LKGEATVSFDDPPSAKAAIDWFDGKEFSGNPIKVSFATRRADFNRGGGNGRGGRGRGGPMGRGGYGGGSGGGGR

-continued

```
GGFPSGGGGGGGQQRAGDWKCPNPTCENMNFSWRNECNQCKAPKPDGPGGGPGGSHMGGNYGDDRRGGRGG

YDRGGYRGRGGDRGGFRGGRGGGDRGGFGPGKMDSRGEHRQDRRERPY
```

```
B) Full Length FUS Protein + mCherry Reporter
SEQ ID NO: 91. Cry2Olig-FUS-mCherry
MKMDKKTIVWFRRDLRIEDNPALAAAAHEGSVFPVFIWCPEEEGQFYPGRASRWWMKQSLAHLSQSLKALGSDLTLI KTHNTISAILDCIRVTGATKVVFNHLYDPVSLVRDHTVKEKLVERGISVQSYNGDLLYEPWEIYCEKGKPFTSFNSYWKKC

LDMSIESVMLPPPWRLMPITAAAEAIWACSIEELGLENEAEKPSNALLTRAWSPGWSNADKLLNEFIEKQLIDYAKNSK

KVVGNSTSLLSPYLHFGEISVRHVFQCARMKQIIWARDKNSEGEESADLFLRGIGLREYSRYICFNFPFTHEQSLLSHLRFF

PWDADVDKFKAWRQGRTGYPLVDAGMRELWATGWMHNRIRVIVSSFAVKFLLLPWKWGMKYFWDTLLDADLEC

DILGWQYISGSIPDGHELDRLDNPALQGAKYDPEGEYIRQWLPELARLPTEWIHHPWDAPLTVLKASGVELGTNYAKPI

VDIDTARELLAKAISRTRGAQIMIGAAAQCRATMYPYDVPDYAMASNDYTQQATQSYGAYPTQPGQGYSQQSSQPY

GQQSYSGYSQSTDTSGYGQSSYSSYGQSQNTGYGTQSTPQGYGSTGGYGSSQSSQSSYGQQSSYPGYGQQPAPSSTS

GSYGSSSSYGQPQSGSYSQQPSYGGQQQSYGQQQSYNPPQGYGQQNQYNSSSGGGGGGGGGGNYGQDQSS

MSSGGGSGGGYGNQDQSGGGSGGYGQQDRGGRGRGGSGGGGGGGGGGYNRSSGGYEPRGRGGGRGGRGGM

GGSDRGGFNKFGGPRDQGSRHDSEQDNSDNNTIFVQGLGENVTIESVADYFKQIGIIKTNKKTGQPMINLYTDRETGK

LKGEATVSFDDPPSAKAAIDWFDGKEFSGNPIKVSFATRRADFNRGGGNGRGGRGRGGPMGRGGYGGGGSGGGR

GGFPSGGGGGGGQQRAGDWKCPNPTCENMNFSWRNECNQCKAPKDGPGGGPGGSHMGGNYGDDRRGGRGG

YDRGGYRGRGGDRGGFRGGRGGGDRGGFGPGKMDSRGEHRQDRRERPYWDPPVATMVSKGEEDNMAIIKEFMR

FKVHMEGSVNGHEFEIEGEGEGRPYEGTQTAKLKVTKGGPLPFAWDILSPQFMYGSKAYVKHPADIPDYLKLSFPEGFK

WERVMNFEDGGVVTVTQDSSLQDGEFIYKVKLRGTNFPSDGPVMQKKTMGWEASSERMYPEDGALKGEIKQRLKLK

DGGHYDAEVKTTYKAKKPVQLPGAYNVNIKLDITSHNEDYTIVEQYERAEGRHSTGGMDELYK
```

```
Amino Acid Sequences of the Vaucheria frigida (Yellow-green alga)
(Conferva frigida) Aureochrome1 protein (Gene is AUREO1):
SEQ ID NO: 92. VfAU1 (A8QW55):
MNGLTPPLMFCSRSDDPSSTSNINLDDVFADVFFNSNGELLDIDEIDDFGDNTCPKSSMSVDDDASSQVFQGHLFGNA LSSIALSDSGDLSTGIYESQGNASRGKSLRTKSSGSISSELTEAQKVERRERNREHAKRSRVRKKFLLESLQQSVNELNHEN NCLKESIREHLGPRGDSLIAQCSPEADTLLTDNPSKANRILEDPDYSLVKALQMAQQNFVITDASLPDNPIVYASRGFLTL

TGYSLDQILGRNCRFLQGPETDPRAVDKIRNAITKGVDTSVCLLNYRQDGTTFWNLFFVAGLRDSKGNIVNYVGVQSKV

SEDYAKLLVNEQNIEYKGVRTSNMLRRK
```

```
SEQ ID NO: 93. VfAU1-LOV domain:
PDYSLVKALQMAQQNFVITDASLPDNPIVYASRGFLTLTGYSLDQILGRNCRFLQGPETDPRAVDKIRNAITKGVDTSVC

LLNYRQDGTTFWNLFFVAGLRDSKGNIVNYVGVQSKVSEDYAKLLVNEQNIEYKGVRTSNMLRRK
```

```
SEQ ID NO: 94. VfAU1-DNA sequence-VfAU1-LOV domain (No Start codon):
Cctgactacagtctcgtgaaggctctgcaaatggcacaacagaattttgtcattacagacgcctccctcccagacaaccctatcg tctacgccagtagagggtttctgacactgacaggctattctctcgaccagatcctgggcaggaactgcaggtttctgcaagggcc agaaacagacccaagagctgtggataagatcaggaatgccatcaccaaaggcgttgataccagtgtctgtctgctgaattataga caggatggcacaaccttctggaatctcttcttcgtggctggactcagagattctaagggcaatattgtcaactacgtcggagtgc agtcaaaggtgagcgaagattatgccaagctgctggtcaacgagcagaacattgagtacaaaggtgtgcgcaccagtaacatgct gcgcagaaag
```

```
SEQ ID NO: 95. TDP-43 (TAR DNA-binding protein-43)
MSEYIRVTEDENDEPIEIPSEDDGTVLLSTVTAQFPGACGLRYRNPVSQCMRGVRLVEGILHAPDAGWGNLVYVVNYP

KDNKRKMDETDASSAVKVKRAVQKTSDLIVLGLPWKTTEQDLKEYFSTFGEVLMVQVKKDLKTGHSKGFGFVRFTEYE

TQVKVMSQRHMIDGRWCDCKLPNSKQSQDEPLRSRKVFVGRCTEDMTEDELREFFSQYGDVMDVFIPKPFRAFAFVT
```

```
FADDQIAQSLCGEDLIIKGISVHISNAEPKHNSNRQLERSGRFGGNPGGFGNQGGFGNSRGGGAGLGNNQGSNMGG

GMNFGAFSINPAMMAAAQAALQSSWGMMGMLASQQNQSGPSGNNQNQGNMQREPNQAFGSGNNSYSGSNS

GAAIGWGSASNAGSGSGFNGGFGSSMDSKSSGWGM

SEQ ID NO: 96. TDP-43 (amino acids 105-414)
MDLIVLGLPWKTTEQDLKEYFSTFGEVLMVQVKKDLKTGHSKGFGFVRFTEYETQVKVMSQRHMIDGRWCDCKLPNS KQSQDEPLRSRKVFVGRCTEDMTEDELREFFSQYGDVMDVFIPKPFRAFAFVTFADDQIAQSLCGEDLIIKGISVHISNAE

PKHNSNRQLERSGRFGGNPGGFGNQGGFGNSRGGGAGLGNNQGSNMGGGMNFGAFSINPAMMAAAQAALQSS

WGMMGMLASQQNQSGPSGNNQNQGNMQREPNQAFGSGNNSYSGSNSGAAIGWGSASNAGSGSGFNGGFGSS

MDSKSSGWGM

SEQ ID NO: 97. TDP-43 (amino acids 191-414)
MRKVFVGRCTEDMTEDELREFFSQYGDVMDVFIPKPFRAFAFVTFADDQIAQSLCGEDLIIKGISVHISNAEPKHNSNR

QLERSGRFGGNPGGFGNQGGFGNSRGGGAGLGNNQGSNMGGGMNFGAFSINPAMMAAAQAALQSSWGMMG

MLASQQNQSGPSGNNQNQGNMQREPNQAFGSGNNSYSGSNSGAAIGWGSASNAGSGSGFNGGFGSSMDSKSSG

WGM

SEQ ID NO: 98. TDP-43 (amino acids 274 to 414)
MGRFGGNPGGFGNQGGFGNSRGGGAGLGNNQGSNMGGGMNFGAFSINPAMMAAAQAALQSSWGMMGMLA

SQQNQSGPSGNNQNQGNMQREPNQAFGSGNNSYSGSNSGAAIGWGSASNAGSGSGFNGGFGSSMDSKSSGWG

M

SEQ ID NO: 99. AsLOV2
GEFLATTLERIEKNFVITDP RLPDNPIIFASDSFLQLTEY SREEILGRNCRFLQGPETDR ATVRKIRDAIDNQTEVTVQL

INYTKSGKKFWNLFHLQPMR DQKGDVQYFIGVQLDGTEHV RDAAEREGVMLIKKTAENID

EAAKELPDANLRPEDLWANH G

SEQ ID NO: 100. EL222
MLDMGQDRPI DGSGAPGADD TRVEVQPPAQ WVLDLIEASP IASVVSDPRL ADNPLIAINQ AFTDLTGYSE

EECVGRNCRF LAGSGTEPWL TDKIRQGVRE HKPVLVEILN YKKDGTPFRN AVLVAPIYDD DDELLYFLGS

QVEVDDDQPN MGMARRERAA EMLKTLSPRQ LEVTTLVASG LRNKEVAARL GLSEKTVKMH RGLVMEKLNL

KTSADLVRIA VEAGI

SEQ ID NO: 101. Ytva
MASFQSFGIP GQLEVIKKAL DHVRVGVVIT DPALEDNPIV YVNQGFVQMT GYETEEILGK NCRFLQGKHT

DPAEVDNIRT ALQNKEPVTV QIQNYKKDGT MFWNELNIDP MEIEDKTYFV GIQNDITKQK

EYEKLLEDSL TEITALSTPI VPIRNGISAL PLVGNLTEER FNSIVCTLTN ILSTSKDDYL IIDLSGLAQV

NEQTADQIFK LSHLLKLTGT ELIITGIKPE LAMKMNKLDA NFSSLKTYSN VKDAVKVLPI M

SEQ ID NO: 102. RsLOV
MDQKQFEKIRAVFDRSGVALTLVDMSLPEQPVVLANPPFLRMTGYTEGQILGFNCRFLQRGDENAQARAD

IRDALKLGRELQVVLRNYRANDEPFDNLLFLHPVGGRPDAPDYFLGSQFELGRSGNSEEAAAAGHAGALT

GELARIGTVAARLEMDSRRHLAQAAAALVRAWERRG
```

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A nucleotide sequence encoding a chimeric polypeptide, comprising: a first nucleotide sequence encoding a light-induced oligomerization domain and a second nucleotide sequence encoding a low complexity domain from a neurodegenerative disease target protein; wherein the light-induced oligomerization domain is CRY2OLIG, or a fragment thereof and wherein the low complexity domain from a neurodegenerative disease target protein is TDP-43.

2. An expression vector encoding a chimeric polypeptide, the expression vector comprising: the nucleotide sequence of claim 1.

3. An isolated cell comprising the nucleotide sequence of claim 1.

4. A chimeric polypeptide comprising a light-induced oligomerization domain and a low complexity domain from a neurodegenerative disease target protein; wherein the light-induced oligomerization domain is CRY2OLIG, or a fragment thereof; and wherein the low complexity domain from a neurodegenerative disease target protein is TDP-43.

5. A method of inducing a neurodegenerative disease pathology in a cell, comprising the steps of:
   introducing into the cell an expression vector encoding a chimeric polypeptide, the expression vector comprising: the nucleotide sequence of claim 1, wherein the nucleotide sequence is operably linked to a promoter;
   expressing the chimeric polypeptide; and
   inducing oligomerization of the chimeric polypeptide by stimulation with blue light.

6. A method of screening for an agent that modulates protein aggregation, comprising the steps of:
   introducing into a cell an expression vector encoding a chimeric polypeptide, the expression vector comprising: the nucleotide sequence of claim 1, wherein the nucleotide sequence is operably linked to a promoter;
   expressing the chimeric polypeptide;
   introducing the agent into a culture media comprising the cell;
   inducing oligomerization of the chimeric polypeptide by stimulation with blue light; and
   determining modulation of protein aggregation by the agent.

7. The nucleotide sequence of claim 1, wherein the first nucleotide sequence encodes a light-induced oligomerization domain comprising at least 90% sequence identity to SEQ ID NO: 2.

8. The nucleotide sequence of claim 1, wherein the first nucleotide sequence encodes a light-induced oligomerization domain comprising SEQ ID NO: 2.

9. The nucleotide sequence of claim 1, wherein the first nucleotide sequence and the second nucleotide sequence encode a chimeric polypeptide comprising at least 90% sequence identity to SEQ ID NO: 6.

10. The nucleotide sequence of claim 1, wherein the first nucleotide sequence and the second nucleotide sequence encode a chimeric polypeptide comprising SEQ ID NO: 6.

11. The nucleotide sequence of claim 1, wherein the first nucleotide sequence and the second nucleotide sequence encode a chimeric polypeptide comprising at least 90% sequence identity to SEQ ID NO: 7.

12. The nucleotide sequence of claim 1, wherein the first nucleotide sequence and the second nucleotide sequence encode a chimeric polypeptide comprising SEQ ID NO: 7.

13. The nucleotide sequence of claim 1, wherein the second nucleotide sequence encodes a low complexity domain comprising at least 90% sequence identity to SEQ ID NO: 95.

14. The nucleotide sequence of claim 1, wherein the second nucleotide sequence encodes a low complexity domain comprising SEQ ID NO: 95.

* * * * *

SEQUENCE LISTING

<160> NUMBER OF SEQ ID NOS: 102

<210> SEQ ID NO 1

<400> SEQUENCE: 1

000

<210> SEQ ID NO 2
<211> LENGTH: 498
<212> TYPE: PRT
<213> ORGANISM: Arabidopsis

<400> SEQUENCE: 2

```
Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
            35                  40                  45

Gly Arg Ala Ser Arg Trp Trp Met Lys Gln Ser Leu Ala His Leu Ser
50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335
```

```
Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
            370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
            405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
            450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
            485                 490                 495

Ala Ala

<210> SEQ ID NO 3
<211> LENGTH: 119
<212> TYPE: PRT
<213> ORGANISM: Neurospora

<400> SEQUENCE: 3

Met Thr Ser Cys Ala Leu Ile Leu Cys Asp Leu Lys Gln Lys Asp Thr
1               5                   10                  15

Pro Ile Val Tyr Ala Ser Glu Ala Phe Leu Tyr Met Thr Gly Tyr Ser
            20                  25                  30

Asn Ala Glu Val Leu Gly Arg Asn Cys Arg Phe Leu Gln Ser Pro Asp
        35                  40                  45

Gly Met Val Lys Pro Lys Ser Thr Arg Lys Tyr Val Asp Ser Asn Thr
    50                  55                  60

Ile Asn Thr Met Arg Lys Ala Ile Asp Arg Asn Ala Glu Val Gln Val
65                  70                  75                  80

Glu Val Val Asn Phe Lys Lys Asn Gly Gln Arg Phe Val Asn Phe Leu
            85                  90                  95

Thr Met Ile Pro Val Arg Asp Glu Thr Gly Glu Tyr Arg Tyr Ser Met
            100                 105                 110

Gly Phe Gln Cys Glu Thr Glu
        115

<210> SEQ ID NO 4
<211> LENGTH: 150
<212> TYPE: PRT
<213> ORGANISM: Neurospora

<400> SEQUENCE: 4

His Thr Leu Tyr Ala Pro Gly Gly Tyr Asp Ile Met Gly Tyr Leu Ile
1               5                   10                  15

Gln Ile Met Asn Arg Pro Asn Pro Gln Val Glu Leu Gly Pro Val Asp
            20                  25                  30
```

Thr Ser Cys Ala Leu Ile Leu Cys Asp Leu Lys Gln Lys Asp Thr Pro
                35                  40                  45

Ile Val Tyr Ala Ser Glu Ala Phe Leu Tyr Met Thr Gly Tyr Ser Asn
 50                  55                  60

Ala Glu Val Leu Gly Arg Asn Cys Arg Phe Leu Gln Ser Pro Asp Gly
 65                  70                  75                  80

Met Val Lys Pro Lys Ser Thr Arg Lys Tyr Val Asp Ser Asn Thr Ile
                 85                  90                  95

Asn Thr Met Arg Lys Ala Ile Asp Arg Asn Ala Glu Val Gln Val Glu
                100                 105                 110

Val Val Asn Phe Lys Lys Asn Gly Gln Arg Phe Val Asn Phe Leu Thr
                115                 120                 125

Met Ile Pro Val Arg Asp Glu Thr Gly Glu Tyr Arg Tyr Ser Met Gly
                130                 135                 140

Phe Gln Cys Glu Thr Glu
145                 150

<210> SEQ ID NO 5
<211> LENGTH: 150
<212> TYPE: PRT
<213> ORGANISM: Neurospora

<400> SEQUENCE: 5

His Thr Leu Tyr Ala Pro Gly Gly Tyr Asp Ile Met Gly Trp Leu Ile
 1               5                  10                  15

Gln Ile Met Asn Arg Pro Asn Pro Gln Val Glu Leu Gly Pro Val Asp
                 20                  25                  30

Thr Ser Cys Ala Leu Ile Leu Cys Asp Leu Lys Gln Lys Asp Thr Pro
                35                  40                  45

Ile Val Tyr Ala Ser Glu Ala Phe Leu Tyr Met Thr Gly Tyr Ser Asn
 50                  55                  60

Ala Glu Val Leu Gly Arg Asn Cys Arg Phe Leu Gln Ser Pro Asp Gly
 65                  70                  75                  80

Met Val Lys Pro Lys Ser Thr Arg Lys Tyr Val Asp Ser Asn Thr Ile
                 85                  90                  95

Asn Thr Met Arg Lys Ala Ile Asp Arg Asn Ala Glu Val Gln Val Glu
                100                 105                 110

Val Val Asn Phe Lys Lys Asn Gly Gln Arg Phe Val Asn Phe Leu Thr
                115                 120                 125

Met Ile Pro Val Arg Asp Glu Thr Gly Glu Tyr Arg Tyr Ser Met Gly
                130                 135                 140

Phe Gln Cys Glu Thr Glu
145                 150

<210> SEQ ID NO 6
<211> LENGTH: 915
<212> TYPE: PRT
<213> ORGANISM: Artificial Sequence
<220> FEATURE:
<223> OTHER INFORMATION: synthetic construct

<400> SEQUENCE: 6

Met Lys Met Asp Lys Lys Thr Ile Val Trp Phe Arg Arg Asp Leu Arg
 1               5                  10                  15

Ile Glu Asp Asn Pro Ala Leu Ala Ala Ala His Glu Gly Ser Val
                 20                  25                  30

Phe Pro Val Phe Ile Trp Cys Pro Glu Glu Glu Gly Gln Phe Tyr Pro

-continued

```
                35                  40                  45
Gly Arg Ala Ser Arg Trp Trp Met Lys Gln Ser Leu Ala His Leu Ser
 50                  55                  60

Gln Ser Leu Lys Ala Leu Gly Ser Asp Leu Thr Leu Ile Lys Thr His
 65                  70                  75                  80

Asn Thr Ile Ser Ala Ile Leu Asp Cys Ile Arg Val Thr Gly Ala Thr
                     85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
                115                 120                 125

Tyr Asn Gly Asp Leu Leu Tyr Glu Pro Trp Glu Ile Tyr Cys Glu Lys
130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
                195                 200                 205

Ala Trp Ser Pro Gly Trp Ser Asn Ala Asp Lys Leu Leu Asn Glu Phe
210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Glu Ser Ala Asp Leu Phe Leu
                275                 280                 285

Arg Gly Ile Gly Leu Arg Glu Tyr Ser Arg Tyr Ile Cys Phe Asn Phe
                290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
                355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
                435                 440                 445

Trp Asp Ala Pro Leu Thr Val Leu Lys Ala Ser Gly Val Glu Leu Gly
450                 455                 460
```

```
Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Arg Gly Met Ser Glu Tyr Ile Arg Val Thr Glu Asp Glu
            500                 505                 510

Asn Asp Glu Pro Ile Glu Ile Pro Ser Glu Asp Gly Thr Val Leu
            515                 520                 525

Leu Ser Thr Val Thr Ala Gln Phe Pro Gly Ala Cys Gly Leu Arg Tyr
530                 535                 540

Arg Asn Pro Val Ser Gln Cys Met Arg Gly Val Arg Leu Val Glu Gly
545                 550                 555                 560

Ile Leu His Ala Pro Asp Ala Gly Trp Gly Asn Leu Val Tyr Val Val
                565                 570                 575

Asn Tyr Pro Lys Asp Asn Lys Arg Lys Met Asp Glu Thr Asp Ala Ser
            580                 585                 590

Ser Ala Val Lys Val Lys Arg Ala Val Gln Lys Thr Ser Asp Leu Ile
            595                 600                 605

Val Leu Gly Leu Pro Trp Lys Thr Thr Glu Gln Asp Leu Lys Glu Tyr
610                 615                 620

Phe Ser Thr Phe Gly Glu Val Leu Met Val Gln Val Lys Lys Asp Leu
625                 630                 635                 640

Lys Thr Gly His Ser Lys Gly Phe Gly Phe Val Arg Phe Thr Glu Tyr
                645                 650                 655

Glu Thr Gln Val Lys Val Met Ser Gln Arg His Met Ile Asp Gly Arg
            660                 665                 670

Trp Cys Asp Cys Lys Leu Pro Asn Ser Lys Gln Ser Gln Asp Glu Pro
            675                 680                 685

Leu Arg Ser Arg Lys Val Phe Val Gly Arg Cys Thr Glu Asp Met Thr
690                 695                 700

Glu Asp Glu Leu Arg Glu Phe Phe Ser Gln Tyr Gly Asp Val Met Asp
705                 710                 715                 720

Val Phe Ile Pro Lys Pro Phe Arg Ala Phe Ala Phe Val Thr Phe Ala
                725                 730                 735

Asp Asp Gln Ile Ala Gln Ser Leu Cys Gly Glu Asp Leu Ile Ile Lys
            740                 745                 750

Gly Ile Ser Val His Ile Ser Asn Ala Glu Pro Lys His Asn Ser Asn
            755                 760                 765

Arg Gln Leu Glu Arg Ser Gly Arg Phe Gly Gly Asn Pro Gly Gly Phe
            770                 775                 780

Gly Asn Gln Gly Gly Phe Gly Asn Ser Arg Gly Gly Gly Ala Gly Leu
785                 790                 795                 800

Gly Asn Asn Gln Gly Ser Asn Met Gly Gly Gly Met Asn Phe Gly Ala
                805                 810                 815

Phe Ser Ile Asn Pro Ala Met Met Ala Ala Ala Gln Ala Ala Leu Gln
            820                 825                 830

Ser Ser Trp Gly Met Met Gly Met Leu Ala Ser Gln Gln Asn Gln Ser
            835                 840                 845

Gly Pro Ser Gly Asn Asn Gln Asn Gln Gly Asn Met Gln Arg Glu Pro
            850                 855                 860

Asn Gln Ala Phe Gly Ser Gly Asn Asn Ser Tyr Ser Gly Ser Asn Ser
865                 870                 875                 880
```

```
Gly Ala Ala Ile Gly Trp Gly Ser Ala Ser Asn Ala Gly Ser Gly Ser
                885                 890                 895

Gly Phe Asn Gly Gly Phe Gly Ser Ser Met Asp Ser Lys Ser Ser Gly
                900                 905                 910

Trp Gly Met
        915

<210> SEQ ID NO 7
<211> LENGTH: 916
<212> TYPE: PRT
<213> ORGANISM: Artificial Sequence
<220> FEATURE:
<223> OTHER INFORMATION: synthetic construct

<400> SEQUENCE: 7

Met Ser Glu Tyr Ile Arg Val Thr Glu Asp Glu Asn Asp Pro Ile
1               5                   10                  15

Glu Ile Pro Ser Glu Asp Asp Gly Thr Val Leu Leu Ser Thr Val Thr
                20                  25                  30

Ala Gln Phe Pro Gly Ala Cys Gly Leu Arg Tyr Arg Asn Pro Val Ser
                35                  40                  45

Gln Cys Met Arg Gly Val Arg Leu Val Glu Gly Ile Leu His Ala Pro
50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
                100                 105                 110

Trp Lys Thr Thr Glu Gln Asp Leu Lys Glu Tyr Phe Ser Thr Phe Gly
                115                 120                 125

Glu Val Leu Met Val Gln Val Lys Lys Asp Leu Lys Thr Gly His Ser
                130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
                180                 185                 190

Val Phe Val Gly Arg Cys Thr Glu Asp Met Thr Glu Asp Glu Leu Arg
                195                 200                 205

Glu Phe Phe Ser Gln Tyr Gly Asp Val Met Asp Val Phe Ile Pro Lys
                210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
                260                 265                 270

Ser Gly Arg Phe Gly Gly Asn Pro Gly Gly Phe Gly Asn Gln Gly Gly
                275                 280                 285

Phe Gly Asn Ser Arg Gly Gly Gly Ala Gly Leu Gly Asn Asn Gln Gly
                290                 295                 300

Ser Asn Met Gly Gly Gly Met Asn Phe Gly Ala Phe Ser Ile Asn Pro
305                 310                 315                 320
```

```
Ala Met Met Ala Ala Ala Gln Ala Ala Leu Gln Ser Ser Trp Gly Met
            325                 330                 335
Met Gly Met Leu Ala Ser Gln Gln Asn Gln Ser Gly Pro Ser Gly Asn
            340                 345                 350
Asn Gln Asn Gln Gly Asn Met Gln Arg Glu Pro Asn Gln Ala Phe Gly
            355                 360                 365
Ser Gly Asn Asn Ser Tyr Ser Gly Ser Asn Ser Gly Ala Ala Ile Gly
            370                 375                 380
Trp Gly Ser Ala Ser Asn Ala Gly Ser Gly Ser Gly Phe Asn Gly Gly
385                 390                 395                 400
Phe Gly Ser Ser Met Asp Ser Lys Ser Ser Gly Trp Gly Met Leu Glu
            405                 410                 415
Ala Thr Met Lys Met Asp Lys Lys Thr Ile Val Trp Phe Arg Arg Asp
            420                 425                 430
Leu Arg Ile Glu Asp Asn Pro Ala Leu Ala Ala Ala His Glu Gly
            435                 440                 445
Ser Val Phe Pro Val Phe Ile Trp Cys Pro Glu Glu Gly Gln Phe
        450                 455                 460
Tyr Pro Gly Arg Ala Ser Arg Trp Trp Met Lys Gln Ser Leu Ala His
465                 470                 475                 480
Leu Ser Gln Ser Leu Lys Ala Leu Gly Ser Asp Leu Thr Leu Ile Lys
            485                 490                 495
Thr His Asn Thr Ile Ser Ala Ile Leu Asp Cys Ile Arg Val Thr Gly
            500                 505                 510
Ala Thr Lys Val Val Phe Asn His Leu Tyr Asp Pro Val Ser Leu Val
            515                 520                 525
Arg Asp His Thr Val Lys Glu Lys Leu Val Glu Arg Gly Ile Ser Val
530                 535                 540
Gln Ser Tyr Asn Gly Asp Leu Leu Tyr Glu Pro Trp Glu Ile Tyr Cys
545                 550                 555                 560
Glu Lys Gly Lys Pro Phe Thr Ser Phe Asn Ser Tyr Trp Lys Lys Cys
            565                 570                 575
Leu Asp Met Ser Ile Glu Ser Val Met Leu Pro Pro Trp Arg Leu
            580                 585                 590
Met Pro Ile Thr Ala Ala Ala Glu Ala Ile Trp Ala Cys Ser Ile Glu
            595                 600                 605
Glu Leu Gly Leu Glu Asn Glu Ala Lys Pro Ser Asn Ala Leu Leu
            610                 615                 620
Thr Arg Ala Trp Ser Pro Gly Trp Ser Asn Ala Asp Lys Leu Leu Asn
625                 630                 635                 640
Glu Phe Ile Glu Lys Gln Leu Ile Asp Tyr Ala Lys Asn Ser Lys Lys
            645                 650                 655
Val Val Gly Asn Ser Thr Ser Leu Leu Ser Pro Tyr Leu His Phe Gly
            660                 665                 670
Glu Ile Ser Val Arg His Val Phe Gln Cys Ala Arg Met Lys Gln Ile
            675                 680                 685
Ile Trp Ala Arg Asp Lys Asn Ser Glu Gly Glu Glu Ser Ala Asp Leu
            690                 695                 700
Phe Leu Arg Gly Ile Gly Leu Arg Glu Tyr Ser Arg Tyr Ile Cys Phe
705                 710                 715                 720
Asn Phe Pro Phe Thr His Glu Gln Ser Leu Leu Ser His Leu Arg Phe
            725                 730                 735
Phe Pro Trp Asp Ala Asp Val Asp Lys Phe Lys Ala Trp Arg Gln Gly
```

```
                        740                 745                 750
Arg Thr Gly Tyr Pro Leu Val Asp Ala Gly Met Arg Glu Leu Trp Ala
            755                 760                 765

Thr Gly Trp Met His Asn Arg Ile Arg Val Ile Val Ser Ser Phe Ala
            770                 775                 780

Val Lys Phe Leu Leu Leu Pro Trp Lys Trp Gly Met Lys Tyr Phe Trp
785                 790                 795                 800

Asp Thr Leu Leu Asp Ala Asp Leu Glu Cys Asp Ile Leu Gly Trp Gln
            805                 810                 815

Tyr Ile Ser Gly Ser Ile Pro Asp Gly His Glu Leu Asp Arg Leu Asp
            820                 825                 830

Asn Pro Ala Leu Gln Gly Ala Lys Tyr Asp Pro Glu Gly Glu Tyr Ile
            835                 840                 845

Arg Gln Trp Leu Pro Glu Leu Ala Arg Leu Pro Thr Glu Trp Ile His
            850                 855                 860

His Pro Trp Asp Ala Pro Leu Thr Val Leu Lys Ala Ser Gly Val Glu
865                 870                 875                 880

Leu Gly Thr Asn Tyr Ala Lys Pro Ile Val Asp Ile Asp Thr Ala Arg
            885                 890                 895

Glu Leu Leu Ala Lys Ala Ile Ser Arg Thr Arg Gly Ala Gln Ile Met
            900                 905                 910

Ile Gly Ala Ala
            915

<210> SEQ ID NO 8
<211> LENGTH: 644
<212> TYPE: PRT
<213> ORGANISM: Artificial Sequence
<220> FEATURE:
<223> OTHER INFORMATION: synthetic construct

<400> SEQUENCE: 8

Met Gly Arg Phe Gly Gly Asn Pro Gly Gly Phe Gly Asn Gln Gly Gly
1               5                   10                  15

Phe Gly Asn Ser Arg Gly Gly Ala Gly Leu Gly Asn Asn Gln Gly
                20                  25                  30

Ser Asn Met Gly Gly Gly Met Asn Phe Gly Ala Phe Ser Ile Asn Pro
            35                  40                  45

Ala Met Met Ala Ala Ala Gln Ala Ala Leu Gln Ser Ser Trp Gly Met
    50                  55                  60

Met Gly Met Leu Ala Ser Gln Gln Asn Gln Ser Gly Pro Ser Gly Asn
65                  70                  75                  80

Asn Gln Asn Gln Gly Asn Met Gln Arg Glu Pro Asn Gln Ala Phe Gly
                85                  90                  95

Ser Gly Asn Asn Ser Tyr Ser Gly Ser Asn Ser Gly Ala Ala Ile Gly
            100                 105                 110

Trp Gly Ser Ala Ser Asn Ala Gly Ser Gly Ser Gly Phe Asn Gly Gly
            115                 120                 125

Phe Gly Ser Ser Met Asp Ser Lys Ser Ser Gly Trp Gly Met Leu Glu
            130                 135                 140

Ala Thr Met Lys Met Asp Lys Lys Thr Ile Val Trp Phe Arg Arg Asp
145                 150                 155                 160

Leu Arg Ile Glu Asp Asn Pro Ala Leu Ala Ala Ala His Glu Gly
                165                 170                 175

Ser Val Phe Pro Val Phe Ile Trp Cys Pro Glu Glu Glu Gly Gln Phe
```

-continued

```
            180                 185                 190
Tyr Pro Gly Arg Ala Ser Arg Trp Trp Met Lys Gln Ser Leu Ala His
                195                 200                 205
Leu Ser Gln Ser Leu Lys Ala Leu Gly Ser Asp Leu Thr Leu Ile Lys
            210                 215                 220
Thr His Asn Thr Ile Ser Ala Ile Leu Asp Cys Ile Arg Val Thr Gly
225                 230                 235                 240
Ala Thr Lys Val Val Phe Asn His Leu Tyr Asp Pro Val Ser Leu Val
                245                 250                 255
Arg Asp His Thr Val Lys Glu Lys Leu Val Glu Arg Gly Ile Ser Val
                260                 265                 270
Gln Ser Tyr Asn Gly Asp Leu Leu Tyr Glu Pro Trp Glu Ile Tyr Cys
            275                 280                 285
Glu Lys Gly Lys Pro Phe Thr Ser Phe Asn Ser Tyr Trp Lys Lys Cys
            290                 295                 300
Leu Asp Met Ser Ile Glu Ser Val Met Leu Pro Pro Trp Arg Leu
305                 310                 315                 320
Met Pro Ile Thr Ala Ala Ala Glu Ala Ile Trp Ala Cys Ser Ile Glu
                325                 330                 335
Glu Leu Gly Leu Glu Asn Glu Ala Glu Lys Pro Ser Asn Ala Leu Leu
            340                 345                 350
Thr Arg Ala Trp Ser Pro Gly Trp Ser Asn Ala Asp Lys Leu Leu Asn
            355                 360                 365
Glu Phe Ile Glu Lys Gln Leu Ile Asp Tyr Ala Lys Asn Ser Lys Lys
        370                 375                 380
Val Val Gly Asn Ser Thr Ser Leu Leu Ser Pro Tyr Leu His Phe Gly
385                 390                 395                 400
Glu Ile Ser Val Arg His Val Phe Gln Cys Ala Arg Met Lys Gln Ile
                405                 410                 415
Ile Trp Ala Arg Asp Lys Asn Ser Glu Gly Glu Ser Ala Asp Leu
            420                 425                 430
Phe Leu Arg Gly Ile Gly Leu Arg Glu Tyr Ser Arg Tyr Ile Cys Phe
            435                 440                 445
Asn Phe Pro Phe Thr His Glu Gln Ser Leu Leu Ser His Leu Arg Phe
            450                 455                 460
Phe Pro Trp Asp Ala Asp Val Asp Lys Phe Lys Ala Trp Arg Gln Gly
465                 470                 475                 480
Arg Thr Gly Tyr Pro Leu Val Asp Ala Gly Met Arg Glu Leu Trp Ala
                485                 490                 495
Thr Gly Trp Met His Asn Arg Ile Arg Val Ile Val Ser Ser Phe Ala
            500                 505                 510
Val Lys Phe Leu Leu Leu Pro Trp Lys Trp Gly Met Lys Tyr Phe Trp
            515                 520                 525
Asp Thr Leu Leu Asp Ala Asp Leu Glu Cys Asp Ile Leu Gly Trp Gln
            530                 535                 540
Tyr Ile Ser Gly Ser Ile Pro Asp Gly His Glu Leu Asp Arg Leu Asp
545                 550                 555                 560
Asn Pro Ala Leu Gln Gly Ala Lys Tyr Asp Pro Glu Gly Glu Tyr Ile
                565                 570                 575
Arg Gln Trp Leu Pro Glu Leu Ala Arg Leu Pro Thr Glu Trp Ile His
            580                 585                 590
His Pro Trp Asp Ala Pro Leu Thr Val Leu Lys Ala Ser Gly Val Glu
            595                 600                 605
```

```
Leu Gly Thr Asn Tyr Ala Lys Pro Ile Val Asp Ile Asp Thr Ala Arg
            610                 615                 620

Glu Leu Leu Ala Lys Ala Ile Ser Arg Thr Arg Gly Ala Gln Ile Met
625                 630                 635                 640

Ile Gly Ala Ala

<210> SEQ ID NO 9
<211> LENGTH: 727
<212> TYPE: PRT
<213> ORGANISM: Artificial Sequence
<220> FEATURE:
<223> OTHER INFORMATION: synthetic construct

<400> SEQUENCE: 9

Met Arg Lys Val Phe Val Gly Arg Cys Thr Glu Asp Met Thr Glu Asp
1               5                   10                  15

Glu Leu Arg Glu Phe Phe Ser Gln Tyr Gly Asp Val Met Asp Val Phe
            20                  25                  30

Ile Pro Lys Pro Phe Arg Ala Phe Ala Phe Val Thr Phe Ala Asp Asp
            35                  40                  45

Gln Ile Ala Gln Ser Leu Cys Gly Glu Asp Leu Ile Ile Lys Gly Ile
50                  55                  60

Ser Val His Ile Ser Asn Ala Glu Pro Lys His Asn Ser Asn Arg Gln
65                  70                  75                  80

Leu Glu Arg Ser Gly Arg Phe Gly Gly Asn Pro Gly Gly Phe Gly Asn
            85                  90                  95

Gln Gly Gly Phe Gly Asn Ser Arg Gly Gly Gly Ala Gly Leu Gly Asn
            100                 105                 110

Asn Gln Gly Ser Asn Met Gly Gly Gly Met Asn Phe Gly Ala Phe Ser
            115                 120                 125

Ile Asn Pro Ala Met Met Ala Ala Ala Gln Ala Ala Leu Gln Ser Ser
130                 135                 140

Trp Gly Met Met Gly Met Leu Ala Ser Gln Gln Asn Gln Ser Gly Pro
145                 150                 155                 160

Ser Gly Asn Asn Gln Asn Gln Gly Asn Met Gln Arg Glu Pro Asn Gln
            165                 170                 175

Ala Phe Gly Ser Gly Asn Asn Ser Tyr Ser Gly Ser Asn Ser Gly Ala
            180                 185                 190

Ala Ile Gly Trp Gly Ser Ala Ser Asn Ala Gly Ser Gly Ser Gly Phe
            195                 200                 205

Asn Gly Gly Phe Gly Ser Ser Met Asp Ser Lys Ser Ser Gly Trp Gly
            210                 215                 220

Met Leu Glu Ala Thr Met Lys Met Asp Lys Lys Thr Ile Val Trp Phe
225                 230                 235                 240

Arg Arg Asp Leu Arg Ile Glu Asp Asn Pro Ala Leu Ala Ala Ala Ala
            245                 250                 255

His Glu Gly Ser Val Phe Pro Val Phe Ile Trp Cys Pro Glu Glu Glu
            260                 265                 270

Gly Gln Phe Tyr Pro Gly Arg Ala Ser Arg Trp Trp Met Lys Gln Ser
            275                 280                 285

Leu Ala His Leu Ser Gln Ser Leu Lys Ala Leu Gly Ser Asp Leu Thr
            290                 295                 300

Leu Ile Lys Thr His Asn Thr Ile Ser Ala Ile Leu Asp Cys Ile Arg
305                 310                 315                 320
```

```
Val Thr Gly Ala Thr Lys Val Val Phe Asn His Leu Tyr Asp Pro Val
                325                 330                 335

Ser Leu Val Arg Asp His Thr Val Lys Glu Lys Leu Val Glu Arg Gly
                340                 345                 350

Ile Ser Val Gln Ser Tyr Asn Gly Asp Leu Leu Tyr Glu Pro Trp Glu
                355                 360                 365

Ile Tyr Cys Glu Lys Gly Lys Pro Phe Thr Ser Phe Asn Ser Tyr Trp
                370                 375                 380

Lys Lys Cys Leu Asp Met Ser Ile Glu Ser Val Met Leu Pro Pro Pro
385                 390                 395                 400

Trp Arg Leu Met Pro Ile Thr Ala Ala Glu Ala Ile Trp Ala Cys
                405                 410                 415

Ser Ile Glu Glu Leu Gly Leu Glu Asn Glu Ala Glu Lys Pro Ser Asn
                420                 425                 430

Ala Leu Leu Thr Arg Ala Trp Ser Pro Gly Trp Ser Asn Ala Asp Lys
                435                 440                 445

Leu Leu Asn Glu Phe Ile Glu Lys Gln Leu Ile Asp Tyr Ala Lys Asn
                450                 455                 460

Ser Lys Lys Val Val Gly Asn Ser Thr Ser Leu Leu Ser Pro Tyr Leu
465                 470                 475                 480

His Phe Gly Glu Ile Ser Val Arg His Val Phe Gln Cys Ala Arg Met
                485                 490                 495

Lys Gln Ile Ile Trp Ala Arg Asp Lys Asn Ser Glu Gly Glu Glu Ser
                500                 505                 510

Ala Asp Leu Phe Leu Arg Gly Ile Gly Leu Arg Glu Tyr Ser Arg Tyr
                515                 520                 525

Ile Cys Phe Asn Phe Pro Phe Thr His Glu Gln Ser Leu Leu Ser His
                530                 535                 540

Leu Arg Phe Phe Pro Trp Asp Ala Asp Val Asp Lys Phe Lys Ala Trp
545                 550                 555                 560

Arg Gln Gly Arg Thr Gly Tyr Pro Leu Val Asp Ala Gly Met Arg Glu
                565                 570                 575

Leu Trp Ala Thr Gly Trp Met His Asn Arg Ile Arg Val Ile Val Ser
                580                 585                 590

Ser Phe Ala Val Lys Phe Leu Leu Leu Pro Trp Lys Trp Gly Met Lys
                595                 600                 605

Tyr Phe Trp Asp Thr Leu Leu Asp Ala Asp Leu Glu Cys Asp Ile Leu
                610                 615                 620

Gly Trp Gln Tyr Ile Ser Gly Ser Ile Pro Asp Gly His Glu Leu Asp
625                 630                 635                 640

Arg Leu Asp Asn Pro Ala Leu Gln Gly Ala Lys Tyr Asp Pro Glu Gly
                645                 650                 655

Glu Tyr Ile Arg Gln Trp Leu Pro Glu Leu Ala Arg Leu Pro Thr Glu
                660                 665                 670

Trp Ile His His Pro Trp Asp Ala Pro Leu Thr Val Leu Lys Ala Ser
                675                 680                 685

Gly Val Glu Leu Gly Thr Asn Tyr Ala Lys Pro Ile Val Asp Ile Asp
                690                 695                 700

Thr Ala Arg Glu Leu Leu Ala Lys Ala Ile Ser Arg Thr Arg Gly Ala
705                 710                 715                 720

Gln Ile Met Ile Gly Ala Ala
                725
```

<210> SEQ ID NO 10
<211> LENGTH: 813
<212> TYPE: PRT
<213> ORGANISM: Artificial Sequence
<220> FEATURE:
<223> OTHER INFORMATION: synthetic construct

<400> SEQUENCE: 10

```
Met Asp Leu Ile Val Leu Gly Leu Pro Trp Lys Thr Thr Glu Gln Asp
1               5                   10                  15

Leu Lys Glu Tyr Phe Ser Thr Phe Gly Glu Val Leu Met Val Gln Val
                20                  25                  30

Lys Lys Asp Leu Lys Thr Gly His Ser Lys Gly Phe Gly Phe Val Arg
            35                  40                  45

Phe Thr Glu Tyr Glu Thr Gln Val Lys Val Met Ser Gln Arg His Met
    50                  55                  60

Ile Asp Gly Arg Trp Cys Asp Cys Lys Leu Pro Asn Ser Lys Gln Ser
65                  70                  75                  80

Gln Asp Glu Pro Leu Arg Ser Arg Lys Val Phe Val Gly Arg Cys Thr
                85                  90                  95

Glu Asp Met Thr Glu Asp Glu Leu Arg Glu Phe Phe Ser Gln Tyr Gly
            100                 105                 110

Asp Val Met Asp Val Phe Ile Pro Lys Pro Phe Arg Ala Phe Ala Phe
        115                 120                 125

Val Thr Phe Ala Asp Asp Gln Ile Ala Gln Ser Leu Cys Gly Glu Asp
    130                 135                 140

Leu Ile Ile Lys Gly Ile Ser Val His Ile Ser Asn Ala Glu Pro Lys
145                 150                 155                 160

His Asn Ser Asn Arg Gln Leu Glu Arg Ser Gly Arg Phe Gly Gly Asn
                165                 170                 175

Pro Gly Gly Phe Gly Asn Gln Gly Gly Phe Gly Asn Ser Arg Gly Gly
            180                 185                 190

Gly Ala Gly Leu Gly Asn Asn Gln Gly Ser Asn Met Gly Gly Gly Met
        195                 200                 205

Asn Phe Gly Ala Phe Ser Ile Asn Pro Ala Met Met Ala Ala Ala Gln
    210                 215                 220

Ala Ala Leu Gln Ser Ser Trp Gly Met Met Gly Met Leu Ala Ser Gln
225                 230                 235                 240

Gln Asn Gln Ser Gly Pro Ser Gly Asn Asn Gln Asn Gly Asn Met
                245                 250                 255

Gln Arg Glu Pro Asn Gln Ala Phe Gly Ser Gly Asn Asn Ser Tyr Ser
            260                 265                 270

Gly Ser Asn Ser Gly Ala Ala Ile Gly Trp Gly Ser Ala Ser Asn Ala
        275                 280                 285

Gly Ser Gly Ser Gly Phe Asn Gly Gly Phe Gly Ser Ser Met Asp Ser
    290                 295                 300

Lys Ser Ser Gly Trp Gly Met Leu Glu Ala Thr Met Lys Met Asp Lys
305                 310                 315                 320

Lys Thr Ile Val Trp Phe Arg Arg Asp Leu Arg Ile Glu Asp Asn Pro
                325                 330                 335

Ala Leu Ala Ala Ala His Glu Gly Ser Val Phe Pro Val Phe Ile
            340                 345                 350

Trp Cys Pro Glu Glu Glu Gly Gln Phe Tyr Pro Gly Arg Ala Ser Arg
        355                 360                 365

Trp Trp Met Lys Gln Ser Leu Ala His Leu Ser Gln Ser Leu Lys Ala
```

```
                   370                 375                 380
Leu Gly Ser Asp Leu Thr Leu Ile Lys Thr His Asn Thr Ile Ser Ala
385                 390                 395                 400

Ile Leu Asp Cys Ile Arg Val Thr Gly Ala Thr Lys Val Val Phe Asn
                405                 410                 415

His Leu Tyr Asp Pro Val Ser Leu Val Arg Asp His Thr Val Lys Glu
                420                 425                 430

Lys Leu Val Glu Arg Gly Ile Ser Val Gln Ser Tyr Asn Gly Asp Leu
                435                 440                 445

Leu Tyr Glu Pro Trp Glu Ile Tyr Cys Glu Lys Gly Lys Pro Phe Thr
                450                 455                 460

Ser Phe Asn Ser Tyr Trp Lys Lys Cys Leu Asp Met Ser Ile Glu Ser
465                 470                 475                 480

Val Met Leu Pro Pro Pro Trp Arg Leu Met Pro Ile Thr Ala Ala Ala
                485                 490                 495

Glu Ala Ile Trp Ala Cys Ser Ile Glu Glu Leu Gly Leu Glu Asn Glu
                500                 505                 510

Ala Glu Lys Pro Ser Asn Ala Leu Leu Thr Arg Ala Trp Ser Pro Gly
                515                 520                 525

Trp Ser Asn Ala Asp Lys Leu Leu Asn Glu Phe Ile Glu Lys Gln Leu
                530                 535                 540

Ile Asp Tyr Ala Lys Asn Ser Lys Lys Val Val Gly Asn Ser Thr Ser
545                 550                 555                 560

Leu Leu Ser Pro Tyr Leu His Phe Gly Glu Ile Ser Val Arg His Val
                565                 570                 575

Phe Gln Cys Ala Arg Met Lys Gln Ile Ile Trp Ala Arg Asp Lys Asn
                580                 585                 590

Ser Glu Gly Glu Ser Ala Asp Leu Phe Leu Arg Gly Ile Gly Leu
                595                 600                 605

Arg Glu Tyr Ser Arg Tyr Ile Cys Phe Asn Phe Pro Phe Thr His Glu
                610                 615                 620

Gln Ser Leu Leu Ser His Leu Arg Phe Phe Pro Trp Asp Ala Asp Val
625                 630                 635                 640

Asp Lys Phe Lys Ala Trp Arg Gln Gly Arg Thr Gly Tyr Pro Leu Val
                645                 650                 655

Asp Ala Gly Met Arg Glu Leu Trp Ala Thr Gly Trp Met His Asn Arg
                660                 665                 670

Ile Arg Val Ile Val Ser Ser Phe Ala Val Lys Phe Leu Leu Leu Pro
                675                 680                 685

Trp Lys Trp Gly Met Lys Tyr Phe Trp Asp Thr Leu Leu Asp Ala Asp
                690                 695                 700

Leu Glu Cys Asp Ile Leu Gly Trp Gln Tyr Ile Ser Gly Ser Ile Pro
705                 710                 715                 720

Asp Gly His Glu Leu Asp Arg Leu Asp Asn Pro Ala Leu Gln Gly Ala
                725                 730                 735

Lys Tyr Asp Pro Glu Gly Glu Tyr Ile Arg Gln Trp Leu Pro Glu Leu
                740                 745                 750

Ala Arg Leu Pro Thr Glu Trp Ile His His Pro Trp Asp Ala Pro Leu
                755                 760                 765

Thr Val Leu Lys Ala Ser Gly Val Glu Leu Gly Thr Asn Tyr Ala Lys
                770                 775                 780

Pro Ile Val Asp Ile Asp Thr Ala Arg Glu Leu Leu Ala Lys Ala Ile
785                 790                 795                 800
```

-continued

Ser Arg Thr Arg Gly Ala Gln Ile Met Ile Gly Ala Ala
            805                 810

<210> SEQ ID NO 11
<211> LENGTH: 642
<212> TYPE: PRT
<213> ORGANISM: Artificial Sequence
<220> FEATURE:
<223> OTHER INFORMATION: synthetic construct

<400> SEQUENCE: 11

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
        370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Arg Gly Gly Arg Phe Gly Gly Asn Pro Gly Gly Phe Gly
            500                 505                 510

Asn Gln Gly Gly Phe Gly Asn Ser Arg Gly Gly Gly Ala Gly Leu Gly
        515                 520                 525

Asn Asn Gln Gly Ser Asn Met Gly Gly Gly Met Asn Phe Gly Ala Phe
    530                 535                 540

Ser Ile Asn Pro Ala Met Met Ala Ala Ala Gln Ala Ala Leu Gln Ser
545                 550                 555                 560

Ser Trp Gly Met Met Gly Met Leu Ala Ser Gln Gln Asn Gln Ser Gly
                565                 570                 575

Pro Ser Gly Asn Asn Gln Asn Gln Gly Asn Met Gln Arg Glu Pro Asn
            580                 585                 590

Gln Ala Phe Gly Ser Gly Asn Asn Ser Tyr Ser Gly Ser Asn Ser Gly
        595                 600                 605

Ala Ala Ile Gly Trp Gly Ser Ala Ser Asn Ala Gly Ser Gly Ser Gly
    610                 615                 620

Phe Asn Gly Gly Phe Gly Ser Ser Met Asp Ser Lys Ser Ser Gly Trp
625                 630                 635                 640

Gly Met

<210> SEQ ID NO 12
<211> LENGTH: 725
<212> TYPE: PRT
<213> ORGANISM: Artificial Sequence
<220> FEATURE:
<223> OTHER INFORMATION: synthetic construct

<400> SEQUENCE: 12

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

-continued

```
Gln Ser Leu Lys Ala Leu Gly Ser Asp Leu Thr Leu Ile Lys Thr His
 65                  70                  75                  80

Asn Thr Ile Ser Ala Ile Leu Asp Cys Ile Arg Val Thr Gly Ala Thr
                 85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
                195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Glu Ser Ala Asp Leu Phe Leu
    275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
```

```
                    485                 490                 495
Ala Ala Ala Arg Gly Arg Lys Val Phe Val Gly Arg Cys Thr Glu Asp
            500                 505                 510

Met Thr Glu Asp Glu Leu Arg Glu Phe Phe Ser Gln Tyr Gly Asp Val
        515                 520                 525

Met Asp Val Phe Ile Pro Lys Pro Phe Arg Ala Phe Ala Phe Val Thr
    530                 535                 540

Phe Ala Asp Asp Gln Ile Ala Gln Ser Leu Cys Gly Glu Asp Leu Ile
545                 550                 555                 560

Ile Lys Gly Ile Ser Val His Ile Ser Asn Ala Glu Pro Lys His Asn
                565                 570                 575

Ser Asn Arg Gln Leu Glu Arg Ser Arg Phe Gly Gly Asn Pro Gly
            580                 585                 590

Gly Phe Gly Asn Gln Gly Gly Phe Gly Asn Ser Arg Gly Gly Ala
        595                 600                 605

Gly Leu Gly Asn Asn Gln Gly Ser Asn Met Gly Gly Met Asn Phe
    610                 615                 620

Gly Ala Phe Ser Ile Asn Pro Ala Met Met Ala Ala Ala Gln Ala Ala
625                 630                 635                 640

Leu Gln Ser Ser Trp Gly Met Met Gly Met Leu Ala Ser Gln Gln Asn
                645                 650                 655

Gln Ser Gly Pro Ser Gly Asn Asn Gln Asn Gln Gly Asn Met Gln Arg
            660                 665                 670

Glu Pro Asn Gln Ala Phe Gly Ser Gly Asn Asn Ser Tyr Ser Gly Ser
        675                 680                 685

Asn Ser Gly Ala Ala Ile Gly Trp Gly Ser Ala Ser Asn Ala Gly Ser
    690                 695                 700

Gly Ser Gly Phe Asn Gly Gly Phe Gly Ser Ser Met Asp Ser Lys Ser
705                 710                 715                 720

Ser Gly Trp Gly Met
                725

<210> SEQ ID NO 13
<211> LENGTH: 811
<212> TYPE: PRT
<213> ORGANISM: Artificial Sequence
<220> FEATURE:
<223> OTHER INFORMATION: synthetic construct

<400> SEQUENCE: 13

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
```

-continued

```
              115                 120                 125
Tyr Asn Gly Asp Leu Leu Tyr Glu Pro Trp Glu Ile Tyr Cys Glu Lys
    130                 135                 140
Gly Lys Pro Phe Thr Ser Phe Asn Ser Tyr Trp Lys Lys Cys Leu Asp
145                 150                 155                 160
Met Ser Ile Glu Ser Val Met Leu Pro Pro Trp Arg Leu Met Pro
                165                 170                 175
Ile Thr Ala Ala Ala Glu Ala Ile Trp Ala Cys Ser Ile Glu Glu Leu
            180                 185                 190
Gly Leu Glu Asn Glu Ala Glu Lys Pro Ser Asn Ala Leu Leu Thr Arg
        195                 200                 205
Ala Trp Ser Pro Gly Trp Ser Asn Ala Asp Lys Leu Leu Asn Glu Phe
    210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
            260                 265                 270
Ala Arg Asp Lys Asn Ser Glu Gly Glu Glu Ser Ala Asp Leu Phe Leu
        275                 280                 285
Arg Gly Ile Gly Leu Arg Glu Tyr Ser Arg Tyr Ile Cys Phe Asn Phe
    290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
            340                 345                 350
Trp Met His Asn Arg Ile Arg Val Ile Val Ser Ser Phe Ala Val Lys
        355                 360                 365
Phe Leu Leu Leu Pro Trp Lys Trp Gly Met Lys Tyr Phe Trp Asp Thr
    370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
        435                 440                 445
Trp Asp Ala Pro Leu Thr Val Leu Lys Ala Ser Gly Val Glu Leu Gly
    450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Arg Gly Asp Leu Ile Val Leu Gly Leu Pro Trp Lys Thr
            500                 505                 510
Thr Glu Gln Asp Leu Lys Glu Tyr Phe Ser Thr Phe Gly Glu Val Leu
        515                 520                 525
Met Val Gln Val Lys Lys Asp Leu Lys Thr Gly His Ser Lys Gly Phe
    530                 535                 540
```

```
Gly Phe Val Arg Phe Thr Glu Tyr Glu Thr Gln Val Lys Val Met Ser
545                 550                 555                 560

Gln Arg His Met Ile Asp Gly Arg Trp Cys Asp Cys Lys Leu Pro Asn
                565                 570                 575

Ser Lys Gln Ser Gln Asp Glu Pro Leu Arg Ser Arg Lys Val Phe Val
            580                 585                 590

Gly Arg Cys Thr Glu Asp Met Thr Glu Asp Glu Leu Arg Glu Phe Phe
        595                 600                 605

Ser Gln Tyr Gly Asp Val Met Asp Val Phe Ile Pro Lys Pro Phe Arg
    610                 615                 620

Ala Phe Ala Phe Val Thr Phe Ala Asp Asp Gln Ile Ala Gln Ser Leu
625                 630                 635                 640

Cys Gly Glu Asp Leu Ile Ile Lys Gly Ile Ser Val His Ile Ser Asn
                645                 650                 655

Ala Glu Pro Lys His Asn Ser Asn Arg Gln Leu Glu Arg Ser Gly Arg
            660                 665                 670

Phe Gly Gly Asn Pro Gly Gly Phe Gly Asn Gln Gly Phe Gly Asn
        675                 680                 685

Ser Arg Gly Gly Gly Ala Gly Leu Gly Asn Asn Gln Gly Ser Asn Met
    690                 695                 700

Gly Gly Gly Met Asn Phe Gly Ala Phe Ser Ile Asn Pro Ala Met Met
705                 710                 715                 720

Ala Ala Ala Gln Ala Ala Leu Gln Ser Ser Trp Gly Met Met Gly Met
                725                 730                 735

Leu Ala Ser Gln Gln Asn Gln Ser Gly Pro Ser Gly Asn Asn Gln Asn
            740                 745                 750

Gln Gly Asn Met Gln Arg Glu Pro Asn Gln Ala Phe Gly Ser Gly Asn
        755                 760                 765

Asn Ser Tyr Ser Gly Ser Asn Ser Gly Ala Ala Ile Gly Trp Gly Ser
    770                 775                 780

Ala Ser Asn Ala Gly Ser Gly Ser Gly Phe Asn Gly Gly Phe Gly Ser
785                 790                 795                 800

Ser Met Asp Ser Lys Ser Ser Gly Trp Gly Met
                805                 810

<210> SEQ ID NO 14
<211> LENGTH: 1159
<212> TYPE: PRT
<213> ORGANISM: Artificial Sequence
<220> FEATURE:
<223> OTHER INFORMATION: synthetic construct

<400> SEQUENCE: 14

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
                35                  40                  45

Gly Arg Ala Ser Arg Trp Trp Met Lys Gln Ser Leu Ala His Leu Ser
            50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95
```

```
Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
        130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
            195                 200                 205

Ala Trp Ser Pro Gly Trp Ser Asn Ala Asp Lys Leu Leu Asn Glu Phe
        210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Ser Ala Asp Leu Phe Leu
            275                 280                 285

Arg Gly Ile Gly Leu Arg Glu Tyr Ser Arg Tyr Ile Cys Phe Asn Phe
        290                 295                 300

Pro Phe Thr His Glu Gln Ser Leu Leu Ser His Leu Arg Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Arg Gly Met Ser Glu Tyr Ile Arg Val Thr Glu Asp Glu
            500                 505                 510
```

-continued

Asn Asp Glu Pro Ile Glu Ile Pro Ser Glu Asp Gly Thr Val Leu
515                 520                 525

Leu Ser Thr Val Thr Ala Gln Phe Pro Gly Ala Cys Gly Leu Arg Tyr
530                 535                 540

Arg Asn Pro Val Ser Gln Cys Met Arg Gly Val Arg Leu Val Glu Gly
545                 550                 555                 560

Ile Leu His Ala Pro Asp Ala Gly Trp Gly Asn Leu Val Tyr Val Val
                565                 570                 575

Asn Tyr Pro Lys Asp Asn Lys Arg Lys Met Asp Glu Thr Asp Ala Ser
                580                 585                 590

Ser Ala Val Lys Val Lys Arg Ala Val Gln Lys Thr Ser Asp Leu Ile
                595                 600                 605

Val Leu Gly Leu Pro Trp Lys Thr Thr Glu Gln Asp Leu Lys Glu Tyr
                610                 615                 620

Phe Ser Thr Phe Gly Glu Val Leu Met Val Gln Val Lys Lys Asp Leu
625                 630                 635                 640

Lys Thr Gly His Ser Lys Gly Phe Gly Phe Val Arg Phe Thr Glu Tyr
                645                 650                 655

Glu Thr Gln Val Lys Val Met Ser Gln Arg His Met Ile Asp Gly Arg
                660                 665                 670

Trp Cys Asp Cys Lys Leu Pro Asn Ser Lys Gln Ser Gln Asp Glu Pro
                675                 680                 685

Leu Arg Ser Arg Lys Val Phe Val Gly Arg Cys Thr Glu Asp Met Thr
                690                 695                 700

Glu Asp Glu Leu Arg Glu Phe Phe Ser Gln Tyr Gly Asp Val Met Asp
705                 710                 715                 720

Val Phe Ile Pro Lys Pro Phe Arg Ala Phe Ala Phe Val Thr Phe Ala
                725                 730                 735

Asp Asp Gln Ile Ala Gln Ser Leu Cys Gly Glu Asp Leu Ile Ile Lys
                740                 745                 750

Gly Ile Ser Val His Ile Ser Asn Ala Glu Pro Lys His Asn Ser Asn
                755                 760                 765

Arg Gln Leu Glu Arg Ser Gly Arg Phe Gly Gly Asn Pro Gly Gly Phe
                770                 775                 780

Gly Asn Gln Gly Gly Phe Gly Asn Ser Arg Gly Gly Gly Ala Gly Leu
785                 790                 795                 800

Gly Asn Asn Gln Gly Ser Asn Met Gly Gly Met Asn Phe Gly Ala
                805                 810                 815

Phe Ser Ile Asn Pro Ala Met Met Ala Ala Gln Ala Ala Leu Gln
                820                 825                 830

Ser Ser Trp Gly Met Met Gly Met Leu Ala Ser Gln Gln Asn Gln Ser
                835                 840                 845

Gly Pro Ser Gly Asn Asn Gln Asn Gln Gly Asn Met Gln Arg Glu Pro
                850                 855                 860

Asn Gln Ala Phe Gly Ser Gly Asn Asn Ser Tyr Ser Gly Ser Asn Ser
865                 870                 875                 880

Gly Ala Ala Ile Gly Trp Gly Ser Ala Ser Asn Ala Gly Ser Gly Ser
                885                 890                 895

Gly Phe Asn Gly Gly Phe Gly Ser Ser Met Asp Ser Lys Ser Ser Gly
                900                 905                 910

Trp Gly Met Ser Arg Asp Pro Pro Val Ala Thr Met Val Ser Lys Gly
                915                 920                 925

Glu Glu Asp Asn Met Ala Ile Ile Lys Glu Phe Met Arg Phe Lys Val

```
                    930             935             940
His Met Glu Gly Ser Val Asn Gly His Glu Phe Glu Ile Glu Gly Glu
945                 950             955                 960

Gly Glu Gly Arg Pro Tyr Glu Gly Thr Gln Thr Ala Lys Leu Lys Val
                965             970                 975

Thr Lys Gly Gly Pro Leu Pro Phe Ala Trp Asp Ile Leu Ser Pro Gln
                980             985                 990

Phe Met Tyr Gly Ser Lys Ala Tyr Val Lys His Pro Ala Asp Ile Pro
                995             1000                1005

Asp Tyr Leu Lys Leu Ser Phe Pro Glu Gly Phe Lys Trp Glu Arg
        1010            1015                1020

Val Met Asn Phe Glu Asp Gly Gly Val Val Thr Val Thr Gln Asp
        1025            1030                1035

Ser Ser Leu Gln Asp Gly Glu Phe Ile Tyr Lys Val Lys Leu Arg
        1040            1045                1050

Gly Thr Asn Phe Pro Ser Asp Gly Pro Val Met Gln Lys Lys Thr
        1055            1060                1065

Met Gly Trp Glu Ala Ser Ser Glu Arg Met Tyr Pro Glu Asp Gly
        1070            1075                1080

Ala Leu Lys Gly Glu Ile Lys Gln Arg Leu Lys Leu Lys Asp Gly
        1085            1090                1095

Gly His Tyr Asp Ala Glu Val Lys Thr Thr Tyr Lys Ala Lys Lys
        1100            1105                1110

Pro Val Gln Leu Pro Gly Ala Tyr Asn Val Asn Ile Lys Leu Asp
        1115            1120                1125

Ile Thr Ser His Asn Glu Asp Tyr Thr Ile Val Glu Gln Tyr Glu
        1130            1135                1140

Arg Ala Glu Gly Arg His Ser Thr Gly Gly Met Asp Glu Leu Tyr
        1145            1150                1155

Lys

<210> SEQ ID NO 15
<211> LENGTH: 1160
<212> TYPE: PRT
<213> ORGANISM: Artificial Sequence
<220> FEATURE:
<223> OTHER INFORMATION: synthetic construct

<400> SEQUENCE: 15

Met Ser Glu Tyr Ile Arg Val Thr Asp Glu Asn Asp Glu Pro Ile
1               5                   10                  15

Glu Ile Pro Ser Glu Asp Asp Gly Thr Val Leu Leu Ser Thr Val Thr
                20              25                  30

Ala Gln Phe Pro Gly Ala Cys Gly Leu Arg Tyr Arg Asn Pro Val Ser
                35              40                  45

Gln Cys Met Arg Gly Val Arg Leu Val Glu Gly Ile Leu His Ala Pro
                50              55                  60

Asp Ala Gly Trp Gly Asn Leu Val Tyr Val Val Asn Tyr Pro Lys Asp
65              70                  75                  80

Asn Lys Arg Lys Met Asp Glu Thr Asp Ala Ser Ser Ala Val Lys Val
                85              90                  95

Lys Arg Ala Val Gln Lys Thr Ser Asp Leu Ile Val Leu Gly Leu Pro
                100             105                 110

Trp Lys Thr Thr Glu Gln Asp Leu Lys Glu Tyr Phe Ser Thr Phe Gly
                115             120                 125
```

-continued

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
                180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
                260                 265                 270

Ser Gly Arg Phe Gly Gly Asn Pro Gly Gly Phe Gly Asn Gln Gly Gly
        275                 280                 285

Phe Gly Asn Ser Arg Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
                340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met Leu Glu
                405                 410                 415

Ala Thr Met Lys Met Asp Lys Lys Thr Ile Val Trp Phe Arg Arg Asp
                420                 425                 430

Leu Arg Ile Glu Asp Asn Pro Ala Leu Ala Ala Ala His Glu Gly
        435                 440                 445

Ser Val Phe Pro Val Phe Ile Trp Cys Pro Glu Glu Glu Gly Gln Phe
    450                 455                 460

Tyr Pro Gly Arg Ala Ser Arg Trp Trp Met Lys Gln Ser Leu Ala His
465                 470                 475                 480

Leu Ser Gln Ser Leu Lys Ala Leu Gly Ser Asp Leu Thr Leu Ile Lys
                485                 490                 495

Thr His Asn Thr Ile Ser Ala Ile Leu Asp Cys Ile Arg Val Thr Gly
                500                 505                 510

Ala Thr Lys Val Val Phe Asn His Leu Tyr Asp Pro Val Ser Leu Val
        515                 520                 525

Arg Asp His Thr Val Lys Glu Lys Leu Val Glu Arg Gly Ile Ser Val
530                 535                 540

```
Gln Ser Tyr Asn Gly Asp Leu Leu Tyr Glu Pro Trp Glu Ile Tyr Cys
545                 550                 555                 560

Glu Lys Gly Lys Pro Phe Thr Ser Phe Asn Ser Tyr Trp Lys Lys Cys
                565                 570                 575

Leu Asp Met Ser Ile Glu Ser Val Met Leu Pro Pro Trp Arg Leu
            580                 585                 590

Met Pro Ile Thr Ala Ala Ala Glu Ala Ile Trp Ala Cys Ser Ile Glu
            595                 600                 605

Glu Leu Gly Leu Glu Asn Glu Ala Glu Lys Pro Ser Asn Ala Leu Leu
            610                 615                 620

Thr Arg Ala Trp Ser Pro Gly Trp Ser Asn Ala Asp Lys Leu Leu Asn
625                 630                 635                 640

Glu Phe Ile Glu Lys Gln Leu Ile Asp Tyr Ala Lys Asn Ser Lys Lys
                645                 650                 655

Val Val Gly Asn Ser Thr Ser Leu Leu Ser Pro Tyr Leu His Phe Gly
                660                 665                 670

Glu Ile Ser Val Arg His Val Phe Gln Cys Ala Arg Met Lys Gln Ile
            675                 680                 685

Ile Trp Ala Arg Asp Lys Asn Ser Glu Gly Glu Ser Ala Asp Leu
            690                 695                 700

Phe Leu Arg Gly Ile Gly Leu Arg Glu Tyr Ser Arg Tyr Ile Cys Phe
705                 710                 715                 720

Asn Phe Pro Phe Thr His Glu Gln Ser Leu Leu Ser His Leu Arg Phe
                725                 730                 735

Phe Pro Trp Asp Ala Asp Val Asp Lys Phe Lys Ala Trp Arg Gln Gly
                740                 745                 750

Arg Thr Gly Tyr Pro Leu Val Asp Ala Gly Met Arg Glu Leu Trp Ala
            755                 760                 765

Thr Gly Trp Met His Asn Arg Ile Arg Val Ile Val Ser Ser Phe Ala
            770                 775                 780

Val Lys Phe Leu Leu Leu Pro Trp Lys Trp Gly Met Lys Tyr Phe Trp
785                 790                 795                 800

Asp Thr Leu Leu Asp Ala Asp Leu Glu Cys Asp Ile Leu Gly Trp Gln
                805                 810                 815

Tyr Ile Ser Gly Ser Ile Pro Asp Gly His Glu Leu Asp Arg Leu Asp
            820                 825                 830

Asn Pro Ala Leu Gln Gly Ala Lys Tyr Asp Pro Glu Gly Glu Tyr Ile
            835                 840                 845

Arg Gln Trp Leu Pro Glu Leu Ala Arg Leu Pro Thr Glu Trp Ile His
850                 855                 860

His Pro Trp Asp Ala Pro Leu Thr Val Leu Lys Ala Ser Gly Val Glu
865                 870                 875                 880

Leu Gly Thr Asn Tyr Ala Lys Pro Ile Val Asp Ile Asp Thr Ala Arg
                885                 890                 895

Glu Leu Leu Ala Lys Ala Ile Ser Arg Thr Arg Gly Ala Gln Ile Met
            900                 905                 910

Ile Gly Ala Ala Ala Arg Asp Pro Pro Val Ala Thr Met Val Ser Lys
            915                 920                 925

Gly Glu Glu Asp Asn Met Ala Ile Ile Lys Glu Phe Met Arg Phe Lys
            930                 935                 940

Val His Met Glu Gly Ser Val Asn Gly His Glu Phe Glu Ile Glu Gly
945                 950                 955                 960

Glu Gly Glu Gly Arg Pro Tyr Glu Gly Thr Gln Thr Ala Lys Leu Lys
```

```
                965                 970                 975
Val Thr Lys Gly Gly Pro Leu Pro Phe Ala Trp Asp Ile Leu Ser Pro
            980                 985                 990

Gln Phe Met Tyr Gly Ser Lys Ala Tyr Val Lys His Pro Ala Asp Ile
        995                1000                1005

Pro Asp Tyr Leu Lys Leu Ser Phe Pro Glu Gly Phe Lys Trp Glu
   1010                1015                1020

Arg Val Met Asn Phe Glu Asp Gly Gly Val Val Thr Val Thr Gln
   1025                1030                1035

Asp Ser Ser Leu Gln Asp Gly Glu Phe Ile Tyr Lys Val Lys Leu
   1040                1045                1050

Arg Gly Thr Asn Phe Pro Ser Asp Gly Pro Val Met Gln Lys Lys
   1055                1060                1065

Thr Met Gly Trp Glu Ala Ser Ser Glu Arg Met Tyr Pro Glu Asp
   1070                1075                1080

Gly Ala Leu Lys Gly Glu Ile Lys Gln Arg Leu Lys Leu Lys Asp
   1085                1090                1095

Gly Gly His Tyr Asp Ala Glu Val Lys Thr Thr Tyr Lys Ala Lys
   1100                1105                1110

Lys Pro Val Gln Leu Pro Gly Ala Tyr Asn Val Asn Ile Lys Leu
   1115                1120                1125

Asp Ile Thr Ser His Asn Glu Asp Tyr Thr Ile Val Glu Gln Tyr
   1130                1135                1140

Glu Arg Ala Glu Gly Arg His Ser Thr Gly Gly Met Asp Glu Leu
   1145                1150                1155

Tyr Lys
   1160

<210> SEQ ID NO 16
<211> LENGTH: 1152
<212> TYPE: PRT
<213> ORGANISM: Artificial Sequence
<220> FEATURE:
<223> OTHER INFORMATION: synthetic construct

<400> SEQUENCE: 16

Met Val Ser Lys Gly Glu Glu Asp Asn Met Ala Ile Ile Lys Glu Phe
1               5                  10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
```

-continued

```
            145                 150                 155                 160
        Ala Leu Lys Gly Glu Ile Lys Gln Arg Leu Lys Leu Lys Asp Gly Gly
                        165                 170                 175
        His Tyr Asp Ala Glu Val Lys Thr Thr Tyr Lys Ala Lys Lys Pro Val
                        180                 185                 190
        Gln Leu Pro Gly Ala Tyr Asn Val Asn Ile Lys Leu Asp Ile Thr Ser
                        195                 200                 205
        His Asn Glu Asp Tyr Thr Ile Val Glu Gln Tyr Glu Arg Ala Glu Gly
                210                 215                 220
        Arg His Ser Thr Gly Gly Met Asp Glu Leu Tyr Lys Met Ser Glu Tyr
        225                 230                 235                 240
        Ile Arg Val Thr Glu Asp Asn Asp Glu Pro Ile Glu Ile Pro Ser
                        245                 250                 255
        Glu Asp Asp Gly Thr Val Leu Leu Ser Thr Val Thr Ala Gln Phe Pro
                        260                 265                 270
        Gly Ala Cys Gly Leu Arg Tyr Arg Asn Pro Val Ser Gln Cys Met Arg
                        275                 280                 285
        Gly Val Arg Leu Val Glu Gly Ile Leu His Ala Pro Asp Ala Gly Trp
                        290                 295                 300
        Gly Asn Leu Val Tyr Val Val Asn Tyr Pro Lys Asp Asn Lys Arg Lys
        305                 310                 315                 320
        Met Asp Glu Thr Asp Ala Ser Ser Ala Val Lys Val Lys Arg Ala Val
                        325                 330                 335
        Gln Lys Thr Ser Asp Leu Ile Val Leu Gly Leu Pro Trp Lys Thr Thr
                        340                 345                 350
        Glu Gln Asp Leu Lys Glu Tyr Phe Ser Thr Phe Gly Glu Val Leu Met
                        355                 360                 365
        Val Gln Val Lys Lys Asp Leu Lys Thr Gly His Ser Lys Gly Phe Gly
                        370                 375                 380
        Phe Val Arg Phe Thr Glu Tyr Glu Thr Gln Val Lys Val Met Ser Gln
        385                 390                 395                 400
        Arg His Met Ile Asp Gly Arg Trp Cys Asp Cys Lys Leu Pro Asn Ser
                        405                 410                 415
        Lys Gln Ser Gln Asp Glu Pro Leu Arg Ser Arg Lys Val Phe Val Gly
                        420                 425                 430
        Arg Cys Thr Glu Asp Met Thr Glu Asp Glu Leu Arg Glu Phe Phe Ser
                        435                 440                 445
        Gln Tyr Gly Asp Val Met Asp Val Phe Ile Pro Lys Pro Phe Arg Ala
                450                 455                 460
        Phe Ala Phe Val Thr Phe Ala Asp Asp Gln Ile Ala Gln Ser Leu Cys
        465                 470                 475                 480
        Gly Glu Asp Leu Ile Ile Lys Gly Ile Ser Val His Ile Ser Asn Ala
                        485                 490                 495
        Glu Pro Lys His Asn Ser Asn Arg Gln Leu Glu Arg Ser Gly Arg Phe
                        500                 505                 510
        Gly Gly Asn Pro Gly Gly Phe Gly Asn Gln Gly Gly Phe Gly Asn Ser
                        515                 520                 525
        Arg Gly Gly Gly Ala Gly Leu Gly Asn Asn Gln Gly Ser Asn Met Gly
                        530                 535                 540
        Gly Gly Met Asn Phe Gly Ala Phe Ser Ile Asn Pro Ala Met Met Ala
        545                 550                 555                 560
        Ala Ala Gln Ala Ala Leu Gln Ser Ser Trp Gly Met Met Gly Met Leu
                        565                 570                 575
```

```
Ala Ser Gln Gln Asn Gln Ser Gly Pro Ser Gly Asn Gln Asn Gln
            580                 585                 590

Gly Asn Met Gln Arg Glu Pro Asn Gln Ala Phe Gly Ser Gly Asn Asn
        595                 600                 605

Ser Tyr Ser Gly Ser Asn Ser Gly Ala Ala Ile Gly Trp Gly Ser Ala
    610                 615                 620

Ser Asn Ala Gly Ser Gly Ser Phe Asn Gly Gly Phe Gly Ser Ser
625                 630                 635                 640

Met Asp Ser Lys Ser Ser Gly Trp Gly Met Leu Glu Ala Thr Met Lys
                645                 650                 655

Met Asp Lys Lys Thr Ile Val Trp Phe Arg Arg Asp Leu Arg Ile Glu
            660                 665                 670

Asp Asn Pro Ala Leu Ala Ala Ala His Glu Gly Ser Val Phe Pro
        675                 680                 685

Val Phe Ile Trp Cys Pro Glu Glu Gly Gln Phe Tyr Pro Gly Arg
    690                 695                 700

Ala Ser Arg Trp Trp Met Lys Gln Ser Leu Ala His Leu Ser Gln Ser
705                 710                 715                 720

Leu Lys Ala Leu Gly Ser Asp Leu Thr Leu Ile Lys Thr His Asn Thr
                725                 730                 735

Ile Ser Ala Ile Leu Asp Cys Ile Arg Val Thr Gly Ala Thr Lys Val
            740                 745                 750

Val Phe Asn His Leu Tyr Asp Pro Val Ser Leu Val Arg Asp His Thr
        755                 760                 765

Val Lys Glu Lys Leu Val Glu Arg Gly Ile Ser Val Gln Ser Tyr Asn
    770                 775                 780

Gly Asp Leu Leu Tyr Glu Pro Trp Glu Ile Tyr Cys Glu Lys Gly Lys
785                 790                 795                 800

Pro Phe Thr Ser Phe Asn Ser Tyr Trp Lys Lys Cys Leu Asp Met Ser
                805                 810                 815

Ile Glu Ser Val Met Leu Pro Pro Trp Arg Leu Met Pro Ile Thr
            820                 825                 830

Ala Ala Ala Glu Ala Ile Trp Ala Cys Ser Ile Glu Glu Leu Gly Leu
        835                 840                 845

Glu Asn Glu Ala Glu Lys Pro Ser Asn Ala Leu Leu Thr Arg Ala Trp
    850                 855                 860

Ser Pro Gly Trp Ser Asn Ala Asp Lys Leu Leu Asn Glu Phe Ile Glu
865                 870                 875                 880

Lys Gln Leu Ile Asp Tyr Ala Lys Asn Ser Lys Val Val Gly Asn
                885                 890                 895

Ser Thr Ser Leu Leu Ser Pro Tyr Leu His Phe Gly Glu Ile Ser Val
            900                 905                 910

Arg His Val Phe Gln Cys Ala Arg Met Lys Gln Ile Ile Trp Ala Arg
        915                 920                 925

Asp Lys Asn Ser Glu Gly Glu Glu Ser Ala Asp Leu Phe Leu Arg Gly
    930                 935                 940

Ile Gly Leu Arg Glu Tyr Ser Arg Tyr Ile Cys Phe Asn Phe Pro Phe
945                 950                 955                 960

Thr His Glu Gln Ser Leu Leu Ser His Leu Arg Phe Phe Pro Trp Asp
                965                 970                 975

Ala Asp Val Asp Lys Phe Lys Ala Trp Arg Gln Gly Arg Thr Gly Tyr
            980                 985                 990
```

```
Pro Leu Val Asp Ala Gly Met Arg Glu Leu Trp Ala Thr Gly Trp Met
        995                1000                1005

His Asn Arg Ile Arg Val Ile Val Ser Ser Phe Ala Val Lys Phe
        1010                1015                1020

Leu Leu Leu Pro Trp Lys Trp Gly Met Lys Tyr Phe Trp Asp Thr
        1025                1030                1035

Leu Leu Asp Ala Asp Leu Glu Cys Asp Ile Leu Gly Trp Gln Tyr
        1040                1045                1050

Ile Ser Gly Ser Ile Pro Asp Gly His Glu Leu Asp Arg Leu Asp
        1055                1060                1065

Asn Pro Ala Leu Gln Gly Ala Lys Tyr Asp Pro Glu Gly Glu Tyr
        1070                1075                1080

Ile Arg Gln Trp Leu Pro Glu Leu Ala Arg Leu Pro Thr Glu Trp
        1085                1090                1095

Ile His His Pro Trp Asp Ala Pro Leu Thr Val Leu Lys Ala Ser
        1100                1105                1110

Gly Val Glu Leu Gly Thr Asn Tyr Ala Lys Pro Ile Val Asp Ile
        1115                1120                1125

Asp Thr Ala Arg Glu Leu Leu Ala Lys Ala Ile Ser Arg Thr Arg
        1130                1135                1140

Gly Ala Gln Ile Met Ile Gly Ala Ala
        1145                1150

<210> SEQ ID NO 17
<211> LENGTH: 888
<212> TYPE: PRT
<213> ORGANISM: Artificial Sequence
<220> FEATURE:
<223> OTHER INFORMATION: synthetic construct

<400> SEQUENCE: 17

Met Gly Arg Phe Gly Gly Asn Pro Gly Gly Phe Gly Asn Gln Gly Gly
1               5                   10                  15

Phe Gly Asn Ser Arg Gly Gly Ala Gly Leu Gly Asn Asn Gln Gly
                20                  25                  30

Ser Asn Met Gly Gly Gly Met Asn Phe Gly Ala Phe Ser Ile Asn Pro
            35                  40                  45

Ala Met Met Ala Ala Ala Gln Ala Ala Leu Gln Ser Ser Trp Gly Met
    50                  55                  60

Met Gly Met Leu Ala Ser Gln Gln Asn Gln Ser Gly Pro Ser Gly Asn
65                  70                  75                  80

Asn Gln Asn Gln Gly Asn Met Gln Arg Glu Pro Asn Gln Ala Phe Gly
                85                  90                  95

Ser Gly Asn Asn Ser Tyr Ser Gly Ser Asn Ser Gly Ala Ala Ile Gly
                100                 105                 110

Trp Gly Ser Ala Ser Asn Ala Gly Ser Gly Ser Phe Asn Gly Gly
            115                 120                 125

Phe Gly Ser Ser Met Asp Ser Lys Ser Ser Gly Trp Gly Met Leu Glu
    130                 135                 140

Ala Thr Met Lys Met Asp Lys Lys Thr Ile Val Trp Phe Arg Arg Asp
145                 150                 155                 160

Leu Arg Ile Glu Asp Asn Pro Ala Leu Ala Ala Ala His Glu Gly
                165                 170                 175

Ser Val Phe Pro Val Phe Ile Trp Cys Pro Glu Glu Glu Gly Gln Phe
                180                 185                 190
```

```
Tyr Pro Gly Arg Ala Ser Arg Trp Trp Met Lys Gln Ser Leu Ala His
        195                 200                 205

Leu Ser Gln Ser Leu Lys Ala Leu Gly Ser Asp Leu Thr Leu Ile Lys
    210                 215                 220

Thr His Asn Thr Ile Ser Ala Ile Leu Asp Cys Ile Arg Val Thr Gly
225                 230                 235                 240

Ala Thr Lys Val Val Phe Asn His Leu Tyr Asp Pro Val Ser Leu Val
                245                 250                 255

Arg Asp His Thr Val Lys Glu Lys Leu Val Glu Arg Gly Ile Ser Val
            260                 265                 270

Gln Ser Tyr Asn Gly Asp Leu Leu Tyr Glu Pro Trp Glu Ile Tyr Cys
        275                 280                 285

Glu Lys Gly Lys Pro Phe Thr Ser Phe Asn Ser Tyr Trp Lys Lys Cys
    290                 295                 300

Leu Asp Met Ser Ile Glu Ser Val Met Leu Pro Pro Trp Arg Leu
305                 310                 315                 320

Met Pro Ile Thr Ala Ala Glu Ala Ile Trp Ala Cys Ser Ile Glu
                325                 330                 335

Glu Leu Gly Leu Glu Asn Glu Ala Lys Pro Ser Asn Ala Leu Leu
            340                 345                 350

Thr Arg Ala Trp Ser Pro Gly Trp Ser Asn Ala Asp Lys Leu Leu Asn
        355                 360                 365

Glu Phe Ile Glu Lys Gln Leu Ile Asp Tyr Ala Lys Asn Ser Lys Lys
    370                 375                 380

Val Val Gly Asn Ser Thr Ser Leu Leu Ser Pro Tyr Leu His Phe Gly
385                 390                 395                 400

Glu Ile Ser Val Arg His Val Phe Gln Cys Ala Arg Met Lys Gln Ile
                405                 410                 415

Ile Trp Ala Arg Asp Lys Asn Ser Glu Gly Glu Ser Ala Asp Leu
            420                 425                 430

Phe Leu Arg Gly Ile Gly Leu Arg Glu Tyr Ser Arg Tyr Ile Cys Phe
        435                 440                 445

Asn Phe Pro Phe Thr His Glu Gln Ser Leu Leu Ser His Leu Arg Phe
    450                 455                 460

Phe Pro Trp Asp Ala Asp Val Asp Lys Phe Lys Ala Trp Arg Gln Gly
465                 470                 475                 480

Arg Thr Gly Tyr Pro Leu Val Asp Ala Gly Met Arg Glu Leu Trp Ala
                485                 490                 495

Thr Gly Trp Met His Asn Arg Ile Arg Val Ile Val Ser Ser Phe Ala
            500                 505                 510

Val Lys Phe Leu Leu Leu Pro Trp Lys Trp Gly Met Lys Tyr Phe Trp
        515                 520                 525

Asp Thr Leu Leu Asp Ala Asp Leu Glu Cys Asp Ile Leu Gly Trp Gln
    530                 535                 540

Tyr Ile Ser Gly Ser Ile Pro Asp Gly His Glu Leu Asp Arg Leu Asp
545                 550                 555                 560

Asn Pro Ala Leu Gln Gly Ala Lys Tyr Asp Pro Glu Gly Glu Tyr Ile
                565                 570                 575

Arg Gln Trp Leu Pro Glu Leu Ala Arg Leu Pro Thr Glu Trp Ile His
            580                 585                 590

His Pro Trp Asp Ala Pro Leu Thr Val Leu Lys Ala Ser Gly Val Glu
        595                 600                 605

Leu Gly Thr Asn Tyr Ala Lys Pro Ile Val Asp Ile Asp Thr Ala Arg
```

```
                610                 615                 620
Glu Leu Leu Ala Lys Ala Ile Ser Arg Thr Arg Gly Ala Gln Ile Met
625                 630                 635                 640

Ile Gly Ala Ala Ala Arg Asp Pro Val Ala Thr Met Val Ser Lys
                645                 650                 655

Gly Glu Glu Asp Asn Met Ala Ile Ile Lys Glu Phe Met Arg Phe Lys
                660                 665                 670

Val His Met Glu Gly Ser Val Asn Gly His Glu Phe Glu Ile Glu Gly
                675                 680                 685

Glu Gly Glu Gly Arg Pro Tyr Glu Gly Thr Gln Thr Ala Lys Leu Lys
                690                 695                 700

Val Thr Lys Gly Gly Pro Leu Pro Phe Ala Trp Asp Ile Leu Ser Pro
705                 710                 715                 720

Gln Phe Met Tyr Gly Ser Lys Ala Tyr Val Lys His Pro Ala Asp Ile
                725                 730                 735

Pro Asp Tyr Leu Lys Leu Ser Phe Pro Glu Gly Phe Lys Trp Glu Arg
                740                 745                 750

Val Met Asn Phe Glu Asp Gly Gly Val Val Thr Val Thr Gln Asp Ser
                755                 760                 765

Ser Leu Gln Asp Gly Glu Phe Ile Tyr Lys Val Lys Leu Arg Gly Thr
770                 775                 780

Asn Phe Pro Ser Asp Gly Pro Val Met Gln Lys Lys Thr Met Gly Trp
785                 790                 795                 800

Glu Ala Ser Ser Glu Arg Met Tyr Pro Glu Asp Gly Ala Leu Lys Gly
                805                 810                 815

Glu Ile Lys Gln Arg Leu Lys Leu Lys Asp Gly Gly His Tyr Asp Ala
                820                 825                 830

Glu Val Lys Thr Thr Tyr Lys Ala Lys Lys Pro Val Gln Leu Pro Gly
                835                 840                 845

Ala Tyr Asn Val Asn Ile Lys Leu Asp Ile Thr Ser His Asn Glu Asp
                850                 855                 860

Tyr Thr Ile Val Glu Gln Tyr Glu Arg Ala Glu Gly Arg His Ser Thr
865                 870                 875                 880

Gly Gly Met Asp Glu Leu Tyr Lys
                885

<210> SEQ ID NO 18
<211> LENGTH: 971
<212> TYPE: PRT
<213> ORGANISM: Artificial Sequence
<220> FEATURE:
<223> OTHER INFORMATION: synthetic construct

<400> SEQUENCE: 18

Met Arg Lys Val Phe Val Gly Arg Cys Thr Glu Asp Met Thr Glu Asp
1               5                   10                  15

Glu Leu Arg Glu Phe Phe Ser Gln Tyr Gly Asp Val Met Asp Val Phe
                20                  25                  30

Ile Pro Lys Pro Phe Arg Ala Phe Ala Phe Val Thr Phe Ala Asp Asp
                35                  40                  45

Gln Ile Ala Gln Ser Leu Cys Gly Glu Asp Leu Ile Ile Lys Gly Ile
                50                  55                  60

Ser Val His Ile Ser Asn Ala Glu Pro Lys His Asn Ser Asn Arg Gln
65                  70                  75                  80

Leu Glu Arg Ser Gly Arg Phe Gly Gly Asn Pro Gly Gly Phe Gly Asn
```

```
            85                  90                  95
Gln Gly Gly Phe Gly Asn Ser Arg Gly Gly Ala Gly Leu Gly Asn
            100                 105                 110

Asn Gln Gly Ser Asn Met Gly Gly Met Asn Phe Gly Ala Phe Ser
            115                 120                 125

Ile Asn Pro Ala Met Met Ala Ala Gln Ala Ala Leu Gln Ser Ser
            130                 135                 140

Trp Gly Met Met Gly Met Leu Ala Ser Gln Gln Asn Gln Ser Gly Pro
145                 150                 155                 160

Ser Gly Asn Asn Gln Asn Gln Gly Asn Met Gln Arg Glu Pro Asn Gln
                    165                 170                 175

Ala Phe Gly Ser Gly Asn Asn Ser Tyr Ser Gly Ser Asn Ser Gly Ala
                    180                 185                 190

Ala Ile Gly Trp Gly Ser Ala Ser Asn Ala Gly Ser Gly Ser Gly Phe
                    195                 200                 205

Asn Gly Gly Phe Gly Ser Ser Met Asp Ser Lys Ser Ser Gly Trp Gly
                    210                 215                 220

Met Leu Glu Ala Thr Met Lys Met Asp Lys Lys Thr Ile Val Trp Phe
225                 230                 235                 240

Arg Arg Asp Leu Arg Ile Glu Asp Asn Pro Ala Leu Ala Ala Ala Ala
                    245                 250                 255

His Glu Gly Ser Val Phe Pro Val Phe Ile Trp Cys Pro Glu Glu Glu
                    260                 265                 270

Gly Gln Phe Tyr Pro Gly Arg Ala Ser Arg Trp Trp Met Lys Gln Ser
                    275                 280                 285

Leu Ala His Leu Ser Gln Ser Leu Lys Ala Leu Gly Ser Asp Leu Thr
                    290                 295                 300

Leu Ile Lys Thr His Asn Thr Ile Ser Ala Ile Leu Asp Cys Ile Arg
305                 310                 315                 320

Val Thr Gly Ala Thr Lys Val Val Phe Asn His Leu Tyr Asp Pro Val
                    325                 330                 335

Ser Leu Val Arg Asp His Thr Val Lys Glu Lys Leu Val Glu Arg Gly
                    340                 345                 350

Ile Ser Val Gln Ser Tyr Asn Gly Asp Leu Leu Tyr Glu Pro Trp Glu
                    355                 360                 365

Ile Tyr Cys Glu Lys Gly Lys Pro Phe Thr Ser Phe Asn Ser Tyr Trp
                    370                 375                 380

Lys Lys Cys Leu Asp Met Ser Ile Glu Ser Val Met Leu Pro Pro Pro
385                 390                 395                 400

Trp Arg Leu Met Pro Ile Thr Ala Ala Ala Glu Ala Ile Trp Ala Cys
                    405                 410                 415

Ser Ile Glu Glu Leu Gly Leu Glu Asn Glu Ala Glu Lys Pro Ser Asn
                    420                 425                 430

Ala Leu Leu Thr Arg Ala Trp Ser Pro Gly Trp Ser Asn Ala Asp Lys
                    435                 440                 445

Leu Leu Asn Glu Phe Ile Glu Lys Gln Leu Ile Asp Tyr Ala Lys Asn
                    450                 455                 460

Ser Lys Lys Val Val Gly Asn Ser Thr Ser Leu Leu Ser Pro Tyr Leu
465                 470                 475                 480

His Phe Gly Glu Ile Ser Val Arg His Val Phe Gln Cys Ala Arg Met
                    485                 490                 495

Lys Gln Ile Ile Trp Ala Arg Asp Lys Asn Ser Glu Gly Glu Glu Ser
                    500                 505                 510
```

```
Ala Asp Leu Phe Leu Arg Gly Ile Gly Leu Arg Glu Tyr Ser Arg Tyr
        515                 520                 525

Ile Cys Phe Asn Phe Pro Phe Thr His Glu Gln Ser Leu Leu Ser His
        530                 535                 540

Leu Arg Phe Phe Pro Trp Asp Ala Asp Val Asp Lys Phe Lys Ala Trp
545                 550                 555                 560

Arg Gln Gly Arg Thr Gly Tyr Pro Leu Val Asp Ala Gly Met Arg Glu
                565                 570                 575

Leu Trp Ala Thr Gly Trp Met His Asn Arg Ile Arg Val Ile Val Ser
                580                 585                 590

Ser Phe Ala Val Lys Phe Leu Leu Pro Trp Lys Trp Gly Met Lys
        595                 600                 605

Tyr Phe Trp Asp Thr Leu Leu Asp Ala Asp Leu Glu Cys Asp Ile Leu
        610                 615                 620

Gly Trp Gln Tyr Ile Ser Gly Ser Ile Pro Asp Gly His Glu Leu Asp
625                 630                 635                 640

Arg Leu Asp Asn Pro Ala Leu Gln Gly Ala Lys Tyr Asp Pro Glu Gly
                645                 650                 655

Glu Tyr Ile Arg Gln Trp Leu Pro Glu Leu Ala Arg Leu Pro Thr Glu
                660                 665                 670

Trp Ile His His Pro Trp Asp Ala Pro Leu Thr Val Leu Lys Ala Ser
                675                 680                 685

Gly Val Glu Leu Gly Thr Asn Tyr Ala Lys Pro Ile Val Asp Ile Asp
690                 695                 700

Thr Ala Arg Glu Leu Leu Ala Lys Ala Ile Ser Arg Thr Arg Gly Ala
705                 710                 715                 720

Gln Ile Met Ile Gly Ala Ala Ala Arg Asp Pro Pro Val Ala Thr Met
                725                 730                 735

Val Ser Lys Gly Glu Glu Asp Asn Met Ala Ile Ile Lys Glu Phe Met
                740                 745                 750

Arg Phe Lys Val His Met Glu Gly Ser Val Asn Gly His Glu Phe Glu
        755                 760                 765

Ile Glu Gly Glu Gly Glu Gly Arg Pro Tyr Glu Gly Thr Gln Thr Ala
        770                 775                 780

Lys Leu Lys Val Thr Lys Gly Gly Pro Leu Pro Phe Ala Trp Asp Ile
785                 790                 795                 800

Leu Ser Pro Gln Phe Met Tyr Gly Ser Lys Ala Tyr Val Lys His Pro
                805                 810                 815

Ala Asp Ile Pro Asp Tyr Leu Lys Leu Ser Phe Pro Glu Gly Phe Lys
                820                 825                 830

Trp Glu Arg Val Met Asn Phe Glu Asp Gly Gly Val Val Thr Val Thr
        835                 840                 845

Gln Asp Ser Ser Leu Gln Asp Gly Glu Phe Ile Tyr Lys Val Lys Leu
850                 855                 860

Arg Gly Thr Asn Phe Pro Ser Asp Gly Pro Val Met Gln Lys Lys Thr
865                 870                 875                 880

Met Gly Trp Glu Ala Ser Ser Glu Arg Met Tyr Pro Glu Asp Gly Ala
                885                 890                 895

Leu Lys Gly Glu Ile Lys Gln Arg Leu Lys Leu Lys Asp Gly Gly His
                900                 905                 910

Tyr Asp Ala Glu Val Lys Thr Thr Tyr Lys Ala Lys Lys Pro Val Gln
        915                 920                 925
```

-continued

```
Leu Pro Gly Ala Tyr Asn Val Asn Ile Lys Leu Asp Ile Thr Ser His
            930                 935                 940

Asn Glu Asp Tyr Thr Ile Val Glu Gln Tyr Glu Arg Ala Glu Gly Arg
945                 950                 955                 960

His Ser Thr Gly Gly Met Asp Glu Leu Tyr Lys
                965                 970

<210> SEQ ID NO 19
<211> LENGTH: 1057
<212> TYPE: PRT
<213> ORGANISM: Artificial Sequence
<220> FEATURE:
<223> OTHER INFORMATION: synthetic construct

<400> SEQUENCE: 19

Met Asp Leu Ile Val Leu Gly Leu Pro Trp Lys Thr Thr Glu Gln Asp
1               5                   10                  15

Leu Lys Glu Tyr Phe Ser Thr Phe Gly Glu Val Leu Met Val Gln Val
                20                  25                  30

Lys Lys Asp Leu Lys Thr Gly His Ser Lys Gly Phe Gly Phe Val Arg
            35                  40                  45

Phe Thr Glu Tyr Glu Thr Gln Val Lys Val Met Ser Gln Arg His Met
        50                  55                  60

Ile Asp Gly Arg Trp Cys Asp Cys Lys Leu Pro Asn Ser Lys Gln Ser
65                  70                  75                  80

Gln Asp Glu Pro Leu Arg Ser Arg Lys Val Phe Val Gly Arg Cys Thr
                85                  90                  95

Glu Asp Met Thr Glu Asp Glu Leu Arg Glu Phe Phe Ser Gln Tyr Gly
            100                 105                 110

Asp Val Met Asp Val Phe Ile Pro Lys Pro Phe Arg Ala Phe Ala Phe
        115                 120                 125

Val Thr Phe Ala Asp Asp Gln Ile Ala Gln Ser Leu Cys Gly Glu Asp
130                 135                 140

Leu Ile Ile Lys Gly Ile Ser Val His Ile Ser Asn Ala Glu Pro Lys
145                 150                 155                 160

His Asn Ser Asn Arg Gln Leu Glu Arg Ser Gly Arg Phe Gly Gly Asn
                165                 170                 175

Pro Gly Gly Phe Gly Asn Gln Gly Gly Phe Gly Asn Ser Arg Gly Gly
            180                 185                 190

Gly Ala Gly Leu Gly Asn Asn Gln Gly Ser Asn Met Gly Gly Gly Met
        195                 200                 205

Asn Phe Gly Ala Phe Ser Ile Asn Pro Ala Met Met Ala Ala Ala Gln
    210                 215                 220

Ala Ala Leu Gln Ser Ser Trp Gly Met Met Gly Met Leu Ala Ser Gln
225                 230                 235                 240

Gln Asn Gln Ser Gly Pro Ser Gly Asn Asn Gln Asn Gln Gly Asn Met
                245                 250                 255

Gln Arg Glu Pro Asn Gln Ala Phe Gly Ser Gly Asn Asn Ser Tyr Ser
            260                 265                 270

Gly Ser Asn Ser Gly Ala Ala Ile Gly Trp Gly Ser Ala Ser Asn Ala
        275                 280                 285

Gly Ser Gly Ser Gly Phe Asn Gly Gly Phe Gly Ser Ser Met Asp Ser
    290                 295                 300

Lys Ser Ser Gly Trp Gly Met Leu Glu Ala Thr Met Lys Met Asp Lys
305                 310                 315                 320
```

```
Lys Thr Ile Val Trp Phe Arg Arg Asp Leu Arg Ile Glu Asp Asn Pro
                325                 330                 335

Ala Leu Ala Ala Ala His Glu Gly Ser Val Phe Pro Val Phe Ile
            340                 345                 350

Trp Cys Pro Glu Glu Glu Gly Gln Phe Tyr Pro Gly Arg Ala Ser Arg
            355                 360                 365

Trp Trp Met Lys Gln Ser Leu Ala His Leu Ser Gln Ser Leu Lys Ala
            370                 375                 380

Leu Gly Ser Asp Leu Thr Leu Ile Lys Thr His Asn Thr Ile Ser Ala
385                 390                 395                 400

Ile Leu Asp Cys Ile Arg Val Thr Gly Ala Thr Lys Val Val Phe Asn
                405                 410                 415

His Leu Tyr Asp Pro Val Ser Leu Val Arg Asp His Thr Val Lys Glu
            420                 425                 430

Lys Leu Val Glu Arg Gly Ile Ser Val Gln Ser Tyr Asn Gly Asp Leu
            435                 440                 445

Leu Tyr Glu Pro Trp Glu Ile Tyr Cys Glu Lys Gly Lys Pro Phe Thr
            450                 455                 460

Ser Phe Asn Ser Tyr Trp Lys Lys Cys Leu Asp Met Ser Ile Glu Ser
465                 470                 475                 480

Val Met Leu Pro Pro Pro Trp Arg Leu Met Pro Ile Thr Ala Ala Ala
                485                 490                 495

Glu Ala Ile Trp Ala Cys Ser Ile Glu Leu Gly Leu Glu Asn Glu
            500                 505                 510

Ala Glu Lys Pro Ser Asn Ala Leu Leu Thr Arg Ala Trp Ser Pro Gly
            515                 520                 525

Trp Ser Asn Ala Asp Lys Leu Leu Asn Glu Phe Ile Glu Lys Gln Leu
            530                 535                 540

Ile Asp Tyr Ala Lys Asn Ser Lys Lys Val Val Gly Asn Ser Thr Ser
545                 550                 555                 560

Leu Leu Ser Pro Tyr Leu His Phe Gly Glu Ile Ser Val Arg His Val
                565                 570                 575

Phe Gln Cys Ala Arg Met Lys Gln Ile Ile Trp Ala Arg Asp Lys Asn
            580                 585                 590

Ser Glu Gly Glu Glu Ser Ala Asp Leu Phe Leu Arg Gly Ile Gly Leu
            595                 600                 605

Arg Glu Tyr Ser Arg Tyr Ile Cys Phe Asn Phe Pro Phe Thr His Glu
            610                 615                 620

Gln Ser Leu Leu Ser His Leu Arg Phe Phe Pro Trp Asp Ala Asp Val
625                 630                 635                 640

Asp Lys Phe Lys Ala Trp Arg Gln Gly Arg Thr Gly Tyr Pro Leu Val
                645                 650                 655

Asp Ala Gly Met Arg Glu Leu Trp Ala Thr Gly Trp Met His Asn Arg
            660                 665                 670

Ile Arg Val Ile Val Ser Ser Phe Ala Val Lys Phe Leu Leu Leu Pro
            675                 680                 685

Trp Lys Trp Gly Met Lys Tyr Phe Trp Asp Thr Leu Leu Asp Ala Asp
            690                 695                 700

Leu Glu Cys Asp Ile Leu Gly Trp Gln Tyr Ile Ser Gly Ser Ile Pro
705                 710                 715                 720

Asp Gly His Glu Leu Asp Arg Leu Asp Asn Pro Ala Leu Gln Gly Ala
                725                 730                 735

Lys Tyr Asp Pro Glu Gly Glu Tyr Ile Arg Gln Trp Leu Pro Glu Leu
```

```
                740                 745                 750
Ala Arg Leu Pro Thr Glu Trp Ile His His Pro Trp Asp Ala Pro Leu
            755                 760                 765

Thr Val Leu Lys Ala Ser Gly Val Glu Leu Gly Thr Asn Tyr Ala Lys
            770                 775                 780

Pro Ile Val Asp Ile Asp Thr Ala Arg Glu Leu Leu Ala Lys Ala Ile
785                 790                 795                 800

Ser Arg Thr Arg Gly Ala Gln Ile Met Ile Gly Ala Ala Arg Asp
                805                 810                 815

Pro Pro Val Ala Thr Met Val Ser Lys Gly Glu Glu Asp Asn Met Ala
            820                 825                 830

Ile Ile Lys Glu Phe Met Arg Phe Lys Val His Met Glu Gly Ser Val
            835                 840                 845

Asn Gly His Glu Phe Glu Ile Glu Gly Glu Gly Glu Gly Arg Pro Tyr
            850                 855                 860

Glu Gly Thr Gln Thr Ala Lys Leu Lys Val Thr Lys Gly Gly Pro Leu
865                 870                 875                 880

Pro Phe Ala Trp Asp Ile Leu Ser Pro Gln Phe Met Tyr Gly Ser Lys
                885                 890                 895

Ala Tyr Val Lys His Pro Ala Asp Ile Pro Asp Tyr Leu Lys Leu Ser
            900                 905                 910

Phe Pro Glu Gly Phe Lys Trp Glu Arg Val Met Asn Phe Glu Asp Gly
            915                 920                 925

Gly Val Val Thr Val Thr Gln Asp Ser Ser Leu Gln Asp Gly Glu Phe
            930                 935                 940

Ile Tyr Lys Val Lys Leu Arg Gly Thr Asn Phe Pro Ser Asp Gly Pro
945                 950                 955                 960

Val Met Gln Lys Lys Thr Met Gly Trp Glu Ala Ser Ser Glu Arg Met
                965                 970                 975

Tyr Pro Glu Asp Gly Ala Leu Lys Gly Glu Ile Lys Gln Arg Leu Lys
            980                 985                 990

Leu Lys Asp Gly Gly His Tyr Asp  Ala Glu Val Lys Thr  Thr Tyr Lys
            995                 1000                1005

Ala Lys  Lys Pro Val Gln Leu  Pro Gly Ala Tyr Asn  Val Asn Ile
    1010                1015                1020

Lys Leu Asp Ile Thr Ser His  Asn Glu Asp Tyr Thr  Ile Val Glu
    1025                1030                1035

Gln Tyr  Glu Arg Ala Glu Gly  Arg His Ser Thr Gly  Gly Met Asp
    1040                1045                1050

Glu Leu  Tyr Lys
    1055

<210> SEQ ID NO 20
<211> LENGTH: 878
<212> TYPE: PRT
<213> ORGANISM: Artificial Sequence
<220> FEATURE:
<223> OTHER INFORMATION: synthetic construct

<400> SEQUENCE: 20

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
```

```
            35                  40                  45
Ala Lys Leu Lys Val Thr Lys Gly Gly Pro Leu Pro Phe Ala Trp Asp
 50                  55                  60
Ile Leu Ser Pro Gln Phe Met Tyr Gly Ser Lys Ala Tyr Val Lys His
 65                  70                  75                  80
Pro Ala Asp Ile Pro Asp Tyr Leu Lys Leu Ser Phe Pro Glu Gly Phe
                 85                  90                  95
Lys Trp Glu Arg Val Met Asn Phe Glu Asp Gly Gly Val Val Thr Val
                100                 105                 110
Thr Gln Asp Ser Ser Leu Gln Asp Gly Glu Phe Ile Tyr Lys Val Lys
            115                 120                 125
Leu Arg Gly Thr Asn Phe Pro Ser Asp Gly Pro Val Met Gln Lys Lys
        130                 135                 140
Thr Met Gly Trp Glu Ala Ser Ser Glu Arg Met Tyr Pro Glu Asp Gly
    145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
                180                 185                 190
Gln Leu Pro Gly Ala Tyr Asn Val Asn Ile Lys Leu Asp Ile Thr Ser
            195                 200                 205
His Asn Glu Asp Tyr Thr Ile Val Glu Gln Tyr Glu Arg Ala Glu Gly
        210                 215                 220
Arg His Ser Thr Gly Gly Met Asp Glu Leu Tyr Lys Met Lys Met Asp
225                 230                 235                 240
Lys Lys Thr Ile Val Trp Phe Arg Arg Asp Leu Arg Ile Glu Asp Asn
                245                 250                 255
Pro Ala Leu Ala Ala Ala Ala His Glu Gly Ser Val Phe Pro Val Phe
                260                 265                 270
Ile Trp Cys Pro Glu Glu Gly Gln Phe Tyr Pro Gly Arg Ala Ser
            275                 280                 285
Arg Trp Trp Met Lys Gln Ser Leu Ala His Leu Ser Gln Ser Leu Lys
        290                 295                 300
Ala Leu Gly Ser Asp Leu Thr Leu Ile Lys Thr His Asn Thr Ile Ser
305                 310                 315                 320
Ala Ile Leu Asp Cys Ile Arg Val Thr Gly Ala Thr Lys Val Val Phe
                325                 330                 335
Asn His Leu Tyr Asp Pro Val Ser Leu Val Arg Asp His Thr Val Lys
                340                 345                 350
Glu Lys Leu Val Glu Arg Gly Ile Ser Val Gln Ser Tyr Asn Gly Asp
            355                 360                 365
Leu Leu Tyr Glu Pro Trp Glu Ile Tyr Cys Glu Lys Gly Lys Pro Phe
        370                 375                 380
Thr Ser Phe Asn Ser Tyr Trp Lys Lys Cys Leu Asp Met Ser Ile Glu
385                 390                 395                 400
Ser Val Met Leu Pro Pro Trp Arg Leu Met Pro Ile Thr Ala Ala
                405                 410                 415
Ala Glu Ala Ile Trp Ala Cys Ser Ile Glu Glu Leu Gly Leu Glu Asn
                420                 425                 430
Glu Ala Glu Lys Pro Ser Asn Ala Leu Leu Thr Arg Ala Trp Ser Pro
            435                 440                 445
Gly Trp Ser Asn Ala Asp Lys Leu Leu Asn Glu Phe Ile Glu Lys Gln
        450                 455                 460
```

```
Leu Ile Asp Tyr Ala Lys Asn Ser Lys Lys Val Val Gly Asn Ser Thr
465                 470                 475                 480

Ser Leu Leu Ser Pro Tyr Leu His Phe Gly Glu Ile Ser Val Arg His
                485                 490                 495

Val Phe Gln Cys Ala Arg Met Lys Gln Ile Ile Trp Ala Arg Asp Lys
            500                 505                 510

Asn Ser Glu Gly Glu Ser Ala Asp Leu Phe Leu Arg Gly Ile Gly
        515                 520                 525

Leu Arg Glu Tyr Ser Arg Tyr Ile Cys Phe Asn Phe Pro Phe Thr His
530                 535                 540

Glu Gln Ser Leu Leu Ser His Leu Arg Phe Phe Pro Trp Asp Ala Asp
545                 550                 555                 560

Val Asp Lys Phe Lys Ala Trp Arg Gln Gly Arg Thr Gly Tyr Pro Leu
                565                 570                 575

Val Asp Ala Gly Met Arg Glu Leu Trp Ala Thr Gly Trp Met His Asn
            580                 585                 590

Arg Ile Arg Val Ile Val Ser Ser Phe Ala Val Lys Phe Leu Leu Leu
                595                 600                 605

Pro Trp Lys Trp Gly Met Lys Tyr Phe Trp Asp Thr Leu Leu Asp Ala
610                 615                 620

Asp Leu Glu Cys Asp Ile Leu Gly Trp Gln Tyr Ile Ser Gly Ser Ile
625                 630                 635                 640

Pro Asp Gly His Glu Leu Asp Arg Leu Asp Asn Pro Ala Leu Gln Gly
                645                 650                 655

Ala Lys Tyr Asp Pro Glu Gly Glu Tyr Ile Arg Gln Trp Leu Pro Glu
            660                 665                 670

Leu Ala Arg Leu Pro Thr Glu Trp Ile His His Pro Trp Asp Ala Pro
                675                 680                 685

Leu Thr Val Leu Lys Ala Ser Gly Val Glu Leu Gly Thr Asn Tyr Ala
690                 695                 700

Lys Pro Ile Val Asp Ile Asp Thr Ala Arg Glu Leu Leu Ala Lys Ala
705                 710                 715                 720

Ile Ser Arg Thr Arg Gly Ala Gln Ile Met Ile Gly Ala Ala Ala Arg
                725                 730                 735

Gly Gly Arg Phe Gly Gly Asn Pro Gly Gly Phe Gly Asn Gln Gly Gly
            740                 745                 750

Phe Gly Asn Ser Arg Gly Gly Ala Gly Leu Gly Asn Asn Gln Gly
                755                 760                 765

Ser Asn Met Gly Gly Gly Met Asn Phe Gly Ala Phe Ser Ile Asn Pro
770                 775                 780

Ala Met Met Ala Ala Gln Ala Ala Leu Gln Ser Ser Trp Gly Met
785                 790                 795                 800

Met Gly Met Leu Ala Ser Gln Gln Asn Gln Ser Gly Pro Ser Gly Asn
                805                 810                 815

Asn Gln Asn Gln Gly Asn Met Gln Arg Glu Pro Asn Gln Ala Phe Gly
            820                 825                 830

Ser Gly Asn Asn Ser Tyr Ser Gly Ser Asn Ser Gly Ala Ala Ile Gly
            835                 840                 845

Trp Gly Ser Ala Ser Asn Ala Gly Ser Gly Ser Gly Phe Asn Gly Gly
    850                 855                 860

Phe Gly Ser Ser Met Asp Ser Lys Ser Ser Gly Trp Gly Met
865                 870                 875
```

<210> SEQ ID NO 21
<211> LENGTH: 961
<212> TYPE: PRT
<213> ORGANISM: Artificial Sequence
<220> FEATURE:
<223> OTHER INFORMATION: synthetic construct

<400> SEQUENCE: 21

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Met Lys Met Asp
225                 230                 235                 240

Lys Lys Thr Ile Val Trp Phe Arg Arg Asp Leu Arg Ile Glu Asp Asn
                245                 250                 255

Pro Ala Leu Ala Ala Ala His Glu Gly Ser Val Phe Pro Val Phe
            260                 265                 270

Ile Trp Cys Pro Glu Glu Gly Gln Phe Tyr Pro Gly Arg Ala Ser
            275                 280                 285

Arg Trp Trp Met Lys Gln Ser Leu Ala His Leu Ser Gln Ser Leu Lys
    290                 295                 300

Ala Leu Gly Ser Asp Leu Thr Leu Ile Lys Thr His Asn Thr Ile Ser
305                 310                 315                 320

Ala Ile Leu Asp Cys Ile Arg Val Thr Gly Ala Thr Lys Val Val Phe
                325                 330                 335

Asn His Leu Tyr Asp Pro Val Ser Leu Val Arg Asp His Thr Val Lys
            340                 345                 350

Glu Lys Leu Val Glu Arg Gly Ile Ser Val Gln Ser Tyr Asn Gly Asp
        355                 360                 365
```

-continued

```
Leu Leu Tyr Glu Pro Trp Glu Ile Tyr Cys Glu Lys Gly Lys Pro Phe
370                 375                 380

Thr Ser Phe Asn Ser Tyr Trp Lys Lys Cys Leu Asp Met Ser Ile Glu
385                 390                 395                 400

Ser Val Met Leu Pro Pro Trp Arg Leu Met Pro Ile Thr Ala Ala
            405                 410                 415

Ala Glu Ala Ile Trp Ala Cys Ser Ile Glu Glu Leu Gly Leu Glu Asn
            420                 425                 430

Glu Ala Glu Lys Pro Ser Asn Ala Leu Leu Thr Arg Ala Trp Ser Pro
            435                 440                 445

Gly Trp Ser Asn Ala Asp Lys Leu Leu Asn Glu Phe Ile Glu Lys Gln
450                 455                 460

Leu Ile Asp Tyr Ala Lys Asn Ser Lys Lys Val Val Gly Asn Ser Thr
465                 470                 475                 480

Ser Leu Leu Ser Pro Tyr Leu His Phe Gly Glu Ile Ser Val Arg His
                485                 490                 495

Val Phe Gln Cys Ala Arg Met Lys Gln Ile Ile Trp Ala Arg Asp Lys
            500                 505                 510

Asn Ser Glu Gly Glu Glu Ser Ala Asp Leu Phe Leu Arg Gly Ile Gly
            515                 520                 525

Leu Arg Glu Tyr Ser Arg Tyr Ile Cys Phe Asn Phe Pro Phe Thr His
530                 535                 540

Glu Gln Ser Leu Leu Ser His Leu Arg Phe Phe Pro Trp Asp Ala Asp
545                 550                 555                 560

Val Asp Lys Phe Lys Ala Trp Arg Gln Gly Arg Thr Gly Tyr Pro Leu
                565                 570                 575

Val Asp Ala Gly Met Arg Glu Leu Trp Ala Thr Gly Trp Met His Asn
            580                 585                 590

Arg Ile Arg Val Ile Val Ser Ser Phe Ala Val Lys Phe Leu Leu Leu
            595                 600                 605

Pro Trp Lys Trp Gly Met Lys Tyr Phe Trp Asp Thr Leu Leu Asp Ala
            610                 615                 620

Asp Leu Glu Cys Asp Ile Leu Gly Trp Gln Tyr Ile Ser Gly Ser Ile
625                 630                 635                 640

Pro Asp Gly His Glu Leu Asp Arg Leu Asp Asn Pro Ala Leu Gln Gly
                645                 650                 655

Ala Lys Tyr Asp Pro Glu Gly Glu Tyr Ile Arg Gln Trp Leu Pro Glu
            660                 665                 670

Leu Ala Arg Leu Pro Thr Glu Trp Ile His His Pro Trp Asp Ala Pro
            675                 680                 685

Leu Thr Val Leu Lys Ala Ser Gly Val Glu Leu Gly Thr Asn Tyr Ala
690                 695                 700

Lys Pro Ile Val Asp Ile Asp Thr Ala Arg Glu Leu Leu Ala Lys Ala
705                 710                 715                 720

Ile Ser Arg Thr Arg Gly Ala Gln Ile Met Ile Gly Ala Ala Ala Arg
                725                 730                 735

Gly Arg Lys Val Phe Val Gly Arg Cys Thr Glu Asp Met Thr Glu Asp
            740                 745                 750

Glu Leu Arg Glu Phe Phe Ser Gln Tyr Gly Asp Val Met Asp Val Phe
            755                 760                 765

Ile Pro Lys Pro Phe Arg Ala Phe Ala Phe Val Thr Phe Ala Asp Asp
770                 775                 780

Gln Ile Ala Gln Ser Leu Cys Gly Glu Asp Leu Ile Ile Lys Gly Ile
```

```
                785                 790                 795                 800
Ser Val His Ile Ser Asn Ala Glu Pro Lys His Asn Ser Asn Arg Gln
                805                 810                 815

Leu Glu Arg Ser Gly Arg Phe Gly Gly Asn Pro Gly Gly Phe Gly Asn
            820                 825                 830

Gln Gly Gly Phe Gly Asn Ser Arg Gly Gly Ala Gly Leu Gly Asn
            835                 840                 845

Asn Gln Gly Ser Asn Met Gly Gly Met Asn Phe Gly Ala Phe Ser
850                 855                 860

Ile Asn Pro Ala Met Met Ala Ala Gln Ala Ala Leu Gln Ser Ser
865                 870                 875                 880

Trp Gly Met Met Gly Met Leu Ala Ser Gln Gln Asn Gln Ser Gly Pro
            885                 890                 895

Ser Gly Asn Asn Gln Asn Gln Gly Asn Met Gln Arg Glu Pro Asn Gln
            900                 905                 910

Ala Phe Gly Ser Gly Asn Asn Ser Tyr Ser Gly Ser Asn Ser Gly Ala
            915                 920                 925

Ala Ile Gly Trp Gly Ser Ala Ser Asn Ala Gly Ser Gly Ser Gly Phe
930                 935                 940

Asn Gly Gly Phe Gly Ser Ser Met Asp Ser Lys Ser Ser Gly Trp Gly
945                 950                 955                 960

Met
```

<210> SEQ ID NO 22
<211> LENGTH: 1047
<212> TYPE: PRT
<213> ORGANISM: Artificial Sequence
<220> FEATURE:
<223> OTHER INFORMATION: synthetic construct

<400> SEQUENCE: 22

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190
```

-continued

```
Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Arg Ala Glu Gly
    210                 215                 220

Arg His Ser Thr Gly Gly Met Asp Glu Leu Tyr Lys Met Lys Met Asp
225                 230                 235                 240

Lys Lys Thr Ile Val Trp Phe Arg Arg Asp Leu Arg Ile Glu Asp Asn
                245                 250                 255

Pro Ala Leu Ala Ala Ala His Glu Gly Ser Val Phe Pro Val Phe
            260                 265                 270

Ile Trp Cys Pro Glu Glu Glu Gly Gln Phe Tyr Pro Gly Arg Ala Ser
        275                 280                 285

Arg Trp Trp Met Lys Gln Ser Leu Ala His Leu Ser Gln Ser Leu Lys
    290                 295                 300

Ala Leu Gly Ser Asp Leu Thr Leu Ile Lys Thr His Asn Thr Ile Ser
305                 310                 315                 320

Ala Ile Leu Asp Cys Ile Arg Val Thr Gly Ala Thr Lys Val Val Phe
                325                 330                 335

Asn His Leu Tyr Asp Pro Val Ser Leu Val Arg Asp His Thr Val Lys
            340                 345                 350

Glu Lys Leu Val Glu Arg Gly Ile Ser Val Gln Ser Tyr Asn Gly Asp
        355                 360                 365

Leu Leu Tyr Glu Pro Trp Glu Ile Tyr Cys Glu Lys Gly Lys Pro Phe
    370                 375                 380

Thr Ser Phe Asn Ser Tyr Trp Lys Lys Cys Leu Asp Met Ser Ile Glu
385                 390                 395                 400

Ser Val Met Leu Pro Pro Pro Trp Arg Leu Met Pro Ile Thr Ala Ala
                405                 410                 415

Ala Glu Ala Ile Trp Ala Cys Ser Ile Glu Glu Leu Gly Leu Glu Asn
            420                 425                 430

Glu Ala Glu Lys Pro Ser Asn Ala Leu Leu Thr Arg Ala Trp Ser Pro
        435                 440                 445

Gly Trp Ser Asn Ala Asp Lys Leu Leu Asn Glu Phe Ile Glu Lys Gln
    450                 455                 460

Leu Ile Asp Tyr Ala Lys Asn Ser Lys Lys Val Val Gly Asn Ser Thr
465                 470                 475                 480

Ser Leu Leu Ser Pro Tyr Leu His Phe Gly Glu Ile Ser Val Arg His
                485                 490                 495

Val Phe Gln Cys Ala Arg Met Lys Gln Ile Ile Trp Ala Arg Asp Lys
            500                 505                 510

Asn Ser Glu Gly Glu Glu Ser Ala Asp Leu Phe Leu Arg Gly Ile Gly
        515                 520                 525

Leu Arg Glu Tyr Ser Arg Tyr Ile Cys Phe Asn Phe Pro Phe Thr His
    530                 535                 540

Glu Gln Ser Leu Leu Ser His Leu Arg Phe Phe Pro Trp Asp Ala Asp
545                 550                 555                 560

Val Asp Lys Phe Lys Ala Trp Arg Gln Gly Arg Thr Gly Tyr Pro Leu
                565                 570                 575

Val Asp Ala Gly Met Arg Glu Leu Trp Ala Thr Gly Trp Met His Asn
            580                 585                 590

Arg Ile Arg Val Ile Val Ser Ser Phe Ala Val Lys Phe Leu Leu Leu
        595                 600                 605
```

```
Pro Trp Lys Trp Gly Met Lys Tyr Phe Trp Asp Thr Leu Asp Ala
610             615                 620

Asp Leu Glu Cys Asp Ile Leu Gly Trp Gln Tyr Ile Ser Gly Ser Ile
625             630                 635                 640

Pro Asp Gly His Glu Leu Asp Arg Leu Asp Asn Pro Ala Leu Gln Gly
                645                 650                 655

Ala Lys Tyr Asp Pro Glu Gly Glu Tyr Ile Arg Gln Trp Leu Pro Glu
            660                 665                 670

Leu Ala Arg Leu Pro Thr Glu Trp Ile His His Pro Trp Asp Ala Pro
            675                 680                 685

Leu Thr Val Leu Lys Ala Ser Gly Val Glu Leu Gly Thr Asn Tyr Ala
690                 695                 700

Lys Pro Ile Val Asp Ile Asp Thr Ala Arg Glu Leu Leu Ala Lys Ala
705             710                 715                 720

Ile Ser Arg Thr Arg Gly Ala Gln Ile Met Ile Gly Ala Ala Ala Arg
                725                 730                 735

Gly Asp Leu Ile Val Leu Gly Leu Pro Trp Lys Thr Thr Glu Gln Asp
            740                 745                 750

Leu Lys Glu Tyr Phe Ser Thr Phe Gly Glu Val Leu Met Val Gln Val
            755                 760                 765

Lys Lys Asp Leu Lys Thr Gly His Ser Lys Gly Phe Gly Phe Val Arg
770             775                 780

Phe Thr Glu Tyr Glu Thr Gln Val Lys Val Met Ser Gln Arg His Met
785             790                 795                 800

Ile Asp Gly Arg Trp Cys Asp Cys Lys Leu Pro Asn Ser Lys Gln Ser
            805                 810                 815

Gln Asp Glu Pro Leu Arg Ser Arg Lys Val Phe Val Gly Arg Cys Thr
            820                 825                 830

Glu Asp Met Thr Glu Asp Glu Leu Arg Glu Phe Phe Ser Gln Tyr Gly
            835                 840                 845

Asp Val Met Asp Val Phe Ile Pro Lys Pro Phe Arg Ala Phe Ala Phe
            850                 855                 860

Val Thr Phe Ala Asp Asp Gln Ile Ala Gln Ser Leu Cys Gly Glu Asp
865             870                 875                 880

Leu Ile Ile Lys Gly Ile Ser Val His Ile Ser Asn Ala Glu Pro Lys
            885                 890                 895

His Asn Ser Asn Arg Gln Leu Glu Arg Ser Gly Arg Phe Gly Gly Asn
            900                 905                 910

Pro Gly Gly Phe Gly Asn Gln Gly Gly Phe Gly Asn Ser Arg Gly Gly
            915                 920                 925

Gly Ala Gly Leu Gly Asn Asn Gln Gly Ser Asn Met Gly Gly Gly Met
930                 935                 940

Asn Phe Gly Ala Phe Ser Ile Asn Pro Ala Met Met Ala Ala Ala Gln
945                 950                 955                 960

Ala Ala Leu Gln Ser Ser Trp Gly Met Met Gly Met Leu Ala Ser Gln
                965                 970                 975

Gln Asn Gln Ser Gly Pro Ser Gly Asn Asn Gln Asn Gln Gly Asn Met
            980                 985                 990

Gln Arg Glu Pro Asn Gln Ala Phe Gly Ser Gly Asn Asn Ser Tyr Ser
            995                 1000                1005

Gly Ser Asn Ser Gly Ala Ala Ile Gly Trp Gly Ser Ala Ser Asn
    1010                1015                1020

Ala Gly Ser Gly Ser Gly Phe Asn Gly Gly Phe Gly Ser Ser Met
```

-continued

```
               1025                1030                1035

Asp Ser Lys Ser Ser Gly Trp Gly Met
        1040                1045

<210> SEQ ID NO 23
<211> LENGTH: 886
<212> TYPE: PRT
<213> ORGANISM: Artificial Sequence
<220> FEATURE:
<223> OTHER INFORMATION: synthetic construct

<400> SEQUENCE: 23

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
```

```
             340                 345                 350
Trp Met His Asn Arg Ile Arg Val Ile Val Ser Ser Phe Ala Val Lys
            355                 360                 365
Phe Leu Leu Leu Pro Trp Lys Trp Gly Met Lys Tyr Phe Trp Asp Thr
            370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                    405                 410                 415
Ala Leu Gln Gly Ala Lys Tyr Asp Pro Glu Gly Glu Tyr Ile Arg Gln
                420                 425                 430
Trp Leu Pro Glu Leu Ala Arg Leu Pro Thr Glu Trp Ile His His Pro
            435                 440                 445
Trp Asp Ala Pro Leu Thr Val Leu Lys Ala Ser Gly Val Glu Leu Gly
            450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Arg Gly Gly Arg Phe Gly Gly Asn Pro Gly Gly Phe Gly
                500                 505                 510
Asn Gln Gly Gly Phe Gly Asn Ser Arg Gly Gly Ala Gly Leu Gly
                515                 520                 525
Asn Asn Gln Gly Ser Asn Met Gly Gly Met Asn Phe Gly Ala Phe
            530                 535                 540
Ser Ile Asn Pro Ala Met Met Ala Ala Ala Ala Leu Gln Ser
545                 550                 555                 560
Ser Trp Gly Met Met Gly Met Leu Ala Ser Gln Gln Asn Gln Ser Gly
                565                 570                 575
Pro Ser Gly Asn Asn Gln Asn Gln Gly Asn Met Gln Arg Glu Pro Asn
            580                 585                 590
Gln Ala Phe Gly Ser Gly Asn Asn Ser Tyr Ser Gly Ser Asn Ser Gly
                595                 600                 605
Ala Ala Ile Gly Trp Gly Ser Ala Ser Asn Ala Gly Ser Gly Ser Gly
            610                 615                 620
Phe Asn Gly Gly Phe Gly Ser Ser Met Asp Ser Lys Ser Ser Gly Trp
625                 630                 635                 640
Gly Met Ser Arg Asp Pro Pro Val Ala Thr Met Val Ser Lys Gly Glu
                645                 650                 655
Glu Asp Asn Met Ala Ile Ile Lys Glu Phe Met Arg Phe Lys Val His
                660                 665                 670
Met Glu Gly Ser Val Asn Gly His Glu Phe Glu Ile Glu Gly Glu Gly
            675                 680                 685
Glu Gly Arg Pro Tyr Glu Gly Thr Gln Thr Ala Lys Leu Lys Val Thr
            690                 695                 700
Lys Gly Gly Pro Leu Pro Phe Ala Trp Asp Ile Leu Ser Pro Gln Phe
705                 710                 715                 720
Met Tyr Gly Ser Lys Ala Tyr Val Lys His Pro Ala Asp Ile Pro Asp
                725                 730                 735
Tyr Leu Lys Leu Ser Phe Pro Glu Gly Phe Lys Trp Glu Arg Val Met
                740                 745                 750
Asn Phe Glu Asp Gly Gly Val Val Thr Val Thr Gln Asp Ser Ser Leu
            755                 760                 765
```

```
Gln Asp Gly Glu Phe Ile Tyr Lys Val Lys Leu Arg Gly Thr Asn Phe
        770                 775                 780

Pro Ser Asp Gly Pro Val Met Gln Lys Lys Thr Met Gly Trp Glu Ala
785                 790                 795                 800

Ser Ser Glu Arg Met Tyr Pro Glu Asp Gly Ala Leu Lys Gly Glu Ile
            805                 810                 815

Lys Gln Arg Leu Lys Leu Lys Asp Gly His Tyr Asp Ala Glu Val
            820                 825                 830

Lys Thr Thr Tyr Lys Ala Lys Lys Pro Val Gln Leu Pro Gly Ala Tyr
            835                 840                 845

Asn Val Asn Ile Lys Leu Asp Ile Thr Ser His Asn Glu Asp Tyr Thr
        850                 855                 860

Ile Val Glu Gln Tyr Glu Arg Ala Glu Gly Arg His Ser Thr Gly Gly
865                 870                 875                 880

Met Asp Glu Leu Tyr Lys
                885

<210> SEQ ID NO 24
<211> LENGTH: 969
<212> TYPE: PRT
<213> ORGANISM: Artificial Sequence
<220> FEATURE:
<223> OTHER INFORMATION: synthetic construct

<400> SEQUENCE: 24

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240
```

```
Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Arg Gly Arg Lys Val Phe Val Gly Arg Cys Thr Glu Asp
            500                 505                 510

Met Thr Glu Asp Glu Leu Arg Glu Phe Phe Ser Gln Tyr Gly Asp Val
        515                 520                 525

Met Asp Val Phe Ile Pro Lys Pro Phe Arg Ala Phe Ala Phe Val Thr
    530                 535                 540

Phe Ala Asp Asp Gln Ile Ala Gln Ser Leu Cys Gly Glu Asp Leu Ile
545                 550                 555                 560

Ile Lys Gly Ile Ser Val His Ile Ser Asn Ala Glu Pro Lys His Asn
                565                 570                 575

Ser Asn Arg Gln Leu Glu Arg Ser Gly Arg Phe Gly Asn Pro Gly
            580                 585                 590

Gly Phe Gly Asn Gln Gly Gly Phe Gly Asn Ser Arg Gly Gly Ala
        595                 600                 605

Gly Leu Gly Asn Asn Gln Gly Ser Asn Met Gly Gly Gly Met Asn Phe
    610                 615                 620

Gly Ala Phe Ser Ile Asn Pro Ala Met Met Ala Ala Gln Ala Ala
625                 630                 635                 640

Leu Gln Ser Ser Trp Gly Met Gly Met Leu Ala Ser Gln Gln Asn
                645                 650                 655
```

```
Gln Ser Gly Pro Ser Gly Asn Asn Gln Asn Gly Asn Met Gln Arg
            660                 665                 670

Glu Pro Asn Gln Ala Phe Gly Ser Gly Asn Asn Ser Tyr Ser Gly Ser
        675                 680                 685

Asn Ser Gly Ala Ala Ile Gly Trp Gly Ser Ala Ser Asn Ala Gly Ser
690                 695                 700

Gly Ser Gly Phe Asn Gly Phe Gly Ser Ser Met Asp Ser Lys Ser
705                 710                 715                 720

Ser Gly Trp Gly Met Ser Arg Asp Pro Val Ala Thr Met Val Ser
            725                 730                 735

Lys Gly Glu Glu Asp Asn Met Ala Ile Ile Lys Glu Phe Met Arg Phe
        740                 745                 750

Lys Val His Met Glu Gly Ser Val Asn Gly His Glu Phe Glu Ile Glu
        755                 760                 765

Gly Glu Gly Glu Gly Arg Pro Tyr Glu Gly Thr Gln Thr Ala Lys Leu
        770                 775                 780

Lys Val Thr Lys Gly Gly Pro Leu Pro Phe Ala Trp Asp Ile Leu Ser
785                 790                 795                 800

Pro Gln Phe Met Tyr Gly Ser Lys Ala Tyr Val Lys His Pro Ala Asp
            805                 810                 815

Ile Pro Asp Tyr Leu Lys Leu Ser Phe Pro Glu Gly Phe Lys Trp Glu
            820                 825                 830

Arg Val Met Asn Phe Glu Asp Gly Gly Val Val Thr Val Thr Gln Asp
            835                 840                 845

Ser Ser Leu Gln Asp Gly Glu Phe Ile Tyr Lys Val Lys Leu Arg Gly
850                 855                 860

Thr Asn Phe Pro Ser Asp Gly Pro Val Met Gln Lys Lys Thr Met Gly
865                 870                 875                 880

Trp Glu Ala Ser Ser Glu Arg Met Tyr Pro Glu Asp Gly Ala Leu Lys
            885                 890                 895

Gly Glu Ile Lys Gln Arg Leu Lys Leu Lys Asp Gly His Tyr Asp
        900                 905                 910

Ala Glu Val Lys Thr Thr Tyr Lys Ala Lys Lys Pro Val Gln Leu Pro
        915                 920                 925

Gly Ala Tyr Asn Val Asn Ile Lys Leu Asp Ile Thr Ser His Asn Glu
        930                 935                 940

Asp Tyr Thr Ile Val Glu Gln Tyr Glu Arg Ala Glu Gly Arg His Ser
945                 950                 955                 960

Thr Gly Gly Met Asp Glu Leu Tyr Lys
                965

<210> SEQ ID NO 25
<211> LENGTH: 1057
<212> TYPE: PRT
<213> ORGANISM: Artificial Sequence
<220> FEATURE:
<223> OTHER INFORMATION: synthetic construct

<400> SEQUENCE: 25

Met Asp Leu Ile Val Leu Gly Leu Pro Trp Lys Thr Thr Glu Gln Asp
1               5                   10                  15

Leu Lys Glu Tyr Phe Ser Thr Phe Gly Glu Val Leu Met Val Gln Val
            20                  25                  30

Lys Lys Asp Leu Lys Thr Gly His Ser Lys Gly Phe Gly Phe Val Arg
        35                  40                  45
```

```
Phe Thr Glu Tyr Glu Thr Gln Val Lys Val Met Ser Gln Arg His Met
 50                  55                  60

Ile Asp Gly Arg Trp Cys Asp Cys Lys Leu Pro Asn Ser Lys Gln Ser
 65                  70                  75                  80

Gln Asp Glu Pro Leu Arg Ser Arg Lys Val Phe Val Gly Arg Cys Thr
                 85                  90                  95

Glu Asp Met Thr Glu Asp Glu Leu Arg Glu Phe Phe Ser Gln Tyr Gly
                100                 105                 110

Asp Val Met Asp Val Phe Ile Pro Lys Pro Phe Arg Ala Phe Ala Phe
                115                 120                 125

Val Thr Phe Ala Asp Asp Gln Ile Ala Gln Ser Leu Cys Gly Glu Asp
    130                 135                 140

Leu Ile Ile Lys Gly Ile Ser Val His Ile Ser Asn Ala Glu Pro Lys
145                 150                 155                 160

His Asn Ser Asn Arg Gln Leu Glu Arg Ser Arg Phe Gly Gly Asn
                165                 170                 175

Pro Gly Gly Phe Gly Asn Gln Gly Gly Phe Gly Asn Ser Arg Gly Gly
                180                 185                 190

Gly Ala Gly Leu Gly Asn Asn Gln Gly Ser Asn Met Gly Gly Gly Met
                195                 200                 205

Asn Phe Gly Ala Phe Ser Ile Asn Pro Ala Met Met Ala Ala Ala Gln
                210                 215                 220

Ala Ala Leu Gln Ser Ser Trp Gly Met Met Gly Met Leu Ala Ser Gln
225                 230                 235                 240

Gln Asn Gln Ser Gly Pro Ser Gly Asn Asn Gln Asn Gln Gly Asn Met
                245                 250                 255

Gln Arg Glu Pro Asn Gln Ala Phe Gly Ser Gly Asn Asn Ser Tyr Ser
                260                 265                 270

Gly Ser Asn Ser Gly Ala Ala Ile Gly Trp Gly Ser Ala Ser Asn Ala
                275                 280                 285

Gly Ser Gly Ser Gly Phe Asn Gly Gly Phe Gly Ser Ser Met Asp Ser
                290                 295                 300

Lys Ser Ser Gly Trp Gly Met Leu Glu Ala Thr Met Lys Met Asp Lys
305                 310                 315                 320

Lys Thr Ile Val Trp Phe Arg Arg Asp Leu Arg Ile Glu Asp Asn Pro
                325                 330                 335

Ala Leu Ala Ala Ala His Glu Gly Ser Val Phe Pro Val Phe Ile
                340                 345                 350

Trp Cys Pro Glu Glu Gly Gln Phe Tyr Pro Gly Arg Ala Ser Arg
                355                 360                 365

Trp Trp Met Lys Gln Ser Leu Ala His Leu Ser Gln Ser Leu Lys Ala
                370                 375                 380

Leu Gly Ser Asp Leu Thr Leu Ile Lys Thr His Asn Thr Ile Ser Ala
385                 390                 395                 400

Ile Leu Asp Cys Ile Arg Val Thr Gly Ala Thr Lys Val Val Phe Asn
                405                 410                 415

His Leu Tyr Asp Pro Val Ser Leu Val Arg Asp His Thr Val Lys Glu
                420                 425                 430

Lys Leu Val Glu Arg Gly Ile Ser Val Gln Ser Tyr Asn Gly Asp Leu
                435                 440                 445

Leu Tyr Glu Pro Trp Glu Ile Tyr Cys Glu Lys Gly Lys Pro Phe Thr
                450                 455                 460

Ser Phe Asn Ser Tyr Trp Lys Lys Cys Leu Asp Met Ser Ile Glu Ser
```

```
          465                 470                 475                 480
Val Met Leu Pro Pro Pro Trp Arg Leu Met Pro Ile Thr Ala Ala Ala
                    485                 490                 495
Glu Ala Ile Trp Ala Cys Ser Ile Glu Glu Leu Gly Leu Glu Asn Glu
                    500                 505                 510
Ala Glu Lys Pro Ser Asn Ala Leu Leu Thr Arg Ala Trp Ser Pro Gly
                    515                 520                 525
Trp Ser Asn Ala Asp Lys Leu Leu Asn Glu Phe Ile Glu Lys Gln Leu
                    530                 535                 540
Ile Asp Tyr Ala Lys Asn Ser Lys Lys Val Val Gly Asn Ser Thr Ser
545                 550                 555                 560
Leu Leu Ser Pro Tyr Leu His Phe Gly Glu Ile Ser Val Arg His Val
                    565                 570                 575
Phe Gln Cys Ala Arg Met Lys Gln Ile Ile Trp Ala Arg Asp Lys Asn
                    580                 585                 590
Ser Glu Gly Glu Glu Ser Ala Asp Leu Phe Leu Arg Gly Ile Gly Leu
                    595                 600                 605
Arg Glu Tyr Ser Arg Tyr Ile Cys Phe Asn Phe Pro Phe Thr His Glu
                    610                 615                 620
Gln Ser Leu Leu Ser His Leu Arg Phe Phe Pro Trp Asp Ala Asp Val
625                 630                 635                 640
Asp Lys Phe Lys Ala Trp Arg Gln Gly Arg Thr Gly Tyr Pro Leu Val
                    645                 650                 655
Asp Ala Gly Met Arg Glu Leu Trp Ala Thr Gly Trp Met His Asn Arg
                    660                 665                 670
Ile Arg Val Ile Val Ser Ser Phe Ala Val Lys Phe Leu Leu Leu Pro
                    675                 680                 685
Trp Lys Trp Gly Met Lys Tyr Phe Trp Asp Thr Leu Leu Asp Ala Asp
                    690                 695                 700
Leu Glu Cys Asp Ile Leu Gly Trp Gln Tyr Ile Ser Gly Ser Ile Pro
705                 710                 715                 720
Asp Gly His Glu Leu Asp Arg Leu Asp Asn Pro Ala Leu Gln Gly Ala
                    725                 730                 735
Lys Tyr Asp Pro Glu Gly Glu Tyr Ile Arg Gln Trp Leu Pro Glu Leu
                    740                 745                 750
Ala Arg Leu Pro Thr Glu Trp Ile His His Pro Trp Asp Ala Pro Leu
                    755                 760                 765
Thr Val Leu Lys Ala Ser Gly Val Glu Leu Gly Thr Asn Tyr Ala Lys
                    770                 775                 780
Pro Ile Val Asp Ile Asp Thr Ala Arg Glu Leu Leu Ala Lys Ala Ile
785                 790                 795                 800
Ser Arg Thr Arg Gly Ala Gln Ile Met Ile Gly Ala Ala Ser Arg Asp
                    805                 810                 815
Pro Pro Val Ala Thr Met Val Ser Lys Gly Glu Glu Asp Asn Met Ala
                    820                 825                 830
Ile Ile Lys Glu Phe Met Arg Phe Lys Val His Met Glu Gly Ser Val
                    835                 840                 845
Asn Gly His Glu Phe Glu Ile Glu Gly Glu Gly Glu Gly Arg Pro Tyr
                    850                 855                 860
Glu Gly Thr Gln Thr Ala Lys Leu Lys Val Thr Lys Gly Gly Pro Leu
865                 870                 875                 880
Pro Phe Ala Trp Asp Ile Leu Ser Pro Gln Phe Met Tyr Gly Ser Lys
                    885                 890                 895
```

Ala Tyr Val Lys His Pro Ala Asp Ile Pro Asp Tyr Leu Lys Leu Ser
            900                 905                 910

Phe Pro Glu Gly Phe Lys Trp Glu Arg Val Met Asn Phe Glu Asp Gly
            915                 920                 925

Gly Val Val Thr Val Thr Gln Asp Ser Ser Leu Gln Asp Gly Glu Phe
            930                 935                 940

Ile Tyr Lys Val Lys Leu Arg Gly Thr Asn Phe Pro Ser Asp Gly Pro
945                 950                 955                 960

Val Met Gln Lys Lys Thr Met Gly Trp Glu Ala Ser Ser Glu Arg Met
            965                 970                 975

Tyr Pro Glu Asp Gly Ala Leu Lys Gly Glu Ile Lys Gln Arg Leu Lys
            980                 985                 990

Leu Lys Asp Gly Gly His Tyr Asp Ala Glu Val Lys Thr Thr Tyr Lys
            995                 1000                1005

Ala Lys Lys Pro Val Gln Leu Pro Gly Ala Tyr Asn Val Asn Ile
            1010                1015                1020

Lys Leu Asp Ile Thr Ser His Asn Glu Asp Tyr Thr Ile Val Glu
            1025                1030                1035

Gln Tyr Glu Arg Ala Glu Gly Arg His Ser Thr Gly Gly Met Asp
            1040                1045                1050

Glu Leu Tyr Lys
            1055

<210> SEQ ID NO 26
<211> LENGTH: 566
<212> TYPE: PRT
<213> ORGANISM: Artificial Sequence
<220> FEATURE:
<223> OTHER INFORMATION: synthetic construct

<400> SEQUENCE: 26

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Ala Met Ser Glu Tyr Ile Arg Val Thr
145                 150                 155                 160

Glu Asp Glu Asn Asp Glu Pro Ile Glu Ile Pro Ser Glu Asp Gly
                165                 170                 175

Thr Val Leu Leu Ser Thr Val Thr Ala Gln Phe Pro Gly Ala Cys Gly
            180                 185                 190

```
Leu Arg Tyr Arg Asn Pro Val Ser Gln Cys Met Arg Gly Val Arg Leu
            195                 200                 205

Val Glu Gly Ile Leu His Ala Pro Asp Ala Gly Trp Gly Asn Leu Val
    210                 215                 220

Tyr Val Val Asn Tyr Pro Lys Asp Asn Arg Lys Met Asp Glu Thr
225                 230                 235                 240

Asp Ala Ser Ser Ala Val Lys Val Lys Arg Ala Val Gln Lys Thr Ser
                245                 250                 255

Asp Leu Ile Val Leu Gly Leu Pro Trp Lys Thr Thr Glu Gln Asp Leu
                260                 265                 270

Lys Glu Tyr Phe Ser Thr Phe Gly Glu Val Leu Met Val Gln Val Lys
            275                 280                 285

Lys Asp Leu Lys Thr Gly His Ser Lys Gly Phe Gly Phe Val Arg Phe
            290                 295                 300

Thr Glu Tyr Glu Thr Gln Val Lys Val Met Ser Gln Arg His Met Ile
305                 310                 315                 320

Asp Gly Arg Trp Cys Asp Cys Lys Leu Pro Asn Ser Lys Gln Ser Gln
                325                 330                 335

Asp Glu Pro Leu Arg Ser Arg Lys Val Phe Val Gly Arg Cys Thr Glu
                340                 345                 350

Asp Met Thr Glu Asp Glu Leu Arg Glu Phe Phe Ser Gln Tyr Gly Asp
            355                 360                 365

Val Met Asp Val Phe Ile Pro Lys Pro Phe Arg Ala Phe Ala Phe Val
370                 375                 380

Thr Phe Ala Asp Asp Gln Ile Ala Gln Ser Leu Cys Gly Glu Asp Leu
385                 390                 395                 400

Ile Ile Lys Gly Ile Ser Val His Ile Ser Asn Ala Glu Pro Lys His
                405                 410                 415

Asn Ser Asn Arg Gln Leu Glu Arg Ser Gly Arg Phe Gly Gly Asn Pro
                420                 425                 430

Gly Gly Phe Gly Asn Gln Gly Gly Phe Gly Asn Ser Arg Gly Gly Gly
            435                 440                 445

Ala Gly Leu Gly Asn Asn Gln Gly Ser Asn Met Gly Gly Gly Met Asn
            450                 455                 460

Phe Gly Ala Phe Ser Ile Asn Pro Ala Met Met Ala Ala Ala Gln Ala
465                 470                 475                 480

Ala Leu Gln Ser Ser Trp Gly Met Met Gly Met Leu Ala Ser Gln Gln
                485                 490                 495

Asn Gln Ser Gly Pro Ser Gly Asn Asn Gln Asn Gln Gly Asn Met Gln
                500                 505                 510

Arg Glu Pro Asn Gln Ala Phe Gly Ser Gly Asn Asn Ser Tyr Ser Gly
            515                 520                 525

Ser Asn Ser Gly Ala Ala Ile Gly Trp Gly Ser Ala Ser Asn Ala Gly
            530                 535                 540

Ser Gly Ser Gly Phe Asn Gly Gly Phe Gly Ser Ser Met Asp Ser Lys
545                 550                 555                 560

Ser Ser Gly Trp Gly Met
                565
```

<210> SEQ ID NO 27
<211> LENGTH: 569
<212> TYPE: PRT
<213> ORGANISM: Artificial Sequence
<220> FEATURE:

<223> OTHER INFORMATION: synthetic construct

<400> SEQUENCE: 27

```
Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400
```

```
Phe Gly Ser Ser Met Asp Ser Lys Ser Ser Gly Trp Gly Met Phe Arg
                405                 410                 415

Ala Gln Arg His Thr Leu Tyr Ala Pro Gly Gly Tyr Asp Ile Met Gly
            420                 425                 430

Trp Leu Ile Gln Ile Met Asn Arg Pro Asn Pro Gln Val Glu Leu Gly
        435                 440                 445

Pro Val Asp Thr Ser Cys Ala Leu Ile Leu Cys Asp Leu Lys Gln Lys
    450                 455                 460

Asp Thr Pro Ile Val Tyr Ala Ser Glu Ala Phe Leu Tyr Met Thr Gly
465                 470                 475                 480

Tyr Ser Asn Ala Glu Val Leu Gly Arg Asn Cys Arg Phe Leu Gln Ser
                485                 490                 495

Pro Asp Gly Met Val Lys Pro Lys Ser Thr Arg Lys Tyr Val Asp Ser
            500                 505                 510

Asn Thr Ile Asn Thr Met Arg Lys Ala Ile Asp Arg Asn Ala Glu Val
        515                 520                 525

Gln Val Glu Val Val Asn Phe Lys Lys Asn Gly Gln Arg Phe Val Asn
    530                 535                 540

Phe Leu Thr Met Ile Pro Val Arg Asp Glu Thr Gly Glu Tyr Arg Tyr
545                 550                 555                 560

Ser Met Gly Phe Gln Cys Glu Thr Glu
                565

<210> SEQ ID NO 28
<211> LENGTH: 466
<212> TYPE: PRT
<213> ORGANISM: Artificial Sequence
<220> FEATURE:
<223> OTHER INFORMATION: synthetic construct

<400> SEQUENCE: 28

Met Asp Leu Ile Val Leu Gly Leu Pro Trp Lys Thr Thr Glu Gln Asp
1               5                   10                  15

Leu Lys Glu Tyr Phe Ser Thr Phe Gly Glu Val Leu Met Val Gln Val
            20                  25                  30

Lys Lys Asp Leu Lys Thr Gly His Ser Lys Gly Phe Gly Phe Val Arg
        35                  40                  45

Phe Thr Glu Tyr Glu Thr Gln Val Lys Val Met Ser Gln Arg His Met
    50                  55                  60

Ile Asp Gly Arg Trp Cys Asp Cys Lys Leu Pro Asn Ser Lys Gln Ser
65                  70                  75                  80

Gln Asp Glu Pro Leu Arg Ser Arg Lys Val Phe Val Gly Arg Cys Thr
                85                  90                  95

Glu Asp Met Thr Glu Asp Glu Leu Arg Glu Phe Phe Ser Gln Tyr Gly
            100                 105                 110

Asp Val Met Asp Val Phe Ile Pro Lys Pro Phe Arg Ala Phe Ala Phe
        115                 120                 125

Val Thr Phe Ala Asp Asp Gln Ile Ala Gln Ser Leu Cys Gly Glu Asp
    130                 135                 140

Leu Ile Ile Lys Gly Ile Ser Val His Ile Ser Asn Ala Glu Pro Lys
145                 150                 155                 160

His Asn Ser Asn Arg Gln Leu Glu Arg Ser Gly Arg Phe Gly Gly Asn
                165                 170                 175

Pro Gly Gly Phe Gly Asn Gln Gly Gly Phe Gly Asn Ser Arg Gly Gly
            180                 185                 190
```

```
Gly Ala Gly Leu Gly Asn Asn Gln Gly Ser Asn Met Gly Gly Met
            195                 200                 205

Asn Phe Gly Ala Phe Ser Ile Asn Pro Ala Met Met Ala Ala Gln
        210                 215                 220

Ala Ala Leu Gln Ser Ser Trp Gly Met Met Gly Met Leu Ala Ser Gln
225                 230                 235                 240

Gln Asn Gln Ser Gly Pro Ser Gly Asn Asn Gln Asn Gly Asn Met
                245                 250                 255

Gln Arg Glu Pro Asn Gln Ala Phe Gly Ser Gly Asn Ser Tyr Ser
            260                 265                 270

Gly Ser Asn Ser Gly Ala Ala Ile Gly Trp Gly Ser Ala Ser Asn Ala
        275                 280                 285

Gly Ser Gly Ser Gly Phe Asn Gly Gly Phe Gly Ser Ser Met Asp Ser
290                 295                 300

Lys Ser Ser Gly Trp Gly Met Phe Arg Ala Gln Arg His Thr Leu Tyr
305                 310                 315                 320

Ala Pro Gly Gly Tyr Asp Ile Met Gly Trp Leu Ile Gln Ile Met Asn
                325                 330                 335

Arg Pro Asn Pro Gln Val Glu Leu Gly Pro Val Asp Thr Ser Cys Ala
            340                 345                 350

Leu Ile Leu Cys Asp Leu Lys Gln Lys Asp Thr Pro Ile Val Tyr Ala
        355                 360                 365

Ser Glu Ala Phe Leu Tyr Met Thr Gly Tyr Ser Asn Ala Glu Val Leu
        370                 375                 380

Gly Arg Asn Cys Arg Phe Leu Gln Ser Pro Asp Gly Met Val Lys Pro
385                 390                 395                 400

Lys Ser Thr Arg Lys Tyr Val Asp Ser Asn Thr Ile Asn Thr Met Arg
                405                 410                 415

Lys Ala Ile Asp Arg Asn Ala Glu Val Gln Val Glu Val Val Asn Phe
            420                 425                 430

Lys Lys Asn Gly Gln Arg Phe Val Asn Phe Leu Thr Met Ile Pro Val
        435                 440                 445

Arg Asp Glu Thr Gly Glu Tyr Arg Tyr Ser Met Gly Phe Gln Cys Glu
    450                 455                 460

Thr Glu
465

<210> SEQ ID NO 29
<211> LENGTH: 380
<212> TYPE: PRT
<213> ORGANISM: Artificial Sequence
<220> FEATURE:
<223> OTHER INFORMATION: synthetic construct

<400> SEQUENCE: 29

Met Arg Lys Val Phe Val Gly Arg Cys Thr Glu Asp Met Thr Glu Asp
1               5                   10                  15

Glu Leu Arg Glu Phe Phe Ser Gln Tyr Gly Asp Val Met Asp Val Phe
            20                  25                  30

Ile Pro Lys Pro Phe Arg Ala Phe Ala Phe Val Thr Phe Ala Asp Asp
        35                  40                  45

Gln Ile Ala Gln Ser Leu Cys Gly Glu Asp Leu Ile Ile Lys Gly Ile
    50                  55                  60

Ser Val His Ile Ser Asn Ala Glu Pro Lys His Asn Ser Asn Arg Gln
65                  70                  75                  80
```

```
Leu Glu Arg Ser Gly Arg Phe Gly Gly Asn Pro Gly Gly Phe Gly Asn
                85                  90                  95

Gln Gly Gly Phe Gly Asn Ser Arg Gly Gly Ala Gly Leu Gly Asn
           100                 105                 110

Asn Gln Gly Ser Asn Met Gly Gly Gly Met Asn Phe Gly Ala Phe Ser
           115                 120                 125

Ile Asn Pro Ala Met Met Ala Ala Gln Ala Leu Gln Ser Ser
           130                 135                 140

Trp Gly Met Met Gly Met Leu Ala Ser Gln Gln Asn Gln Ser Gly Pro
145                 150                 155                 160

Ser Gly Asn Asn Gln Asn Gln Gly Asn Met Gln Arg Glu Pro Asn Gln
                165                 170                 175

Ala Phe Gly Ser Gly Asn Asn Ser Tyr Ser Gly Ser Asn Ser Gly Ala
                180                 185                 190

Ala Ile Gly Trp Gly Ser Ala Ser Asn Ala Gly Ser Gly Ser Gly Phe
                195                 200                 205

Asn Gly Gly Phe Gly Ser Ser Met Asp Ser Lys Ser Ser Gly Trp Gly
                210                 215                 220

Met Phe Arg Ala Gln Arg His Thr Leu Tyr Ala Pro Gly Gly Tyr Asp
225                 230                 235                 240

Ile Met Gly Trp Leu Ile Gln Ile Met Asn Arg Pro Asn Pro Gln Val
                245                 250                 255

Glu Leu Gly Pro Val Asp Thr Ser Cys Ala Leu Ile Leu Cys Asp Leu
                260                 265                 270

Lys Gln Lys Asp Thr Pro Ile Val Tyr Ala Ser Glu Ala Phe Leu Tyr
                275                 280                 285

Met Thr Gly Tyr Ser Asn Ala Glu Val Leu Gly Arg Asn Cys Arg Phe
                290                 295                 300

Leu Gln Ser Pro Asp Gly Met Val Lys Pro Lys Ser Thr Arg Lys Tyr
305                 310                 315                 320

Val Asp Ser Asn Thr Ile Asn Thr Met Arg Lys Ala Ile Asp Arg Asn
                325                 330                 335

Ala Glu Val Gln Val Glu Val Val Asn Phe Lys Lys Asn Gly Gln Arg
                340                 345                 350

Phe Val Asn Phe Leu Thr Met Ile Pro Val Arg Asp Glu Thr Gly Glu
                355                 360                 365

Tyr Arg Tyr Ser Met Gly Phe Gln Cys Glu Thr Glu
                370                 375                 380

<210> SEQ ID NO 30
<211> LENGTH: 297
<212> TYPE: PRT
<213> ORGANISM: Artificial Sequence
<220> FEATURE:
<223> OTHER INFORMATION: synthetic construct

<400> SEQUENCE: 30

Met Gly Arg Phe Gly Gly Asn Pro Gly Gly Phe Gly Asn Gln Gly Gly
1               5                   10                  15

Phe Gly Asn Ser Arg Gly Gly Ala Gly Leu Gly Asn Asn Gln Gly
            20                  25                  30

Ser Asn Met Gly Gly Gly Met Asn Phe Gly Ala Phe Ser Ile Asn Pro
            35                  40                  45

Ala Met Met Ala Ala Ala Gln Ala Leu Gln Ser Ser Trp Gly Met
50                  55                  60
```

```
Met Gly Met Leu Ala Ser Gln Gln Asn Gln Ser Gly Pro Ser Gly Asn
 65                  70                  75                  80

Asn Gln Asn Gln Gly Asn Met Gln Arg Glu Pro Asn Gln Ala Phe Gly
                 85                  90                  95

Ser Gly Asn Asn Ser Tyr Ser Gly Ser Asn Ser Gly Ala Ala Ile Gly
            100                 105                 110

Trp Gly Ser Ala Ser Asn Ala Gly Ser Gly Ser Gly Phe Asn Gly Gly
        115                 120                 125

Phe Gly Ser Ser Met Asp Ser Lys Ser Ser Gly Trp Gly Met Phe Arg
    130                 135                 140

Ala Gln Arg His Thr Leu Tyr Ala Pro Gly Gly Tyr Asp Ile Met Gly
145                 150                 155                 160

Trp Leu Ile Gln Ile Met Asn Arg Pro Asn Pro Gln Val Glu Leu Gly
                165                 170                 175

Pro Val Asp Thr Ser Cys Ala Leu Ile Leu Cys Asp Leu Lys Gln Lys
            180                 185                 190

Asp Thr Pro Ile Val Tyr Ala Ser Glu Ala Phe Leu Tyr Met Thr Gly
        195                 200                 205

Tyr Ser Asn Ala Glu Val Leu Gly Arg Asn Cys Arg Phe Leu Gln Ser
210                 215                 220

Pro Asp Gly Met Val Lys Pro Lys Ser Thr Arg Lys Tyr Val Asp Ser
225                 230                 235                 240

Asn Thr Ile Asn Thr Met Arg Lys Ala Ile Asp Arg Asn Ala Glu Val
                245                 250                 255

Gln Val Glu Val Val Asn Phe Lys Lys Asn Gly Gln Arg Phe Val Asn
            260                 265                 270

Phe Leu Thr Met Ile Pro Val Arg Asp Glu Thr Gly Glu Tyr Arg Tyr
        275                 280                 285

Ser Met Gly Phe Gln Cys Glu Thr Glu
    290                 295

<210> SEQ ID NO 31
<211> LENGTH: 462
<212> TYPE: PRT
<213> ORGANISM: Artificial Sequence
<220> FEATURE:
<223> OTHER INFORMATION: synthetic construct

<400> SEQUENCE: 31

Met His Thr Leu Tyr Ala Pro Gly Gly Tyr Asp Ile Met Gly Trp Leu
 1               5                  10                  15

Ile Gln Ile Met Asn Arg Pro Asn Pro Gln Val Glu Leu Gly Pro Val
                20                  25                  30

Asp Thr Ser Cys Ala Leu Ile Leu Cys Asp Leu Lys Gln Lys Asp Thr
            35                  40                  45

Pro Ile Val Tyr Ala Ser Glu Ala Phe Leu Tyr Met Thr Gly Tyr Ser
        50                  55                  60

Asn Ala Glu Val Leu Gly Arg Asn Cys Arg Phe Leu Gln Ser Pro Asp
 65                  70                  75                  80

Gly Met Val Lys Pro Lys Ser Thr Arg Lys Tyr Val Asp Ser Asn Thr
                 85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125
```

Thr Met Ile Pro Val Arg Asp Glu Thr Gly Glu Tyr Arg Tyr Ser Met
            130                 135                 140

Gly Phe Gln Cys Glu Thr Glu Ala Asp Leu Ile Val Leu Gly Leu Pro
145                 150                 155                 160

Trp Lys Thr Thr Glu Gln Asp Leu Lys Glu Tyr Phe Ser Thr Phe Gly
                165                 170                 175

Glu Val Leu Met Val Gln Val Lys Lys Asp Leu Lys Thr Gly His Ser
            180                 185                 190

Lys Gly Phe Gly Phe Val Arg Phe Thr Glu Tyr Glu Thr Gln Val Lys
                195                 200                 205

Val Met Ser Gln Arg His Met Ile Asp Gly Arg Trp Cys Asp Cys Lys
210                 215                 220

Leu Pro Asn Ser Lys Gln Ser Gln Asp Glu Pro Leu Arg Ser Arg Lys
225                 230                 235                 240

Val Phe Val Gly Arg Cys Thr Glu Asp Met Thr Glu Asp Glu Leu Arg
                245                 250                 255

Glu Phe Phe Ser Gln Tyr Gly Asp Val Met Asp Val Phe Ile Pro Lys
                260                 265                 270

Pro Phe Arg Ala Phe Ala Phe Val Thr Phe Ala Asp Asp Gln Ile Ala
                275                 280                 285

Gln Ser Leu Cys Gly Glu Asp Leu Ile Ile Lys Gly Ile Ser Val His
            290                 295                 300

Ile Ser Asn Ala Glu Pro Lys His Asn Ser Asn Arg Gln Leu Glu Arg
305                 310                 315                 320

Ser Gly Arg Phe Gly Gly Asn Pro Gly Gly Phe Gly Asn Gln Gly Gly
                325                 330                 335

Phe Gly Asn Ser Arg Gly Gly Gly Ala Gly Leu Gly Asn Asn Gln Gly
            340                 345                 350

Ser Asn Met Gly Gly Gly Met Asn Phe Gly Ala Phe Ser Ile Asn Pro
            355                 360                 365

Ala Met Met Ala Ala Ala Gln Ala Ala Leu Gln Ser Ser Trp Gly Met
            370                 375                 380

Met Gly Met Leu Ala Ser Gln Gln Asn Gln Ser Gly Pro Ser Gly Asn
385                 390                 395                 400

Asn Gln Asn Gln Gly Asn Met Gln Arg Glu Pro Asn Gln Ala Phe Gly
                405                 410                 415

Ser Gly Asn Asn Ser Tyr Ser Gly Ser Asn Ser Gly Ala Ala Ile Gly
                420                 425                 430

Trp Gly Ser Ala Ser Asn Ala Gly Ser Gly Ser Gly Phe Asn Gly Gly
            435                 440                 445

Phe Gly Ser Ser Met Asp Ser Lys Ser Ser Gly Trp Gly Met
450                 455                 460

<210> SEQ ID NO 32
<211> LENGTH: 376
<212> TYPE: PRT
<213> ORGANISM: Artificial Sequence
<220> FEATURE:
<223> OTHER INFORMATION: synthetic construct

<400> SEQUENCE: 32

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

```
Asp Thr Ser Cys Ala Leu Ile Leu Cys Asp Leu Lys Gln Lys Asp Thr
            35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
            115                 120                 125

Thr Met Ile Pro Val Arg Asp Glu Thr Gly Glu Tyr Arg Tyr Ser Met
    130                 135                 140

Gly Phe Gln Cys Glu Thr Glu Ala Arg Lys Val Phe Val Gly Arg Cys
145                 150                 155                 160

Thr Glu Asp Met Thr Glu Asp Glu Leu Arg Glu Phe Phe Ser Gln Tyr
                165                 170                 175

Gly Asp Val Met Asp Val Phe Ile Pro Lys Pro Phe Arg Ala Phe Ala
            180                 185                 190

Phe Val Thr Phe Ala Asp Asp Gln Ile Ala Gln Ser Leu Cys Gly Glu
    195                 200                 205

Asp Leu Ile Ile Lys Gly Ile Ser Val His Ile Ser Asn Ala Glu Pro
    210                 215                 220

Lys His Asn Ser Asn Arg Gln Leu Glu Arg Ser Gly Arg Phe Gly Gly
225                 230                 235                 240

Asn Pro Gly Gly Phe Gly Asn Gln Gly Gly Phe Gly Asn Ser Arg Gly
                245                 250                 255

Gly Gly Ala Gly Leu Gly Asn Asn Gln Gly Ser Asn Met Gly Gly Gly
            260                 265                 270

Met Asn Phe Gly Ala Phe Ser Ile Asn Pro Ala Met Met Ala Ala Ala
    275                 280                 285

Gln Ala Ala Leu Gln Ser Ser Trp Gly Met Met Gly Met Leu Ala Ser
290                 295                 300

Gln Gln Asn Gln Ser Gly Pro Ser Gly Asn Asn Gln Asn Gln Gly Asn
305                 310                 315                 320

Met Gln Arg Glu Pro Asn Gln Ala Phe Gly Ser Gly Asn Asn Ser Tyr
                325                 330                 335

Ser Gly Ser Asn Ser Gly Ala Ala Ile Gly Trp Gly Ser Ala Ser Asn
            340                 345                 350

Ala Gly Ser Gly Ser Gly Phe Asn Gly Gly Phe Gly Ser Ser Met Asp
    355                 360                 365

Ser Lys Ser Ser Gly Trp Gly Met
    370                 375

<210> SEQ ID NO 33
<211> LENGTH: 292
<212> TYPE: PRT
<213> ORGANISM: Artificial Sequence
<220> FEATURE:
<223> OTHER INFORMATION: synthetic construct

<400> SEQUENCE: 33

His Thr Leu Tyr Ala Pro Gly Gly Tyr Asp Ile Met Gly Trp Leu Ile
1               5                   10                  15
```

```
Gln Ile Met Asn Arg Pro Asn Pro Gln Val Glu Leu Gly Pro Val Asp
             20                  25                  30

Thr Ser Cys Ala Leu Ile Leu Cys Asp Leu Lys Gln Lys Asp Thr Pro
         35                  40                  45

Ile Val Tyr Ala Ser Glu Ala Phe Leu Tyr Met Thr Gly Tyr Ser Asn
 50                  55                  60

Ala Glu Val Leu Gly Arg Asn Cys Arg Phe Leu Gln Ser Pro Asp Gly
 65                  70                  75                  80

Met Val Lys Pro Lys Ser Thr Arg Lys Tyr Val Asp Ser Asn Thr Ile
                 85                  90                  95

Asn Thr Met Arg Lys Ala Ile Asp Arg Asn Ala Glu Val Gln Val Glu
                100                 105                 110

Val Val Asn Phe Lys Lys Asn Gly Gln Arg Phe Val Asn Phe Leu Thr
            115                 120                 125

Met Ile Pro Val Arg Asp Glu Thr Gly Glu Tyr Arg Tyr Ser Met Gly
130                 135                 140

Phe Gln Cys Glu Thr Glu Ala Gly Arg Phe Gly Gly Asn Pro Gly Gly
145                 150                 155                 160

Phe Gly Asn Gln Gly Gly Phe Gly Asn Ser Arg Gly Gly Ala Gly
                165                 170                 175

Leu Gly Asn Asn Gln Gly Ser Asn Met Gly Gly Met Asn Phe Gly
                180                 185                 190

Ala Phe Ser Ile Asn Pro Ala Met Met Ala Ala Gln Ala Ala Leu
                195                 200                 205

Gln Ser Ser Trp Gly Met Met Gly Met Leu Ala Ser Gln Gln Asn Gln
210                 215                 220

Ser Gly Pro Ser Gly Asn Asn Gln Asn Gln Gly Asn Met Gln Arg Glu
225                 230                 235                 240

Pro Asn Gln Ala Phe Gly Ser Gly Asn Asn Ser Tyr Ser Gly Ser Asn
                245                 250                 255

Ser Gly Ala Ala Ile Gly Trp Gly Ser Ala Ser Asn Ala Gly Ser Gly
                260                 265                 270

Ser Gly Phe Asn Gly Gly Phe Gly Ser Ser Met Asp Ser Lys Ser Ser
                275                 280                 285

Gly Trp Gly Met
    290
```

<210> SEQ ID NO 34
<211> LENGTH: 808
<212> TYPE: PRT
<213> ORGANISM: Artificial Sequence
<220> FEATURE:
<223> OTHER INFORMATION: synthetic construct

<400> SEQUENCE: 34

```
Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
                20                  25                  30

Asp Thr Ser Cys Ala Leu Ile Leu Cys Asp Leu Lys Gln Lys Asp Thr
            35                  40                  45

Pro Ile Val Tyr Ala Ser Glu Ala Phe Leu Tyr Met Thr Gly Tyr Ser
        50                  55                  60

Asn Ala Glu Val Leu Gly Arg Asn Cys Arg Phe Leu Gln Ser Pro Asp
65                  70                  75                  80
```

-continued

```
Gly Met Val Lys Pro Lys Ser Thr Arg Lys Tyr Val Asp Ser Asn Thr
             85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Ala Met Ser Glu Tyr Ile Arg Val Thr
145                 150                 155                 160

Glu Asp Glu Asn Asp Glu Pro Ile Glu Ile Pro Ser Glu Asp Asp Gly
                165                 170                 175

Thr Val Leu Leu Ser Thr Val Thr Ala Gln Phe Pro Gly Ala Cys Gly
            180                 185                 190

Leu Arg Tyr Arg Asn Pro Val Ser Gln Cys Met Arg Gly Val Arg Leu
        195                 200                 205

Val Glu Gly Ile Leu His Ala Pro Asp Ala Gly Trp Gly Asn Leu Val
    210                 215                 220

Tyr Val Val Asn Tyr Pro Lys Asp Asn Lys Arg Lys Met Asp Glu Thr
225                 230                 235                 240

Asp Ala Ser Ser Ala Val Lys Val Lys Arg Ala Val Gln Lys Thr Ser
                245                 250                 255

Asp Leu Ile Val Leu Gly Leu Pro Trp Lys Thr Thr Glu Gln Asp Leu
            260                 265                 270

Lys Glu Tyr Phe Ser Thr Phe Gly Glu Val Leu Met Val Gln Val Lys
        275                 280                 285

Lys Asp Leu Lys Thr Gly His Ser Lys Gly Phe Gly Phe Val Arg Phe
    290                 295                 300

Thr Glu Tyr Glu Thr Gln Val Lys Val Met Ser Gln Arg His Met Ile
305                 310                 315                 320

Asp Gly Arg Trp Cys Asp Cys Lys Leu Pro Asn Ser Lys Gln Ser Gln
                325                 330                 335

Asp Glu Pro Leu Arg Ser Arg Lys Val Phe Val Gly Arg Cys Thr Glu
            340                 345                 350

Asp Met Thr Glu Asp Glu Leu Arg Glu Phe Phe Ser Gln Tyr Gly Asp
        355                 360                 365

Val Met Asp Val Phe Ile Pro Lys Pro Phe Arg Ala Phe Ala Phe Val
    370                 375                 380

Thr Phe Ala Asp Asp Gln Ile Ala Gln Ser Leu Cys Gly Glu Asp Leu
385                 390                 395                 400

Ile Ile Lys Gly Ile Ser Val His Ile Ser Asn Ala Glu Pro Lys His
                405                 410                 415

Asn Ser Asn Arg Gln Leu Glu Arg Ser Gly Arg Phe Gly Gly Asn Pro
            420                 425                 430

Gly Gly Phe Gly Asn Gln Gly Gly Phe Gly Asn Ser Arg Gly Gly Gly
        435                 440                 445

Ala Gly Leu Gly Asn Asn Gln Gly Ser Asn Met Gly Gly Gly Met Asn
    450                 455                 460

Phe Gly Ala Phe Ser Ile Asn Pro Ala Met Met Ala Ala Ala Gln Ala
465                 470                 475                 480

Ala Leu Gln Ser Ser Trp Gly Met Met Gly Met Leu Ala Ser Gln Gln
                485                 490                 495

Asn Gln Ser Gly Pro Ser Gly Asn Asn Gln Asn Gln Gly Asn Met Gln
```

```
                500             505             510
    Arg Glu Pro Asn Gln Ala Phe Gly Ser Gly Asn Asn Ser Tyr Ser Gly
            515                 520                 525
    Ser Asn Ser Gly Ala Ala Ile Gly Trp Gly Ser Ala Ser Asn Ala Gly
            530                 535                 540
    Ser Gly Ser Gly Phe Asn Gly Gly Phe Gly Ser Ser Met Asp Ser Lys
545                 550                 555                 560
    Ser Ser Gly Trp Gly Met Phe Ala Pro Val Ala Thr Met Val Ser Lys
                565                 570                 575
    Gly Glu Glu Asp Asn Met Ala Ile Ile Lys Glu Phe Met Arg Phe Lys
                580                 585                 590
    Val His Met Glu Gly Ser Val Asn Gly His Glu Phe Glu Ile Glu Gly
                595                 600                 605
    Glu Gly Glu Gly Arg Pro Tyr Glu Gly Thr Gln Thr Ala Lys Leu Lys
                610                 615                 620
    Val Thr Lys Gly Gly Pro Leu Pro Phe Ala Trp Asp Ile Leu Ser Pro
625                 630                 635                 640
    Gln Phe Met Tyr Gly Ser Lys Ala Tyr Val Lys His Pro Ala Asp Ile
                645                 650                 655
    Pro Asp Tyr Leu Lys Leu Ser Phe Pro Glu Gly Phe Lys Trp Glu Arg
                660                 665                 670
    Val Met Asn Phe Glu Asp Gly Gly Val Val Thr Val Thr Gln Asp Ser
                675                 680                 685
    Ser Leu Gln Asp Gly Glu Phe Ile Tyr Lys Val Lys Leu Arg Gly Thr
                690                 695                 700
    Asn Phe Pro Ser Asp Gly Pro Val Met Gln Lys Lys Thr Met Gly Trp
705                 710                 715                 720
    Glu Ala Ser Ser Glu Arg Met Tyr Pro Glu Asp Gly Ala Leu Lys Gly
                725                 730                 735
    Glu Ile Lys Gln Arg Leu Lys Leu Lys Asp Gly Gly His Tyr Asp Ala
                740                 745                 750
    Glu Val Lys Thr Thr Tyr Lys Ala Lys Lys Pro Val Gln Leu Pro Gly
                755                 760                 765
    Ala Tyr Asn Val Asn Ile Lys Leu Asp Ile Thr Ser His Asn Glu Asp
                770                 775                 780
    Tyr Thr Ile Val Glu Gln Tyr Glu Arg Ala Glu Gly Arg His Ser Thr
785                 790                 795                 800
    Gly Gly Met Asp Glu Leu Tyr Lys
                805

<210> SEQ ID NO 35
<211> LENGTH: 809
<212> TYPE: PRT
<213> ORGANISM: Artificial Sequence
<220> FEATURE:
<223> OTHER INFORMATION: synthetic construct

<400> SEQUENCE: 35

Met Val Ser Lys Gly Glu Glu Asp Asn Met Ala Ile Ile Lys Glu Phe
1               5                   10                  15
Met Arg Phe Lys Val His Met Glu Gly Ser Val Asn Gly His Glu Phe
                20                  25                  30
Glu Ile Glu Gly Glu Gly Glu Gly Arg Pro Tyr Glu Gly Thr Gln Thr
            35                  40                  45
Ala Lys Leu Lys Val Thr Lys Gly Gly Pro Leu Pro Phe Ala Trp Asp
```

-continued

```
                 50                  55                  60
Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
                115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Asn Val Asn Ile Lys Leu Asp Ile Thr Ser
                195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys Ser Gly Leu Lys
225                 230                 235                 240

Met Ser Glu Tyr Ile Arg Val Thr Glu Asp Glu Asn Asp Glu Pro Ile
                245                 250                 255

Glu Ile Pro Ser Glu Asp Gly Thr Val Leu Leu Ser Thr Val Thr
                260                 265                 270

Ala Gln Phe Pro Gly Ala Cys Gly Leu Arg Tyr Arg Asn Pro Val Ser
                275                 280                 285

Gln Cys Met Arg Gly Val Arg Leu Val Glu Gly Ile Leu His Ala Pro
                290                 295                 300

Asp Ala Gly Trp Gly Asn Leu Val Tyr Val Val Asn Tyr Pro Lys Asp
305                 310                 315                 320

Asn Lys Arg Lys Met Asp Glu Thr Asp Ala Ser Ser Ala Val Lys Val
                325                 330                 335

Lys Arg Ala Val Gln Lys Thr Ser Asp Leu Ile Val Leu Gly Leu Pro
                340                 345                 350

Trp Lys Thr Thr Glu Gln Asp Leu Lys Glu Tyr Phe Ser Thr Phe Gly
                355                 360                 365

Glu Val Leu Met Val Gln Val Lys Lys Asp Leu Lys Thr Gly His Ser
370                 375                 380

Lys Gly Phe Gly Phe Val Arg Phe Thr Glu Tyr Glu Thr Gln Val Lys
385                 390                 395                 400

Val Met Ser Gln Arg His Met Ile Asp Gly Arg Trp Cys Asp Cys Lys
                405                 410                 415

Leu Pro Asn Ser Lys Gln Ser Gln Asp Glu Pro Leu Arg Ser Arg Lys
                420                 425                 430

Val Phe Val Gly Arg Cys Thr Glu Asp Met Thr Glu Asp Glu Leu Arg
                435                 440                 445

Glu Phe Phe Ser Gln Tyr Gly Asp Val Met Asp Val Phe Ile Pro Lys
                450                 455                 460

Pro Phe Arg Ala Phe Ala Phe Val Thr Phe Ala Asp Asp Gln Ile Ala
465                 470                 475                 480
```

-continued

```
Gln Ser Leu Cys Gly Glu Asp Leu Ile Ile Lys Gly Ile Ser Val His
            485                 490                 495

Ile Ser Asn Ala Glu Pro Lys His Asn Ser Asn Arg Gln Leu Glu Arg
            500                 505                 510

Ser Gly Arg Phe Gly Gly Asn Pro Gly Gly Phe Gly Asn Gln Gly Gly
            515                 520                 525

Phe Gly Asn Ser Arg Gly Gly Ala Gly Leu Gly Asn Asn Gln Gly
            530                 535             540

Ser Asn Met Gly Gly Gly Met Asn Phe Gly Ala Phe Ser Ile Asn Pro
545                 550                 555                 560

Ala Met Met Ala Ala Gln Ala Ala Leu Gln Ser Ser Trp Gly Met
            565                 570                 575

Met Gly Met Leu Ala Ser Gln Gln Asn Gln Ser Gly Pro Ser Gly Asn
            580                 585                 590

Asn Gln Asn Gln Gly Asn Met Gln Arg Glu Pro Asn Gln Ala Phe Gly
            595                 600                 605

Ser Gly Asn Asn Ser Tyr Ser Gly Ser Asn Ser Gly Ala Ala Ile Gly
            610                 615                 620

Trp Gly Ser Ala Ser Asn Ala Gly Ser Gly Ser Gly Phe Asn Gly Gly
625                 630                 635                 640

Phe Gly Ser Ser Met Asp Ser Lys Ser Ser Gly Trp Gly Met Phe Arg
                645                 650                 655

Ala Gln Arg His Thr Leu Tyr Ala Pro Gly Gly Tyr Asp Ile Met Gly
                660                 665                 670

Trp Leu Ile Gln Ile Met Asn Arg Pro Asn Pro Gln Val Glu Leu Gly
                675                 680                 685

Pro Val Asp Thr Ser Cys Ala Leu Ile Leu Cys Asp Leu Lys Gln Lys
            690                 695                 700

Asp Thr Pro Ile Val Tyr Ala Ser Glu Ala Phe Leu Tyr Met Thr Gly
705                 710                 715                 720

Tyr Ser Asn Ala Glu Val Leu Gly Arg Asn Cys Arg Phe Leu Gln Ser
                725                 730                 735

Pro Asp Gly Met Val Lys Pro Lys Ser Thr Arg Lys Tyr Val Asp Ser
            740                 745                 750

Asn Thr Ile Asn Thr Met Arg Lys Ala Ile Asp Arg Asn Ala Glu Val
            755                 760                 765

Gln Val Glu Val Val Asn Phe Lys Lys Asn Gly Gln Arg Phe Val Asn
            770                 775                 780

Phe Leu Thr Met Ile Pro Val Arg Asp Glu Thr Gly Glu Tyr Arg Tyr
785                 790                 795                 800

Ser Met Gly Phe Gln Cys Glu Thr Glu
                805

<210> SEQ ID NO 36
<211> LENGTH: 705
<212> TYPE: PRT
<213> ORGANISM: Artificial Sequence
<220> FEATURE:
<223> OTHER INFORMATION: synthetic construct

<400> SEQUENCE: 36

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30
```

-continued

Glu Ile Glu Gly Glu Gly Gly Arg Pro Tyr Gly Thr Gln Thr
         35                  40                  45

Ala Lys Leu Lys Val Thr Lys Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
             100                 105                 110

Thr Gln Asp Ser Ser Leu Gln Asp Gly Glu Phe Ile Tyr Lys Val Lys
             115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                 165                 170                 175

His Tyr Asp Ala Glu Val Lys Thr Thr Tyr Lys Ala Lys Lys Pro Val
             180                 185                 190

Gln Leu Pro Gly Ala Tyr Asn Val Asn Ile Lys Leu Asp Ile Thr Ser
             195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys Ser Gly Leu Lys
225                 230                 235                 240

Asp Leu Ile Val Leu Gly Leu Pro Trp Lys Thr Thr Glu Gln Asp Leu
                 245                 250                 255

Lys Glu Tyr Phe Ser Thr Phe Gly Glu Val Leu Met Val Gln Val Lys
             260                 265                 270

Lys Asp Leu Lys Thr Gly His Ser Lys Gly Phe Gly Phe Val Arg Phe
             275                 280                 285

Thr Glu Tyr Glu Thr Gln Val Lys Val Met Ser Gln Arg His Met Ile
290                 295                 300

Asp Gly Arg Trp Cys Asp Cys Lys Leu Pro Asn Ser Lys Gln Ser Gln
305                 310                 315                 320

Asp Glu Pro Leu Arg Ser Arg Lys Val Phe Val Gly Arg Cys Thr Glu
                 325                 330                 335

Asp Met Thr Glu Asp Glu Leu Arg Glu Phe Phe Ser Gln Tyr Gly Asp
             340                 345                 350

Val Met Asp Val Phe Ile Pro Lys Pro Phe Arg Ala Phe Ala Phe Val
             355                 360                 365

Thr Phe Ala Asp Asp Gln Ile Ala Gln Ser Leu Cys Gly Glu Asp Leu
370                 375                 380

Ile Ile Lys Gly Ile Ser Val His Ile Ser Asn Ala Glu Pro Lys His
385                 390                 395                 400

Asn Ser Asn Arg Gln Leu Glu Arg Ser Gly Arg Phe Gly Gly Asn Pro
                 405                 410                 415

Gly Gly Phe Gly Asn Gln Gly Gly Phe Gly Asn Ser Arg Gly Gly Gly
             420                 425                 430

Ala Gly Leu Gly Asn Asn Gln Gly Ser Asn Met Gly Gly Gly Met Asn
             435                 440                 445

-continued

```
Phe Gly Ala Phe Ser Ile Asn Pro Ala Met Met Ala Ala Gln Ala
    450                 455                 460
Ala Leu Gln Ser Ser Trp Gly Met Met Gly Met Leu Ala Ser Gln Gln
465                 470                 475                 480
Asn Gln Ser Gly Pro Ser Gly Asn Asn Gln Asn Gly Asn Met Gln
                485                 490                 495
Arg Glu Pro Asn Gln Ala Phe Gly Ser Gly Asn Asn Ser Tyr Ser Gly
                500                 505                 510
Ser Asn Ser Gly Ala Ala Ile Gly Trp Gly Ser Ala Ser Asn Ala Gly
            515                 520                 525
Ser Gly Ser Gly Phe Asn Gly Gly Phe Gly Ser Ser Met Asp Ser Lys
    530                 535                 540
Ser Ser Gly Trp Gly Met Phe Arg Ala Gln Arg His Thr Leu Tyr Ala
545                 550                 555                 560
Pro Gly Gly Tyr Asp Ile Met Gly Trp Leu Ile Gln Ile Met Asn Arg
                565                 570                 575
Pro Asn Pro Gln Val Glu Leu Gly Pro Val Asp Thr Ser Cys Ala Leu
                580                 585                 590
Ile Leu Cys Asp Leu Lys Gln Lys Asp Thr Pro Ile Val Tyr Ala Ser
            595                 600                 605
Glu Ala Phe Leu Tyr Met Thr Gly Tyr Ser Asn Ala Glu Val Leu Gly
    610                 615                 620
Arg Asn Cys Arg Phe Leu Gln Ser Pro Asp Gly Met Val Lys Pro Lys
625                 630                 635                 640
Ser Thr Arg Lys Tyr Val Asp Ser Asn Thr Ile Asn Thr Met Arg Lys
                645                 650                 655
Ala Ile Asp Arg Asn Ala Glu Val Gln Val Glu Val Val Asn Phe Lys
                660                 665                 670
Lys Asn Gly Gln Arg Phe Val Asn Phe Leu Thr Met Ile Pro Val Arg
            675                 680                 685
Asp Glu Thr Gly Glu Tyr Arg Tyr Ser Met Gly Phe Gln Cys Glu Thr
    690                 695                 700
Glu
705

<210> SEQ ID NO 37
<211> LENGTH: 619
<212> TYPE: PRT
<213> ORGANISM: Artificial Sequence
<220> FEATURE:
<223> OTHER INFORMATION: synthetic construct

<400> SEQUENCE: 37

Met Val Ser Lys Gly Glu Glu Asp Asn Met Ala Ile Ile Lys Glu Phe
1               5                   10                  15
Met Arg Phe Lys Val His Met Glu Gly Ser Val Asn Gly His Glu Phe
                20                  25                  30
Glu Ile Glu Gly Glu Gly Glu Gly Arg Pro Tyr Glu Gly Thr Gln Thr
            35                  40                  45
Ala Lys Leu Lys Val Thr Lys Gly Gly Pro Leu Pro Phe Ala Trp Asp
    50                  55                  60
Ile Leu Ser Pro Gln Phe Met Tyr Gly Ser Lys Ala Tyr Val Lys His
65                  70                  75                  80
Pro Ala Asp Ile Pro Asp Tyr Leu Lys Leu Ser Phe Pro Glu Gly Phe
                85                  90                  95
```

-continued

```
Lys Trp Glu Arg Val Met Asn Phe Glu Asp Gly Val Thr Val
                100                 105                 110
Thr Gln Asp Ser Ser Leu Gln Asp Gly Glu Phe Ile Tyr Lys Val Lys
        115                 120                 125
Leu Arg Gly Thr Asn Phe Pro Ser Asp Gly Pro Val Met Gln Lys Lys
    130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
            180                 185                 190
Gln Leu Pro Gly Ala Tyr Asn Val Asn Ile Lys Leu Asp Ile Thr Ser
        195                 200                 205
His Asn Glu Asp Tyr Thr Ile Val Glu Gln Tyr Glu Arg Ala Glu Gly
    210                 215                 220
Arg His Ser Thr Gly Gly Met Asp Glu Leu Tyr Lys Ser Gly Leu Lys
225                 230                 235                 240
Arg Lys Val Phe Val Gly Arg Cys Thr Glu Asp Met Thr Glu Asp Glu
                245                 250                 255
Leu Arg Glu Phe Phe Ser Gln Tyr Gly Asp Val Met Asp Val Phe Ile
            260                 265                 270
Pro Lys Pro Phe Arg Ala Phe Ala Phe Val Thr Phe Ala Asp Asp Gln
        275                 280                 285
Ile Ala Gln Ser Leu Cys Gly Glu Asp Leu Ile Ile Lys Gly Ile Ser
    290                 295                 300
Val His Ile Ser Asn Ala Glu Pro Lys His Asn Ser Asn Arg Gln Leu
305                 310                 315                 320
Glu Arg Ser Gly Arg Phe Gly Asn Pro Gly Gly Phe Gly Asn Gln
                325                 330                 335
Gly Gly Phe Gly Asn Ser Arg Gly Gly Gly Ala Gly Leu Gly Asn Asn
            340                 345                 350
Gln Gly Ser Asn Met Gly Gly Gly Met Asn Phe Gly Ala Phe Ser Ile
        355                 360                 365
Asn Pro Ala Met Met Ala Ala Ala Gln Ala Ala Leu Gln Ser Ser Trp
    370                 375                 380
Gly Met Met Gly Met Leu Ala Ser Gln Gln Asn Gln Ser Gly Pro Ser
385                 390                 395                 400
Gly Asn Asn Gln Asn Gln Gly Asn Met Gln Arg Glu Pro Asn Gln Ala
                405                 410                 415
Phe Gly Ser Gly Asn Asn Ser Tyr Ser Gly Ser Asn Ser Gly Ala Ala
            420                 425                 430
Ile Gly Trp Gly Ser Ala Ser Asn Ala Gly Ser Gly Ser Gly Phe Asn
        435                 440                 445
Gly Gly Phe Gly Ser Ser Met Asp Ser Lys Ser Ser Gly Trp Gly Met
    450                 455                 460
Phe Arg Ala Gln Arg His Thr Leu Tyr Ala Pro Gly Gly Tyr Asp Ile
465                 470                 475                 480
Met Gly Trp Leu Ile Gln Ile Met Asn Arg Pro Asn Pro Gln Val Glu
                485                 490                 495
Leu Gly Pro Val Asp Thr Ser Cys Ala Leu Ile Leu Cys Asp Leu Lys
            500                 505                 510
Gln Lys Asp Thr Pro Ile Val Tyr Ala Ser Glu Ala Phe Leu Tyr Met
```

```
                 515                 520                 525

Thr Gly Tyr Ser Asn Ala Glu Val Leu Gly Arg Asn Cys Arg Phe Leu
    530                 535                 540

Gln Ser Pro Asp Gly Met Val Lys Pro Lys Ser Thr Arg Lys Tyr Val
545                 550                 555                 560

Asp Ser Asn Thr Ile Asn Thr Met Arg Lys Ala Ile Asp Arg Asn Ala
                565                 570                 575

Glu Val Gln Val Glu Val Val Asn Phe Lys Lys Asn Gly Gln Arg Phe
            580                 585                 590

Val Asn Phe Leu Thr Met Ile Pro Val Arg Asp Glu Thr Gly Glu Tyr
        595                 600                 605

Arg Tyr Ser Met Gly Phe Gln Cys Glu Thr Glu
610                 615

<210> SEQ ID NO 38
<211> LENGTH: 536
<212> TYPE: PRT
<213> ORGANISM: Artificial Sequence
<220> FEATURE:
<223> OTHER INFORMATION: synthetic construct

<400> SEQUENCE: 38

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
        210                 215                 220

Arg His Ser Thr Gly Gly Met Asp Glu Leu Tyr Lys Ser Gly Leu Lys
225                 230                 235                 240

Gly Arg Phe Gly Gly Asn Pro Gly Gly Phe Gly Asn Gln Gly Gly Phe
                245                 250                 255

Gly Asn Ser Arg Gly Gly Gly Ala Gly Leu Gly Asn Asn Gln Gly Ser
```

-continued

```
                260                 265                 270
Asn Met Gly Gly Gly Met Asn Phe Gly Ala Phe Ser Ile Asn Pro Ala
                275                 280                 285
Met Met Ala Ala Ala Gln Ala Ala Leu Gln Ser Ser Trp Gly Met Met
            290                 295                 300
Gly Met Leu Ala Ser Gln Gln Asn Gln Ser Gly Pro Ser Gly Asn Asn
305                 310                 315                 320
Gln Asn Gln Gly Asn Met Gln Arg Glu Pro Asn Gln Ala Phe Gly Ser
                325                 330                 335
Gly Asn Asn Ser Tyr Ser Gly Ser Asn Ser Gly Ala Ala Ile Gly Trp
                340                 345                 350
Gly Ser Ala Ser Asn Ala Gly Ser Gly Ser Phe Asn Gly Gly Phe
            355                 360                 365
Gly Ser Ser Met Asp Ser Lys Ser Ser Gly Trp Gly Met Phe Arg Ala
            370                 375                 380
Gln Arg His Thr Leu Tyr Ala Pro Gly Gly Tyr Asp Ile Met Gly Trp
385                 390                 395                 400
Leu Ile Gln Ile Met Asn Arg Pro Asn Pro Gln Val Glu Leu Gly Pro
                405                 410                 415
Val Asp Thr Ser Cys Ala Leu Ile Leu Cys Asp Leu Lys Gln Lys Asp
                420                 425                 430
Thr Pro Ile Val Tyr Ala Ser Glu Ala Phe Leu Tyr Met Thr Gly Tyr
                435                 440                 445
Ser Asn Ala Glu Val Leu Gly Arg Asn Cys Arg Phe Leu Gln Ser Pro
450                 455                 460
Asp Gly Met Val Lys Pro Lys Ser Thr Arg Lys Tyr Val Asp Ser Asn
465                 470                 475                 480
Thr Ile Asn Thr Met Arg Lys Ala Ile Asp Arg Asn Ala Glu Val Gln
                485                 490                 495
Val Glu Val Val Asn Phe Lys Lys Asn Gly Gln Arg Phe Val Asn Phe
                500                 505                 510
Leu Thr Met Ile Pro Val Arg Asp Glu Thr Gly Glu Tyr Arg Tyr Ser
                515                 520                 525
Met Gly Phe Gln Cys Glu Thr Glu
        530                 535
```

<210> SEQ ID NO 39
<211> LENGTH: 704
<212> TYPE: PRT
<213> ORGANISM: Artificial Sequence
<220> FEATURE:
<223> OTHER INFORMATION: synthetic construct

<400> SEQUENCE: 39

```
Met His Thr Leu Tyr Ala Pro Gly Gly Tyr Asp Ile Met Gly Trp Leu
1               5                   10                  15
Ile Gln Ile Met Asn Arg Pro Asn Pro Gln Val Glu Leu Gly Pro Val
                20                  25                  30
Asp Thr Ser Cys Ala Leu Ile Leu Cys Asp Leu Lys Gln Lys Asp Thr
            35                  40                  45
Pro Ile Val Tyr Ala Ser Glu Ala Phe Leu Tyr Met Thr Gly Tyr Ser
        50                  55                  60
Asn Ala Glu Val Leu Gly Arg Asn Cys Arg Phe Leu Gln Ser Pro Asp
65                  70                  75                  80
Gly Met Val Lys Pro Lys Ser Thr Arg Lys Tyr Val Asp Ser Asn Thr
```

-continued

```
                      85                  90                  95
Ile Asn Thr Met Arg Lys Ala Ile Asp Arg Asn Ala Glu Val Gln Val
                100                 105                 110
Glu Val Val Asn Phe Lys Lys Asn Gly Gln Arg Phe Val Asn Phe Leu
                115                 120                 125
Thr Met Ile Pro Val Arg Asp Glu Thr Gly Glu Tyr Arg Tyr Ser Met
                130                 135                 140
Gly Phe Gln Cys Glu Thr Glu Ala Asp Leu Ile Val Leu Gly Leu Pro
145                 150                 155                 160
Trp Lys Thr Thr Glu Gln Asp Leu Lys Glu Tyr Phe Ser Thr Phe Gly
                165                 170                 175
Glu Val Leu Met Val Gln Val Lys Lys Asp Leu Lys Thr Gly His Ser
                180                 185                 190
Lys Gly Phe Gly Phe Val Arg Phe Thr Glu Tyr Glu Thr Gln Val Lys
                195                 200                 205
Val Met Ser Gln Arg His Met Ile Asp Gly Arg Trp Cys Asp Cys Lys
                210                 215                 220
Leu Pro Asn Ser Lys Gln Ser Gln Asp Glu Pro Leu Arg Ser Arg Lys
225                 230                 235                 240
Val Phe Val Gly Arg Cys Thr Glu Asp Met Thr Glu Asp Glu Leu Arg
                245                 250                 255
Glu Phe Phe Ser Gln Tyr Gly Asp Val Met Asp Val Phe Ile Pro Lys
                260                 265                 270
Pro Phe Arg Ala Phe Ala Phe Val Thr Phe Ala Asp Asp Gln Ile Ala
                275                 280                 285
Gln Ser Leu Cys Gly Glu Asp Leu Ile Ile Lys Gly Ile Ser Val His
                290                 295                 300
Ile Ser Asn Ala Glu Pro Lys His Asn Ser Asn Arg Gln Leu Glu Arg
305                 310                 315                 320
Ser Gly Arg Phe Gly Gly Asn Pro Gly Gly Phe Gly Asn Gln Gly Gly
                325                 330                 335
Phe Gly Asn Ser Arg Gly Gly Gly Ala Gly Leu Gly Asn Asn Gln Gly
                340                 345                 350
Ser Asn Met Gly Gly Gly Met Asn Phe Gly Ala Phe Ser Ile Asn Pro
                355                 360                 365
Ala Met Met Ala Ala Ala Gln Ala Ala Leu Gln Ser Ser Trp Gly Met
                370                 375                 380
Met Gly Met Leu Ala Ser Gln Gln Asn Gln Ser Gly Pro Ser Gly Asn
385                 390                 395                 400
Asn Gln Asn Gln Gly Asn Met Gln Arg Glu Pro Asn Gln Ala Phe Gly
                405                 410                 415
Ser Gly Asn Asn Ser Tyr Ser Gly Ser Asn Ser Gly Ala Ala Ile Gly
                420                 425                 430
Trp Gly Ser Ala Ser Asn Ala Gly Ser Gly Ser Gly Phe Asn Gly Gly
                435                 440                 445
Phe Gly Ser Ser Met Asp Ser Lys Ser Ser Gly Trp Gly Met Phe Ala
                450                 455                 460
Pro Val Ala Thr Met Val Ser Lys Gly Glu Glu Asp Asn Met Ala Ile
465                 470                 475                 480
Ile Lys Glu Phe Met Arg Phe Lys Val His Met Glu Gly Ser Val Asn
                485                 490                 495
Gly His Glu Phe Glu Ile Glu Gly Glu Gly Glu Gly Arg Pro Tyr Glu
                500                 505                 510
```

```
Gly Thr Gln Thr Ala Lys Leu Lys Val Thr Lys Gly Gly Pro Leu Pro
            515                 520                 525

Phe Ala Trp Asp Ile Leu Ser Pro Gln Phe Met Tyr Gly Ser Lys Ala
        530                 535                 540

Tyr Val Lys His Pro Ala Asp Ile Pro Asp Tyr Leu Lys Leu Ser Phe
545                 550                 555                 560

Pro Glu Gly Phe Lys Trp Glu Arg Val Met Asn Phe Glu Asp Gly Gly
                565                 570                 575

Val Val Thr Val Thr Gln Asp Ser Ser Leu Gln Asp Gly Glu Phe Ile
            580                 585                 590

Tyr Lys Val Lys Leu Arg Gly Thr Asn Phe Pro Ser Asp Gly Pro Val
        595                 600                 605

Met Gln Lys Lys Thr Met Gly Trp Glu Ala Ser Ser Glu Arg Met Tyr
    610                 615                 620

Pro Glu Asp Gly Ala Leu Lys Gly Glu Ile Lys Gln Arg Leu Lys Leu
625                 630                 635                 640

Lys Asp Gly Gly His Tyr Asp Ala Glu Val Lys Thr Thr Tyr Lys Ala
                645                 650                 655

Lys Lys Pro Val Gln Leu Pro Gly Ala Tyr Asn Val Asn Ile Lys Leu
            660                 665                 670

Asp Ile Thr Ser His Asn Glu Asp Tyr Thr Ile Val Glu Gln Tyr Glu
        675                 680                 685

Arg Ala Glu Gly Arg His Ser Thr Gly Gly Met Asp Glu Leu Tyr Lys
    690                 695                 700

<210> SEQ ID NO 40
<211> LENGTH: 618
<212> TYPE: PRT
<213> ORGANISM: Artificial Sequence
<220> FEATURE:
<223> OTHER INFORMATION: synthetic construct

<400> SEQUENCE: 40

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Ala Arg Lys Val Phe Val Gly Arg Cys
145                 150                 155                 160

Thr Glu Asp Met Thr Glu Asp Glu Leu Arg Glu Phe Phe Ser Gln Tyr
                165                 170                 175
```

```
Gly Asp Val Met Asp Val Phe Ile Pro Lys Pro Phe Arg Ala Phe Ala
            180                 185                 190

Phe Val Thr Phe Ala Asp Asp Gln Ile Ala Gln Ser Leu Cys Gly Glu
        195                 200                 205

Asp Leu Ile Ile Lys Gly Ile Ser Val His Ile Ser Asn Ala Glu Pro
    210                 215                 220

Lys His Asn Ser Asn Arg Gln Leu Glu Arg Ser Gly Arg Phe Gly Gly
225                 230                 235                 240

Asn Pro Gly Gly Phe Gly Asn Gln Gly Gly Phe Gly Asn Ser Arg Gly
                245                 250                 255

Gly Gly Ala Gly Leu Gly Asn Asn Gln Gly Ser Asn Met Gly Gly Gly
            260                 265                 270

Met Asn Phe Gly Ala Phe Ser Ile Asn Pro Ala Met Met Ala Ala Ala
        275                 280                 285

Gln Ala Ala Leu Gln Ser Ser Trp Gly Met Met Gly Met Leu Ala Ser
    290                 295                 300

Gln Gln Asn Gln Ser Gly Pro Ser Gly Asn Asn Gln Asn Gln Gly Asn
305                 310                 315                 320

Met Gln Arg Glu Pro Asn Gln Ala Phe Gly Ser Gly Asn Asn Ser Tyr
                325                 330                 335

Ser Gly Ser Asn Ser Gly Ala Ala Ile Gly Trp Gly Ser Ala Ser Asn
            340                 345                 350

Ala Gly Ser Gly Ser Gly Phe Asn Gly Gly Phe Gly Ser Ser Met Asp
        355                 360                 365

Ser Lys Ser Ser Gly Trp Gly Met Phe Ala Pro Val Ala Thr Met Val
    370                 375                 380

Ser Lys Gly Glu Glu Asp Asn Met Ala Ile Ile Lys Glu Phe Met Arg
385                 390                 395                 400

Phe Lys Val His Met Glu Gly Ser Val Asn Gly His Glu Phe Glu Ile
                405                 410                 415

Glu Gly Glu Gly Glu Gly Arg Pro Tyr Glu Gly Thr Gln Thr Ala Lys
            420                 425                 430

Leu Lys Val Thr Lys Gly Gly Pro Leu Pro Phe Ala Trp Asp Ile Leu
        435                 440                 445

Ser Pro Gln Phe Met Tyr Gly Ser Lys Ala Tyr Val Lys His Pro Ala
    450                 455                 460

Asp Ile Pro Asp Tyr Leu Lys Leu Ser Phe Pro Glu Gly Phe Lys Trp
465                 470                 475                 480

Glu Arg Val Met Asn Phe Glu Asp Gly Gly Val Val Thr Val Thr Gln
                485                 490                 495

Asp Ser Ser Leu Gln Asp Gly Glu Phe Ile Tyr Lys Val Lys Leu Arg
            500                 505                 510

Gly Thr Asn Phe Pro Ser Asp Gly Pro Val Met Gln Lys Lys Thr Met
        515                 520                 525

Gly Trp Glu Ala Ser Ser Glu Arg Met Tyr Pro Glu Asp Gly Ala Leu
    530                 535                 540

Lys Gly Glu Ile Lys Gln Arg Leu Lys Leu Lys Asp Gly Gly His Tyr
545                 550                 555                 560

Asp Ala Glu Val Lys Thr Thr Tyr Lys Ala Lys Lys Pro Val Gln Leu
                565                 570                 575

Pro Gly Ala Tyr Asn Val Asn Ile Lys Leu Asp Ile Thr Ser His Asn
            580                 585                 590
```

```
Glu Asp Tyr Thr Ile Val Glu Gln Tyr Glu Arg Ala Glu Gly Arg His
            595                 600                 605

Ser Thr Gly Gly Met Asp Glu Leu Tyr Lys
    610                 615

<210> SEQ ID NO 41
<211> LENGTH: 535
<212> TYPE: PRT
<213> ORGANISM: Artificial Sequence
<220> FEATURE:
<223> OTHER INFORMATION: synthetic construct

<400> SEQUENCE: 41

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
                20                  25                  30

Asp Thr Ser Cys Ala Leu Ile Leu Cys Asp Leu Lys Gln Lys Asp Thr
            35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
                100                 105                 110

Glu Val Val Asn Phe Lys Lys Asn Gly Gln Arg Phe Val Asn Phe Leu
            115                 120                 125

Thr Met Ile Pro Val Arg Asp Glu Thr Gly Glu Tyr Arg Tyr Ser Met
        130                 135                 140

Gly Phe Gln Cys Glu Thr Glu Ala Gly Arg Phe Gly Gly Asn Pro Gly
145                 150                 155                 160

Gly Phe Gly Asn Gln Gly Gly Phe Gly Asn Ser Arg Gly Gly Gly Ala
                165                 170                 175

Gly Leu Gly Asn Asn Gln Gly Ser Asn Met Gly Gly Gly Met Asn Phe
            180                 185                 190

Gly Ala Phe Ser Ile Asn Pro Ala Met Met Ala Ala Ala Gln Ala Ala
        195                 200                 205

Leu Gln Ser Ser Trp Gly Met Met Gly Met Leu Ala Ser Gln Gln Asn
    210                 215                 220

Gln Ser Gly Pro Ser Gly Asn Asn Gln Asn Gly Asn Met Gln Arg
225                 230                 235                 240

Glu Pro Asn Gln Ala Phe Gly Ser Gly Asn Asn Ser Tyr Ser Gly Ser
                245                 250                 255

Asn Ser Gly Ala Ala Ile Gly Trp Gly Ser Ala Ser Asn Ala Gly Ser
            260                 265                 270

Gly Ser Gly Phe Asn Gly Gly Phe Gly Ser Ser Met Asp Ser Lys Ser
        275                 280                 285

Ser Gly Trp Gly Met Phe Ala Pro Val Ala Thr Met Val Ser Lys Gly
    290                 295                 300

Glu Glu Asp Asn Met Ala Ile Ile Lys Glu Phe Met Arg Phe Lys Val
305                 310                 315                 320

His Met Glu Gly Ser Val Asn Gly His Glu Phe Glu Ile Glu Gly Glu
                325                 330                 335
```

Gly Glu Gly Arg Pro Tyr Glu Gly Thr Gln Thr Ala Lys Leu Lys Val
            340                 345                 350

Thr Lys Gly Gly Pro Leu Pro Phe Ala Trp Asp Ile Leu Ser Pro Gln
        355                 360                 365

Phe Met Tyr Gly Ser Lys Ala Tyr Val Lys His Pro Ala Asp Ile Pro
    370                 375                 380

Asp Tyr Leu Lys Leu Ser Phe Pro Glu Gly Phe Lys Trp Glu Arg Val
385                 390                 395                 400

Met Asn Phe Glu Asp Gly Gly Val Val Thr Val Thr Gln Asp Ser Ser
                405                 410                 415

Leu Gln Asp Gly Glu Phe Ile Tyr Lys Val Lys Leu Arg Gly Thr Asn
            420                 425                 430

Phe Pro Ser Asp Gly Pro Val Met Gln Lys Lys Thr Met Gly Trp Glu
        435                 440                 445

Ala Ser Ser Glu Arg Met Tyr Pro Glu Asp Gly Ala Leu Lys Gly Glu
    450                 455                 460

Ile Lys Gln Arg Leu Lys Leu Lys Asp Gly Gly His Tyr Asp Ala Glu
465                 470                 475                 480

Val Lys Thr Thr Tyr Lys Ala Lys Lys Pro Val Gln Leu Pro Gly Ala
                485                 490                 495

Tyr Asn Val Asn Ile Lys Leu Asp Ile Thr Ser His Asn Glu Asp Tyr
            500                 505                 510

Thr Ile Val Glu Gln Tyr Glu Arg Ala Glu Gly Arg His Ser Thr Gly
        515                 520                 525

Gly Met Asp Glu Leu Tyr Lys
    530                 535

<210> SEQ ID NO 42
<211> LENGTH: 639
<212> TYPE: PRT
<213> ORGANISM: Artificial Sequence
<220> FEATURE:
<223> OTHER INFORMATION: synthetic construct

<400> SEQUENCE: 42

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

```
Met Ser Ile Glu Ser Val Met Leu Pro Pro Trp Arg Leu Met Pro
            165                 170                 175
Ile Thr Ala Ala Ala Glu Ala Ile Trp Ala Cys Ser Ile Glu Glu Leu
        180                 185                 190
Gly Leu Glu Asn Glu Ala Glu Lys Pro Ser Asn Ala Leu Leu Thr Arg
            195                 200                 205
Ala Trp Ser Pro Gly Trp Ser Asn Ala Asp Lys Leu Leu Asn Glu Phe
    210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
            260                 265                 270
Ala Arg Asp Lys Asn Ser Glu Gly Glu Glu Ser Ala Asp Leu Phe Leu
        275                 280                 285
Arg Gly Ile Gly Leu Arg Glu Tyr Ser Arg Tyr Ile Cys Phe Asn Phe
    290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
            340                 345                 350
Trp Met His Asn Arg Ile Arg Val Ile Val Ser Ser Phe Ala Val Lys
        355                 360                 365
Phe Leu Leu Leu Pro Trp Lys Trp Gly Met Lys Tyr Phe Trp Asp Thr
    370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
        435                 440                 445
Trp Asp Ala Pro Leu Thr Val Leu Lys Ala Ser Gly Val Glu Leu Gly
    450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Met Asp Val Phe Met Lys Gly Leu Ser Lys Ala Lys Glu
            500                 505                 510
Gly Val Val Ala Ala Glu Lys Thr Lys Gln Gly Val Ala Glu Ala
        515                 520                 525
Ala Gly Lys Thr Lys Glu Gly Val Leu Tyr Val Gly Ser Lys Thr Lys
    530                 535                 540
Glu Gly Val Val His Gly Val Ala Thr Val Ala Glu Lys Thr Lys Glu
545                 550                 555                 560
Gln Val Thr Asn Val Gly Gly Ala Val Val Thr Gly Val Thr Ala Val
                565                 570                 575
Ala Gln Lys Thr Val Glu Gly Ala Gly Ser Ile Ala Ala Ala Thr Gly
```

```
                       580                 585                 590
Phe Val Lys Lys Asp Gln Leu Gly Lys Asn Glu Glu Gly Ala Pro Gln
                   595                 600                 605

Glu Gly Ile Leu Glu Asp Met Pro Val Asp Pro Asp Asn Glu Ala Tyr
               610                 615                 620

Glu Met Pro Ser Glu Glu Gly Tyr Gln Asp Tyr Glu Pro Glu Ala
625                 630                 635

<210> SEQ ID NO 43
<211> LENGTH: 644
<212> TYPE: PRT
<213> ORGANISM: Artificial Sequence
<220> FEATURE:
<223> OTHER INFORMATION: synthetic construct

<400> SEQUENCE: 43

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Asp Pro Pro Val
        130                 135                 140

Ala Thr Met Lys Met Asp Lys Lys Thr Ile Val Trp Phe Arg Arg Asp
145                 150                 155                 160

Leu Arg Ile Glu Asp Asn Pro Ala Leu Ala Ala Ala His Glu Gly
                165                 170                 175

Ser Val Phe Pro Val Phe Ile Trp Cys Pro Glu Glu Glu Gly Gln Phe
            180                 185                 190

Tyr Pro Gly Arg Ala Ser Arg Trp Trp Met Lys Gln Ser Leu Ala His
        195                 200                 205

Leu Ser Gln Ser Leu Lys Ala Leu Gly Ser Asp Leu Thr Leu Ile Lys
    210                 215                 220

Thr His Asn Thr Ile Ser Ala Ile Leu Asp Cys Ile Arg Val Thr Gly
225                 230                 235                 240

Ala Thr Lys Val Val Phe Asn His Leu Tyr Asp Pro Val Ser Leu Val
                245                 250                 255

Arg Asp His Thr Val Lys Glu Lys Leu Val Glu Arg Gly Ile Ser Val
            260                 265                 270

Gln Ser Tyr Asn Gly Asp Leu Leu Tyr Glu Pro Trp Glu Ile Tyr Cys
        275                 280                 285

Glu Lys Gly Lys Pro Phe Thr Ser Phe Asn Ser Tyr Trp Lys Lys Cys
    290                 295                 300

Leu Asp Met Ser Ile Glu Ser Val Met Leu Pro Pro Pro Trp Arg Leu
```

```
305                 310                 315                 320
Met Pro Ile Thr Ala Ala Ala Glu Ala Ile Trp Ala Cys Ser Ile Glu
                325                 330                 335

Glu Leu Gly Leu Glu Asn Glu Ala Glu Lys Pro Ser Asn Ala Leu Leu
                340                 345                 350

Thr Arg Ala Trp Ser Pro Gly Trp Ser Asn Ala Asp Lys Leu Leu Asn
                355                 360                 365

Glu Phe Ile Glu Lys Gln Leu Ile Asp Tyr Ala Lys Asn Ser Lys Lys
                370                 375                 380

Val Val Gly Asn Ser Thr Ser Leu Leu Ser Pro Tyr Leu His Phe Gly
385                 390                 395                 400

Glu Ile Ser Val Arg His Val Phe Gln Cys Ala Arg Met Lys Gln Ile
                405                 410                 415

Ile Trp Ala Arg Asp Lys Asn Ser Glu Gly Glu Ser Ala Asp Leu
                420                 425                 430

Phe Leu Arg Gly Ile Gly Leu Arg Glu Tyr Ser Arg Tyr Ile Cys Phe
                435                 440                 445

Asn Phe Pro Phe Thr His Glu Gln Ser Leu Leu Ser His Leu Arg Phe
                450                 455                 460

Phe Pro Trp Asp Ala Asp Val Asp Lys Phe Lys Ala Trp Arg Gln Gly
465                 470                 475                 480

Arg Thr Gly Tyr Pro Leu Val Asp Ala Gly Met Arg Glu Leu Trp Ala
                485                 490                 495

Thr Gly Trp Met His Asn Arg Ile Arg Val Ile Val Ser Ser Phe Ala
                500                 505                 510

Val Lys Phe Leu Leu Leu Pro Trp Lys Trp Gly Met Lys Tyr Phe Trp
                515                 520                 525

Asp Thr Leu Leu Asp Ala Asp Leu Glu Cys Asp Ile Leu Gly Trp Gln
                530                 535                 540

Tyr Ile Ser Gly Ser Ile Pro Asp Gly His Glu Leu Asp Arg Leu Asp
545                 550                 555                 560

Asn Pro Ala Leu Gln Gly Ala Lys Tyr Asp Pro Glu Gly Glu Tyr Ile
                565                 570                 575

Arg Gln Trp Leu Pro Glu Leu Ala Arg Leu Pro Thr Glu Trp Ile His
                580                 585                 590

His Pro Trp Asp Ala Pro Leu Thr Val Leu Lys Ala Ser Gly Val Glu
                595                 600                 605

Leu Gly Thr Asn Tyr Ala Lys Pro Ile Val Asp Ile Asp Thr Ala Arg
                610                 615                 620

Glu Leu Leu Ala Lys Ala Ile Ser Arg Thr Arg Gly Ala Gln Ile Met
625                 630                 635                 640

Ile Gly Ala Ala
```

<210> SEQ ID NO 44
<211> LENGTH: 881
<212> TYPE: PRT
<213> ORGANISM: Artificial Sequence
<220> FEATURE:
<223> OTHER INFORMATION: synthetic construct

<400> SEQUENCE: 44

```
Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30
```

-continued

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
50                      55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
                115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
        210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
        340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
        420                 425                 430

Trp Leu Pro Glu Leu Ala Arg Leu Pro Thr Glu Trp Ile His His Pro
435                 440                 445

-continued

```
Trp Asp Ala Pro Leu Thr Val Leu Lys Ala Ser Gly Val Glu Leu Gly
    450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                    485                 490                 495
Ala Ala Ala Met Asp Val Phe Met Lys Gly Leu Ser Lys Ala Lys Glu
                500                 505                 510
Gly Val Val Ala Ala Ala Glu Lys Thr Lys Gln Gly Val Ala Glu Ala
            515                 520                 525
Ala Gly Lys Thr Lys Glu Gly Val Leu Tyr Val Gly Ser Lys Thr Lys
        530                 535                 540
Glu Gly Val Val His Gly Val Ala Thr Val Ala Glu Lys Thr Lys Glu
545                 550                 555                 560
Gln Val Thr Asn Val Gly Gly Ala Val Val Thr Gly Val Thr Ala Val
                    565                 570                 575
Ala Gln Lys Thr Val Glu Gly Ala Gly Ser Ile Ala Ala Ala Thr Gly
                580                 585                 590
Phe Val Lys Lys Asp Gln Leu Gly Lys Asn Glu Glu Gly Ala Pro Gln
            595                 600                 605
Glu Gly Ile Leu Glu Asp Met Pro Val Asp Pro Asp Asn Glu Ala Tyr
        610                 615                 620
Glu Met Pro Ser Glu Glu Gly Tyr Gln Asp Tyr Glu Pro Glu Ala Asp
625                 630                 635                 640
Pro Pro Val Ala Thr Met Val Ser Lys Gly Glu Glu Asp Asn Met Ala
                    645                 650                 655
Ile Ile Lys Glu Phe Met Arg Phe Lys Val His Met Glu Gly Ser Val
                660                 665                 670
Asn Gly His Glu Phe Glu Ile Glu Gly Glu Gly Glu Gly Arg Pro Tyr
            675                 680                 685
Glu Gly Thr Gln Thr Ala Lys Leu Lys Val Thr Lys Gly Gly Pro Leu
        690                 695                 700
Pro Phe Ala Trp Asp Ile Leu Ser Pro Gln Phe Met Tyr Gly Ser Lys
705                 710                 715                 720
Ala Tyr Val Lys His Pro Ala Asp Ile Pro Asp Tyr Leu Lys Leu Ser
                    725                 730                 735
Phe Pro Glu Gly Phe Lys Trp Glu Arg Val Met Asn Phe Glu Asp Gly
                740                 745                 750
Gly Val Val Thr Val Thr Gln Asp Ser Ser Leu Gln Asp Gly Glu Phe
            755                 760                 765
Ile Tyr Lys Val Lys Leu Arg Gly Thr Asn Phe Pro Ser Asp Gly Pro
        770                 775                 780
Val Met Gln Lys Lys Thr Met Gly Trp Glu Ala Ser Ser Glu Arg Met
785                 790                 795                 800
Tyr Pro Glu Asp Gly Ala Leu Lys Gly Glu Ile Lys Gln Arg Leu Lys
                    805                 810                 815
Leu Lys Asp Gly Gly His Tyr Asp Ala Glu Val Lys Thr Thr Tyr Lys
                820                 825                 830
Ala Lys Lys Pro Val Gln Leu Pro Gly Ala Tyr Asn Val Asn Ile Lys
            835                 840                 845
Leu Asp Ile Thr Ser His Asn Glu Asp Tyr Thr Ile Val Glu Gln Tyr
        850                 855                 860
Glu Arg Ala Glu Gly Arg His Ser Thr Gly Gly Met Asp Glu Leu Tyr
```

```
                    865                 870                875                880

Lys

<210> SEQ ID NO 45
<211> LENGTH: 882
<212> TYPE: PRT
<213> ORGANISM: Artificial Sequence
<220> FEATURE:
<223> OTHER INFORMATION: synthetic construct

<400> SEQUENCE: 45

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350
```

```
Trp Met His Asn Arg Ile Arg Val Ile Val Ser Ser Phe Ala Val Lys
            355                 360                 365
Phe Leu Leu Leu Pro Trp Lys Trp Gly Met Lys Tyr Phe Trp Asp Thr
370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
        435                 440                 445
Trp Asp Ala Pro Leu Thr Val Leu Lys Ala Ser Gly Val Glu Leu Gly
    450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Arg Asp Pro Pro Val Ala Thr Met Val Ser Lys Gly Glu
            500                 505                 510
Glu Asp Asn Met Ala Ile Ile Lys Glu Phe Met Arg Phe Lys Val His
        515                 520                 525
Met Glu Gly Ser Val Asn Gly His Glu Phe Glu Ile Glu Gly Glu Gly
    530                 535                 540
Glu Gly Arg Pro Tyr Glu Gly Thr Gln Thr Ala Lys Leu Lys Val Thr
545                 550                 555                 560
Lys Gly Gly Pro Leu Pro Phe Ala Trp Asp Ile Leu Ser Pro Gln Phe
                565                 570                 575
Met Tyr Gly Ser Lys Ala Tyr Val Lys His Pro Ala Asp Ile Pro Asp
            580                 585                 590
Tyr Leu Lys Leu Ser Phe Pro Glu Gly Phe Lys Trp Glu Arg Val Met
        595                 600                 605
Asn Phe Glu Asp Gly Gly Val Val Thr Val Thr Gln Asp Ser Ser Leu
    610                 615                 620
Gln Asp Gly Glu Phe Ile Tyr Lys Val Lys Leu Arg Gly Thr Asn Phe
625                 630                 635                 640
Pro Ser Asp Gly Pro Val Met Gln Lys Lys Thr Met Gly Trp Glu Ala
                645                 650                 655
Ser Ser Glu Arg Met Tyr Pro Glu Asp Gly Ala Leu Lys Gly Glu Ile
            660                 665                 670
Lys Gln Arg Leu Lys Leu Lys Asp Gly Gly His Tyr Asp Ala Glu Val
        675                 680                 685
Lys Thr Thr Tyr Lys Ala Lys Lys Pro Val Gln Leu Pro Gly Ala Tyr
    690                 695                 700
Asn Val Asn Ile Lys Leu Asp Ile Thr Ser His Asn Glu Asp Tyr Thr
705                 710                 715                 720
Ile Val Glu Gln Tyr Glu Arg Ala Glu Gly Arg His Ser Thr Gly Gly
                725                 730                 735
Met Asp Glu Leu Tyr Lys Met Asp Val Phe Met Lys Gly Leu Ser Lys
            740                 745                 750
Ala Lys Glu Gly Val Val Ala Ala Glu Lys Thr Lys Gln Gly Val
        755                 760                 765
```

Ala Glu Ala Ala Gly Lys Thr Lys Glu Gly Val Leu Tyr Val Gly Ser
770                 775                 780

Lys Thr Lys Glu Gly Val Val His Gly Val Ala Thr Val Ala Glu Lys
785                 790                 795                 800

Thr Lys Glu Gln Val Thr Asn Val Gly Gly Ala Val Val Thr Gly Val
                805                 810                 815

Thr Ala Val Ala Gln Lys Thr Val Glu Gly Ala Gly Ser Ile Ala Ala
            820                 825                 830

Ala Thr Gly Phe Val Lys Lys Asp Gln Leu Gly Lys Asn Glu Glu Gly
        835                 840                 845

Ala Pro Gln Glu Gly Ile Leu Glu Asp Met Pro Val Asp Pro Asp Asn
850                 855                 860

Glu Ala Tyr Glu Met Pro Ser Glu Gly Tyr Gln Asp Tyr Glu Pro
865                 870                 875                 880

Glu Ala

<210> SEQ ID NO 46
<211> LENGTH: 881
<212> TYPE: PRT
<213> ORGANISM: Artificial Sequence
<220> FEATURE:
<223> OTHER INFORMATION: synthetic construct

<400> SEQUENCE: 46

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Asp Pro Pro Val
    130                 135                 140

Ala Thr Met Lys Met Asp Lys Lys Thr Ile Val Trp Phe Arg Arg Asp
145                 150                 155                 160

Leu Arg Ile Glu Asp Asn Pro Ala Leu Ala Ala Ala His Glu Gly
                165                 170                 175

Ser Val Phe Pro Val Phe Ile Trp Cys Pro Glu Glu Gly Gln Phe
            180                 185                 190

Tyr Pro Gly Arg Ala Ser Arg Trp Trp Met Lys Gln Ser Leu Ala His
        195                 200                 205

Leu Ser Gln Ser Leu Lys Ala Leu Gly Ser Asp Leu Thr Leu Ile Lys
    210                 215                 220

Thr His Asn Thr Ile Ser Ala Ile Leu Asp Cys Ile Arg Val Thr Gly
225                 230                 235                 240

Ala Thr Lys Val Val Phe Asn His Leu Tyr Asp Pro Val Ser Leu Val

```
            245                 250                 255
Arg Asp His Thr Val Lys Glu Lys Leu Val Glu Arg Gly Ile Ser Val
            260                 265                 270

Gln Ser Tyr Asn Gly Asp Leu Leu Tyr Glu Pro Trp Glu Ile Tyr Cys
            275                 280                 285

Glu Lys Gly Lys Pro Phe Thr Ser Phe Asn Ser Tyr Trp Lys Lys Cys
            290                 295                 300

Leu Asp Met Ser Ile Glu Ser Val Met Leu Pro Pro Trp Arg Leu
305                 310                 315                 320

Met Pro Ile Thr Ala Ala Glu Ala Ile Trp Ala Cys Ser Ile Glu
            325                 330                 335

Glu Leu Gly Leu Glu Asn Glu Ala Glu Lys Pro Ser Asn Ala Leu Leu
            340                 345                 350

Thr Arg Ala Trp Ser Pro Gly Trp Ser Asn Ala Asp Lys Leu Leu Asn
            355                 360                 365

Glu Phe Ile Glu Lys Gln Leu Ile Asp Tyr Ala Lys Asn Ser Lys Lys
            370                 375                 380

Val Val Gly Asn Ser Thr Ser Leu Leu Ser Pro Tyr Leu His Phe Gly
385                 390                 395                 400

Glu Ile Ser Val Arg His Val Phe Gln Cys Ala Arg Met Lys Gln Ile
                405                 410                 415

Ile Trp Ala Arg Asp Lys Asn Ser Glu Gly Glu Ser Ala Asp Leu
            420                 425                 430

Phe Leu Arg Gly Ile Gly Leu Arg Glu Tyr Ser Arg Tyr Ile Cys Phe
            435                 440                 445

Asn Phe Pro Phe Thr His Glu Gln Ser Leu Leu Ser His Leu Arg Phe
            450                 455                 460

Phe Pro Trp Asp Ala Asp Val Asp Lys Phe Lys Ala Trp Arg Gln Gly
465                 470                 475                 480

Arg Thr Gly Tyr Pro Leu Val Asp Ala Gly Met Arg Glu Leu Trp Ala
                485                 490                 495

Thr Gly Trp Met His Asn Arg Ile Arg Val Ile Val Ser Ser Phe Ala
            500                 505                 510

Val Lys Phe Leu Leu Leu Pro Trp Lys Trp Gly Met Lys Tyr Phe Trp
            515                 520                 525

Asp Thr Leu Leu Asp Ala Asp Leu Glu Cys Asp Ile Leu Gly Trp Gln
            530                 535                 540

Tyr Ile Ser Gly Ser Ile Pro Asp Gly His Glu Leu Asp Arg Leu Asp
545                 550                 555                 560

Asn Pro Ala Leu Gln Gly Ala Lys Tyr Asp Pro Glu Gly Glu Tyr Ile
            565                 570                 575

Arg Gln Trp Leu Pro Glu Leu Ala Arg Leu Pro Thr Glu Trp Ile His
            580                 585                 590

His Pro Trp Asp Ala Pro Leu Thr Val Leu Lys Ala Ser Gly Val Glu
            595                 600                 605

Leu Gly Thr Asn Tyr Ala Lys Pro Ile Val Asp Ile Asp Thr Ala Arg
            610                 615                 620

Glu Leu Leu Ala Lys Ala Ile Ser Arg Thr Arg Gly Ala Gln Ile Met
625                 630                 635                 640

Ile Gly Ala Ala Ala Met Val Ser Lys Gly Glu Glu Asp Asn Met Ala
                645                 650                 655

Ile Ile Lys Glu Phe Met Arg Phe Lys Val His Met Glu Gly Ser Val
            660                 665                 670
```

Asn Gly His Glu Phe Glu Ile Glu Gly Glu Gly Arg Pro Tyr
            675                 680                 685

Glu Gly Thr Gln Thr Ala Lys Leu Lys Val Thr Lys Gly Gly Pro Leu
690                 695                 700

Pro Phe Ala Trp Asp Ile Leu Ser Pro Gln Phe Met Tyr Gly Ser Lys
705                 710                 715                 720

Ala Tyr Val Lys His Pro Ala Asp Ile Pro Asp Tyr Leu Lys Leu Ser
                725                 730                 735

Phe Pro Glu Gly Phe Lys Trp Glu Arg Val Met Asn Phe Glu Asp Gly
            740                 745                 750

Gly Val Val Thr Val Thr Gln Asp Ser Ser Leu Gln Asp Gly Glu Phe
        755                 760                 765

Ile Tyr Lys Val Lys Leu Arg Gly Thr Asn Phe Pro Ser Asp Gly Pro
    770                 775                 780

Val Met Gln Lys Lys Thr Met Gly Trp Glu Ala Ser Ser Glu Arg Met
785                 790                 795                 800

Tyr Pro Glu Asp Gly Ala Leu Lys Gly Glu Ile Lys Gln Arg Leu Lys
                805                 810                 815

Leu Lys Asp Gly Gly His Tyr Asp Ala Glu Val Lys Thr Thr Tyr Lys
            820                 825                 830

Ala Lys Lys Pro Val Gln Leu Pro Gly Ala Tyr Asn Val Asn Ile Lys
        835                 840                 845

Leu Asp Ile Thr Ser His Asn Glu Asp Tyr Thr Ile Val Glu Gln Tyr
    850                 855                 860

Glu Arg Ala Glu Gly Arg His Ser Thr Gly Gly Met Asp Glu Leu Tyr
865                 870                 875                 880

Lys

<210> SEQ ID NO 47
<211> LENGTH: 291
<212> TYPE: PRT
<213> ORGANISM: Artificial Sequence
<220> FEATURE:
<223> OTHER INFORMATION: synthetic construct

<400> SEQUENCE: 47

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Phe His Thr Leu
    130                 135                 140

```
Tyr Ala Pro Gly Gly Tyr Asp Ile Met Gly Trp Leu Ile Gln Ile Met
145                 150                 155                 160

Asn Arg Pro Asn Pro Gln Val Glu Leu Gly Pro Val Asp Thr Ser Cys
                165                 170                 175

Ala Leu Ile Leu Cys Asp Leu Lys Gln Lys Asp Thr Pro Ile Val Tyr
            180                 185                 190

Ala Ser Glu Ala Phe Leu Tyr Met Thr Gly Tyr Ser Asn Ala Glu Val
        195                 200                 205

Leu Gly Arg Asn Cys Arg Phe Leu Gln Ser Pro Asp Gly Met Val Lys
    210                 215                 220

Pro Lys Ser Thr Arg Lys Tyr Val Asp Ser Asn Thr Ile Asn Thr Met
225                 230                 235                 240

Arg Lys Ala Ile Asp Arg Asn Ala Glu Val Gln Val Glu Val Val Asn
                245                 250                 255

Phe Lys Lys Asn Gly Gln Arg Phe Val Asn Phe Leu Thr Met Ile Pro
            260                 265                 270

Val Arg Asp Glu Thr Gly Glu Tyr Arg Tyr Ser Met Gly Phe Gln Cys
        275                 280                 285

Glu Thr Glu
    290

<210> SEQ ID NO 48
<211> LENGTH: 292
<212> TYPE: PRT
<213> ORGANISM: Artificial Sequence
<220> FEATURE:
<223> OTHER INFORMATION: synthetic construct

<400> SEQUENCE: 48

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
            20                  25                  30

Asp Thr Ser Cys Ala Leu Ile Leu Cys Asp Leu Lys Gln Lys Asp Thr
        35                  40                  45

Pro Ile Val Tyr Ala Ser Glu Ala Phe Leu Tyr Met Thr Gly Tyr Ser
    50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
    130                 135                 140

Gly Phe Gln Cys Glu Thr Glu Ala Met Asp Val Phe Met Lys Gly Leu
145                 150                 155                 160

Ser Lys Ala Lys Glu Gly Val Val Ala Ala Glu Lys Thr Lys Gln
                165                 170                 175

Gly Val Ala Glu Ala Ala Gly Lys Thr Lys Glu Gly Val Leu Tyr Val
            180                 185                 190

Gly Ser Lys Thr Lys Glu Gly Val Val His Gly Val Ala Thr Val Ala
        195                 200                 205
```

```
Glu Lys Thr Lys Glu Gln Val Thr Asn Val Gly Gly Ala Val Val Thr
    210                 215                 220
Gly Val Thr Ala Val Ala Gln Lys Thr Val Glu Gly Ala Gly Ser Ile
225                 230                 235                 240
Ala Ala Ala Thr Gly Phe Val Lys Lys Asp Gln Leu Gly Lys Asn Glu
                245                 250                 255
Glu Gly Ala Pro Gln Glu Gly Ile Leu Glu Asp Met Pro Val Asp Pro
                260                 265                 270
Asp Asn Glu Ala Tyr Glu Met Pro Ser Glu Gly Tyr Gln Asp Tyr
                275                 280                 285
Glu Pro Glu Ala
    290
```

<210> SEQ ID NO 49
<211> LENGTH: 528
<212> TYPE: PRT
<213> ORGANISM: Artificial Sequence
<220> FEATURE:
<223> OTHER INFORMATION: synthetic construct

<400> SEQUENCE: 49

```
Met Val Ser Lys Gly Glu Glu Asp Asn Met Ala Ile Ile Lys Glu Phe
1               5                   10                  15
Met Arg Phe Lys Val His Met Glu Gly Ser Val Asn Gly His Glu Phe
                20                  25                  30
Glu Ile Glu Gly Glu Gly Glu Gly Arg Pro Tyr Glu Gly Thr Gln Thr
            35                  40                  45
Ala Lys Leu Lys Val Thr Lys Gly Gly Pro Leu Pro Phe Ala Trp Asp
50                  55                  60
Ile Leu Ser Pro Gln Phe Met Tyr Gly Ser Lys Ala Tyr Val Lys His
65                  70                  75                  80
Pro Ala Asp Ile Pro Asp Tyr Leu Lys Leu Ser Phe Pro Glu Gly Phe
                85                  90                  95
Lys Trp Glu Arg Val Met Asn Phe Glu Asp Gly Gly Val Val Thr Val
                100                 105                 110
Thr Gln Asp Ser Ser Leu Gln Asp Gly Glu Phe Ile Tyr Lys Val Lys
            115                 120                 125
Leu Arg Gly Thr Asn Phe Pro Ser Asp Gly Pro Val Met Gln Lys Lys
130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
                180                 185                 190
Gln Leu Pro Gly Ala Tyr Asn Val Asn Ile Lys Leu Asp Ile Thr Ser
            195                 200                 205
His Asn Glu Asp Tyr Thr Ile Val Glu Gln Tyr Glu Arg Ala Glu Gly
210                 215                 220
Arg His Ser Thr Gly Gly Met Asp Glu Leu Tyr Ser Lys Met Asp Val
225                 230                 235                 240
Phe Met Lys Gly Leu Ser Lys Ala Lys Glu Gly Val Val Ala Ala Ala
                245                 250                 255
Glu Lys Thr Lys Gln Gly Val Ala Glu Ala Ala Gly Lys Thr Lys Glu
                260                 265                 270
```

Gly Val Leu Tyr Val Gly Ser Lys Thr Lys Glu Gly Val His Gly
            275                 280                 285

Val Ala Thr Val Ala Glu Lys Thr Lys Glu Gln Val Thr Asn Val Gly
        290                 295                 300

Gly Ala Val Val Thr Gly Val Thr Ala Val Ala Gln Lys Thr Val Glu
305                 310                 315                 320

Gly Ala Gly Ser Ile Ala Ala Ala Thr Gly Phe Val Lys Lys Asp Gln
                325                 330                 335

Leu Gly Lys Asn Glu Glu Gly Ala Pro Gln Gly Ile Leu Glu Asp
            340                 345                 350

Met Pro Val Asp Pro Asp Asn Glu Ala Tyr Glu Met Pro Ser Glu Glu
        355                 360                 365

Gly Tyr Gln Asp Tyr Glu Pro Glu Ala Phe His Thr Leu Tyr Ala Pro
            370                 375                 380

Gly Gly Tyr Asp Ile Met Gly Trp Leu Ile Gln Ile Met Asn Arg Pro
385                 390                 395                 400

Asn Pro Gln Val Glu Leu Gly Pro Val Asp Thr Ser Cys Ala Leu Ile
                405                 410                 415

Leu Cys Asp Leu Lys Gln Lys Asp Thr Pro Ile Val Tyr Ala Ser Glu
            420                 425                 430

Ala Phe Leu Tyr Met Thr Gly Tyr Ser Asn Ala Glu Val Leu Gly Arg
        435                 440                 445

Asn Cys Arg Phe Leu Gln Ser Pro Asp Gly Met Val Lys Pro Lys Ser
            450                 455                 460

Thr Arg Lys Tyr Val Asp Ser Asn Thr Ile Asn Thr Met Arg Lys Ala
465                 470                 475                 480

Ile Asp Arg Asn Ala Glu Val Gln Val Glu Val Val Asn Phe Lys Lys
                485                 490                 495

Asn Gly Gln Arg Phe Val Asn Phe Leu Thr Met Ile Pro Val Arg Asp
            500                 505                 510

Glu Thr Gly Glu Tyr Arg Tyr Ser Met Gly Phe Gln Cys Glu Thr Glu
        515                 520                 525

<210> SEQ ID NO 50
<211> LENGTH: 547
<212> TYPE: PRT
<213> ORGANISM: Artificial Sequence
<220> FEATURE:
<223> OTHER INFORMATION: synthetic construct

<400> SEQUENCE: 50

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

```
Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys Ser Gly Leu Arg
225                 230                 235                 240

Ser Arg Ala Gln Arg His Thr Leu Tyr Ala Pro Gly Gly Tyr Asp Ile
                245                 250                 255

Met Gly Trp Leu Ile Gln Ile Met Asn Arg Pro Asn Pro Gln Val Glu
            260                 265                 270

Leu Gly Pro Val Asp Thr Ser Cys Ala Leu Ile Leu Cys Asp Leu Lys
        275                 280                 285

Gln Lys Asp Thr Pro Ile Val Tyr Ala Ser Glu Ala Phe Leu Tyr Met
        290                 295                 300

Thr Gly Tyr Ser Asn Ala Glu Val Leu Gly Arg Asn Cys Arg Phe Leu
305                 310                 315                 320

Gln Ser Pro Asp Gly Met Val Lys Pro Lys Ser Thr Arg Lys Tyr Val
                325                 330                 335

Asp Ser Asn Thr Ile Asn Thr Met Arg Lys Ala Ile Asp Arg Asn Ala
            340                 345                 350

Glu Val Gln Val Glu Val Asn Phe Lys Lys Asn Gly Gln Arg Phe
        355                 360                 365

Val Asn Phe Leu Thr Met Ile Pro Val Arg Asp Glu Thr Gly Glu Tyr
370                 375                 380

Arg Tyr Ser Met Gly Phe Gln Cys Glu Thr Glu Ala Leu Glu Phe Cys
385                 390                 395                 400

Ser Arg Arg Tyr Arg Gly Pro Met Asp Val Phe Met Lys Gly Leu Ser
                405                 410                 415

Lys Ala Lys Glu Gly Val Val Ala Ala Ala Glu Lys Thr Lys Gln Gly
            420                 425                 430

Val Ala Glu Ala Ala Gly Lys Thr Lys Glu Gly Val Leu Tyr Val Gly
        435                 440                 445

Ser Lys Thr Lys Glu Gly Val Val His Gly Val Ala Thr Val Ala Glu
        450                 455                 460

Lys Thr Lys Glu Gln Val Thr Asn Val Gly Gly Ala Val Val Thr Gly
465                 470                 475                 480

Val Thr Ala Val Ala Gln Lys Thr Val Glu Gly Ala Gly Ser Ile Ala
                485                 490                 495

Ala Ala Thr Gly Phe Val Lys Lys Asp Gln Leu Gly Lys Asn Glu Glu
            500                 505                 510

Gly Ala Pro Gln Glu Gly Ile Leu Glu Asp Met Pro Val Asp Pro Asp
        515                 520                 525

Asn Glu Ala Tyr Glu Met Pro Ser Glu Glu Gly Tyr Gln Asp Tyr Glu
```

-continued

```
                530                 535                 540
Pro Glu Ala
545

<210> SEQ ID NO 51
<211> LENGTH: 534
<212> TYPE: PRT
<213> ORGANISM: Artificial Sequence
<220> FEATURE:
<223> OTHER INFORMATION: synthetic construct

<400> SEQUENCE: 51

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
                20                  25                  30

Asp Thr Ser Cys Ala Leu Ile Leu Cys Asp Leu Lys Gln Lys Asp Thr
            35                  40                  45

Pro Ile Val Tyr Ala Ser Glu Ala Phe Leu Tyr Met Thr Gly Tyr Ser
        50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
            100                 105                 110

Glu Val Val Asn Phe Lys Lys Asn Gly Gln Arg Phe Val Asn Phe Leu
        115                 120                 125

Thr Met Ile Pro Val Arg Asp Glu Thr Gly Glu Tyr Arg Tyr Ser Met
130                 135                 140

Gly Phe Gln Cys Glu Thr Glu Ala Met Asp Val Phe Met Lys Gly Leu
145                 150                 155                 160

Ser Lys Ala Lys Glu Gly Val Val Ala Ala Glu Lys Thr Lys Gln
                165                 170                 175

Gly Val Ala Glu Ala Ala Gly Lys Thr Lys Glu Gly Val Leu Tyr Val
            180                 185                 190

Gly Ser Lys Thr Lys Glu Gly Val Val His Gly Val Ala Thr Val Ala
        195                 200                 205

Glu Lys Thr Lys Glu Gln Val Thr Asn Val Gly Gly Ala Val Val Thr
    210                 215                 220

Gly Val Thr Ala Val Ala Gln Lys Thr Val Glu Gly Ala Gly Ser Ile
225                 230                 235                 240

Ala Ala Ala Thr Gly Phe Val Lys Lys Asp Gln Leu Gly Lys Asn Glu
                245                 250                 255

Glu Gly Ala Pro Gln Glu Gly Ile Leu Glu Asp Met Pro Val Asp Pro
            260                 265                 270

Asp Asn Glu Ala Tyr Glu Met Pro Ser Glu Glu Gly Tyr Gln Asp Tyr
        275                 280                 285

Glu Pro Glu Ala Phe Ala Pro Val Ala Thr Met Val Ser Lys Gly Glu
    290                 295                 300

Glu Asp Asn Met Ala Ile Ile Lys Glu Phe Met Arg Phe Lys Val His
305                 310                 315                 320

Met Glu Gly Ser Val Asn Gly His Glu Phe Glu Ile Glu Gly Glu Gly
                325                 330                 335

Glu Gly Arg Pro Tyr Glu Gly Thr Gln Thr Ala Lys Leu Lys Val Thr
```

```
                340                 345                 350
Lys Gly Gly Pro Leu Pro Phe Ala Trp Asp Ile Leu Ser Pro Gln Phe
            355                 360                 365

Met Tyr Gly Ser Lys Ala Tyr Val Lys His Pro Ala Asp Ile Pro Asp
370                 375                 380

Tyr Leu Lys Leu Ser Phe Pro Glu Gly Phe Lys Trp Glu Arg Val Met
385                 390                 395                 400

Asn Phe Glu Asp Gly Gly Val Val Thr Val Thr Gln Asp Ser Ser Leu
            405                 410                 415

Gln Asp Gly Glu Phe Ile Tyr Lys Val Lys Leu Arg Gly Thr Asn Phe
            420                 425                 430

Pro Ser Asp Gly Pro Val Met Gln Lys Lys Thr Met Gly Trp Glu Ala
            435                 440                 445

Ser Ser Glu Arg Met Tyr Pro Glu Asp Gly Ala Leu Lys Gly Glu Ile
            450                 455                 460

Lys Gln Arg Leu Lys Leu Lys Asp Gly Gly His Tyr Asp Ala Glu Val
465                 470                 475                 480

Lys Thr Thr Tyr Lys Ala Lys Lys Pro Val Gln Leu Pro Gly Ala Tyr
            485                 490                 495

Asn Val Asn Ile Lys Leu Asp Ile Thr Ser His Asn Glu Asp Tyr Thr
            500                 505                 510

Ile Val Glu Gln Tyr Glu Arg Ala Glu Gly Arg His Ser Thr Gly Gly
            515                 520                 525

Met Asp Glu Leu Tyr Lys
            530

<210> SEQ ID NO 52
<211> LENGTH: 558
<212> TYPE: PRT
<213> ORGANISM: Artificial Sequence
<220> FEATURE:
<223> OTHER INFORMATION: synthetic construct

<400> SEQUENCE: 52

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Leu Leu Pro Val
        130                 135                 140

Ala Thr Met Val Ser Lys Gly Glu Glu Asp Asn Met Ala Ile Ile Lys
145                 150                 155                 160

Glu Phe Met Arg Phe Lys Val His Met Glu Gly Ser Val Asn Gly His
```

```
            165                 170                 175
Glu Phe Glu Ile Glu Gly Glu Gly Gly Arg Pro Tyr Glu Gly Thr
            180                 185                 190

Gln Thr Ala Lys Leu Lys Val Thr Lys Gly Pro Leu Pro Phe Ala
            195                 200                 205

Trp Asp Ile Leu Ser Pro Gln Phe Met Tyr Gly Ser Lys Ala Tyr Val
            210                 215                 220

Lys His Pro Ala Asp Ile Pro Asp Tyr Leu Lys Leu Ser Phe Pro Glu
225                 230                 235                 240

Gly Phe Lys Trp Glu Arg Val Met Asn Phe Glu Asp Gly Gly Val Val
                    245                 250                 255

Thr Val Thr Gln Asp Ser Ser Leu Gln Asp Gly Glu Phe Ile Tyr Lys
            260                 265                 270

Val Lys Leu Arg Gly Thr Asn Phe Pro Ser Asp Gly Pro Val Met Gln
            275                 280                 285

Lys Lys Thr Met Gly Trp Glu Ala Ser Ser Glu Arg Met Tyr Pro Glu
            290                 295                 300

Asp Gly Ala Leu Lys Gly Glu Ile Lys Gln Arg Leu Lys Leu Lys Asp
305                 310                 315                 320

Gly Gly His Tyr Asp Ala Glu Val Lys Thr Thr Tyr Lys Ala Lys Lys
                    325                 330                 335

Pro Val Gln Leu Pro Gly Ala Tyr Asn Val Asn Ile Lys Leu Asp Ile
            340                 345                 350

Thr Ser His Asn Glu Asp Tyr Thr Ile Val Glu Gln Tyr Glu Arg Ala
            355                 360                 365

Glu Gly Arg His Ser Thr Gly Gly Met Asp Glu Leu Tyr Lys Ser Gly
            370                 375                 380

Leu Arg Ser Arg Ala Gln Ala Ser Asn Ser Ala Val Asp Gly Thr Ala
385                 390                 395                 400

Gly Pro Met His Thr Leu Tyr Ala Pro Gly Gly Tyr Asp Ile Met Gly
                    405                 410                 415

Tyr Leu Ile Gln Ile Met Asn Arg Pro Asn Pro Gln Val Glu Leu Gly
            420                 425                 430

Pro Val Asp Thr Ser Cys Ala Leu Ile Leu Cys Asp Leu Lys Gln Lys
            435                 440                 445

Asp Thr Pro Ile Val Tyr Ala Ser Glu Ala Phe Leu Tyr Met Thr Gly
450                 455                 460

Tyr Ser Asn Ala Glu Val Leu Gly Arg Asn Cys Arg Phe Leu Gln Ser
465                 470                 475                 480

Pro Asp Gly Met Val Lys Pro Lys Ser Thr Arg Lys Tyr Val Asp Ser
                    485                 490                 495

Asn Thr Ile Asn Thr Met Arg Lys Ala Ile Asp Arg Asn Ala Glu Val
            500                 505                 510

Gln Val Glu Val Val Asn Phe Lys Lys Asn Gly Gln Arg Phe Val Asn
            515                 520                 525

Phe Leu Thr Met Ile Pro Val Arg Asp Glu Thr Gly Glu Tyr Arg Tyr
            530                 535                 540

Ser Met Gly Phe Gln Cys Glu Thr Glu Gly Ile His Arg Ile
545                 550                 555

<210> SEQ ID NO 53
<211> LENGTH: 551
<212> TYPE: PRT
<213> ORGANISM: Artificial Sequence
```

<220> FEATURE:
<223> OTHER INFORMATION: synthetic construct

<400> SEQUENCE: 53

```
Met Val Ser Lys Gly Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
            210                 215                 220

Arg His Ser Thr Gly Gly Met Asp Glu Leu Tyr Lys Ser Gly Leu Arg
225                 230                 235                 240

Ser Arg Ala Gln Met Asp Val Phe Met Lys Gly Leu Ser Lys Ala Lys
                245                 250                 255

Glu Gly Val Val Ala Ala Glu Lys Thr Lys Gln Gly Val Ala Glu
                260                 265                 270

Ala Ala Gly Lys Thr Lys Glu Gly Val Leu Tyr Val Gly Ser Lys Thr
            275                 280                 285

Lys Glu Gly Val Val His Gly Val Ala Thr Val Ala Glu Lys Thr Lys
            290                 295                 300

Glu Gln Val Thr Asn Val Gly Gly Ala Val Val Thr Gly Val Thr Ala
305                 310                 315                 320

Val Ala Gln Lys Thr Val Glu Gly Ala Gly Ser Ile Ala Ala Ala Thr
                325                 330                 335

Gly Phe Val Lys Lys Asp Gln Leu Gly Lys Asn Glu Glu Gly Ala Pro
                340                 345                 350

Gln Glu Gly Ile Leu Glu Asp Met Pro Val Asp Pro Asp Asn Glu Ala
            355                 360                 365

Tyr Glu Met Pro Ser Glu Glu Gly Tyr Gln Asp Tyr Glu Pro Glu Ala
            370                 375                 380

Ser Asn Ser Ala Val Asp Gly Thr Ala Gly Pro Met His Thr Leu Tyr
385                 390                 395                 400
```

Ala Pro Gly Gly Tyr Asp Ile Met Gly Tyr Leu Ile Gln Ile Met Asn
             405                 410                 415

Arg Pro Asn Pro Gln Val Glu Leu Gly Pro Val Asp Thr Ser Cys Ala
         420                 425                 430

Leu Ile Leu Cys Asp Leu Lys Gln Lys Asp Thr Pro Ile Val Tyr Ala
     435                 440                 445

Ser Glu Ala Phe Leu Tyr Met Thr Gly Tyr Ser Asn Ala Glu Val Leu
450                 455                 460

Gly Arg Asn Cys Arg Phe Leu Gln Ser Pro Asp Gly Met Val Lys Pro
465                 470                 475                 480

Lys Ser Thr Arg Lys Tyr Val Asp Ser Asn Thr Ile Asn Thr Met Arg
                485                 490                 495

Lys Ala Ile Asp Arg Asn Ala Glu Val Gln Val Glu Val Val Asn Phe
            500                 505                 510

Lys Lys Asn Gly Gln Arg Phe Val Asn Phe Leu Thr Met Ile Pro Val
        515                 520                 525

Arg Asp Glu Thr Gly Glu Tyr Arg Tyr Ser Met Gly Phe Gln Cys Glu
    530                 535                 540

Thr Glu Gly Ile His Arg Ile
545                 550

<210> SEQ ID NO 54
<211> LENGTH: 551
<212> TYPE: PRT
<213> ORGANISM: Artificial Sequence
<220> FEATURE:
<223> OTHER INFORMATION: synthetic construct

<400> SEQUENCE: 54

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Ser Gly Leu Arg
225                 230                 235                 240

Ser Arg Ala Gln Ala Ser Asn Ser Ala Val Asp Gly Thr Ala Gly Pro
                245                 250                 255

Met His Thr Leu Tyr Ala Pro Gly Gly Tyr Asp Ile Met Gly Tyr Leu
            260                 265                 270

Ile Gln Ile Met Asn Arg Pro Asn Pro Gln Val Glu Leu Gly Pro Val
        275                 280                 285

Asp Thr Ser Cys Ala Leu Ile Leu Cys Asp Leu Lys Gln Lys Asp Thr
    290                 295                 300

Pro Ile Val Tyr Ala Ser Glu Ala Phe Leu Tyr Met Thr Gly Tyr Ser
305                 310                 315                 320

Asn Ala Glu Val Leu Gly Arg Asn Cys Arg Phe Leu Gln Ser Pro Asp
                325                 330                 335

Gly Met Val Lys Pro Lys Ser Thr Arg Lys Tyr Val Asp Ser Asn Thr
            340                 345                 350

Ile Asn Thr Met Arg Lys Ala Ile Asp Arg Asn Ala Glu Val Gln Val
        355                 360                 365

Glu Val Val Asn Phe Lys Lys Asn Gly Gln Arg Phe Val Asn Phe Leu
    370                 375                 380

Thr Met Ile Pro Val Arg Asp Glu Thr Gly Glu Tyr Arg Tyr Ser Met
385                 390                 395                 400

Gly Phe Gln Cys Glu Thr Glu Gly Met Asp Val Phe Met Lys Gly Leu
                405                 410                 415

Ser Lys Ala Lys Glu Gly Val Val Ala Ala Glu Lys Thr Lys Gln
            420                 425                 430

Gly Val Ala Glu Ala Gly Lys Thr Lys Glu Gly Val Leu Tyr Val
            435                 440                 445

Gly Ser Lys Thr Lys Glu Gly Val Val His Gly Val Ala Thr Val Ala
    450                 455                 460

Glu Lys Thr Lys Glu Gln Val Thr Asn Val Gly Gly Ala Val Val Thr
465                 470                 475                 480

Gly Val Thr Ala Val Ala Gln Lys Thr Val Glu Gly Ala Gly Ser Ile
                485                 490                 495

Ala Ala Ala Thr Gly Phe Val Lys Lys Asp Gln Leu Gly Lys Asn Glu
            500                 505                 510

Glu Gly Ala Pro Gln Glu Gly Ile Leu Glu Asp Met Pro Val Asp Pro
        515                 520                 525

Asp Asn Glu Ala Tyr Glu Met Pro Ser Glu Glu Gly Tyr Gln Asp Tyr
    530                 535                 540

Glu Pro Glu Ala His Arg Ile
545                 550

<210> SEQ ID NO 55
<211> LENGTH: 702
<212> TYPE: PRT
<213> ORGANISM: Artificial Sequence
<220> FEATURE:
<223> OTHER INFORMATION: synthetic construct

<400> SEQUENCE: 55

Met Val Ser Lys Gly Glu Glu Asp Asn Met Ala Ile Ile Lys Glu Phe
1               5                   10                  15

```
Met Arg Phe Lys Val His Met Glu Gly Ser Val Asn Gly His Glu Phe
             20                  25                  30
Glu Ile Glu Gly Glu Gly Glu Gly Arg Pro Tyr Glu Gly Thr Gln Thr
         35                  40                  45
Ala Lys Leu Lys Val Thr Lys Gly Gly Pro Leu Pro Phe Ala Trp Asp
 50                  55                  60
Ile Leu Ser Pro Gln Phe Met Tyr Gly Ser Lys Ala Tyr Val Lys His
65                  70                  75                  80
Pro Ala Asp Ile Pro Asp Tyr Leu Lys Leu Ser Phe Pro Glu Gly Phe
                 85                  90                  95
Lys Trp Glu Arg Val Met Asn Phe Glu Asp Gly Gly Val Val Thr Val
            100                 105                 110
Thr Gln Asp Ser Ser Leu Gln Asp Gly Glu Phe Ile Tyr Lys Val Lys
        115                 120                 125
Leu Arg Gly Thr Asn Phe Pro Ser Asp Gly Pro Val Met Gln Lys Lys
130                 135                 140
Thr Met Gly Trp Glu Ala Ser Ser Glu Arg Met Tyr Pro Glu Asp Gly
145                 150                 155                 160
Ala Leu Lys Gly Glu Ile Lys Gln Arg Leu Lys Leu Lys Asp Gly Gly
                165                 170                 175
His Tyr Asp Ala Glu Val Lys Thr Thr Tyr Lys Ala Lys Lys Pro Val
            180                 185                 190
Gln Leu Pro Gly Ala Tyr Asn Val Asn Ile Lys Leu Asp Ile Thr Ser
        195                 200                 205
His Asn Glu Asp Tyr Thr Ile Val Glu Gln Tyr Glu Arg Ala Glu Gly
210                 215                 220
Arg His Ser Thr Gly Gly Met Asp Glu Leu Tyr Lys Ser Gly Leu Arg
225                 230                 235                 240
Ser Arg Ala Gln Ala Ser Asn Ser Ala Val Asp Gly Thr Ala Gly Pro
                245                 250                 255
Met Ala Glu Pro Arg Gln Glu Phe Glu Val Met Glu Asp His Ala Gly
            260                 265                 270
Thr Tyr Gly Leu Gly Asp Arg Lys Asp Gln Gly Gly Tyr Thr Met His
        275                 280                 285
Gln Asp Gln Glu Gly Asp Thr Asp Ala Gly Leu Lys Glu Ser Pro Leu
290                 295                 300
Gln Thr Pro Thr Glu Asp Gly Ser Glu Glu Pro Gly Ser Glu Thr Ser
305                 310                 315                 320
Asp Ala Lys Ser Thr Pro Thr Ala Glu Asp Val Thr Ala Pro Leu Val
                325                 330                 335
Asp Glu Gly Ala Pro Gly Lys Gln Ala Ala Gln Pro His Thr Glu
            340                 345                 350
Ile Pro Glu Gly Thr Thr Ala Glu Glu Ala Gly Ile Gly Asp Thr Pro
        355                 360                 365
Ser Leu Glu Asp Glu Ala Ala Gly His Val Thr Gln Ala Arg Met Val
370                 375                 380
Ser Lys Ser Lys Asp Gly Thr Gly Ser Asp Asp Lys Lys Ala Lys Gly
385                 390                 395                 400
Ala Asp Gly Lys Thr Lys Ile Ala Thr Pro Arg Gly Ala Ala Pro Pro
                405                 410                 415
Gly Gln Lys Gly Gln Ala Asn Ala Thr Arg Ile Pro Ala Lys Thr Pro
            420                 425                 430
```

```
Pro Ala Pro Lys Thr Pro Pro Ser Ser Gly Glu Pro Pro Lys Ser Gly
            435                 440                 445

Asp Arg Ser Gly Tyr Ser Ser Pro Gly Ser Pro Gly Thr Pro Gly Ser
450                 455                 460

Arg Ser Arg Thr Pro Ser Leu Pro Thr Pro Pro Thr Arg Glu Pro Lys
465                 470                 475                 480

Lys Val Ala Val Val Arg Thr Pro Pro Lys Ser Pro Ser Ser Ala Lys
                485                 490                 495

Ser Arg Leu Gln Thr Ala Pro Val Pro Met Pro Asp Leu Lys Asn Val
            500                 505                 510

Lys Ser Lys Ile Gly Ser Thr Glu Asn Leu Lys His Gln Pro Gly Gly
            515                 520                 525

Gly Lys Val Gln Ile Ile Asn Lys Lys Leu Asp Leu Ser Asn Val Gln
            530                 535                 540

Ser Lys Cys Gly Ser Lys Asp Asn Ile Lys His Val Pro Gly Gly Gly
545                 550                 555                 560

Ser Val Gln Ile Val Tyr Lys Pro Val Asp Leu Ser Lys Val Thr Ser
                565                 570                 575

Lys Cys Gly Ser Leu Gly Asn Ile His His Lys Pro Gly Gly Gly Gln
            580                 585                 590

Val Glu Val Lys Ser Glu Lys Leu Asp Phe Lys Asp Arg Val Gln Ser
            595                 600                 605

Lys Ile Gly Ser Leu Asp Asn Ile Thr His Val Pro Gly Gly Gly Asn
            610                 615                 620

Lys Lys Ile Glu Thr His Lys Leu Thr Phe Arg Glu Asn Ala Lys Ala
625                 630                 635                 640

Lys Thr Asp His Gly Ala Glu Ile Val Tyr Lys Ser Pro Val Val Ser
                645                 650                 655

Gly Asp Thr Ser Pro Arg His Leu Ser Asn Val Ser Ser Thr Gly Ser
            660                 665                 670

Ile Asp Met Val Asp Ser Pro Gln Leu Ala Thr Leu Ala Asp Glu Val
            675                 680                 685

Ser Ala Ser Leu Ala Lys Gln Gly Leu Gly Ile His Arg Ile
690                 695                 700

<210> SEQ ID NO 56
<211> LENGTH: 879
<212> TYPE: PRT
<213> ORGANISM: Artificial Sequence
<220> FEATURE:
<223> OTHER INFORMATION: synthetic construct

<400> SEQUENCE: 56

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95
```

-continued

```
Lys Trp Glu Arg Val Met Asn Phe Glu Asp Gly Val Val Thr Val
                100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Ser Gly Leu Arg
225                 230                 235                 240

Ser Arg Ala Gln Ala Ser Asn Ser Ala Val Asp Gly Thr Ala Gly Pro
                245                 250                 255

Met Pro Asp Tyr Ser Leu Val Lys Ala Leu Gln Met Ala Gln Gln Asn
            260                 265                 270

Phe Val Ile Thr Asp Ala Ser Leu Pro Asp Asn Pro Ile Val Tyr Ala
        275                 280                 285

Ser Arg Gly Phe Leu Thr Leu Thr Gly Tyr Ser Leu Asp Gln Ile Leu
    290                 295                 300

Gly Arg Asn Cys Arg Phe Leu Gln Gly Pro Glu Thr Asp Pro Arg Ala
305                 310                 315                 320

Val Asp Lys Ile Arg Asn Ala Ile Thr Lys Gly Val Asp Thr Ser Val
                325                 330                 335

Cys Leu Leu Asn Tyr Arg Gln Asp Gly Thr Thr Phe Trp Asn Leu Phe
            340                 345                 350

Phe Val Ala Gly Leu Arg Asp Ser Lys Gly Asn Ile Val Asn Tyr Val
        355                 360                 365

Gly Val Gln Ser Lys Val Ser Glu Asp Tyr Ala Lys Leu Leu Val Asn
    370                 375                 380

Glu Gln Asn Ile Glu Tyr Lys Gly Val Arg Thr Ser Asn Met Leu Arg
385                 390                 395                 400

Arg Lys Pro Gly Gly Ile His Arg Ile Met Ala Glu Pro Arg Gln Glu
                405                 410                 415

Phe Glu Val Met Glu Asp His Ala Gly Thr Tyr Gly Leu Gly Asp Arg
            420                 425                 430

Lys Asp Gln Gly Gly Tyr Thr Met His Gln Asp Gln Glu Gly Asp Thr
        435                 440                 445

Asp Ala Gly Leu Lys Glu Ser Pro Leu Gln Thr Pro Thr Glu Asp Gly
    450                 455                 460

Ser Glu Glu Pro Gly Ser Glu Thr Ser Asp Ala Lys Ser Thr Pro Thr
465                 470                 475                 480

Ala Glu Asp Val Thr Ala Pro Leu Val Asp Gly Ala Pro Gly Lys
                485                 490                 495

Gln Ala Ala Ala Gln Pro His Thr Glu Ile Pro Glu Gly Thr Thr Ala
            500                 505                 510

Glu Glu Ala Gly Ile Gly Asp Thr Pro Ser Leu Glu Asp Glu Ala Ala
```

```
            515                 520                 525
Gly His Val Thr Gln Ala Arg Met Val Ser Lys Ser Lys Asp Gly Thr
            530                 535                 540
Gly Ser Asp Asp Lys Lys Ala Lys Gly Ala Asp Gly Lys Thr Lys Ile
545                 550                 555                 560
Ala Thr Pro Arg Gly Ala Ala Pro Pro Gly Gln Lys Gly Gln Ala Asn
                565                 570                 575
Ala Thr Arg Ile Pro Ala Lys Thr Pro Pro Ala Pro Lys Thr Pro Pro
            580                 585                 590
Ser Ser Gly Glu Pro Pro Lys Ser Gly Asp Arg Ser Gly Tyr Ser Ser
            595                 600                 605
Pro Gly Ser Pro Gly Thr Pro Gly Ser Arg Ser Arg Thr Pro Ser Leu
            610                 615                 620
Pro Thr Pro Pro Thr Arg Glu Pro Lys Lys Val Ala Val Val Arg Thr
625                 630                 635                 640
Pro Pro Lys Ser Pro Ser Ser Ala Lys Ser Arg Leu Gln Thr Ala Pro
                645                 650                 655
Val Pro Met Pro Asp Leu Lys Asn Val Lys Ser Lys Ile Gly Ser Thr
            660                 665                 670
Glu Asn Leu Lys His Gln Pro Gly Gly Gly Lys Val Gln Ile Ile Asn
            675                 680                 685
Lys Lys Leu Asp Leu Ser Asn Val Gln Ser Lys Cys Gly Ser Lys Asp
690                 695                 700
Asn Ile Lys His Val Pro Gly Gly Gly Ser Val Gln Ile Val Tyr Lys
705                 710                 715                 720
Pro Val Asp Leu Ser Lys Val Thr Ser Lys Cys Gly Ser Leu Gly Asn
                725                 730                 735
Ile His His Lys Pro Gly Gly Gly Gln Val Glu Val Lys Ser Glu Lys
            740                 745                 750
Leu Asp Phe Lys Asp Arg Val Gln Ser Lys Ile Gly Ser Leu Asp Asn
            755                 760                 765
Ile Thr His Val Pro Gly Gly Gly Asn Lys Lys Ile Glu Thr His Lys
            770                 775                 780
Leu Thr Phe Arg Glu Asn Ala Lys Ala Lys Thr Asp His Gly Ala Glu
785                 790                 795                 800
Ile Val Tyr Lys Ser Pro Val Val Ser Gly Asp Thr Ser Pro Arg His
                805                 810                 815
Leu Ser Asn Val Ser Ser Thr Gly Ser Ile Asp Met Val Asp Ser Pro
            820                 825                 830
Gln Leu Ala Thr Leu Ala Asp Glu Val Ser Ala Ser Leu Ala Lys Gln
            835                 840                 845
Gly Leu Ile Thr Asp His Asn Gln Pro Tyr His Ile Cys Arg Gly Phe
            850                 855                 860
Thr Cys Phe Lys Lys Pro Pro Thr Pro Pro Glu Pro Glu Thr
865                 870                 875

<210> SEQ ID NO 57
<211> LENGTH: 852
<212> TYPE: PRT
<213> ORGANISM: Artificial Sequence
<220> FEATURE:
<223> OTHER INFORMATION: synthetic construct

<400> SEQUENCE: 57

Met Val Ser Lys Gly Glu Glu Asp Asn Met Ala Ile Ile Lys Glu Phe
```

-continued

```
  1               5                  10                 15
Met Arg Phe Lys Val His Met Glu Gly Ser Val Asn Gly His Glu Phe
             20                 25                 30
Glu Ile Glu Gly Glu Gly Gly Arg Pro Tyr Glu Gly Thr Gln Thr
             35                 40                 45
Ala Lys Leu Lys Val Thr Lys Gly Gly Pro Leu Pro Phe Ala Trp Asp
         50                 55                 60
Ile Leu Ser Pro Gln Phe Met Tyr Gly Ser Lys Ala Tyr Val Lys His
65                 70                 75                 80
Pro Ala Asp Ile Pro Asp Tyr Leu Lys Leu Ser Phe Pro Glu Gly Phe
                 85                 90                 95
Lys Trp Glu Arg Val Met Asn Phe Glu Asp Gly Gly Val Val Thr Val
                100                105                110
Thr Gln Asp Ser Ser Leu Gln Asp Gly Glu Phe Ile Tyr Lys Val Lys
                115                120                125
Leu Arg Gly Thr Asn Phe Pro Ser Asp Gly Pro Val Met Gln Lys Lys
            130                135                140
Thr Met Gly Trp Glu Ala Ser Ser Glu Arg Met Tyr Pro Glu Asp Gly
145                150                155                160
Ala Leu Lys Gly Glu Ile Lys Gln Arg Leu Lys Leu Lys Asp Gly Gly
                165                170                175
His Tyr Asp Ala Glu Val Lys Thr Thr Tyr Lys Ala Lys Lys Pro Val
                180                185                190
Gln Leu Pro Gly Ala Tyr Asn Val Asn Ile Lys Leu Asp Ile Thr Ser
            195                200                205
His Asn Glu Asp Tyr Thr Ile Val Glu Gln Tyr Glu Arg Ala Glu Gly
    210                215                220
Arg His Ser Thr Gly Gly Met Asp Glu Leu Tyr Lys Ser Gly Leu Arg
225                230                235                240
Ser Arg Ala Gln Ala Ser Asn Ser Ala Val Asp Gly Thr Ala Gly Pro
                245                250                255
Met His Thr Leu Tyr Ala Pro Gly Gly Tyr Asp Ile Met Gly Trp Leu
            260                265                270
Ile Gln Ile Met Asn Arg Pro Asn Pro Gln Val Glu Leu Gly Pro Val
        275                280                285
Asp Thr Ser Cys Ala Leu Ile Leu Cys Asp Leu Lys Gln Lys Asp Thr
            290                295                300
Pro Ile Val Tyr Ala Ser Glu Ala Phe Leu Tyr Met Thr Gly Tyr Ser
305                310                315                320
Asn Ala Glu Val Leu Gly Arg Asn Cys Arg Phe Leu Gln Ser Pro Asp
                325                330                335
Gly Met Val Lys Pro Lys Ser Thr Arg Lys Tyr Val Asp Ser Asn Thr
            340                345                350
Ile Asn Thr Met Arg Lys Ala Ile Asp Arg Asn Ala Glu Val Gln Val
        355                360                365
Glu Val Val Asn Phe Lys Lys Asn Gly Gln Arg Phe Val Asn Phe Leu
        370                375                380
Thr Met Ile Pro Val Arg Asp Glu Thr Gly Glu Tyr Arg Tyr Ser Met
385                390                395                400
Gly Phe Gln Cys Glu Thr Glu Gly Met Ala Glu Pro Arg Gln Glu Phe
                405                410                415
Glu Val Met Glu Asp His Ala Gly Thr Tyr Gly Leu Gly Asp Arg Lys
            420                425                430
```

```
Asp Gln Gly Gly Tyr Thr Met His Gln Asp Gln Glu Gly Asp Thr Asp
            435                 440                 445
Ala Gly Leu Lys Glu Ser Pro Leu Gln Thr Pro Thr Glu Asp Gly Ser
        450                 455                 460
Glu Glu Pro Gly Ser Glu Thr Ser Asp Ala Lys Ser Thr Pro Thr Ala
465                 470                 475                 480
Glu Asp Val Thr Ala Pro Leu Val Asp Glu Gly Ala Pro Gly Lys Gln
                485                 490                 495
Ala Ala Ala Gln Pro His Thr Glu Ile Pro Glu Gly Thr Thr Ala Glu
            500                 505                 510
Glu Ala Gly Ile Gly Asp Thr Pro Ser Leu Glu Asp Glu Ala Ala Gly
        515                 520                 525
His Val Thr Gln Ala Arg Met Val Ser Lys Ser Lys Asp Gly Thr Gly
    530                 535                 540
Ser Asp Asp Lys Lys Ala Lys Gly Ala Asp Gly Lys Thr Lys Ile Ala
545                 550                 555                 560
Thr Pro Arg Gly Ala Ala Pro Pro Gly Gln Lys Gly Gln Ala Asn Ala
                565                 570                 575
Thr Arg Ile Pro Ala Lys Thr Pro Pro Ala Pro Lys Thr Pro Pro Ser
            580                 585                 590
Ser Gly Glu Pro Pro Lys Ser Gly Asp Arg Ser Gly Tyr Ser Ser Pro
        595                 600                 605
Gly Ser Pro Gly Thr Pro Gly Ser Arg Ser Arg Thr Pro Ser Leu Pro
    610                 615                 620
Thr Pro Pro Thr Arg Glu Pro Lys Lys Val Ala Val Val Arg Thr Pro
625                 630                 635                 640
Pro Lys Ser Pro Ser Ser Ala Lys Ser Arg Leu Gln Thr Ala Pro Val
                645                 650                 655
Pro Met Pro Asp Leu Lys Asn Val Lys Ser Lys Ile Gly Ser Thr Glu
            660                 665                 670
Asn Leu Lys His Gln Pro Gly Gly Gly Lys Val Gln Ile Ile Asn Lys
        675                 680                 685
Lys Leu Asp Leu Ser Asn Val Gln Ser Lys Cys Gly Ser Lys Asp Asn
    690                 695                 700
Ile Lys His Val Pro Gly Gly Gly Ser Val Gln Ile Val Tyr Lys Pro
705                 710                 715                 720
Val Asp Leu Ser Lys Val Thr Ser Lys Cys Gly Ser Leu Gly Asn Ile
                725                 730                 735
His His Lys Pro Gly Gly Gly Gln Val Glu Val Lys Ser Glu Lys Leu
            740                 745                 750
Asp Phe Lys Asp Arg Val Gln Ser Lys Ile Gly Ser Leu Asp Asn Ile
        755                 760                 765
Thr His Val Pro Gly Gly Gly Asn Lys Lys Ile Glu Thr His Lys Leu
    770                 775                 780
Thr Phe Arg Glu Asn Ala Lys Ala Lys Thr Asp His Gly Ala Glu Ile
785                 790                 795                 800
Val Tyr Lys Ser Pro Val Val Ser Gly Asp Thr Ser Pro Arg His Leu
                805                 810                 815
Ser Asn Val Ser Ser Thr Gly Ser Ile Asp Met Val Asp Ser Pro Gln
            820                 825                 830
Leu Ala Thr Leu Ala Asp Glu Val Ser Ala Ser Leu Ala Lys Gln Gly
        835                 840                 845
```

Leu His Arg Ile
    850

<210> SEQ ID NO 58
<211> LENGTH: 853
<212> TYPE: PRT
<213> ORGANISM: Artificial Sequence
<220> FEATURE:
<223> OTHER INFORMATION: synthetic construct

<400> SEQUENCE: 58

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Ser Gly Leu Thr
225                 230                 235                 240

Met Ala Glu Pro Arg Gln Glu Phe Glu Val Met Glu Asp His Ala Gly
                245                 250                 255

Thr Tyr Gly Leu Gly Asp Arg Lys Asp Gln Gly Gly Tyr Thr Met His
            260                 265                 270

Gln Asp Gln Glu Gly Asp Thr Asp Ala Gly Leu Lys Glu Ser Pro Leu
        275                 280                 285

Gln Thr Pro Thr Glu Asp Gly Ser Glu Glu Pro Gly Ser Glu Thr Ser
    290                 295                 300

Asp Ala Lys Ser Thr Pro Thr Ala Glu Asp Val Thr Ala Pro Leu Val
305                 310                 315                 320

Asp Glu Gly Ala Pro Gly Lys Gln Ala Ala Gln Pro His Thr Glu
                325                 330                 335

Ile Pro Glu Gly Thr Thr Ala Glu Glu Ala Gly Ile Gly Asp Thr Pro
            340                 345                 350

-continued

Ser Leu Glu Asp Glu Ala Ala Gly His Val Thr Gln Ala Arg Met Val
        355                 360                 365

Ser Lys Ser Lys Asp Gly Thr Gly Ser Asp Lys Lys Ala Lys Gly
    370                 375                 380

Ala Asp Gly Lys Thr Lys Ile Ala Thr Pro Arg Gly Ala Ala Pro Pro
385                 390                 395                 400

Gly Gln Lys Gly Gln Ala Asn Ala Thr Arg Ile Pro Ala Lys Thr Pro
                405                 410                 415

Pro Ala Pro Lys Thr Pro Pro Ser Ser Gly Glu Pro Lys Ser Gly
            420                 425                 430

Asp Arg Ser Gly Tyr Ser Ser Pro Gly Ser Pro Gly Thr Pro Gly Ser
            435                 440                 445

Arg Ser Arg Thr Pro Ser Leu Pro Thr Pro Thr Arg Glu Pro Lys
    450                 455                 460

Lys Val Ala Val Val Arg Thr Pro Pro Lys Ser Pro Ser Ser Ala Lys
465                 470                 475                 480

Ser Arg Leu Gln Thr Ala Pro Val Pro Met Pro Asp Leu Lys Asn Val
                485                 490                 495

Lys Ser Lys Ile Gly Ser Thr Glu Asn Leu Lys His Gln Pro Gly Gly
            500                 505                 510

Gly Lys Val Gln Ile Ile Asn Lys Lys Leu Asp Leu Ser Asn Val Gln
            515                 520                 525

Ser Lys Cys Gly Ser Lys Asp Asn Ile Lys His Val Pro Gly Gly Gly
    530                 535                 540

Ser Val Gln Ile Val Tyr Lys Pro Val Asp Leu Ser Lys Val Thr Ser
545                 550                 555                 560

Lys Cys Gly Ser Leu Gly Asn Ile His His Lys Pro Gly Gly Gly Gln
            565                 570                 575

Val Glu Val Lys Ser Glu Lys Leu Asp Phe Lys Asp Arg Val Gln Ser
            580                 585                 590

Lys Ile Gly Ser Leu Asp Asn Ile Thr His Val Pro Gly Gly Gly Asn
    595                 600                 605

Lys Lys Ile Glu Thr His Lys Leu Thr Phe Arg Glu Asn Ala Lys Ala
610                 615                 620

Lys Thr Asp His Gly Ala Glu Ile Val Tyr Lys Ser Pro Val Val Ser
625                 630                 635                 640

Gly Asp Thr Ser Pro Arg His Leu Ser Asn Val Ser Ser Thr Gly Ser
                645                 650                 655

Ile Asp Met Val Asp Ser Pro Gln Leu Ala Thr Leu Ala Asp Glu Val
            660                 665                 670

Ser Ala Ser Leu Ala Lys Gln Gly Leu Arg Arg Ala Gln Arg His Thr
            675                 680                 685

Leu Tyr Ala Pro Gly Gly Tyr Asp Ile Met Gly Trp Leu Ile Gln Ile
    690                 695                 700

Met Asn Arg Pro Asn Pro Gln Val Glu Leu Gly Pro Val Asp Thr Ser
705                 710                 715                 720

Cys Ala Leu Ile Leu Cys Asp Leu Lys Gln Lys Asp Thr Pro Ile Val
                725                 730                 735

Tyr Ala Ser Glu Ala Phe Leu Tyr Met Thr Gly Tyr Ser Asn Ala Glu
            740                 745                 750

Val Leu Gly Arg Asn Cys Arg Phe Leu Gln Ser Pro Asp Gly Met Val
            755                 760                 765

Lys Pro Lys Ser Thr Arg Lys Tyr Val Asp Ser Asn Thr Ile Asn Thr

```
                770                 775                 780
Met Arg Lys Ala Ile Asp Arg Asn Ala Glu Val Gln Val Glu Val Val
785                 790                 795                 800

Asn Phe Lys Lys Asn Gly Gln Arg Phe Val Asn Phe Leu Thr Met Ile
                805                 810                 815

Pro Val Arg Asp Glu Thr Gly Glu Tyr Arg Tyr Ser Met Gly Phe Gln
                820                 825                 830

Cys Glu Thr Glu Ala Leu Glu Phe Cys Ser Arg Arg Tyr Arg Gly Pro
                835                 840                 845

Gly Ile His Arg Ile
    850

<210> SEQ ID NO 59
<211> LENGTH: 853
<212> TYPE: PRT
<213> ORGANISM: Artificial Sequence
<220> FEATURE:
<223> OTHER INFORMATION: synthetic construct

<400> SEQUENCE: 59

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190

Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
        210                 215                 220

Arg His Ser Thr Gly Gly Met Asp Glu Leu Tyr Lys Ser Gly Leu Arg
225                 230                 235                 240

Ser Arg Ala Gln Arg His Thr Leu Tyr Ala Pro Gly Gly Tyr Asp Ile
                245                 250                 255

Met Gly Trp Leu Ile Gln Ile Met Asn Arg Pro Asn Pro Gln Val Glu
                260                 265                 270

Leu Gly Pro Val Asp Thr Ser Cys Ala Leu Ile Leu Cys Asp Leu Lys
```

```
                275                 280                 285
Gln Lys Asp Thr Pro Ile Val Tyr Ala Ser Glu Ala Phe Leu Tyr Met
290                 295                 300

Thr Gly Tyr Ser Asn Ala Glu Val Leu Gly Arg Asn Cys Arg Phe Leu
305                 310                 315                 320

Gln Ser Pro Asp Gly Met Val Lys Pro Lys Ser Thr Arg Lys Tyr Val
                325                 330                 335

Asp Ser Asn Thr Ile Asn Thr Met Arg Lys Ala Ile Asp Arg Asn Ala
                340                 345                 350

Glu Val Gln Val Glu Val Val Asn Phe Lys Lys Asn Gly Gln Arg Phe
                355                 360                 365

Val Asn Phe Leu Thr Met Ile Pro Val Arg Asp Glu Thr Gly Glu Tyr
                370                 375                 380

Arg Tyr Ser Met Gly Phe Gln Cys Glu Thr Glu Ala Leu Ala Met Ala
385                 390                 395                 400

Glu Pro Arg Gln Glu Phe Glu Val Met Glu Asp His Ala Gly Thr Tyr
                405                 410                 415

Gly Leu Gly Asp Arg Lys Asp Gln Gly Gly Tyr Thr Met His Gln Asp
                420                 425                 430

Gln Glu Gly Asp Thr Asp Ala Gly Leu Lys Glu Ser Pro Leu Gln Thr
                435                 440                 445

Pro Thr Glu Asp Gly Ser Glu Glu Pro Gly Ser Glu Thr Ser Asp Ala
450                 455                 460

Lys Ser Thr Pro Thr Ala Glu Asp Val Thr Ala Pro Leu Val Asp Glu
465                 470                 475                 480

Gly Ala Pro Gly Lys Gln Ala Ala Ala Gln Pro His Thr Glu Ile Pro
                485                 490                 495

Glu Gly Thr Thr Ala Glu Glu Ala Gly Ile Gly Asp Thr Pro Ser Leu
                500                 505                 510

Glu Asp Glu Ala Ala Gly His Val Thr Gln Ala Arg Met Val Ser Lys
                515                 520                 525

Ser Lys Asp Gly Thr Gly Ser Asp Asp Lys Lys Ala Lys Gly Ala Asp
530                 535                 540

Gly Lys Thr Lys Ile Ala Thr Pro Arg Gly Ala Ala Pro Pro Gly Gln
545                 550                 555                 560

Lys Gly Gln Ala Asn Ala Thr Arg Ile Pro Ala Lys Thr Pro Pro Ala
                565                 570                 575

Pro Lys Thr Pro Pro Ser Ser Gly Glu Pro Pro Lys Ser Gly Asp Arg
                580                 585                 590

Ser Gly Tyr Ser Ser Pro Gly Ser Pro Gly Thr Pro Gly Ser Arg Ser
                595                 600                 605

Arg Thr Pro Ser Leu Pro Thr Pro Pro Thr Arg Glu Pro Lys Lys Val
                610                 615                 620

Ala Val Val Arg Thr Pro Pro Lys Ser Pro Ser Ser Ala Lys Ser Arg
625                 630                 635                 640

Leu Gln Thr Ala Pro Val Pro Met Pro Asp Leu Lys Asn Val Lys Ser
                645                 650                 655

Lys Ile Gly Ser Thr Glu Asn Leu Lys His Gln Pro Gly Gly Gly Lys
                660                 665                 670

Val Gln Ile Ile Asn Lys Lys Leu Asp Leu Ser Asn Val Gln Ser Lys
                675                 680                 685

Cys Gly Ser Lys Asp Asn Ile Lys His Val Pro Gly Gly Gly Ser Val
                690                 695                 700
```

-continued

```
Gln Ile Val Tyr Lys Pro Val Asp Leu Ser Lys Val Thr Ser Lys Cys
705                 710                 715                 720

Gly Ser Leu Gly Asn Ile His His Lys Pro Gly Gly Gly Gln Val Glu
                725                 730                 735

Val Lys Ser Glu Lys Leu Asp Phe Lys Asp Arg Val Gln Ser Lys Ile
            740                 745                 750

Gly Ser Leu Asp Asn Ile Thr His Val Pro Gly Gly Gly Asn Lys Lys
        755                 760                 765

Ile Glu Thr His Lys Leu Thr Phe Arg Glu Asn Ala Lys Ala Lys Thr
770                 775                 780

Asp His Gly Ala Glu Ile Val Tyr Lys Ser Pro Val Val Ser Gly Asp
785                 790                 795                 800

Thr Ser Pro Arg His Leu Ser Asn Val Ser Ser Thr Gly Ser Ile Asp
                805                 810                 815

Met Val Asp Ser Pro Gln Leu Ala Thr Leu Ala Asp Glu Val Ser Ala
            820                 825                 830

Ser Leu Ala Lys Gln Gly Leu Arg Cys Ser Arg Arg Tyr Arg Gly Pro
        835                 840                 845

Gly Ile His Arg Ile
    850

<210> SEQ ID NO 60
<211> LENGTH: 859
<212> TYPE: PRT
<213> ORGANISM: Artificial Sequence
<220> FEATURE:
<223> OTHER INFORMATION: synthetic construct

<400> SEQUENCE: 60

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205
```

```
Arg Ser Arg Thr Pro Ser Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
    355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu Ala Leu Pro Val Ala Thr Met
    435                 440                 445

Val Ser Lys Gly Glu Glu Asp Asn Met Ala Ile Ile Lys Glu Phe Met
    450                 455                 460

Arg Phe Lys Val His Met Glu Gly Ser Val Asn Gly His Glu Phe Glu
465                 470                 475                 480

Ile Glu Gly Glu Gly Glu Gly Arg Pro Tyr Glu Gly Thr Gln Thr Ala
                485                 490                 495

Lys Leu Lys Val Thr Lys Gly Gly Pro Leu Pro Phe Ala Trp Asp Ile
            500                 505                 510

Leu Ser Pro Gln Phe Met Tyr Gly Ser Lys Ala Tyr Val Lys His Pro
    515                 520                 525

Ala Asp Ile Pro Asp Tyr Leu Lys Leu Ser Phe Pro Glu Gly Phe Lys
    530                 535                 540

Trp Glu Arg Val Met Asn Phe Glu Asp Gly Gly Val Val Thr Val Thr
545                 550                 555                 560

Gln Asp Ser Ser Leu Gln Asp Gly Glu Phe Ile Tyr Lys Val Lys Leu
                565                 570                 575

Arg Gly Thr Asn Phe Pro Ser Asp Gly Pro Val Met Gln Lys Lys Thr
            580                 585                 590

Met Gly Trp Glu Ala Ser Ser Glu Arg Met Tyr Pro Glu Asp Gly Ala
    595                 600                 605

Leu Lys Gly Glu Ile Lys Gln Arg Leu Lys Leu Lys Asp Gly Gly His
    610                 615                 620
```

Tyr Asp Ala Glu Val Lys Thr Thr Tyr Lys Ala Lys Lys Pro Val Gln
625                 630                 635                 640

Leu Pro Gly Ala Tyr Asn Val Asn Ile Lys Leu Asp Ile Thr Ser His
            645                 650                 655

Asn Glu Asp Tyr Thr Ile Val Glu Gln Tyr Glu Arg Ala Glu Gly Arg
        660                 665                 670

His Ser Thr Gly Gly Met Asp Glu Leu Tyr Lys Ser Gly Leu Arg Ser
    675                 680                 685

Arg Ala Gln Arg His Thr Leu Tyr Ala Pro Gly Gly Tyr Asp Ile Met
690                 695                 700

Gly Trp Leu Ile Gln Ile Met Asn Arg Pro Asn Pro Gln Val Glu Leu
705                 710                 715                 720

Gly Pro Val Asp Thr Ser Cys Ala Leu Ile Leu Cys Asp Leu Lys Gln
            725                 730                 735

Lys Asp Thr Pro Ile Val Tyr Ala Ser Glu Ala Phe Leu Tyr Met Thr
        740                 745                 750

Gly Tyr Ser Asn Ala Glu Val Leu Gly Arg Asn Cys Arg Phe Leu Gln
    755                 760                 765

Ser Pro Asp Gly Met Val Lys Pro Lys Ser Thr Arg Lys Tyr Val Asp
770                 775                 780

Ser Asn Thr Ile Asn Thr Met Arg Lys Ala Ile Asp Arg Asn Ala Glu
785                 790                 795                 800

Val Gln Val Glu Val Val Asn Phe Lys Lys Asn Gly Gln Arg Phe Val
            805                 810                 815

Asn Phe Leu Thr Met Ile Pro Val Arg Asp Glu Thr Gly Glu Tyr Arg
        820                 825                 830

Tyr Ser Met Gly Phe Gln Cys Glu Thr Glu Ala Leu Glu Phe Cys Ser
    835                 840                 845

Arg Arg Tyr Arg Gly Pro Gly Ile His Arg Ile
850                 855

<210> SEQ ID NO 61
<211> LENGTH: 1190
<212> TYPE: PRT
<213> ORGANISM: Artificial Sequence
<220> FEATURE:
<223> OTHER INFORMATION: synthetic construct

<400> SEQUENCE: 61

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

```
Tyr Asn Gly Asp Leu Leu Tyr Glu Pro Trp Glu Ile Tyr Cys Glu Lys
    130                 135                 140
Gly Lys Pro Phe Thr Ser Phe Asn Ser Tyr Trp Lys Lys Cys Leu Asp
145                 150                 155                 160
Met Ser Ile Glu Ser Val Met Leu Pro Pro Trp Arg Leu Met Pro
                165                 170                 175
Ile Thr Ala Ala Ala Glu Ala Ile Trp Ala Cys Ser Ile Glu Glu Leu
                180                 185                 190
Gly Leu Glu Asn Glu Ala Glu Lys Pro Ser Asn Ala Leu Leu Thr Arg
                195                 200                 205
Ala Trp Ser Pro Gly Trp Ser Asn Ala Asp Lys Leu Leu Asn Glu Phe
210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
                260                 265                 270
Ala Arg Asp Lys Asn Ser Glu Gly Glu Glu Ser Ala Asp Leu Phe Leu
                275                 280                 285
Arg Gly Ile Gly Leu Arg Glu Tyr Ser Arg Tyr Ile Cys Phe Asn Phe
                290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
                340                 345                 350
Trp Met His Asn Arg Ile Arg Val Ile Val Ser Ser Phe Ala Val Lys
                355                 360                 365
Phe Leu Leu Leu Pro Trp Lys Trp Gly Met Lys Tyr Phe Trp Asp Thr
                370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
                420                 425                 430
Trp Leu Pro Glu Leu Ala Arg Leu Pro Thr Glu Trp Ile His His Pro
                435                 440                 445
Trp Asp Ala Pro Leu Thr Val Leu Lys Ala Ser Gly Val Glu Leu Gly
450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Arg Asp Pro Pro Val Ala Thr Met Val Ser Lys Gly Glu
                500                 505                 510
Glu Asp Asn Met Ala Ile Ile Lys Glu Phe Met Arg Phe Lys Val His
                515                 520                 525
Met Glu Gly Ser Val Asn Gly His Glu Phe Glu Ile Glu Gly Glu Gly
                530                 535                 540
Glu Gly Arg Pro Tyr Glu Gly Thr Gln Thr Ala Lys Leu Lys Val Thr
```

-continued

```
        545                 550                 555                 560
Lys Gly Gly Pro Leu Pro Phe Ala Trp Asp Ile Leu Ser Pro Gln Phe
                565                 570                 575

Met Tyr Gly Ser Lys Ala Tyr Val Lys His Pro Ala Asp Ile Pro Asp
                580                 585                 590

Tyr Leu Lys Leu Ser Phe Pro Glu Gly Phe Lys Trp Glu Arg Val Met
                595                 600                 605

Asn Phe Glu Asp Gly Gly Val Val Thr Val Thr Gln Asp Ser Ser Leu
610                 615                 620

Gln Asp Gly Glu Phe Ile Tyr Lys Val Lys Leu Arg Gly Thr Asn Phe
625                 630                 635                 640

Pro Ser Asp Gly Pro Val Met Gln Lys Lys Thr Met Gly Trp Glu Ala
                645                 650                 655

Ser Ser Glu Arg Met Tyr Pro Glu Asp Gly Ala Leu Lys Gly Glu Ile
                660                 665                 670

Lys Gln Arg Leu Lys Leu Lys Asp Gly Gly His Tyr Asp Ala Glu Val
                675                 680                 685

Lys Thr Thr Tyr Lys Ala Lys Lys Pro Val Gln Leu Pro Gly Ala Tyr
                690                 695                 700

Asn Val Asn Ile Lys Leu Asp Ile Thr Ser His Asn Glu Asp Tyr Thr
705                 710                 715                 720

Ile Val Glu Gln Tyr Glu Arg Ala Glu Gly Arg His Ser Thr Gly Gly
                725                 730                 735

Met Asp Glu Leu Tyr Lys Ser Arg Met Ala Glu Pro Arg Gln Glu Phe
                740                 745                 750

Glu Val Met Glu Asp His Ala Gly Thr Tyr Gly Leu Gly Asp Arg Lys
                755                 760                 765

Asp Gln Gly Gly Tyr Thr Met His Gln Asp Gln Glu Gly Asp Thr Asp
                770                 775                 780

Ala Gly Leu Lys Glu Ser Pro Leu Gln Thr Pro Thr Glu Asp Gly Ser
785                 790                 795                 800

Glu Glu Pro Gly Ser Glu Thr Ser Asp Ala Lys Ser Thr Pro Thr Ala
                805                 810                 815

Glu Asp Val Thr Ala Pro Leu Val Asp Glu Gly Ala Pro Gly Lys Gln
                820                 825                 830

Ala Ala Ala Gln Pro His Thr Glu Ile Pro Glu Gly Thr Thr Ala Glu
                835                 840                 845

Glu Ala Gly Ile Gly Asp Thr Pro Ser Leu Glu Asp Glu Ala Ala Gly
                850                 855                 860

His Val Thr Gln Ala Arg Met Val Ser Lys Ser Lys Asp Gly Thr Gly
865                 870                 875                 880

Ser Asp Asp Lys Lys Ala Lys Gly Ala Asp Gly Lys Thr Lys Ile Ala
                885                 890                 895

Thr Pro Arg Gly Ala Ala Pro Pro Gly Gln Lys Gly Gln Ala Asn Ala
                900                 905                 910

Thr Arg Ile Pro Ala Lys Thr Pro Pro Ala Pro Lys Thr Pro Pro Ser
                915                 920                 925

Ser Gly Glu Pro Pro Lys Ser Gly Asp Arg Ser Gly Tyr Ser Ser Pro
                930                 935                 940

Gly Ser Pro Gly Thr Pro Gly Ser Arg Ser Arg Thr Pro Ser Leu Pro
945                 950                 955                 960

Thr Pro Pro Thr Arg Glu Pro Lys Lys Val Ala Val Val Arg Thr Pro
                965                 970                 975
```

```
Pro Lys Ser Pro Ser Ser Ala Lys Ser Arg Leu Gln Thr Ala Pro Val
                980                 985                 990

Pro Met Pro Asp Leu Lys Asn Val  Lys Ser Lys Ile Gly  Ser Thr Glu
            995                 1000                1005

Asn Leu Lys His Gln Pro Gly  Gly Gly Lys Val Gln  Ile Ile Asn
        1010                1015                1020

Lys Lys Leu Asp Leu Ser Asn  Val Gln Ser Lys Cys  Gly Ser Lys
        1025                1030                1035

Asp Asn Ile Lys His Val Pro  Gly Gly Gly Ser Val  Gln Ile Val
        1040                1045                1050

Tyr Lys Pro Val Asp Leu Ser  Lys Val Thr Ser Lys  Cys Gly Ser
        1055                1060                1065

Leu Gly Asn Ile His His Lys  Pro Gly Gly Gly Gln  Val Glu Val
        1070                1075                1080

Lys Ser Glu Lys Leu Asp Phe  Lys Asp Arg Val Gln  Ser Lys Ile
        1085                1090                1095

Gly Ser Leu Asp Asn Ile Thr  His Val Pro Gly Gly  Gly Asn Lys
        1100                1105                1110

Lys Ile Glu Thr His Lys Leu  Thr Phe Arg Glu Asn  Ala Lys Ala
        1115                1120                1125

Lys Thr Asp His Gly Ala Glu  Ile Val Tyr Lys Ser  Pro Val Val
        1130                1135                1140

Ser Gly Asp Thr Ser Pro Arg  His Leu Ser Asn Val  Ser Ser Thr
        1145                1150                1155

Gly Ser Ile Asp Met Val Asp  Ser Pro Gln Leu Ala  Thr Leu Ala
        1160                1165                1170

Asp Glu Val Ser Ala Ser Leu  Ala Lys Gln Gly Leu  Gly Asp Ser
        1175                1180                1185

Arg Ser
    1190

<210> SEQ ID NO 62
<211> LENGTH: 706
<212> TYPE: PRT
<213> ORGANISM: Artificial Sequence
<220> FEATURE:
<223> OTHER INFORMATION: synthetic construct

<400> SEQUENCE: 62

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125
```

```
Ser Lys Ser Lys Asp Gly Thr Gly Ser Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu Phe Ala Thr Met Val Ser Lys
        435                 440                 445

Gly Glu Glu Asp Asn Met Ala Ile Ile Lys Glu Phe Met Arg Phe Lys
    450                 455                 460

Val His Met Glu Gly Ser Val Asn Gly His Glu Phe Glu Ile Glu Gly
465                 470                 475                 480

Glu Gly Glu Gly Arg Pro Tyr Glu Gly Thr Gln Thr Ala Lys Leu Lys
                485                 490                 495

Val Thr Lys Gly Gly Pro Leu Pro Phe Ala Trp Asp Ile Leu Ser Pro
            500                 505                 510

Gln Phe Met Tyr Gly Ser Lys Ala Tyr Val Lys His Pro Ala Asp Ile
        515                 520                 525

Pro Asp Tyr Leu Lys Leu Ser Phe Pro Glu Gly Phe Lys Trp Glu Arg
    530                 535                 540
```

Val Met Asn Phe Glu Asp Gly Gly Val Val Thr Val Thr Gln Asp Ser
545                 550                 555                 560

Ser Leu Gln Asp Gly Glu Phe Ile Tyr Lys Val Lys Leu Arg Gly Thr
                565                 570                 575

Asn Phe Pro Ser Asp Gly Pro Val Met Gln Lys Lys Thr Met Gly Trp
            580                 585                 590

Glu Ala Ser Ser Glu Arg Met Tyr Pro Glu Asp Gly Ala Leu Lys Gly
        595                 600                 605

Glu Ile Lys Gln Arg Leu Lys Leu Lys Asp Gly Gly His Tyr Asp Ala
    610                 615                 620

Glu Val Lys Thr Thr Tyr Lys Ala Lys Lys Pro Val Gln Leu Pro Gly
625                 630                 635                 640

Ala Tyr Asn Val Asn Ile Lys Leu Asp Ile Thr Ser His Asn Glu Asp
                645                 650                 655

Tyr Thr Ile Val Glu Gln Tyr Glu Arg Ala Glu Gly Arg His Ser Thr
            660                 665                 670

Gly Gly Met Asp Glu Leu Tyr Lys Ser Gly Leu Arg Ser Arg Ala Gln
        675                 680                 685

Ala Ser Asn Ser Ala Val Asp Gly Thr Ala Gly Pro Gly Ser Thr Gly
    690                 695                 700

Ser Arg
705

<210> SEQ ID NO 63
<211> LENGTH: 1193
<212> TYPE: PRT
<213> ORGANISM: Artificial Sequence
<220> FEATURE:
<223> OTHER INFORMATION: synthetic construct

<400> SEQUENCE: 63

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

```
Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu Ala Leu Pro Asp Ser Asp Leu
        435                 440                 445

Glu Ala Thr Met Lys Met Asp Lys Lys Thr Ile Val Trp Phe Arg Arg
    450                 455                 460

Asp Leu Arg Ile Glu Asp Asn Pro Ala Leu Ala Ala Ala His Glu
465                 470                 475                 480

Gly Ser Val Phe Pro Val Phe Ile Trp Cys Pro Glu Glu Gly Gln
                485                 490                 495

Phe Tyr Pro Gly Arg Ala Ser Arg Trp Trp Met Lys Gln Ser Leu Ala
            500                 505                 510

His Leu Ser Gln Ser Leu Lys Ala Leu Gly Ser Asp Leu Thr Leu Ile
        515                 520                 525

Lys Thr His Asn Thr Ile Ser Ala Ile Leu Asp Cys Ile Arg Val Thr
    530                 535                 540

Gly Ala Thr Lys Val Val Phe Asn His Leu Tyr Asp Pro Val Ser Leu
545                 550                 555                 560

Val Arg Asp His Thr Val Lys Glu Lys Leu Val Glu Arg Gly Ile Ser
                565                 570                 575

Val Gln Ser Tyr Asn Gly Asp Leu Leu Tyr Glu Pro Trp Glu Ile Tyr
            580                 585                 590

Cys Glu Lys Gly Lys Pro Phe Thr Ser Phe Asn Ser Tyr Trp Lys Lys
        595                 600                 605

Cys Leu Asp Met Ser Ile Glu Ser Val Met Leu Pro Pro Pro Trp Arg
```

-continued

```
            610                 615                 620
Leu Met Pro Ile Thr Ala Ala Glu Ala Ile Trp Ala Cys Ser Ile
625                 630                 635                 640

Glu Glu Leu Gly Leu Glu Asn Glu Ala Glu Lys Pro Ser Asn Ala Leu
                645                 650                 655

Leu Thr Arg Ala Trp Ser Pro Gly Trp Ser Asn Ala Asp Lys Leu Leu
                660                 665                 670

Asn Glu Phe Ile Glu Lys Gln Leu Ile Asp Tyr Ala Lys Asn Ser Lys
                675                 680                 685

Lys Val Val Gly Asn Ser Thr Ser Leu Leu Ser Pro Tyr Leu His Phe
            690                 695                 700

Gly Glu Ile Ser Val Arg His Val Phe Gln Cys Ala Arg Met Lys Gln
705                 710                 715                 720

Ile Ile Trp Ala Arg Asp Lys Asn Ser Glu Gly Glu Ser Ala Asp
                725                 730                 735

Leu Phe Leu Arg Gly Ile Gly Leu Arg Glu Tyr Ser Arg Tyr Ile Cys
                740                 745                 750

Phe Asn Phe Pro Phe Thr His Glu Gln Ser Leu Leu Ser His Leu Arg
                755                 760                 765

Phe Phe Pro Trp Asp Ala Asp Val Asp Lys Phe Lys Ala Trp Arg Gln
                770                 775                 780

Gly Arg Thr Gly Tyr Pro Leu Val Asp Ala Gly Met Arg Glu Leu Trp
785                 790                 795                 800

Ala Thr Gly Trp Met His Asn Arg Ile Arg Val Ile Val Ser Ser Phe
                805                 810                 815

Ala Val Lys Phe Leu Leu Leu Pro Trp Lys Trp Gly Met Lys Tyr Phe
                820                 825                 830

Trp Asp Thr Leu Leu Asp Ala Asp Leu Glu Cys Asp Ile Leu Gly Trp
                835                 840                 845

Gln Tyr Ile Ser Gly Ser Ile Pro Asp Gly His Glu Leu Asp Arg Leu
            850                 855                 860

Asp Asn Pro Ala Leu Gln Gly Ala Lys Tyr Asp Pro Glu Gly Glu Tyr
865                 870                 875                 880

Ile Arg Gln Trp Leu Pro Glu Leu Ala Arg Leu Pro Thr Glu Trp Ile
                885                 890                 895

His His Pro Trp Asp Ala Pro Leu Thr Val Leu Lys Ala Ser Gly Val
                900                 905                 910

Glu Leu Gly Thr Asn Tyr Ala Lys Pro Ile Val Asp Ile Asp Thr Ala
                915                 920                 925

Arg Glu Leu Leu Ala Lys Ala Ile Ser Arg Thr Arg Gly Ala Gln Ile
930                 935                 940

Met Ile Gly Ala Ala Ala Arg Asp Pro Pro Val Ala Thr Met Val Ser
945                 950                 955                 960

Lys Gly Glu Glu Asp Asn Met Ala Ile Ile Lys Glu Phe Met Arg Phe
                965                 970                 975

Lys Val His Met Glu Gly Ser Val Asn Gly His Glu Phe Glu Ile Glu
                980                 985                 990

Gly Glu Gly Glu Gly Arg Pro Tyr Glu Gly Thr Gln Thr Ala Lys Leu
            995                 1000                1005

Lys Val Thr Lys Gly Gly Pro Leu Pro Phe Ala Trp Asp Ile Leu
        1010                1015                1020

Ser Pro Gln Phe Met Tyr Gly Ser Lys Ala Tyr Val Lys His Pro
        1025                1030                1035
```

-continued

Ala Asp Ile Pro Asp Tyr Leu Lys Leu Ser Phe Pro Glu Gly Phe
    1040                1045                1050

Lys Trp Glu Arg Val Met Asn Phe Glu Asp Gly Gly Val Val Thr
    1055                1060                1065

Val Thr Gln Asp Ser Ser Leu Gln Asp Gly Glu Phe Ile Tyr Lys
    1070                1075                1080

Val Lys Leu Arg Gly Thr Asn Phe Pro Ser Asp Gly Pro Val Met
    1085                1090                1095

Gln Lys Lys Thr Met Gly Trp Glu Ala Ser Ser Glu Arg Met Tyr
    1100                1105                1110

Pro Glu Asp Gly Ala Leu Lys Gly Glu Ile Lys Gln Arg Leu Lys
    1115                1120                1125

Leu Lys Asp Gly Gly His Tyr Asp Ala Glu Val Lys Thr Thr Tyr
    1130                1135                1140

Lys Ala Lys Lys Pro Val Gln Leu Pro Gly Ala Tyr Asn Val Asn
    1145                1150                1155

Ile Lys Leu Asp Ile Thr Ser His Asn Glu Asp Tyr Thr Ile Val
    1160                1165                1170

Glu Gln Tyr Glu Arg Ala Glu Gly Arg His Ser Thr Gly Gly Met
    1175                1180                1185

Asp Glu Leu Tyr Lys
    1190

<210> SEQ ID NO 64
<211> LENGTH: 1184
<212> TYPE: PRT
<213> ORGANISM: Artificial Sequence
<220> FEATURE:
<223> OTHER INFORMATION: synthetic construct

<400> SEQUENCE: 64

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30

Phe Pro Val Phe Ile Trp Cys Pro Glu Glu Gly Gln Phe Tyr Pro
            35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
                180                 185                 190

```
Gly Leu Glu Asn Glu Ala Glu Lys Pro Ser Asn Ala Leu Leu Thr Arg
            195                 200                 205

Ala Trp Ser Pro Gly Trp Ser Asn Ala Asp Lys Leu Leu Asn Glu Phe
210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Ser Ala Asp Leu Phe Leu
            275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
                355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
            450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Pro Met Ala Glu Pro Arg Gln Glu Phe Glu Val Met Glu
                500                 505                 510

Asp His Ala Gly Thr Tyr Gly Leu Gly Asp Arg Lys Asp Gln Gly Gly
            515                 520                 525

Tyr Thr Met His Gln Asp Gln Glu Gly Asp Thr Asp Ala Gly Leu Lys
            530                 535                 540

Glu Ser Pro Leu Gln Thr Pro Thr Glu Asp Gly Ser Glu Glu Pro Gly
545                 550                 555                 560

Ser Glu Thr Ser Asp Ala Lys Ser Thr Pro Thr Ala Glu Asp Val Thr
                565                 570                 575

Ala Pro Leu Val Asp Glu Gly Ala Pro Gly Lys Gln Ala Ala Ala Gln
                580                 585                 590

Pro His Thr Glu Ile Pro Glu Gly Thr Thr Ala Glu Glu Ala Gly Ile
            595                 600                 605
```

```
Gly Asp Thr Pro Ser Leu Glu Asp Glu Ala Ala Gly His Val Thr Gln
610                 615                 620

Ala Arg Met Val Ser Lys Ser Lys Asp Gly Thr Gly Ser Asp Asp Lys
625                 630                 635                 640

Lys Ala Lys Gly Ala Asp Gly Lys Thr Lys Ile Ala Thr Pro Arg Gly
                645                 650                 655

Ala Ala Pro Pro Gly Gln Lys Gly Gln Ala Asn Ala Thr Arg Ile Pro
            660                 665                 670

Ala Lys Thr Pro Pro Ala Pro Lys Thr Pro Ser Ser Gly Glu Pro
        675                 680                 685

Pro Lys Ser Gly Asp Arg Ser Gly Tyr Ser Ser Pro Gly Ser Pro Gly
690                 695                 700

Thr Pro Gly Ser Arg Ser Arg Thr Pro Ser Leu Pro Thr Pro Pro Thr
705                 710                 715                 720

Arg Glu Pro Lys Lys Val Ala Val Val Arg Thr Pro Pro Lys Ser Pro
                725                 730                 735

Ser Ser Ala Lys Ser Arg Leu Gln Thr Ala Pro Val Pro Met Pro Asp
            740                 745                 750

Leu Lys Asn Val Lys Ser Lys Ile Gly Ser Thr Glu Asn Leu Lys His
        755                 760                 765

Gln Pro Gly Gly Gly Lys Val Gln Ile Ile Asn Lys Lys Leu Asp Leu
770                 775                 780

Ser Asn Val Gln Ser Lys Cys Gly Ser Lys Asp Asn Ile Lys His Val
785                 790                 795                 800

Pro Gly Gly Gly Ser Val Gln Ile Val Tyr Lys Pro Val Asp Leu Ser
                805                 810                 815

Lys Val Thr Ser Lys Cys Gly Ser Leu Gly Asn Ile His His Lys Pro
            820                 825                 830

Gly Gly Gly Gln Val Glu Val Lys Ser Glu Lys Leu Asp Phe Lys Asp
        835                 840                 845

Arg Val Gln Ser Lys Ile Gly Ser Leu Asp Asn Ile Thr His Val Pro
850                 855                 860

Gly Gly Gly Asn Lys Lys Ile Glu Thr His Lys Leu Thr Phe Arg Glu
865                 870                 875                 880

Asn Ala Lys Ala Lys Thr Asp His Gly Ala Glu Ile Val Tyr Lys Ser
                885                 890                 895

Pro Val Val Ser Gly Asp Thr Ser Pro Arg His Leu Ser Asn Val Ser
            900                 905                 910

Ser Thr Gly Ser Ile Asp Met Val Asp Ser Pro Gln Leu Ala Thr Leu
        915                 920                 925

Ala Asp Glu Val Ser Ala Ser Leu Ala Lys Gln Gly Leu Gly Asp Pro
930                 935                 940

Pro Val Ala Thr Met Val Ser Lys Gly Glu Glu Asp Asn Met Ala Ile
945                 950                 955                 960

Ile Lys Glu Phe Met Arg Phe Lys Val His Met Glu Gly Ser Val Asn
                965                 970                 975

Gly His Glu Phe Glu Ile Glu Gly Glu Gly Glu Gly Arg Pro Tyr Glu
            980                 985                 990

Gly Thr Gln Thr Ala Lys Leu Lys Val Thr Lys Gly Gly Pro Leu Pro
        995                 1000                1005

Phe Ala Trp Asp Ile Leu Ser Pro Gln Phe Met Tyr Gly Ser Lys
        1010                1015                1020

Ala Tyr Val Lys His Pro Ala Asp Ile Pro Asp Tyr Leu Lys Leu
```

```
              1025                1030                1035

Ser Phe Pro Glu Gly Phe Lys Trp Glu Arg Val Met Asn Phe Glu
     1040                1045                1050

Asp Gly Gly Val Val Thr Val Thr Gln Asp Ser Ser Leu Gln Asp
     1055                1060                1065

Gly Glu Phe Ile Tyr Lys Val Lys Leu Arg Gly Thr Asn Phe Pro
     1070                1075                1080

Ser Asp Gly Pro Val Met Gln Lys Lys Thr Met Gly Trp Glu Ala
     1085                1090                1095

Ser Ser Glu Arg Met Tyr Pro Glu Asp Gly Ala Leu Lys Gly Glu
     1100                1105                1110

Ile Lys Gln Arg Leu Lys Leu Lys Asp Gly Gly His Tyr Asp Ala
     1115                1120                1125

Glu Val Lys Thr Thr Tyr Lys Ala Lys Lys Pro Val Gln Leu Pro
     1130                1135                1140

Gly Ala Tyr Asn Val Asn Ile Lys Leu Asp Ile Thr Ser His Asn
     1145                1150                1155

Glu Asp Tyr Thr Ile Val Glu Gln Tyr Glu Arg Ala Glu Gly Arg
     1160                1165                1170

His Ser Thr Gly Gly Met Asp Glu Leu Tyr Lys
     1175                1180

<210> SEQ ID NO 65
<211> LENGTH: 1190
<212> TYPE: PRT
<213> ORGANISM: Artificial Sequence
<220> FEATURE:
<223> OTHER INFORMATION: synthetic construct

<400> SEQUENCE: 65

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
            35                  40                  45

Gly Arg Ala Ser Arg Trp Trp Met Lys Gln Ser Leu Ala His Leu Ser
     50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
```

```
                195                 200                 205
Ala Trp Ser Pro Gly Trp Ser Asn Ala Asp Lys Leu Leu Asn Glu Phe
210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Ser Ala Asp Leu Phe Leu
            275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Arg Asp Pro Pro Val Ala Thr Met Val Ser Lys Gly Glu
                500                 505                 510

Glu Asp Asn Met Ala Ile Ile Lys Glu Phe Met Arg Phe Lys Val His
            515                 520                 525

Met Glu Gly Ser Val Asn Gly His Glu Phe Glu Ile Glu Gly Glu Gly
530                 535                 540

Glu Gly Arg Pro Tyr Glu Gly Thr Gln Thr Ala Lys Leu Lys Val Thr
545                 550                 555                 560

Lys Gly Gly Pro Leu Pro Phe Ala Trp Asp Ile Leu Ser Pro Gln Phe
                565                 570                 575

Met Tyr Gly Ser Lys Ala Tyr Val Lys His Pro Ala Asp Ile Pro Asp
                580                 585                 590

Tyr Leu Lys Leu Ser Phe Pro Glu Gly Phe Lys Trp Glu Arg Val Met
            595                 600                 605

Asn Phe Glu Asp Gly Gly Val Val Thr Val Thr Gln Asp Ser Ser Leu
610                 615                 620
```

-continued

```
Gln Asp Gly Glu Phe Ile Tyr Lys Val Lys Leu Arg Gly Thr Asn Phe
625                 630                 635                 640

Pro Ser Asp Gly Pro Val Met Gln Lys Lys Thr Met Gly Trp Glu Ala
            645                 650                 655

Ser Ser Glu Arg Met Tyr Pro Glu Asp Gly Ala Leu Lys Gly Glu Ile
        660                 665                 670

Lys Gln Arg Leu Lys Leu Lys Asp Gly Gly His Tyr Asp Ala Glu Val
    675                 680                 685

Lys Thr Thr Tyr Lys Ala Lys Lys Pro Val Gln Leu Pro Gly Ala Tyr
690                 695                 700

Asn Val Asn Ile Lys Leu Asp Ile Thr Ser His Asn Glu Asp Tyr Thr
705                 710                 715                 720

Ile Val Glu Gln Tyr Glu Arg Ala Glu Gly Arg His Ser Thr Gly Gly
                725                 730                 735

Met Asp Glu Leu Tyr Lys Ser Arg Met Ala Glu Pro Arg Gln Glu Phe
            740                 745                 750

Glu Val Met Glu Asp His Ala Gly Thr Tyr Gly Leu Gly Asp Arg Lys
        755                 760                 765

Asp Gln Gly Gly Tyr Thr Met His Gln Asp Gln Glu Gly Asp Thr Asp
    770                 775                 780

Ala Gly Leu Lys Glu Ser Pro Leu Gln Thr Pro Thr Glu Asp Gly Ser
785                 790                 795                 800

Glu Glu Pro Gly Ser Glu Thr Ser Asp Ala Lys Ser Thr Pro Thr Ala
                805                 810                 815

Glu Asp Val Thr Ala Pro Leu Val Asp Glu Gly Ala Pro Gly Lys Gln
            820                 825                 830

Ala Ala Ala Gln Pro His Thr Glu Ile Pro Glu Gly Thr Thr Ala Glu
        835                 840                 845

Glu Ala Gly Ile Gly Asp Thr Pro Ser Leu Glu Asp Glu Ala Ala Gly
    850                 855                 860

His Val Thr Gln Ala Arg Met Val Ser Lys Ser Lys Asp Gly Thr Gly
865                 870                 875                 880

Ser Asp Asp Lys Lys Ala Lys Gly Ala Asp Gly Lys Thr Lys Ile Ala
                885                 890                 895

Thr Pro Arg Gly Ala Ala Pro Pro Gly Gln Lys Gly Gln Ala Asn Ala
            900                 905                 910

Thr Arg Ile Pro Ala Lys Thr Pro Pro Ala Pro Lys Thr Pro Pro Ser
        915                 920                 925

Ser Gly Glu Pro Pro Lys Ser Gly Asp Arg Ser Gly Tyr Ser Ser Pro
    930                 935                 940

Gly Ser Pro Gly Thr Pro Gly Ser Arg Ser Arg Thr Pro Ser Leu Pro
945                 950                 955                 960

Thr Pro Pro Thr Arg Glu Pro Lys Lys Val Ala Val Val Arg Thr Pro
                965                 970                 975

Pro Lys Ser Pro Ser Ser Ala Lys Ser Arg Leu Gln Thr Ala Pro Val
            980                 985                 990

Pro Met Pro Asp Leu Lys Asn Val  Lys Ser Lys Ile Gly  Ser Thr Glu
        995                 1000                1005

Asn Leu  Lys His Gln Pro Gly  Gly Gly Lys Val Gln  Ile Ile Asn
    1010                 1015                1020

Lys Lys  Leu Asp Leu Ser Asn  Val Gln Ser Lys Cys  Gly Ser Lys
    1025                 1030                1035
```

```
Asp Asn Ile Lys His Val Pro Gly Gly Gly Ser Val Gln Ile Val
    1040                1045                1050

Tyr Lys Pro Val Asp Leu Ser Lys Val Thr Ser Lys Cys Gly Ser
    1055                1060                1065

Leu Gly Asn Ile His His Lys Pro Gly Gly Gln Val Glu Val
    1070                1075                1080

Lys Ser Glu Lys Leu Asp Phe Lys Asp Arg Val Gln Ser Lys Ile
    1085                1090                1095

Gly Ser Leu Asp Asn Ile Thr His Val Pro Gly Gly Asn Lys
    1100                1105                1110

Lys Ile Glu Thr His Lys Leu Thr Phe Arg Glu Asn Ala Lys Ala
    1115                1120                1125

Lys Thr Asp His Gly Ala Glu Ile Val Tyr Lys Ser Pro Val Val
    1130                1135                1140

Ser Gly Asp Thr Ser Pro Arg His Leu Ser Asn Val Ser Ser Thr
    1145                1150                1155

Gly Ser Ile Asp Met Val Asp Ser Pro Gln Leu Ala Thr Leu Ala
    1160                1165                1170

Asp Glu Val Ser Ala Ser Leu Ala Lys Gln Gly Leu Gly Asp Ser
    1175                1180                1185

Arg Ser
    1190

<210> SEQ ID NO 66
<211> LENGTH: 853
<212> TYPE: PRT
<213> ORGANISM: Artificial Sequence
<220> FEATURE:
<223> OTHER INFORMATION: synthetic construct

<400> SEQUENCE: 66

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
                180                 185                 190
```

```
Gln Leu Pro Gly Ala Tyr Asn Val Asn Ile Lys Leu Asp Ile Thr Ser
            195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Ser Gly Leu Thr
225                 230                 235                 240

Met Ala Glu Pro Arg Gln Glu Phe Glu Val Met Glu Asp His Ala Gly
                245                 250                 255

Thr Tyr Gly Leu Gly Asp Arg Lys Asp Gln Gly Gly Tyr Thr Met His
            260                 265                 270

Gln Asp Gln Glu Gly Asp Thr Asp Ala Gly Leu Lys Glu Ser Pro Leu
        275                 280                 285

Gln Thr Pro Thr Glu Asp Gly Ser Glu Glu Pro Gly Ser Glu Thr Ser
    290                 295                 300

Asp Ala Lys Ser Thr Pro Thr Ala Glu Asp Val Thr Ala Pro Leu Val
305                 310                 315                 320

Asp Glu Gly Ala Pro Gly Lys Gln Ala Ala Gln Pro His Thr Glu
                325                 330                 335

Ile Pro Glu Gly Thr Thr Ala Glu Glu Ala Gly Ile Gly Asp Thr Pro
            340                 345                 350

Ser Leu Glu Asp Glu Ala Ala Gly His Val Thr Gln Ala Arg Met Val
        355                 360                 365

Ser Lys Ser Lys Asp Gly Thr Gly Ser Asp Asp Lys Lys Ala Lys Gly
    370                 375                 380

Ala Asp Gly Lys Thr Lys Ile Ala Thr Pro Arg Gly Ala Ala Pro Pro
385                 390                 395                 400

Gly Gln Lys Gly Gln Ala Asn Ala Thr Arg Ile Pro Ala Lys Thr Pro
                405                 410                 415

Pro Ala Pro Lys Thr Pro Pro Ser Ser Gly Glu Pro Pro Lys Ser Gly
            420                 425                 430

Asp Arg Ser Gly Tyr Ser Ser Pro Gly Ser Pro Gly Thr Pro Gly Ser
        435                 440                 445

Arg Ser Arg Thr Pro Ser Leu Pro Thr Pro Pro Thr Arg Glu Pro Lys
    450                 455                 460

Lys Val Ala Val Val Arg Thr Pro Pro Lys Ser Pro Ser Ser Ala Lys
465                 470                 475                 480

Ser Arg Leu Gln Thr Ala Pro Val Pro Met Pro Asp Leu Lys Asn Val
                485                 490                 495

Lys Ser Lys Ile Gly Ser Thr Glu Asn Leu Lys His Gln Pro Gly Gly
            500                 505                 510

Gly Lys Val Gln Ile Ile Asn Lys Lys Leu Asp Leu Ser Asn Val Gln
        515                 520                 525

Ser Lys Cys Gly Ser Lys Asp Asn Ile Lys His Val Pro Gly Gly Gly
    530                 535                 540

Ser Val Gln Ile Val Tyr Lys Pro Val Asp Leu Ser Lys Val Thr Ser
545                 550                 555                 560

Lys Cys Gly Ser Leu Gly Asn Ile His His Lys Pro Gly Gly Gly Gln
                565                 570                 575

Val Glu Val Lys Ser Glu Lys Leu Asp Phe Lys Asp Arg Val Gln Ser
            580                 585                 590

Lys Ile Gly Ser Leu Asp Asn Ile Thr His Val Pro Gly Gly Gly Asn
        595                 600                 605

Lys Lys Ile Glu Thr His Lys Leu Thr Phe Arg Glu Asn Ala Lys Ala
```

```
                      610                 615                 620
Lys Thr Asp His Gly Ala Glu Ile Val Tyr Lys Ser Pro Val Val Ser
625                 630                 635                 640

Gly Asp Thr Ser Pro Arg His Leu Ser Asn Val Ser Ser Thr Gly Ser
                645                 650                 655

Ile Asp Met Val Asp Ser Pro Gln Leu Ala Thr Leu Ala Asp Glu Val
            660                 665                 670

Ser Ala Ser Leu Ala Lys Gln Gly Leu Arg Arg Ala Gln Arg His Thr
        675                 680                 685

Leu Tyr Ala Pro Gly Gly Tyr Asp Ile Met Gly Trp Leu Ile Gln Ile
    690                 695                 700

Met Asn Arg Pro Asn Pro Gln Val Glu Leu Gly Pro Val Asp Thr Ser
705                 710                 715                 720

Cys Ala Leu Ile Leu Cys Asp Leu Lys Gln Lys Asp Thr Pro Ile Val
                725                 730                 735

Tyr Ala Ser Glu Ala Phe Leu Tyr Met Thr Gly Tyr Ser Asn Ala Glu
            740                 745                 750

Val Leu Gly Arg Asn Cys Arg Phe Leu Gln Ser Pro Asp Gly Met Val
        755                 760                 765

Lys Pro Lys Ser Thr Arg Lys Tyr Val Asp Ser Asn Thr Ile Asn Thr
    770                 775                 780

Met Arg Lys Ala Ile Asp Arg Asn Ala Glu Val Gln Val Glu Val Val
785                 790                 795                 800

Asn Phe Lys Lys Asn Gly Gln Arg Phe Val Asn Phe Leu Thr Met Ile
                805                 810                 815

Pro Val Arg Asp Glu Thr Gly Glu Tyr Arg Tyr Ser Met Gly Phe Gln
            820                 825                 830

Cys Glu Thr Glu Ala Leu Glu Phe Cys Ser Arg Arg Tyr Arg Gly Pro
        835                 840                 845

Gly Ile His Arg Ile
    850

<210> SEQ ID NO 67
<211> LENGTH: 853
<212> TYPE: PRT
<213> ORGANISM: Artificial Sequence
<220> FEATURE:
<223> OTHER INFORMATION: synthetic construct

<400> SEQUENCE: 67

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
```

-continued

```
               115                 120                 125
Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Ser Gly Leu Arg
225                 230                 235                 240

Ser Arg Ala Gln Arg His Thr Leu Tyr Ala Pro Gly Gly Tyr Asp Ile
                245                 250                 255

Met Gly Trp Leu Ile Gln Ile Met Asn Arg Pro Asn Pro Gln Val Glu
            260                 265                 270

Leu Gly Pro Val Asp Thr Ser Cys Ala Leu Ile Leu Cys Asp Leu Lys
        275                 280                 285

Gln Lys Asp Thr Pro Ile Val Tyr Ala Ser Glu Ala Phe Leu Tyr Met
    290                 295                 300

Thr Gly Tyr Ser Asn Ala Glu Val Leu Gly Arg Asn Cys Arg Phe Leu
305                 310                 315                 320

Gln Ser Pro Asp Gly Met Val Lys Pro Lys Ser Thr Arg Lys Tyr Val
                325                 330                 335

Asp Ser Asn Thr Ile Asn Thr Met Arg Lys Ala Ile Asp Arg Asn Ala
            340                 345                 350

Glu Val Gln Val Glu Val Val Asn Phe Lys Lys Asn Gly Gln Arg Phe
        355                 360                 365

Val Asn Phe Leu Thr Met Ile Pro Val Arg Asp Glu Thr Gly Glu Tyr
    370                 375                 380

Arg Tyr Ser Met Gly Phe Gln Cys Glu Thr Glu Ala Leu Ala Met Ala
385                 390                 395                 400

Glu Pro Arg Gln Glu Phe Glu Val Met Glu Asp His Ala Gly Thr Tyr
                405                 410                 415

Gly Leu Gly Asp Arg Lys Asp Gln Gly Gly Tyr Thr Met His Gln Asp
            420                 425                 430

Gln Glu Gly Asp Thr Asp Ala Gly Leu Lys Glu Ser Pro Leu Gln Thr
        435                 440                 445

Pro Thr Glu Asp Gly Ser Glu Pro Gly Ser Glu Thr Ser Asp Ala
    450                 455                 460

Lys Ser Thr Pro Thr Ala Glu Asp Val Thr Ala Pro Leu Val Asp Glu
465                 470                 475                 480

Gly Ala Pro Gly Lys Gln Ala Ala Gln Pro His Thr Glu Ile Pro
                485                 490                 495

Glu Gly Thr Thr Ala Glu Glu Ala Gly Ile Gly Asp Thr Pro Ser Leu
            500                 505                 510

Glu Asp Glu Ala Ala Gly His Val Thr Gln Ala Arg Met Val Ser Lys
        515                 520                 525

Ser Lys Asp Gly Thr Gly Ser Asp Asp Lys Lys Ala Lys Gly Ala Asp
    530                 535                 540
```

Gly Lys Thr Lys Ile Ala Thr Pro Arg Gly Ala Pro Pro Gly Gln
545                 550                 555                 560

Lys Gly Gln Ala Asn Ala Thr Arg Ile Pro Ala Lys Thr Pro Pro Ala
            565                 570                 575

Pro Lys Thr Pro Pro Ser Ser Gly Glu Pro Pro Lys Ser Gly Asp Arg
            580                 585                 590

Ser Gly Tyr Ser Ser Pro Gly Ser Pro Gly Thr Pro Gly Ser Arg Ser
            595                 600                 605

Arg Thr Pro Ser Leu Pro Thr Pro Pro Thr Arg Glu Pro Lys Lys Val
            610                 615                 620

Ala Val Val Arg Thr Pro Pro Lys Ser Pro Ser Ser Ala Lys Ser Arg
625                 630                 635                 640

Leu Gln Thr Ala Pro Val Pro Met Pro Asp Leu Lys Asn Val Lys Ser
                645                 650                 655

Lys Ile Gly Ser Thr Glu Asn Leu Lys His Gln Pro Gly Gly Gly Lys
            660                 665                 670

Val Gln Ile Ile Asn Lys Lys Leu Asp Leu Ser Asn Val Gln Ser Lys
            675                 680                 685

Cys Gly Ser Lys Asp Asn Ile Lys His Val Pro Gly Gly Gly Ser Val
690                 695                 700

Gln Ile Val Tyr Lys Pro Val Asp Leu Ser Lys Val Thr Ser Lys Cys
705                 710                 715                 720

Gly Ser Leu Gly Asn Ile His His Lys Pro Gly Gly Gly Gln Val Glu
                725                 730                 735

Val Lys Ser Glu Lys Leu Asp Phe Lys Asp Arg Val Gln Ser Lys Ile
            740                 745                 750

Gly Ser Leu Asp Asn Ile Thr His Val Pro Gly Gly Gly Asn Lys Lys
            755                 760                 765

Ile Glu Thr His Lys Leu Thr Phe Arg Glu Asn Ala Lys Ala Lys Thr
770                 775                 780

Asp His Gly Ala Glu Ile Val Tyr Lys Ser Pro Val Val Ser Gly Asp
785                 790                 795                 800

Thr Ser Pro Arg His Leu Ser Asn Val Ser Ser Thr Gly Ser Ile Asp
                805                 810                 815

Met Val Asp Ser Pro Gln Leu Ala Thr Leu Ala Asp Glu Val Ser Ala
            820                 825                 830

Ser Leu Ala Lys Gln Gly Leu Arg Cys Ser Arg Tyr Arg Gly Pro
            835                 840                 845

Gly Ile His Arg Ile
    850

<210> SEQ ID NO 68
<211> LENGTH: 971
<212> TYPE: PRT
<213> ORGANISM: Artificial Sequence
<220> FEATURE:
<223> OTHER INFORMATION: synthetic construct

<400> SEQUENCE: 68

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
            35                  40                  45

```
Gly Arg Ala Ser Arg Trp Trp Met Lys Gln Ser Leu Ala His Leu Ser
 50                  55                  60

Gln Ser Leu Lys Ala Leu Gly Ser Asp Leu Thr Leu Ile Lys Thr His
 65                  70                  75                  80

Asn Thr Ile Ser Ala Ile Leu Asp Cys Ile Arg Val Thr Gly Ala Thr
                 85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
            195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
    275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
    355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
    435                 440                 445

Trp Asp Ala Pro Leu Thr Val Leu Lys Ala Ser Gly Val Glu Leu Gly
450                 455                 460
```

```
Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
            485                 490                 495

Ala Ala Ala Gln Met Ala Glu Pro Arg Gln Glu Phe Glu Val Met Glu
        500                 505                 510

Asp His Ala Gly Thr Tyr Gly Leu Gly Asp Arg Lys Asp Gln Gly Gly
    515                 520                 525

Tyr Thr Met His Gln Asp Gln Glu Gly Asp Thr Asp Ala Gly Leu Lys
530                 535                 540

Glu Ser Pro Leu Gln Thr Pro Thr Glu Asp Gly Ser Glu Glu Pro Gly
545                 550                 555                 560

Ser Glu Thr Ser Asp Ala Lys Ser Thr Pro Thr Ala Glu Asp Val Thr
                565                 570                 575

Ala Pro Leu Val Asp Glu Gly Ala Pro Gly Lys Gln Ala Ala Ala Gln
            580                 585                 590

Pro His Thr Glu Ile Pro Glu Gly Thr Thr Ala Glu Glu Ala Gly Ile
        595                 600                 605

Gly Asp Thr Pro Ser Leu Glu Asp Glu Ala Ala Gly His Val Thr Gln
610                 615                 620

Ala Arg Met Val Ser Lys Ser Lys Asp Gly Thr Gly Ser Asp Asp Lys
625                 630                 635                 640

Lys Ala Lys Gly Ala Asp Gly Lys Thr Lys Ile Ala Thr Pro Arg Gly
                645                 650                 655

Ala Ala Pro Pro Gly Gln Lys Gly Gln Ala Asn Ala Thr Arg Ile Pro
            660                 665                 670

Ala Lys Thr Pro Pro Ala Pro Lys Thr Pro Ser Ser Gly Glu Pro
        675                 680                 685

Pro Lys Ser Gly Asp Arg Ser Gly Tyr Ser Ser Pro Gly Ser Pro Gly
690                 695                 700

Thr Pro Gly Ser Arg Ser Arg Thr Pro Ser Leu Pro Thr Pro Pro Thr
705                 710                 715                 720

Arg Glu Pro Lys Lys Val Ala Val Arg Thr Pro Pro Lys Ser Pro
                725                 730                 735

Ser Ser Ala Lys Ser Arg Leu Gln Thr Ala Pro Val Pro Met Pro Asp
            740                 745                 750

Leu Lys Asn Val Lys Ser Lys Ile Gly Ser Thr Glu Asn Leu Lys His
        755                 760                 765

Gln Pro Gly Gly Gly Lys Val Gln Ile Ile Asn Lys Lys Leu Asp Leu
770                 775                 780

Ser Asn Val Gln Ser Lys Cys Gly Ser Lys Asp Asn Ile Lys His Val
785                 790                 795                 800

Pro Gly Gly Gly Ser Val Gln Ile Val Tyr Lys Pro Val Asp Leu Ser
                805                 810                 815

Lys Val Thr Ser Lys Cys Gly Ser Leu Gly Asn Ile His His Lys Pro
            820                 825                 830

Gly Gly Gly Gln Val Glu Val Lys Ser Glu Lys Leu Asp Phe Lys Asp
        835                 840                 845

Arg Val Gln Ser Lys Ile Gly Ser Leu Asp Asn Ile Thr His Val Pro
850                 855                 860

Gly Gly Gly Asn Lys Lys Ile Glu Thr His Lys Leu Thr Phe Arg Glu
865                 870                 875                 880

Asn Ala Lys Ala Lys Thr Asp His Gly Ala Glu Ile Val Tyr Lys Ser
```

```
                  885                 890                 895
Pro Val Ser Gly Asp Thr Ser Pro Arg His Leu Ser Asn Val Ser
            900                 905                 910

Ser Thr Gly Ser Ile Asp Met Val Asp Ser Pro Gln Leu Ala Thr Leu
            915                 920                 925

Ala Asp Glu Val Ser Ala Ser Leu Ala Lys Gln Gly Leu Ala Thr Leu
930                     935                 940

Asp His Asn Gln Pro Tyr His Ile Cys Arg Gly Phe Thr Cys Phe Lys
945                 950                 955                 960

Lys Pro Pro Thr Pro Pro Glu Pro Glu Thr
                965                 970

<210> SEQ ID NO 69
<211> LENGTH: 583
<212> TYPE: PRT
<213> ORGANISM: Artificial Sequence
<220> FEATURE:
<223> OTHER INFORMATION: synthetic construct

<400> SEQUENCE: 69

Met His Thr Leu Tyr Ala Pro Gly Gly Tyr Asp Ile Met Gly Trp Leu
1               5                   10                  15

Ile Gln Ile Met Asn Arg Pro Asn Pro Gln Val Glu Leu Gly Pro Val
                20                  25                  30

Asp Thr Ser Cys Ala Leu Ile Leu Cys Asp Leu Lys Gln Lys Asp Thr
            35                  40                  45

Pro Ile Val Tyr Ala Ser Glu Ala Phe Leu Tyr Met Thr Gly Tyr Ser
50                  55                  60

Asn Ala Glu Val Leu Gly Arg Asn Cys Arg Phe Leu Gln Ser Pro Asp
65                  70                  75                  80

Gly Met Val Lys Pro Lys Ser Thr Arg Lys Tyr Val Asp Ser Asn Thr
                85                  90                  95

Ile Asn Thr Met Arg Lys Ala Ile Asp Arg Asn Ala Glu Val Gln Val
                100                 105                 110

Glu Val Val Asn Phe Lys Lys Asn Gly Gln Arg Phe Val Asn Phe Leu
            115                 120                 125

Thr Met Ile Pro Val Arg Asp Glu Thr Gly Glu Met Ala Glu Pro Arg
130                 135                 140

Gln Glu Phe Glu Val Met Glu Asp His Ala Gly Thr Tyr Gly Leu Gly
145                 150                 155                 160

Asp Arg Lys Asp Gln Gly Gly Tyr Thr Met His Gln Asp Gln Glu Gly
                165                 170                 175

Asp Thr Asp Ala Gly Leu Lys Glu Ser Pro Leu Gln Thr Pro Thr Glu
            180                 185                 190

Asp Gly Ser Glu Glu Pro Gly Ser Glu Thr Ser Asp Ala Lys Ser Thr
        195                 200                 205

Pro Thr Ala Glu Asp Val Thr Ala Pro Leu Val Asp Glu Gly Ala Pro
    210                 215                 220

Gly Lys Gln Ala Ala Ala Gln Pro His Thr Glu Ile Pro Glu Gly Thr
225                 230                 235                 240

Thr Ala Glu Glu Ala Gly Ile Gly Asp Thr Pro Ser Leu Glu Asp Glu
                245                 250                 255

Ala Ala Gly His Val Thr Gln Ala Arg Met Val Ser Lys Ser Lys Asp
            260                 265                 270

Gly Thr Gly Ser Asp Asp Lys Lys Ala Lys Gly Ala Asp Gly Lys Thr
```

-continued

```
                275                 280                 285
Lys Ile Ala Thr Pro Arg Gly Ala Pro Pro Gly Gln Lys Gly Gln
            290                 295                 300
Ala Asn Ala Thr Arg Ile Pro Ala Lys Thr Pro Pro Ala Pro Lys Thr
305                 310                 315                 320
Pro Pro Ser Ser Gly Glu Pro Pro Lys Ser Gly Asp Arg Ser Gly Tyr
                325                 330                 335
Ser Ser Pro Gly Ser Pro Gly Thr Pro Gly Ser Arg Ser Arg Thr Pro
            340                 345                 350
Ser Leu Pro Thr Pro Pro Thr Arg Glu Pro Lys Lys Val Ala Val Val
            355                 360                 365
Arg Thr Pro Pro Lys Ser Pro Ser Ser Ala Lys Ser Arg Leu Gln Thr
            370                 375                 380
Ala Pro Val Pro Met Pro Asp Leu Lys Asn Val Lys Ser Lys Ile Gly
385                 390                 395                 400
Ser Thr Glu Asn Leu Lys His Gln Pro Gly Gly Gly Lys Val Gln Ile
                405                 410                 415
Ile Asn Lys Lys Leu Asp Leu Ser Asn Val Gln Ser Lys Cys Gly Ser
            420                 425                 430
Lys Asp Asn Ile Lys His Val Pro Gly Gly Gly Ser Val Gln Ile Val
            435                 440                 445
Tyr Lys Pro Val Asp Leu Ser Lys Val Thr Ser Lys Cys Gly Ser Leu
            450                 455                 460
Gly Asn Ile His His Lys Pro Gly Gly Gln Val Glu Val Lys Ser
465                 470                 475                 480
Glu Lys Leu Asp Phe Lys Asp Arg Val Gln Ser Lys Ile Gly Ser Leu
                485                 490                 495
Asp Asn Ile Thr His Val Pro Gly Gly Gly Asn Lys Lys Ile Glu Thr
            500                 505                 510
His Lys Leu Thr Phe Arg Glu Asn Ala Lys Ala Lys Thr Asp His Gly
            515                 520                 525
Ala Glu Ile Val Tyr Lys Ser Pro Val Val Ser Gly Asp Thr Ser Pro
530                 535                 540
Arg His Leu Ser Asn Val Ser Ser Thr Gly Ser Ile Asp Met Val Asp
545                 550                 555                 560
Ser Pro Gln Leu Ala Thr Leu Ala Asp Glu Val Ser Ala Ser Leu Ala
                565                 570                 575
Lys Gln Gly Leu His Arg Ile
            580

<210> SEQ ID NO 70
<211> LENGTH: 969
<212> TYPE: PRT
<213> ORGANISM: Artificial Sequence
<220> FEATURE:
<223> OTHER INFORMATION: synthetic construct

<400> SEQUENCE: 70

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Glu Pro Gly Ser Glu Thr Ser
```

```
                50                  55                  60
Asp Ala Lys Ser Thr Pro Thr Ala Glu Asp Val Thr Ala Pro Leu Val
 65                  70                  75                  80
Asp Glu Gly Ala Pro Gly Lys Gln Ala Ala Gln Pro His Thr Glu
                     85                  90                  95
Ile Pro Glu Gly Thr Thr Ala Glu Glu Ala Gly Ile Gly Asp Thr Pro
                    100                 105                 110
Ser Leu Glu Asp Glu Ala Ala Gly His Val Thr Gln Ala Arg Met Val
                    115                 120                 125
Ser Lys Ser Lys Asp Gly Thr Gly Ser Asp Lys Lys Ala Lys Gly
                    130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                    165                 170                 175
Pro Ala Pro Lys Thr Pro Pro Ser Ser Gly Glu Pro Pro Lys Ser Gly
                    180                 185                 190
Asp Arg Ser Gly Tyr Ser Ser Pro Gly Ser Pro Gly Thr Pro Gly Ser
                    195                 200                 205
Arg Ser Arg Thr Pro Ser Leu Pro Thr Pro Pro Thr Arg Glu Pro Lys
210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                    245                 250                 255
Lys Ser Lys Ile Gly Ser Thr Glu Asn Leu Lys His Gln Pro Gly Gly
                    260                 265                 270
Gly Lys Val Gln Ile Ile Asn Lys Lys Leu Asp Leu Ser Asn Val Gln
                    275                 280                 285
Ser Lys Cys Gly Ser Lys Asp Asn Ile Lys His Val Pro Gly Gly Gly
                    290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                    325                 330                 335
Val Glu Val Lys Ser Glu Lys Leu Asp Phe Lys Asp Arg Val Gln Ser
                    340                 345                 350
Lys Ile Gly Ser Leu Asp Asn Ile Thr His Val Pro Gly Gly Gly Asn
                    355                 360                 365
Lys Lys Ile Glu Thr His Lys Leu Thr Phe Arg Glu Asn Ala Lys Ala
                    370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                    405                 410                 415
Ile Asp Met Val Asp Ser Pro Gln Leu Ala Thr Leu Ala Asp Glu Val
                    420                 425                 430
Ser Ala Ser Leu Ala Lys Gln Gly Leu Met Lys Met Asp Lys Lys Thr
                    435                 440                 445
Ile Val Trp Phe Arg Arg Asp Leu Arg Ile Glu Asp Asn Pro Ala Leu
                    450                 455                 460
Ala Ala Ala Ala His Glu Gly Ser Val Phe Pro Val Phe Ile Trp Cys
465                 470                 475                 480
```

```
Pro Glu Glu Glu Gly Gln Phe Tyr Pro Gly Arg Ala Ser Arg Trp Trp
            485                 490                 495

Met Lys Gln Ser Leu Ala His Leu Ser Gln Ser Leu Lys Ala Leu Gly
        500                 505                 510

Ser Asp Leu Thr Leu Ile Lys Thr His Asn Thr Ile Ser Ala Ile Leu
        515                 520                 525

Asp Cys Ile Arg Val Thr Gly Ala Thr Lys Val Val Phe Asn His Leu
        530                 535                 540

Tyr Asp Pro Val Ser Leu Val Arg Asp His Thr Val Lys Glu Lys Leu
545                 550                 555                 560

Val Glu Arg Gly Ile Ser Val Gln Ser Tyr Asn Gly Asp Leu Leu Tyr
                565                 570                 575

Glu Pro Trp Glu Ile Tyr Cys Glu Lys Gly Lys Pro Phe Thr Ser Phe
            580                 585                 590

Asn Ser Tyr Trp Lys Lys Cys Leu Asp Met Ser Ile Glu Ser Val Met
        595                 600                 605

Leu Pro Pro Pro Trp Arg Leu Met Pro Ile Thr Ala Ala Glu Ala
        610                 615                 620

Ile Trp Ala Cys Ser Ile Glu Glu Leu Gly Leu Glu Asn Glu Ala Glu
625                 630                 635                 640

Lys Pro Ser Asn Ala Leu Leu Thr Arg Ala Trp Ser Pro Gly Trp Ser
                645                 650                 655

Asn Ala Asp Lys Leu Leu Asn Glu Phe Ile Glu Lys Gln Leu Ile Asp
            660                 665                 670

Tyr Ala Lys Asn Ser Lys Lys Val Gly Asn Ser Thr Ser Leu Leu
        675                 680                 685

Ser Pro Tyr Leu His Phe Gly Glu Ile Ser Val Arg His Val Phe Gln
        690                 695                 700

Cys Ala Arg Met Lys Gln Ile Ile Trp Ala Arg Asp Lys Asn Ser Glu
705                 710                 715                 720

Gly Glu Glu Ser Ala Asp Leu Phe Leu Arg Gly Ile Gly Leu Arg Glu
                725                 730                 735

Tyr Ser Arg Tyr Ile Cys Phe Asn Phe Pro Phe Thr His Glu Gln Ser
            740                 745                 750

Leu Leu Ser His Leu Arg Phe Phe Pro Trp Asp Ala Asp Val Asp Lys
        755                 760                 765

Phe Lys Ala Trp Arg Gln Gly Arg Thr Gly Tyr Pro Leu Val Asp Ala
        770                 775                 780

Gly Met Arg Glu Leu Trp Ala Thr Gly Trp Met His Asn Arg Ile Arg
785                 790                 795                 800

Val Ile Val Ser Ser Phe Ala Val Lys Phe Leu Leu Leu Pro Trp Lys
                805                 810                 815

Trp Gly Met Lys Tyr Phe Trp Asp Thr Leu Leu Asp Ala Asp Leu Glu
            820                 825                 830

Cys Asp Ile Leu Gly Trp Gln Tyr Ile Ser Gly Ser Ile Pro Asp Gly
        835                 840                 845

His Glu Leu Asp Arg Leu Asp Asn Pro Ala Leu Gln Gly Ala Lys Tyr
        850                 855                 860

Asp Pro Glu Gly Glu Tyr Ile Arg Gln Trp Leu Pro Glu Leu Ala Arg
865                 870                 875                 880

Leu Pro Thr Glu Trp Ile His Pro Trp Asp Ala Pro Leu Thr Val
                885                 890                 895
```

```
Leu Lys Ala Ser Gly Val Glu Leu Gly Thr Asn Tyr Ala Lys Pro Ile
                900                 905                 910

Val Asp Ile Asp Thr Ala Arg Glu Leu Leu Ala Lys Ala Ile Ser Arg
            915                 920                 925

Thr Arg Gly Ala Gln Ile Met Ile Gly Ala Ala Thr Leu Asp His
        930                 935                 940

Asn Gln Pro Tyr His Ile Cys Arg Gly Phe Thr Cys Phe Lys Lys Pro
945                 950                 955                 960

Pro Thr Pro Pro Pro Glu Pro Glu Thr
                965

<210> SEQ ID NO 71
<211> LENGTH: 604
<212> TYPE: PRT
<213> ORGANISM: Artificial Sequence
<220> FEATURE:
<223> OTHER INFORMATION: synthetic construct

<400> SEQUENCE: 71

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285
```

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
                370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu Pro Asp Tyr Ser Leu Val Lys
                435                 440                 445

Ala Leu Gln Met Ala Gln Asn Phe Val Ile Thr Asp Ala Ser Leu
450                 455                 460

Pro Asp Asn Pro Ile Val Tyr Ala Ser Arg Gly Phe Leu Thr Leu Thr
465                 470                 475                 480

Gly Tyr Ser Leu Asp Gln Ile Leu Gly Arg Asn Cys Arg Phe Leu Gln
                485                 490                 495

Gly Pro Glu Thr Asp Pro Arg Ala Val Asp Lys Ile Arg Asn Ala Ile
                500                 505                 510

Thr Lys Gly Val Asp Thr Ser Val Cys Leu Leu Asn Tyr Arg Gln Asp
                515                 520                 525

Gly Thr Thr Phe Trp Asn Leu Phe Phe Val Ala Gly Leu Arg Asp Ser
                530                 535                 540

Lys Gly Asn Ile Val Asn Tyr Val Gly Val Gln Ser Lys Val Ser Glu
545                 550                 555                 560

Asp Tyr Ala Lys Leu Leu Val Asn Glu Gln Asn Ile Glu Tyr Lys Gly
                565                 570                 575

Val Arg Thr Ser Asn Met Leu Arg Arg Lys Pro Gly Leu Gln Ser Thr
                580                 585                 590

Val Pro Arg Ala Arg Asp Pro Pro Asp Leu Asp Asn
                595                 600

<210> SEQ ID NO 72
<211> LENGTH: 607
<212> TYPE: PRT
<213> ORGANISM: Artificial Sequence
<220> FEATURE:
<223> OTHER INFORMATION: synthetic construct

<400> SEQUENCE: 72

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

-continued

```
Gln Thr Pro Thr Glu Asp Gly Ser Glu Pro Gly Ser Glu Thr Ser
     50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
                275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu His Thr Leu Tyr Ala Pro Gly
    435                 440                 445

Gly Tyr Asp Ile Met Gly Trp Leu Ile Gln Ile Met Asn Arg Pro Asn
450                 455                 460

Pro Gln Val Glu Leu Gly Pro Val Asp Thr Ser Cys Ala Leu Ile Leu
```

```
                465                 470                 475                 480
Cys Asp Leu Lys Gln Lys Asp Thr Pro Ile Val Tyr Ala Ser Glu Ala
                    485                 490                 495

Phe Leu Tyr Met Thr Gly Tyr Ser Asn Ala Glu Val Leu Gly Arg Asn
                500                 505                 510

Cys Arg Phe Leu Gln Ser Pro Asp Gly Met Val Lys Pro Lys Ser Thr
                515                 520                 525

Arg Lys Tyr Val Asp Ser Asn Thr Ile Asn Thr Met Arg Lys Ala Ile
            530                 535                 540

Asp Arg Asn Ala Glu Val Gln Val Glu Val Val Asn Phe Lys Lys Asn
545                 550                 555                 560

Gly Gln Arg Phe Val Asn Phe Leu Thr Met Ile Pro Val Arg Asp Glu
                565                 570                 575

Thr Gly Glu Tyr Arg Tyr Ser Met Gly Phe Gln Cys Glu Thr Glu Leu
                580                 585                 590

Gln Ser Thr Val Pro Arg Ala Arg Asp Pro Pro Asp Leu Asp Asn
                595                 600                 605

<210> SEQ ID NO 73
<211> LENGTH: 607
<212> TYPE: PRT
<213> ORGANISM: Artificial Sequence
<220> FEATURE:
<223> OTHER INFORMATION: synthetic construct

<400> SEQUENCE: 73

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
```

```
            225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
                260                 265                 270
Gly Lys Val Gln Ile Ile Asn Lys Leu Asp Leu Ser Asn Val Gln
                275                 280                 285
Ser Lys Cys Gly Ser Lys Asp Asn Ile Lys His Val Pro Gly Gly Gly
305                 310                 315                 320
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
                340                 345                 350
Lys Ile Gly Ser Leu Asp Asn Ile Thr His Val Pro Gly Gly Gly Asn
                355                 360                 365
Lys Lys Ile Glu Thr His Lys Leu Thr Phe Arg Glu Asn Ala Lys Ala
                370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
                420                 425                 430
Ser Ala Ser Leu Ala Lys Gln Gly Leu His Thr Leu Tyr Ala Pro Gly
                435                 440                 445
Gly Tyr Asp Ile Met Gly Trp Leu Ile Gln Ile Met Asn Arg Pro Asn
                450                 455                 460
Pro Gln Val Glu Leu Gly Pro Val Asp Thr Ser Cys Ala Leu Ile Leu
465                 470                 475                 480
Cys Asp Leu Lys Gln Lys Asp Thr Pro Ile Val Tyr Ala Ser Glu Ala
                485                 490                 495
Phe Leu Tyr Met Thr Gly Tyr Ser Asn Ala Glu Val Leu Gly Arg Asn
                500                 505                 510
Cys Arg Phe Leu Gln Ser Pro Asp Gly Met Val Lys Pro Lys Ser Thr
                515                 520                 525
Arg Lys Tyr Val Asp Ser Asn Thr Ile Asn Thr Met Arg Lys Ala Ile
                530                 535                 540
Asp Arg Asn Ala Glu Val Gln Val Glu Val Val Asn Phe Lys Lys Asn
545                 550                 555                 560
Gly Gln Arg Phe Val Asn Phe Leu Thr Met Ile Pro Val Arg Asp Glu
                565                 570                 575
Thr Gly Glu Tyr Arg Tyr Ser Met Gly Phe Gln Cys Glu Thr Glu Leu
                580                 585                 590
Gln Ser Thr Val Pro Arg Ala Arg Asp Pro Pro Asp Leu Asp Asn
                595                 600                 605
```

<210> SEQ ID NO 74
<211> LENGTH: 608
<212> TYPE: PRT
<213> ORGANISM: Artificial Sequence
<220> FEATURE:
<223> OTHER INFORMATION: synthetic construct -continued

```
<400> SEQUENCE: 74

Met Pro Asp Tyr Ser Leu Val Lys Ala Leu Gln Met Ala Gln Gln Asn
1               5                   10                  15

Phe Val Ile Thr Asp Ala Ser Leu Pro Asp Asn Pro Ile Val Tyr Ala
            20                  25                  30

Ser Arg Gly Phe Leu Thr Leu Thr Gly Tyr Ser Leu Asp Gln Ile Leu
        35                  40                  45

Gly Arg Asn Cys Arg Phe Leu Gln Gly Pro Glu Thr Asp Pro Arg Ala
    50                  55                  60

Val Asp Lys Ile Arg Asn Ala Ile Thr Lys Gly Val Asp Thr Ser Val
65                  70                  75                  80

Cys Leu Leu Asn Tyr Arg Gln Asp Gly Thr Thr Phe Trp Asn Leu Phe
                85                  90                  95

Phe Val Ala Gly Leu Arg Asp Ser Lys Gly Asn Ile Val Asn Tyr Val
            100                 105                 110

Gly Val Gln Ser Lys Val Ser Glu Asp Tyr Ala Lys Leu Leu Val Asn
        115                 120                 125

Glu Gln Asn Ile Glu Tyr Lys Gly Val Arg Thr Ser Asn Met Leu Arg
    130                 135                 140

Arg Lys Pro Gly Ser Leu Met Ala Glu Pro Arg Gln Glu Phe Glu Val
145                 150                 155                 160

Met Glu Asp His Ala Gly Thr Tyr Gly Leu Gly Asp Arg Lys Asp Gln
                165                 170                 175

Gly Gly Tyr Thr Met His Gln Asp Gln Glu Gly Asp Thr Asp Ala Gly
            180                 185                 190

Leu Lys Glu Ser Pro Leu Gln Thr Pro Thr Glu Asp Gly Ser Glu Glu
        195                 200                 205

Pro Gly Ser Glu Thr Ser Asp Ala Lys Ser Thr Pro Thr Ala Glu Asp
    210                 215                 220

Val Thr Ala Pro Leu Val Asp Glu Gly Ala Pro Gly Lys Gln Ala Ala
225                 230                 235                 240

Ala Gln Pro His Thr Glu Ile Pro Glu Gly Thr Thr Ala Glu Glu Ala
                245                 250                 255

Gly Ile Gly Asp Thr Pro Ser Leu Glu Asp Glu Ala Ala Gly His Val
            260                 265                 270

Thr Gln Ala Arg Met Val Ser Lys Ser Lys Asp Gly Thr Gly Ser Asp
        275                 280                 285

Asp Lys Lys Ala Lys Gly Ala Asp Gly Lys Thr Lys Ile Ala Thr Pro
    290                 295                 300

Arg Gly Ala Ala Pro Pro Gly Gln Lys Gly Gln Ala Asn Ala Thr Arg
305                 310                 315                 320

Ile Pro Ala Lys Thr Pro Pro Ala Pro Lys Thr Pro Pro Ser Ser Gly
                325                 330                 335

Glu Pro Pro Lys Ser Gly Asp Arg Ser Gly Tyr Ser Ser Pro Gly Ser
            340                 345                 350

Pro Gly Thr Pro Gly Ser Arg Ser Arg Thr Pro Ser Leu Pro Thr Pro
        355                 360                 365

Pro Thr Arg Glu Pro Lys Lys Val Ala Val Val Arg Thr Pro Pro Lys
    370                 375                 380

Ser Pro Ser Ser Ala Lys Ser Arg Leu Gln Thr Ala Pro Val Pro Met
385                 390                 395                 400

Pro Asp Leu Lys Asn Val Lys Ser Lys Ile Gly Ser Thr Glu Asn Leu
                405                 410                 415
```

```
Lys His Gln Pro Gly Gly Lys Val Gln Ile Ile Asn Lys Lys Leu
                420                 425                 430

Asp Leu Ser Asn Val Gln Ser Lys Cys Gly Ser Lys Asp Asn Ile Lys
                435                 440                 445

His Val Pro Gly Gly Gly Ser Val Gln Ile Val Tyr Lys Pro Val Asp
                450                 455                 460

Leu Ser Lys Val Thr Ser Lys Cys Gly Ser Leu Gly Asn Ile His His
465                 470                 475                 480

Lys Pro Gly Gly Gly Gln Val Glu Val Lys Ser Glu Lys Leu Asp Phe
                485                 490                 495

Lys Asp Arg Val Gln Ser Lys Ile Gly Ser Leu Asp Asn Ile Thr His
                500                 505                 510

Val Pro Gly Gly Gly Asn Lys Lys Ile Glu Thr His Lys Leu Thr Phe
                515                 520                 525

Arg Glu Asn Ala Lys Ala Lys Thr Asp His Gly Ala Glu Ile Val Tyr
                530                 535                 540

Lys Ser Pro Val Val Ser Gly Asp Thr Ser Pro Arg His Leu Ser Asn
545                 550                 555                 560

Val Ser Ser Thr Gly Ser Ile Asp Met Val Asp Ser Pro Gln Leu Ala
                565                 570                 575

Thr Leu Ala Asp Glu Val Ser Ala Ser Leu Ala Lys Gln Gly Leu Ser
                580                 585                 590

Asn Ser Ala Val Asp Gly Thr Ala Gly Pro Gly Ser Thr Gly Ser Arg
                595                 600                 605

<210> SEQ ID NO 75
<211> LENGTH: 1159
<212> TYPE: PRT
<213> ORGANISM: Artificial Sequence
<220> FEATURE:
<223> OTHER INFORMATION: synthetic construct

<400> SEQUENCE: 75

Met Lys Met Asp Lys Lys Thr Ile Val Trp Phe Arg Arg Asp Leu Arg
1               5                   10                  15

Ile Glu Asp Asn Pro Ala Leu Ala Ala Ala Ala His Glu Gly Ser Val
                20                  25                  30

Phe Pro Val Phe Ile Trp Cys Pro Glu Glu Gly Gln Phe Tyr Pro
                35                  40                  45

Gly Arg Ala Ser Arg Trp Trp Met Lys Gln Ser Leu Ala His Leu Ser
            50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
            130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175
```

```
Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Arg Gly Met Ser Glu Tyr Ile Arg Val Thr Glu Asp Glu
            500                 505                 510

Asn Asp Glu Pro Ile Glu Ile Pro Ser Glu Asp Gly Thr Val Leu
        515                 520                 525

Leu Ser Thr Val Thr Ala Gln Phe Pro Gly Ala Cys Gly Leu Arg Tyr
530                 535                 540

Arg Asn Pro Val Ser Gln Cys Met Arg Gly Val Arg Leu Val Glu Gly
545                 550                 555                 560

Ile Leu His Ala Pro Asp Ala Gly Trp Gly Asn Leu Val Tyr Val Val
                565                 570                 575

Asn Tyr Pro Lys Asp Asn Lys Arg Lys Met Asp Glu Thr Asp Ala Ser
            580                 585                 590
```

Ser Ala Val Lys Val Lys Arg Ala Val Gln Lys Thr Ser Asp Leu Ile
            595                 600                 605

Val Leu Gly Leu Pro Trp Lys Thr Thr Glu Gln Asp Leu Lys Glu Tyr
610                 615                 620

Phe Ser Thr Phe Gly Glu Val Leu Met Val Gln Val Lys Lys Asp Leu
625                 630                 635                 640

Lys Thr Gly His Ser Lys Gly Leu Gly Phe Val Arg Phe Thr Glu Tyr
            645                 650                 655

Glu Thr Gln Val Lys Val Met Ser Gln Arg His Met Ile Asp Gly Arg
            660                 665                 670

Trp Cys Asp Cys Lys Leu Pro Asn Ser Lys Gln Ser Gln Asp Glu Pro
            675                 680                 685

Leu Arg Ser Arg Lys Val Phe Val Gly Arg Cys Thr Glu Asp Met Thr
            690                 695                 700

Glu Asp Glu Leu Arg Glu Phe Phe Ser Gln Tyr Gly Asp Val Met Asp
705                 710                 715                 720

Val Phe Ile Pro Lys Pro Phe Arg Ala Phe Ala Phe Val Thr Phe Ala
                    725                 730                 735

Asp Asp Gln Ile Ala Gln Ser Leu Cys Gly Glu Asp Leu Ile Ile Lys
            740                 745                 750

Gly Ile Ser Val His Ile Ser Asn Ala Glu Pro Lys His Asn Ser Asn
            755                 760                 765

Arg Gln Leu Glu Arg Ser Gly Arg Phe Gly Gly Asn Pro Gly Gly Phe
770                 775                 780

Gly Asn Gln Gly Gly Phe Gly Asn Ser Arg Gly Gly Gly Ala Gly Leu
785                 790                 795                 800

Gly Asn Asn Gln Gly Ser Asn Met Gly Gly Gly Met Asn Phe Gly Ala
            805                 810                 815

Phe Ser Ile Asn Pro Ala Met Met Ala Ala Ala Gln Ala Ala Leu Gln
            820                 825                 830

Ser Ser Trp Gly Met Met Gly Met Leu Ala Ser Gln Gln Asn Gln Ser
            835                 840                 845

Gly Pro Ser Gly Asn Asn Gln Asn Gln Gly Asn Met Gln Arg Glu Pro
850                 855                 860

Asn Gln Ala Phe Gly Ser Gly Asn Asn Ser Tyr Ser Gly Ser Asn Ser
865                 870                 875                 880

Gly Ala Ala Ile Gly Trp Gly Ser Ala Ser Asn Ala Gly Ser Gly Ser
                    885                 890                 895

Gly Phe Asn Gly Gly Phe Gly Ser Ser Met Asp Ser Lys Ser Ser Gly
                    900                 905                 910

Trp Gly Met Ser Arg Asp Pro Pro Val Ala Thr Met Val Ser Lys Gly
            915                 920                 925

Glu Glu Asp Asn Met Ala Ile Ile Lys Glu Phe Met Arg Phe Lys Val
930                 935                 940

His Met Glu Gly Ser Val Asn Gly His Glu Phe Glu Ile Glu Gly Glu
945                 950                 955                 960

Gly Glu Gly Arg Pro Tyr Glu Gly Thr Gln Thr Ala Lys Leu Lys Val
                    965                 970                 975

Thr Lys Gly Gly Pro Leu Pro Phe Ala Trp Asp Ile Leu Ser Pro Gln
            980                 985                 990

Phe Met Tyr Gly Ser Lys Ala Tyr  Val Lys His Pro Ala  Asp Ile Pro
            995                 1000                1005

Asp Tyr  Leu Lys Leu Ser Phe  Pro Glu Gly Phe Lys  Trp Glu Arg

```
                    1010                1015                1020
Val Met Asn Phe Glu Asp Gly Gly Val Val Thr Val Thr Gln Asp
            1025                1030                1035

Ser Ser Leu Gln Asp Gly Glu Phe Ile Tyr Lys Val Lys Leu Arg
            1040                1045                1050

Gly Thr Asn Phe Pro Ser Asp Gly Pro Val Met Gln Lys Lys Thr
            1055                1060                1065

Met Gly Trp Glu Ala Ser Ser Glu Arg Met Tyr Pro Glu Asp Gly
            1070                1075                1080

Ala Leu Lys Gly Glu Ile Lys Gln Arg Leu Lys Leu Lys Asp Gly
            1085                1090                1095

Gly His Tyr Asp Ala Glu Val Lys Thr Thr Tyr Lys Ala Lys Lys
            1100                1105                1110

Pro Val Gln Leu Pro Gly Ala Tyr Asn Val Asn Ile Lys Leu Asp
            1115                1120                1125

Ile Thr Ser His Asn Glu Asp Tyr Thr Ile Val Glu Gln Tyr Glu
            1130                1135                1140

Arg Ala Glu Gly Arg His Ser Thr Gly Gly Met Asp Glu Leu Tyr
            1145                1150                1155

Lys

<210> SEQ ID NO 76
<211> LENGTH: 1159
<212> TYPE: PRT
<213> ORGANISM: Artificial Sequence
<220> FEATURE:
<223> OTHER INFORMATION: synthetic construct

<400> SEQUENCE: 76

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
            35                  40                  45

Gly Arg Ala Ser Arg Trp Trp Met Lys Gln Ser Leu Ala His Leu Ser
        50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
        130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
            195                 200                 205
```

-continued

```
Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Ser Ala Asp Leu Phe Leu
        275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
                355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Arg Gly Met Ser Glu Tyr Ile Arg Val Thr Glu Asp Glu
            500                 505                 510

Asn Asp Glu Pro Ile Glu Ile Pro Ser Glu Asp Gly Thr Val Leu
        515                 520                 525

Leu Ser Thr Val Thr Ala Gln Phe Pro Gly Ala Cys Gly Leu Arg Tyr
    530                 535                 540

Arg Asn Pro Val Ser Gln Cys Met Arg Gly Val Arg Leu Val Glu Gly
545                 550                 555                 560

Ile Leu His Ala Pro Asp Ala Gly Trp Gly Asn Leu Val Tyr Val Val
                565                 570                 575

Asn Tyr Pro Lys Asp Asn Lys Arg Lys Met Asp Glu Thr Asp Ala Ser
            580                 585                 590

Ser Ala Val Lys Val Lys Arg Ala Val Gln Lys Thr Ser Asp Leu Ile
        595                 600                 605

Val Leu Gly Leu Pro Trp Lys Thr Thr Glu Gln Asp Leu Lys Glu Tyr
610                 615                 620
```

```
Phe Ser Thr Phe Gly Glu Val Leu Met Val Gln Val Lys Lys Asp Leu
625                 630                 635                 640

Lys Thr Gly His Ser Lys Gly Phe Gly Phe Val Arg Phe Thr Glu Tyr
            645                 650                 655

Glu Thr Gln Val Lys Val Met Ser Gln Arg His Met Ile Asp Gly Arg
                660                 665                 670

Trp Cys Asp Cys Lys Leu Pro Asn Ser Lys Gln Ser Gln Asp Glu Pro
            675                 680                 685

Leu Arg Ser Arg Lys Val Phe Val Gly Arg Cys Thr Glu Asp Met Thr
690                 695                 700

Glu Asp Glu Leu Arg Glu Phe Phe Ser Gln Tyr Gly Asp Val Met Asp
705                 710                 715                 720

Val Phe Ile Pro Lys Pro Phe Arg Ala Leu Ala Phe Val Thr Phe Ala
                725                 730                 735

Asp Asp Gln Ile Ala Gln Ser Leu Cys Gly Glu Asp Leu Ile Ile Lys
                740                 745                 750

Gly Ile Ser Val His Ile Ser Asn Ala Glu Pro Lys His Asn Ser Asn
            755                 760                 765

Arg Gln Leu Glu Arg Ser Gly Arg Phe Gly Gly Asn Pro Gly Gly Phe
770                 775                 780

Gly Asn Gln Gly Gly Phe Gly Asn Ser Arg Gly Gly Ala Gly Leu
785                 790                 795                 800

Gly Asn Asn Gln Gly Ser Asn Met Gly Gly Met Asn Phe Gly Ala
                805                 810                 815

Phe Ser Ile Asn Pro Ala Met Met Ala Ala Gln Ala Ala Leu Gln
            820                 825                 830

Ser Ser Trp Gly Met Met Gly Met Leu Ala Ser Gln Gln Asn Gln Ser
            835                 840                 845

Gly Pro Ser Gly Asn Asn Gln Asn Gln Gly Asn Met Gln Arg Glu Pro
        850                 855                 860

Asn Gln Ala Phe Gly Ser Gly Asn Asn Ser Tyr Ser Gly Ser Asn Ser
865                 870                 875                 880

Gly Ala Ala Ile Gly Trp Gly Ser Ala Ser Asn Ala Gly Ser Gly Ser
                885                 890                 895

Gly Phe Asn Gly Gly Phe Gly Ser Ser Met Asp Ser Lys Ser Ser Gly
            900                 905                 910

Trp Gly Met Ser Arg Asp Pro Pro Val Ala Thr Met Val Ser Lys Gly
            915                 920                 925

Glu Glu Asp Asn Met Ala Ile Ile Lys Glu Phe Met Arg Phe Lys Val
930                 935                 940

His Met Glu Gly Ser Val Asn Gly His Glu Phe Glu Ile Glu Gly Glu
945                 950                 955                 960

Gly Glu Gly Arg Pro Tyr Glu Gly Thr Gln Thr Ala Lys Leu Lys Val
                965                 970                 975

Thr Lys Gly Gly Pro Leu Pro Phe Ala Trp Asp Ile Leu Ser Pro Gln
            980                 985                 990

Phe Met Tyr Gly Ser Lys Ala Tyr  Val Lys His Pro Ala  Asp Ile Pro
            995                 1000                1005

Asp Tyr  Leu Lys Leu Ser Phe  Pro Glu Gly Phe Lys  Trp Glu Arg
    1010                1015                1020

Val Met  Asn Phe Glu Asp Gly  Gly Val Val Thr Val  Thr Gln Asp
    1025                1030                1035

Ser Ser  Leu Gln Asp Gly Glu  Phe Ile Tyr Lys Val  Lys Leu Arg
```

```
            1040                1045                1050

Gly Thr Asn Phe Pro Ser Asp Gly Pro Val Met Gln Lys Lys Thr
    1055                1060                1065

Met Gly Trp Glu Ala Ser Ser Glu Arg Met Tyr Pro Glu Asp Gly
    1070                1075                1080

Ala Leu Lys Gly Glu Ile Lys Gln Arg Leu Lys Leu Lys Asp Gly
    1085                1090                1095

Gly His Tyr Asp Ala Glu Val Lys Thr Thr Tyr Lys Ala Lys Lys
    1100                1105                1110

Pro Val Gln Leu Pro Gly Ala Tyr Asn Val Asn Ile Lys Leu Asp
    1115                1120                1125

Ile Thr Ser His Asn Glu Asp Tyr Thr Ile Val Glu Gln Tyr Glu
    1130                1135                1140

Arg Ala Glu Gly Arg His Ser Thr Gly Gly Met Asp Glu Leu Tyr
    1145                1150                1155

Lys

<210> SEQ ID NO 77
<211> LENGTH: 1157
<212> TYPE: PRT
<213> ORGANISM: Artificial Sequence
<220> FEATURE:
<223> OTHER INFORMATION: synthetic construct

<400> SEQUENCE: 77

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30

Phe Pro Val Phe Ile Trp Cys Pro Glu Glu Gly Gln Phe Tyr Pro
            35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240
```

-continued

```
Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Met Ser Glu Tyr Ile Arg Val Thr Glu Asp Glu Asn
            500                 505                 510

Asp Glu Pro Ile Glu Ile Pro Ser Glu Asp Asp Gly Thr Val Leu Leu
        515                 520                 525

Ser Thr Val Thr Ala Gln Phe Pro Gly Ala Cys Gly Leu Arg Tyr Arg
    530                 535                 540

Asn Pro Val Ser Gln Cys Met Arg Gly Val Arg Leu Val Glu Gly Ile
545                 550                 555                 560

Leu His Ala Pro Asp Ala Gly Trp Gly Asn Leu Val Tyr Val Val Asn
                565                 570                 575

Tyr Pro Lys Asp Asn Lys Arg Lys Met Asp Glu Thr Asp Ala Ser Ser
            580                 585                 590

Ala Val Lys Val Lys Arg Ala Val Gln Lys Thr Ser Asp Leu Ile Val
        595                 600                 605

Leu Gly Leu Pro Trp Lys Thr Thr Glu Gln Asp Leu Lys Glu Tyr Phe
    610                 615                 620

Ser Thr Phe Gly Glu Val Leu Met Val Gln Val Lys Lys Asp Leu Lys
625                 630                 635                 640

Thr Gly His Ser Lys Gly Phe Gly Phe Val Arg Phe Thr Glu Tyr Glu
                645                 650                 655
```

```
Thr Gln Val Lys Val Met Ser Gln Arg His Met Ile Asp Gly Arg Trp
            660                 665                 670

Cys Asp Cys Lys Leu Pro Asn Ser Lys Gln Ser Gln Asp Glu Pro Leu
            675                 680                 685

Arg Ser Arg Lys Val Phe Val Gly Arg Cys Thr Glu Asp Met Thr Glu
        690                 695                 700

Asp Glu Leu Arg Glu Phe Phe Ser Gln Tyr Gly Asp Val Met Asp Val
705                 710                 715                 720

Phe Ile Pro Lys Pro Phe Arg Ala Phe Ala Phe Val Thr Phe Ala Asp
                725                 730                 735

Asp Gln Ile Ala Gln Ser Leu Cys Gly Glu Asp Leu Ile Ile Lys Gly
            740                 745                 750

Ile Ser Val His Ile Ser Asn Ala Glu Pro Lys His Asn Ser Asn Arg
        755                 760                 765

Gln Leu Glu Arg Ser Gly Arg Phe Gly Gly Asn Pro Gly Gly Phe Gly
    770                 775                 780

Asn Gln Gly Gly Phe Gly Asn Ser Arg Gly Gly Gly Ala Gly Leu Gly
785                 790                 795                 800

Asn Asn Gln Gly Ser Asn Met Gly Gly Gly Met Asn Phe Gly Ala Phe
                805                 810                 815

Ser Ile Asn Pro Ala Met Met Ala Ala Ala Gln Ala Ala Leu Gln Ser
            820                 825                 830

Ser Trp Gly Met Met Gly Met Leu Ala Ser Gln Gln Asn Gln Ser Gly
        835                 840                 845

Pro Ser Gly Asn Asn Gln Asn Gln Gly Asn Met Gln Arg Glu Pro Asn
    850                 855                 860

Gln Ala Phe Gly Ser Gly Asn Asn Ser Tyr Ser Gly Ser Asn Ser Gly
865                 870                 875                 880

Ala Ala Ile Gly Trp Gly Ser Ala Ser Asn Ala Gly Ser Gly Ser Gly
                885                 890                 895

Phe Asn Gly Gly Phe Gly Ser Ser Met Asp Ser Lys Ala Ala Gly Trp
            900                 905                 910

Gly Met Trp Asp Pro Pro Val Ala Thr Met Val Ser Lys Gly Glu Glu
        915                 920                 925

Asp Asn Met Ala Ile Ile Lys Glu Phe Met Arg Phe Lys Val His Met
930                 935                 940

Glu Gly Ser Val Asn Gly His Glu Phe Glu Ile Glu Gly Glu Gly Glu
945                 950                 955                 960

Gly Arg Pro Tyr Glu Gly Thr Gln Thr Ala Lys Leu Lys Val Thr Lys
                965                 970                 975

Gly Gly Pro Leu Pro Phe Ala Trp Asp Ile Leu Ser Pro Gln Phe Met
            980                 985                 990

Tyr Gly Ser Lys Ala Tyr Val Lys His Pro Ala Asp Ile Pro Asp Tyr
        995                 1000                1005

Leu Lys Leu Ser Phe Pro Glu Gly Phe Lys Trp Glu Arg Val Met
    1010                1015                1020

Asn Phe Glu Asp Gly Gly Val Val Thr Val Thr Gln Asp Ser Ser
    1025                1030                1035

Leu Gln Asp Gly Glu Phe Ile Tyr Lys Val Lys Leu Arg Gly Thr
    1040                1045                1050

Asn Phe Pro Ser Asp Gly Pro Val Met Gln Lys Lys Thr Met Gly
    1055                1060                1065

Trp Glu Ala Ser Ser Glu Arg Met Tyr Pro Glu Asp Gly Ala Leu
```

```
              1070                1075                1080

Lys Gly Glu Ile Lys Gln Arg Leu Lys Leu Lys Asp Gly Gly His
    1085                1090                1095

Tyr Asp Ala Glu Val Lys Thr Thr Tyr Lys Ala Lys Lys Pro Val
    1100                1105                1110

Gln Leu Pro Gly Ala Tyr Asn Val Asn Ile Lys Leu Asp Ile Thr
    1115                1120                1125

Ser His Asn Glu Asp Tyr Thr Ile Val Glu Gln Tyr Glu Arg Ala
    1130                1135                1140

Glu Gly Arg His Ser Thr Gly Gly Met Asp Glu Leu Tyr Lys
    1145                1150                1155

<210> SEQ ID NO 78
<211> LENGTH: 1157
<212> TYPE: PRT
<213> ORGANISM: Artificial Sequence
<220> FEATURE:
<223> OTHER INFORMATION: synthetic construct

<400> SEQUENCE: 78

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
```

```
              275                 280                 285
Arg Gly Ile Gly Leu Arg Glu Tyr Ser Arg Tyr Ile Cys Phe Asn Phe
            290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
                355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Met Ser Glu Tyr Ile Arg Val Thr Glu Asp Glu Asn
            500                 505                 510

Asp Glu Pro Ile Glu Ile Pro Ser Glu Asp Asp Gly Thr Val Leu Leu
            515                 520                 525

Ser Thr Val Thr Ala Gln Phe Pro Gly Ala Cys Gly Leu Arg Tyr Arg
530                 535                 540

Asn Pro Val Ser Gln Cys Met Arg Gly Val Arg Leu Val Glu Gly Ile
545                 550                 555                 560

Leu His Ala Pro Asp Ala Gly Trp Gly Asn Leu Val Tyr Val Val Asn
                565                 570                 575

Tyr Pro Lys Asp Asn Lys Arg Lys Met Asp Glu Thr Asp Ala Ser Ser
            580                 585                 590

Ala Val Lys Val Lys Arg Ala Val Gln Lys Thr Ser Asp Leu Ile Val
            595                 600                 605

Leu Gly Leu Pro Trp Lys Thr Thr Glu Gln Asp Leu Lys Glu Tyr Phe
            610                 615                 620

Ser Thr Phe Gly Glu Val Leu Met Val Gln Val Lys Lys Asp Leu Lys
625                 630                 635                 640

Thr Gly His Ser Lys Gly Phe Gly Phe Val Arg Phe Thr Glu Tyr Glu
                645                 650                 655

Thr Gln Val Lys Val Met Ser Gln Arg His Met Ile Asp Gly Arg Trp
            660                 665                 670

Cys Asp Cys Lys Leu Pro Asn Ser Lys Gln Ser Gln Asp Glu Pro Leu
            675                 680                 685

Arg Ser Arg Lys Val Phe Val Gly Arg Cys Thr Glu Asp Met Thr Glu
            690                 695                 700
```

-continued

```
Asp Glu Leu Arg Glu Phe Phe Ser Gln Tyr Gly Asp Val Met Asp Val
705                 710                 715                 720

Phe Ile Pro Lys Pro Phe Arg Ala Phe Ala Phe Val Thr Phe Ala Asp
            725                 730                 735

Asp Gln Ile Ala Gln Ser Leu Cys Gly Glu Asp Leu Ile Ile Lys Gly
                740                 745                 750

Ile Ser Val His Ile Ser Asn Ala Glu Pro Lys His Asn Ser Asn Arg
        755                 760                 765

Gln Leu Glu Arg Ser Gly Arg Phe Gly Gly Asn Pro Gly Gly Phe Gly
770                 775                 780

Asn Gln Gly Gly Phe Gly Asn Ser Arg Gly Gly Gly Ala Gly Leu Gly
785                 790                 795                 800

Asn Asn Gln Gly Ser Asn Met Gly Gly Gly Met Asn Phe Gly Ala Phe
                805                 810                 815

Ser Ile Asn Pro Ala Met Met Ala Ala Ala Gln Ala Ala Leu Gln Ser
                820                 825                 830

Ser Trp Gly Met Met Gly Met Leu Ala Ser Gln Gln Asn Gln Ser Gly
            835                 840                 845

Pro Ser Gly Asn Asn Gln Asn Gln Gly Asn Met Gln Arg Glu Pro Asn
        850                 855                 860

Gln Ala Phe Gly Ser Gly Asn Asn Ser Tyr Ser Gly Ser Asn Ser Gly
865                 870                 875                 880

Ala Ala Ile Gly Trp Gly Ser Ala Ser Asn Ala Gly Ser Gly Ser Gly
                885                 890                 895

Phe Asn Gly Gly Phe Gly Ser Ser Met Asp Ser Lys Asp Gly Trp
                900                 905                 910

Gly Met Trp Asp Pro Pro Val Ala Thr Met Val Ser Lys Gly Glu Glu
            915                 920                 925

Asp Asn Met Ala Ile Ile Lys Glu Phe Met Arg Phe Lys Val His Met
930                 935                 940

Glu Gly Ser Val Asn Gly His Glu Phe Glu Ile Glu Gly Glu Gly Glu
945                 950                 955                 960

Gly Arg Pro Tyr Glu Gly Thr Gln Thr Ala Lys Leu Lys Val Thr Lys
                965                 970                 975

Gly Gly Pro Leu Pro Phe Ala Trp Asp Ile Leu Ser Pro Gln Phe Met
            980                 985                 990

Tyr Gly Ser Lys Ala Tyr Val Lys His Pro Ala Asp Ile Pro Asp Tyr
                995                 1000                1005

Leu Lys Leu Ser Phe Pro Glu Gly Phe Lys Trp Glu Arg Val Met
        1010                1015                1020

Asn Phe Glu Asp Gly Gly Val Val Thr Val Thr Gln Asp Ser Ser
        1025                1030                1035

Leu Gln Asp Gly Glu Phe Ile Tyr Lys Val Lys Leu Arg Gly Thr
        1040                1045                1050

Asn Phe Pro Ser Asp Gly Pro Val Met Gln Lys Lys Thr Met Gly
        1055                1060                1065

Trp Glu Ala Ser Ser Glu Arg Met Tyr Pro Glu Asp Gly Ala Leu
        1070                1075                1080

Lys Gly Glu Ile Lys Gln Arg Leu Lys Leu Lys Asp Gly Gly His
        1085                1090                1095

Tyr Asp Ala Glu Val Lys Thr Thr Tyr Lys Ala Lys Lys Pro Val
        1100                1105                1110
```

Gln Leu Pro Gly Ala Tyr Asn Val Asn Ile Lys Leu Asp Ile Thr
    1115                1120                1125

Ser His Asn Glu Asp Tyr Thr Ile Val Glu Gln Tyr Glu Arg Ala
    1130                1135                1140

Glu Gly Arg His Ser Thr Gly Gly Met Asp Glu Leu Tyr Lys
    1145                1150                1155

<210> SEQ ID NO 79
<211> LENGTH: 1156
<212> TYPE: PRT
<213> ORGANISM: Artificial Sequence
<220> FEATURE:
<223> OTHER INFORMATION: synthetic construct

<400> SEQUENCE: 79

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

-continued

Trp Asp Ala Asp Val Asp Lys Phe Lys Ala Trp Arg Gln Gly Arg Thr
            325                 330                 335
Gly Tyr Pro Leu Val Asp Ala Gly Met Arg Glu Leu Trp Ala Thr Gly
            340                 345                 350
Trp Met His Asn Arg Ile Arg Val Ile Val Ser Ser Phe Ala Val Lys
            355                 360                 365
Phe Leu Leu Leu Pro Trp Lys Trp Gly Met Lys Tyr Phe Trp Asp Thr
370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
            435                 440                 445
Trp Asp Ala Pro Leu Thr Val Leu Lys Ala Ser Gly Val Glu Leu Gly
450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Gln Met Ser Glu Tyr Ile Arg Val Thr Glu Asp Glu Asn
            500                 505                 510
Asp Glu Pro Ile Glu Ile Pro Ser Glu Asp Gly Thr Val Leu Leu
            515                 520                 525
Ser Thr Val Thr Ala Gln Phe Pro Gly Ala Cys Gly Leu Arg Tyr Arg
530                 535                 540
Asn Pro Val Ser Gln Cys Met Arg Gly Val Arg Leu Val Glu Gly Ile
545                 550                 555                 560
Leu His Ala Pro Asp Ala Gly Trp Gly Asn Leu Val Tyr Val Val Asn
                565                 570                 575
Tyr Pro Lys Asp Asn Lys Arg Lys Met Asp Glu Thr Asp Ala Ser Ser
            580                 585                 590
Ala Val Lys Val Lys Arg Ala Val Gln Lys Thr Ser Asp Leu Ile Val
            595                 600                 605
Leu Gly Leu Pro Trp Lys Thr Thr Glu Gln Asp Leu Lys Glu Tyr Phe
610                 615                 620
Ser Thr Phe Gly Glu Val Leu Met Val Gln Val Lys Lys Asp Leu Lys
625                 630                 635                 640
Thr Gly His Ser Lys Gly Phe Gly Phe Val Arg Phe Thr Glu Tyr Glu
                645                 650                 655
Thr Gln Val Lys Val Met Ser Gln Arg His Met Ile Asp Gly Arg Trp
            660                 665                 670
Cys Asp Cys Lys Leu Pro Asn Ser Lys Gln Ser Gln Asp Glu Pro Leu
            675                 680                 685
Arg Ser Arg Lys Val Phe Val Gly Arg Cys Thr Glu Asp Met Thr Glu
690                 695                 700
Asp Glu Leu Arg Glu Phe Phe Ser Gln Tyr Gly Asp Val Met Asp Val
705                 710                 715                 720
Phe Ile Pro Lys Pro Phe Arg Ala Phe Ala Phe Val Thr Phe Ala Asp
                725                 730                 735
Asp Gln Ile Ala Gln Ser Leu Cys Gly Glu Asp Leu Ile Ile Lys Gly

```
                 740                 745                 750
Ile Ser Val His Ile Ser Asn Ala Glu Pro Lys His Asn Ser Asn Arg
                755                 760                 765

Gln Leu Glu Arg Ser Gly Arg Phe Gly Gly Asn Pro Gly Gly Phe Gly
                770                 775                 780

Asn Gln Gly Gly Phe Gly Asn Ser Arg Gly Gly Gly Ala Gly Leu Gly
785                 790                 795                 800

Asn Asn Gln Gly Ser Asn Met Gly Gly Gly Met Asn Phe Gly Ala Phe
                805                 810                 815

Ser Ile Asn Pro Val Met Met Ala Ala Ala Gln Ala Ala Leu Gln Ser
                820                 825                 830

Ser Trp Gly Met Met Gly Met Leu Ala Ser Gln Gln Asn Gln Ser Gly
                835                 840                 845

Pro Ser Gly Asn Asn Gln Asn Gln Gly Asn Met Gln Arg Glu Pro Asn
                850                 855                 860

Gln Ala Phe Gly Ser Gly Asn Asn Ser Tyr Ser Gly Ser Asn Ser Gly
865                 870                 875                 880

Ala Ala Ile Gly Trp Gly Ser Ala Ser Asn Ala Gly Ser Gly Ser Gly
                885                 890                 895

Phe Asn Gly Gly Phe Gly Ser Ser Met Asp Ser Lys Ser Ser Gly Trp
                900                 905                 910

Gly Trp Asp Pro Pro Val Ala Thr Met Val Ser Lys Gly Glu Glu Asp
                915                 920                 925

Asn Met Ala Ile Ile Lys Glu Phe Met Arg Phe Lys Val His Met Glu
                930                 935                 940

Gly Ser Val Asn Gly His Glu Phe Glu Ile Glu Gly Glu Gly Glu Gly
945                 950                 955                 960

Arg Pro Tyr Glu Gly Thr Gln Thr Ala Lys Leu Lys Val Thr Lys Gly
                965                 970                 975

Gly Pro Leu Pro Phe Ala Trp Asp Ile Leu Ser Pro Gln Phe Met Tyr
                980                 985                 990

Gly Ser Lys Ala Tyr Val Lys His Pro Ala Asp Ile Pro Asp Tyr Leu
                995                 1000                1005

Lys Leu Ser Phe Pro Glu Gly Phe Lys Trp Glu Arg Val Met Asn
        1010                1015                1020

Phe Glu Asp Gly Gly Val Val Thr Val Thr Gln Asp Ser Ser Leu
        1025                1030                1035

Gln Asp Gly Glu Phe Ile Tyr Lys Val Lys Leu Arg Gly Thr Asn
        1040                1045                1050

Phe Pro Ser Asp Gly Pro Val Met Gln Lys Lys Thr Met Gly Trp
        1055                1060                1065

Glu Ala Ser Ser Glu Arg Met Tyr Pro Glu Asp Gly Ala Leu Lys
        1070                1075                1080

Gly Glu Ile Lys Gln Arg Leu Lys Leu Lys Asp Gly Gly His Tyr
        1085                1090                1095

Asp Ala Glu Val Lys Thr Thr Tyr Lys Ala Lys Lys Pro Val Gln
        1100                1105                1110

Leu Pro Gly Ala Tyr Asn Val Asn Ile Lys Leu Asp Ile Thr Ser
        1115                1120                1125

His Asn Glu Asp Tyr Thr Ile Val Glu Gln Tyr Glu Arg Ala Glu
        1130                1135                1140

Gly Arg His Ser Thr Gly Gly Met Asp Glu Leu Tyr Lys
        1145                1150                1155
```

<210> SEQ ID NO 80
<211> LENGTH: 1156
<212> TYPE: PRT
<213> ORGANISM: Artificial Sequence
<220> FEATURE:
<223> OTHER INFORMATION: synthetic construct

<400> SEQUENCE: 80

```
Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
            35                  40                  45

Gly Arg Ala Ser Arg Trp Trp Met Lys Gln Ser Leu Ala His Leu Ser
        50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
        130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
            195                 200                 205

Ala Trp Ser Pro Gly Trp Ser Asn Ala Asp Lys Leu Leu Asn Glu Phe
        210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
            275                 280                 285

Arg Gly Ile Gly Leu Arg Glu Tyr Ser Arg Tyr Ile Cys Phe Asn Phe
        290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
            355                 360                 365
```

```
Phe Leu Leu Leu Pro Trp Lys Trp Gly Met Lys Tyr Phe Trp Asp Thr
        370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Met Ser Glu Tyr Ile Arg Val Thr Glu Asp Glu Asn
            500                 505                 510

Asp Glu Pro Ile Glu Ile Pro Ser Glu Asp Gly Thr Val Leu Leu
        515                 520                 525

Ser Thr Val Thr Ala Gln Phe Pro Gly Ala Cys Gly Leu Arg Tyr Arg
530                 535                 540

Asn Pro Val Ser Gln Cys Met Arg Gly Val Arg Leu Val Glu Gly Ile
545                 550                 555                 560

Leu His Ala Pro Asp Ala Gly Trp Gly Asn Leu Val Tyr Val Val Asn
                565                 570                 575

Tyr Pro Lys Asp Asn Lys Arg Lys Met Asp Glu Thr Asp Ala Ser Ser
            580                 585                 590

Ala Val Lys Val Lys Arg Ala Val Gln Lys Thr Ser Asp Leu Ile Val
        595                 600                 605

Leu Gly Leu Pro Trp Lys Thr Thr Glu Gln Asp Leu Lys Glu Tyr Phe
610                 615                 620

Ser Thr Phe Gly Glu Val Leu Met Val Gln Val Lys Lys Asp Leu Lys
625                 630                 635                 640

Thr Gly His Ser Lys Gly Phe Gly Phe Val Arg Phe Thr Glu Tyr Glu
                645                 650                 655

Thr Gln Val Lys Val Met Ser Gln Arg His Met Ile Asp Gly Arg Trp
            660                 665                 670

Cys Asp Cys Lys Leu Pro Asn Ser Lys Gln Ser Gln Asp Glu Pro Leu
        675                 680                 685

Arg Ser Arg Lys Val Phe Val Gly Arg Cys Thr Glu Asp Met Thr Glu
690                 695                 700

Asp Glu Leu Arg Glu Phe Phe Ser Gln Tyr Gly Asp Val Met Asp Val
705                 710                 715                 720

Phe Ile Pro Lys Pro Phe Arg Ala Phe Ala Phe Val Thr Phe Ala Asp
                725                 730                 735

Asp Gln Ile Ala Gln Ser Leu Cys Gly Glu Asp Leu Ile Ile Lys Gly
            740                 745                 750

Ile Ser Val His Ile Ser Asn Ala Glu Pro Lys His Asn Ser Asn Arg
        755                 760                 765

Gln Leu Glu Arg Ser Gly Arg Phe Gly Gly Asn Pro Gly Gly Phe Gly
770                 775                 780
```

Asn Gln Gly Gly Phe Gly Asn Ser Arg Gly Gly Ala Gly Leu Gly
785                 790                 795                 800

Asn Asn Gln Gly Ser Asn Met Gly Gly Gly Met Asn Phe Gly Ala Phe
            805                 810                 815

Ser Ile Asn Pro Ala Met Met Ala Ala Gln Ala Ala Leu Gln Ser
        820                 825                 830

Ser Trp Gly Met Val Gly Met Leu Ala Ser Gln Gln Asn Gln Ser Gly
            835                 840                 845

Pro Ser Gly Asn Asn Gln Asn Gly Asn Met Gln Arg Glu Pro Asn
        850                 855                 860

Gln Ala Phe Gly Ser Gly Asn Asn Ser Tyr Ser Gly Ser Asn Ser Gly
865         870                 875                 880

Ala Ala Ile Gly Trp Gly Ser Ala Ser Asn Ala Gly Ser Gly Ser Gly
                885                 890                 895

Phe Asn Gly Gly Phe Gly Ser Ser Met Asp Ser Lys Ser Ser Gly Trp
            900                 905                 910

Gly Trp Asp Pro Pro Val Ala Thr Met Val Ser Lys Gly Glu Glu Asp
            915                 920                 925

Asn Met Ala Ile Ile Lys Glu Phe Met Arg Phe Lys Val His Met Glu
930                 935                 940

Gly Ser Val Asn Gly His Glu Phe Glu Ile Glu Gly Glu Gly Glu Gly
945                 950                 955                 960

Arg Pro Tyr Glu Gly Thr Gln Thr Ala Lys Leu Lys Val Thr Lys Gly
                965                 970                 975

Gly Pro Leu Pro Phe Ala Trp Asp Ile Leu Ser Pro Gln Phe Met Tyr
            980                 985                 990

Gly Ser Lys Ala Tyr Val Lys His Pro Ala Asp Ile Pro Asp Tyr Leu
            995                 1000                1005

Lys Leu Ser Phe Pro Glu Gly Phe Lys Trp Glu Arg Val Met Asn
    1010                1015                1020

Phe Glu Asp Gly Gly Val Val Thr Val Thr Gln Asp Ser Ser Leu
    1025                1030                1035

Gln Asp Gly Glu Phe Ile Tyr Lys Val Lys Leu Arg Gly Thr Asn
    1040                1045                1050

Phe Pro Ser Asp Gly Pro Val Met Gln Lys Lys Thr Met Gly Trp
    1055                1060                1065

Glu Ala Ser Ser Glu Arg Met Tyr Pro Glu Asp Gly Ala Leu Lys
    1070                1075                1080

Gly Glu Ile Lys Gln Arg Leu Lys Leu Lys Asp Gly Gly His Tyr
    1085                1090                1095

Asp Ala Glu Val Lys Thr Thr Tyr Lys Ala Lys Lys Pro Val Gln
    1100                1105                1110

Leu Pro Gly Ala Tyr Asn Val Asn Ile Lys Leu Asp Ile Thr Ser
    1115                1120                1125

His Asn Glu Asp Tyr Thr Ile Val Glu Gln Tyr Glu Arg Ala Glu
    1130                1135                1140

Gly Arg His Ser Thr Gly Gly Met Asp Glu Leu Tyr Lys
    1145                1150                1155

<210> SEQ ID NO 81
<211> LENGTH: 884
<212> TYPE: PRT
<213> ORGANISM: Artificial Sequence
<220> FEATURE:
<223> OTHER INFORMATION: synthetic construct

<400> SEQUENCE: 81

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
            35                  40                  45

Gly Arg Ala Ser Arg Trp Trp Met Lys Gln Ser Leu Ala His Leu Ser
        50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro

```
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
            435                 440                 445
Trp Asp Ala Pro Leu Thr Val Leu Lys Ala Ser Gly Val Glu Leu Gly
            450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Gln Gly Arg Phe Gly Gly Asn Pro Gly Gly Phe Gly Asn
                500                 505                 510
Gln Gly Gly Phe Gly Asn Ser Arg Gly Gly Ala Gly Leu Gly Asn
            515                 520                 525
Asn Gln Gly Ser Asn Met Gly Gly Met Asn Phe Gly Ala Phe Ser
            530                 535                 540
Ile Asn Pro Val Met Met Ala Ala Gln Ala Ala Leu Gln Ser Ser
545                 550                 555                 560
Trp Gly Met Met Gly Met Leu Ala Ser Gln Gln Asn Gln Ser Gly Pro
                565                 570                 575
Ser Gly Asn Asn Gln Asn Gln Gly Asn Met Gln Arg Glu Pro Asn Gln
            580                 585                 590
Ala Phe Gly Ser Gly Asn Asn Ser Tyr Ser Gly Ser Asn Ser Gly Ala
        595                 600                 605
Ala Ile Gly Trp Gly Ser Ala Ser Asn Ala Gly Ser Gly Ser Gly Phe
        610                 615                 620
Asn Gly Gly Phe Gly Ser Ser Met Asp Ser Lys Ser Ser Gly Trp Gly
625                 630                 635                 640
Met Arg Asp Pro Pro Val Ala Thr Met Val Ser Lys Gly Glu Glu Asp
                645                 650                 655
Asn Met Ala Ile Ile Lys Glu Phe Met Arg Phe Lys Val His Met Glu
                660                 665                 670
Gly Ser Val Asn Gly His Glu Phe Glu Ile Glu Gly Glu Gly Glu Gly
            675                 680                 685
Arg Pro Tyr Glu Gly Thr Gln Thr Ala Lys Leu Lys Val Thr Lys Gly
            690                 695                 700
Gly Pro Leu Pro Phe Ala Trp Asp Ile Leu Ser Pro Gln Phe Met Tyr
705                 710                 715                 720
Gly Ser Lys Ala Tyr Val Lys His Pro Ala Asp Ile Pro Asp Tyr Leu
                725                 730                 735
Lys Leu Ser Phe Pro Glu Gly Phe Lys Trp Glu Arg Val Met Asn Phe
            740                 745                 750
Glu Asp Gly Gly Val Val Thr Val Thr Gln Asp Ser Ser Leu Gln Asp
            755                 760                 765
Gly Glu Phe Ile Tyr Lys Val Lys Leu Arg Gly Thr Asn Phe Pro Ser
        770                 775                 780
Asp Gly Pro Val Met Gln Lys Lys Thr Met Gly Trp Glu Ala Ser Ser
785                 790                 795                 800
Glu Arg Met Tyr Pro Glu Asp Gly Ala Leu Lys Gly Glu Ile Lys Gln
                805                 810                 815
Arg Leu Lys Leu Lys Asp Gly Gly His Tyr Asp Ala Glu Val Lys Thr
            820                 825                 830
```

-continued

```
Thr Tyr Lys Ala Lys Lys Pro Val Gln Leu Pro Gly Ala Tyr Asn Val
        835                 840                 845

Asn Ile Lys Leu Asp Ile Thr Ser His Asn Glu Asp Tyr Thr Ile Val
    850                 855                 860

Glu Gln Tyr Glu Arg Ala Glu Gly Arg His Ser Thr Gly Gly Met Asp
865                 870                 875                 880

Glu Leu Tyr Lys

<210> SEQ ID NO 82
<211> LENGTH: 884
<212> TYPE: PRT
<213> ORGANISM: Artificial Sequence
<220> FEATURE:
<223> OTHER INFORMATION: synthetic construct

<400> SEQUENCE: 82

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300
```

```
Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
            325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Gly Arg Phe Gly Gly Asn Pro Gly Gly Phe Gly Asn
            500                 505                 510

Gln Gly Gly Phe Gly Asn Ser Arg Gly Gly Ala Gly Leu Gly Asn
            515                 520                 525

Asn Gln Gly Ser Asn Met Gly Gly Met Asn Phe Gly Ala Phe Ser
            530                 535                 540

Ile Asn Pro Ala Met Met Ala Ala Gln Ala Ala Leu Gln Ser Ser
545                 550                 555                 560

Trp Gly Met Val Gly Met Leu Ala Ser Gln Gln Asn Gln Ser Gly Pro
            565                 570                 575

Ser Gly Asn Asn Gln Asn Gln Gly Asn Met Gln Arg Glu Pro Asn Gln
            580                 585                 590

Ala Phe Gly Ser Gly Asn Asn Ser Tyr Ser Gly Ser Asn Ser Gly Ala
            595                 600                 605

Ala Ile Gly Trp Gly Ser Ala Ser Asn Ala Gly Ser Gly Ser Gly Phe
            610                 615                 620

Asn Gly Gly Phe Gly Ser Ser Met Asp Ser Lys Ser Ser Gly Trp Gly
625                 630                 635                 640

Met Arg Asp Pro Pro Val Ala Thr Met Val Ser Lys Gly Glu Glu Asp
            645                 650                 655

Asn Met Ala Ile Ile Lys Glu Phe Met Arg Phe Lys Val His Met Glu
            660                 665                 670

Gly Ser Val Asn Gly His Glu Phe Glu Ile Glu Gly Glu Gly Glu Gly
            675                 680                 685

Arg Pro Tyr Glu Gly Thr Gln Thr Ala Lys Leu Lys Val Thr Lys Gly
            690                 695                 700

Gly Pro Leu Pro Phe Ala Trp Asp Ile Leu Ser Pro Gln Phe Met Tyr
705                 710                 715                 720

Gly Ser Lys Ala Tyr Val Lys His Pro Ala Asp Ile Pro Asp Tyr Leu
```

```
                          725                 730                 735
Lys Leu Ser Phe Pro Glu Gly Phe Lys Trp Glu Arg Val Met Asn Phe
            740                 745                 750

Glu Asp Gly Gly Val Thr Val Thr Gln Asp Ser Ser Leu Gln Asp
            755                 760                 765

Gly Glu Phe Ile Tyr Lys Val Lys Leu Arg Gly Thr Asn Phe Pro Ser
770                 775                 780

Asp Gly Pro Val Met Gln Lys Lys Thr Met Gly Trp Glu Ala Ser Ser
785                 790                 795                 800

Glu Arg Met Tyr Pro Glu Asp Gly Ala Leu Lys Gly Glu Ile Lys Gln
            805                 810                 815

Arg Leu Lys Leu Lys Asp Gly Gly His Tyr Asp Ala Glu Val Lys Thr
            820                 825                 830

Thr Tyr Lys Ala Lys Lys Pro Val Gln Leu Pro Gly Ala Tyr Asn Val
            835                 840                 845

Asn Ile Lys Leu Asp Ile Thr Ser His Asn Glu Asp Tyr Thr Ile Val
850                 855                 860

Glu Gln Tyr Glu Arg Ala Glu Gly Arg His Ser Thr Gly Gly Met Asp
865                 870                 875                 880

Glu Leu Tyr Lys

<210> SEQ ID NO 83
<211> LENGTH: 884
<212> TYPE: PRT
<213> ORGANISM: Artificial Sequence
<220> FEATURE:
<223> OTHER INFORMATION: synthetic construct

<400> SEQUENCE: 83

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205
```

```
Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                    245                 250                 255

Ser Val Arg His Val Phe Gln Cys Ala Arg Met Lys Gln Ile Ile Trp
                260                 265                 270

Ala Arg Asp Lys Asn Ser Glu Gly Glu Ser Ala Asp Leu Phe Leu
            275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
            450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Gly Arg Phe Gly Gly Asn Pro Gly Gly Phe Gly Asn
            500                 505                 510

Gln Gly Gly Phe Gly Asn Ser Arg Gly Gly Ala Gly Leu Gly Asn
        515                 520                 525

Asn Gln Gly Ser Asn Met Gly Gly Met Asn Phe Gly Ala Phe Ser
        530                 535                 540

Ile Asn Pro Ala Met Met Ala Ala Gln Ala Ala Leu Gln Ser Ser
545                 550                 555                 560

Trp Gly Met Met Gly Met Leu Ala Ser Gln Gln Asn Gln Ser Gly Pro
                565                 570                 575

Ser Gly Asn Asn Gln Asn Gln Gly Asn Met Gln Arg Glu Pro Asn Gln
                580                 585                 590

Ala Phe Gly Ser Gly Asn Asn Ser Tyr Ser Gly Ser Asn Ser Gly Ala
            595                 600                 605

Ala Ile Gly Trp Gly Ser Ala Ser Asn Ala Gly Ser Gly Ser Gly Phe
610                 615                 620
```

```
Asn Gly Gly Phe Gly Ser Ser Met Asp Ser Lys Ala Ala Gly Trp Gly
625                 630                 635                 640

Met Arg Asp Pro Pro Val Ala Thr Met Val Ser Lys Gly Glu Glu Asp
            645                 650                 655

Asn Met Ala Ile Ile Lys Glu Phe Met Arg Phe Lys Val His Met Glu
        660                 665                 670

Gly Ser Val Asn Gly His Glu Phe Glu Ile Glu Gly Glu Gly Glu Gly
    675                 680                 685

Arg Pro Tyr Glu Gly Thr Gln Thr Ala Lys Leu Lys Val Thr Lys Gly
690                 695                 700

Gly Pro Leu Pro Phe Ala Trp Asp Ile Leu Ser Pro Gln Phe Met Tyr
705                 710                 715                 720

Gly Ser Lys Ala Tyr Val Lys His Pro Ala Asp Ile Pro Asp Tyr Leu
            725                 730                 735

Lys Leu Ser Phe Pro Glu Gly Phe Lys Trp Glu Arg Val Met Asn Phe
        740                 745                 750

Glu Asp Gly Gly Val Val Thr Val Thr Gln Asp Ser Ser Leu Gln Asp
    755                 760                 765

Gly Glu Phe Ile Tyr Lys Val Lys Leu Arg Gly Thr Asn Phe Pro Ser
770                 775                 780

Asp Gly Pro Val Met Gln Lys Lys Thr Met Gly Trp Glu Ala Ser Ser
785                 790                 795                 800

Glu Arg Met Tyr Pro Glu Asp Gly Ala Leu Lys Gly Glu Ile Lys Gln
            805                 810                 815

Arg Leu Lys Leu Lys Asp Gly Gly His Tyr Asp Ala Glu Val Lys Thr
        820                 825                 830

Thr Tyr Lys Ala Lys Lys Pro Val Gln Leu Pro Gly Ala Tyr Asn Val
    835                 840                 845

Asn Ile Lys Leu Asp Ile Thr Ser His Asn Glu Asp Tyr Thr Ile Val
850                 855                 860

Glu Gln Tyr Glu Arg Ala Glu Gly Arg His Ser Thr Gly Gly Met Asp
865                 870                 875                 880

Glu Leu Tyr Lys

<210> SEQ ID NO 84
<211> LENGTH: 885
<212> TYPE: PRT
<213> ORGANISM: Artificial Sequence
<220> FEATURE:
<223> OTHER INFORMATION: synthetic construct

<400> SEQUENCE: 84

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
            85                  90                  95

Lys Val Val Phe Asn His Leu Tyr Asp Pro Val Ser Leu Val Arg Asp
```

```
               100                 105                 110
His Thr Val Lys Glu Lys Leu Val Glu Arg Gly Ile Ser Val Gln Ser
            115                 120                 125
Tyr Asn Gly Asp Leu Leu Tyr Glu Pro Trp Glu Ile Tyr Cys Glu Lys
130                 135                 140
Gly Lys Pro Phe Thr Ser Phe Asn Ser Tyr Trp Lys Cys Leu Asp
145                 150                 155                 160
Met Ser Ile Glu Ser Val Met Leu Pro Pro Trp Arg Leu Met Pro
            165                 170                 175
Ile Thr Ala Ala Ala Glu Ala Ile Trp Ala Cys Ser Ile Glu Glu Leu
            180                 185                 190
Gly Leu Glu Asn Glu Ala Glu Lys Pro Ser Asn Ala Leu Leu Thr Arg
            195                 200                 205
Ala Trp Ser Pro Gly Trp Ser Asn Ala Asp Lys Leu Leu Asn Glu Phe
            210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
            260                 265                 270
Ala Arg Asp Lys Asn Ser Glu Gly Glu Glu Ser Ala Asp Leu Phe Leu
            275                 280                 285
Arg Gly Ile Gly Leu Arg Glu Tyr Ser Arg Tyr Ile Cys Phe Asn Phe
            290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
                340                 345                 350
Trp Met His Asn Arg Ile Arg Val Ile Val Ser Ser Phe Ala Val Lys
            355                 360                 365
Phe Leu Leu Leu Pro Trp Lys Trp Gly Met Lys Tyr Phe Trp Asp Thr
370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
                420                 425                 430
Trp Leu Pro Glu Leu Ala Arg Leu Pro Thr Glu Trp Ile His His Pro
            435                 440                 445
Trp Asp Ala Pro Leu Thr Val Leu Lys Ala Ser Gly Val Glu Leu Gly
            450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Pro Gly Arg Phe Gly Gly Asn Pro Gly Gly Phe Gly Asn
                500                 505                 510
Gln Gly Gly Phe Gly Asn Ser Arg Gly Gly Ala Gly Leu Gly Asn
            515                 520                 525
```

```
Asn Gln Gly Ser Asn Met Gly Gly Met Asn Phe Gly Ala Phe Ser
            530                 535                 540

Ile Asn Pro Ala Met Met Ala Ala Gln Ala Ala Leu Gln Ser Ser
545                 550                 555                 560

Trp Gly Met Met Gly Met Leu Ala Ser Gln Gln Asn Gln Ser Gly Pro
                565                 570                 575

Ser Gly Asn Asn Gln Asn Gln Gly Asn Met Gln Arg Glu Pro Asn Gln
            580                 585                 590

Ala Phe Gly Ser Gly Asn Asn Ser Tyr Ser Gly Ser Asn Ser Gly Ala
            595                 600                 605

Ala Ile Gly Trp Gly Ser Ala Ser Asn Ala Gly Ser Gly Ser Gly Phe
            610                 615                 620

Asn Gly Gly Phe Gly Ser Ser Met Asp Ser Lys Asp Asp Gly Trp Gly
625                 630                 635                 640

Met Thr Arg Asp Pro Pro Val Ala Thr Met Val Ser Lys Gly Glu Glu
                645                 650                 655

Asp Asn Met Ala Ile Ile Lys Glu Phe Met Arg Phe Lys Val His Met
            660                 665                 670

Glu Gly Ser Val Asn Gly His Glu Phe Glu Ile Glu Gly Glu Gly Glu
            675                 680                 685

Gly Arg Pro Tyr Glu Gly Thr Gln Thr Ala Lys Leu Lys Val Thr Lys
            690                 695                 700

Gly Gly Pro Leu Pro Phe Ala Trp Asp Ile Leu Ser Pro Gln Phe Met
705                 710                 715                 720

Tyr Gly Ser Lys Ala Tyr Val Lys His Pro Ala Asp Ile Pro Asp Tyr
                725                 730                 735

Leu Lys Leu Ser Phe Pro Glu Gly Phe Lys Trp Glu Arg Val Met Asn
            740                 745                 750

Phe Glu Asp Gly Gly Val Val Thr Val Thr Gln Asp Ser Ser Leu Gln
            755                 760                 765

Asp Gly Glu Phe Ile Tyr Lys Val Lys Leu Arg Gly Thr Asn Phe Pro
            770                 775                 780

Ser Asp Gly Pro Val Met Gln Lys Lys Thr Met Gly Trp Glu Ala Ser
785                 790                 795                 800

Ser Glu Arg Met Tyr Pro Glu Asp Gly Ala Leu Lys Gly Glu Ile Lys
                805                 810                 815

Gln Arg Leu Lys Leu Lys Asp Gly Gly His Tyr Asp Ala Glu Val Lys
            820                 825                 830

Thr Thr Tyr Lys Ala Lys Lys Pro Val Gln Leu Pro Gly Ala Tyr Asn
            835                 840                 845

Val Asn Ile Lys Leu Asp Ile Thr Ser His Asn Glu Asp Tyr Thr Ile
850                 855                 860

Val Glu Gln Tyr Glu Arg Ala Glu Gly Arg His Ser Thr Gly Gly Met
865                 870                 875                 880

Asp Glu Leu Tyr Lys
            885
```

<210> SEQ ID NO 85
<211> LENGTH: 1157
<212> TYPE: PRT
<213> ORGANISM: Artificial Sequence
<220> FEATURE:
<223> OTHER INFORMATION: synthetic construct

<400> SEQUENCE: 85

-continued

```
Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
        130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415
```

-continued

```
Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
                435                 440                 445

Trp Asp Ala Pro Leu Thr Val Leu Lys Ala Ser Gly Val Glu Leu Gly
            450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Met Ser Glu Tyr Ile Arg Val Thr Glu Asp Glu Asn
            500                 505                 510

Asp Glu Pro Ile Glu Ile Pro Ser Glu Asp Gly Thr Val Leu Leu
            515                 520                 525

Ser Thr Val Thr Ala Gln Phe Pro Gly Ala Cys Gly Leu Arg Tyr Arg
            530                 535                 540

Asn Pro Val Ser Gln Cys Met Arg Gly Val Arg Leu Val Glu Gly Ile
545                 550                 555                 560

Leu His Ala Pro Asp Ala Gly Trp Gly Asn Leu Val Tyr Val Asn
                565                 570                 575

Tyr Pro Lys Asp Asn Lys Arg Lys Met Asp Glu Thr Asp Ala Ser Ser
            580                 585                 590

Ala Val Lys Val Lys Arg Ala Val Gln Lys Thr Ser Asp Leu Ile Val
                595                 600                 605

Leu Gly Leu Pro Trp Lys Thr Thr Glu Gln Asp Leu Lys Glu Tyr Phe
610                 615                 620

Ser Thr Phe Gly Glu Val Leu Met Val Gln Val Lys Lys Asp Leu Lys
625                 630                 635                 640

Thr Gly His Ser Lys Gly Leu Gly Leu Val Arg Phe Thr Glu Tyr Glu
                645                 650                 655

Thr Gln Val Lys Val Met Ser Gln Arg His Met Ile Asp Gly Arg Trp
                660                 665                 670

Cys Asp Cys Lys Leu Pro Asn Ser Lys Gln Ser Gln Asp Glu Pro Leu
                675                 680                 685

Arg Ser Arg Lys Val Leu Val Gly Arg Cys Thr Glu Asp Met Thr Glu
            690                 695                 700

Asp Glu Leu Arg Glu Phe Phe Ser Gln Tyr Gly Asp Val Met Asp Val
705                 710                 715                 720

Phe Ile Pro Lys Pro Phe Arg Ala Leu Ala Leu Val Thr Phe Ala Asp
                725                 730                 735

Asp Gln Ile Ala Gln Ser Leu Cys Gly Glu Asp Leu Ile Ile Lys Gly
                740                 745                 750

Ile Ser Val His Ile Ser Asn Ala Glu Pro Lys His Asn Ser Asn Arg
                755                 760                 765

Gln Leu Glu Arg Ser Gly Arg Phe Gly Gly Asn Pro Gly Gly Phe Gly
770                 775                 780

Asn Gln Gly Gly Phe Gly Asn Ser Arg Gly Gly Ala Gly Leu Gly
785                 790                 795                 800

Asn Asn Gln Gly Ser Asn Met Gly Gly Met Asn Phe Gly Ala Phe
                805                 810                 815

Ser Ile Asn Pro Ala Met Met Ala Ala Ala Gln Ala Ala Leu Gln Ser
                820                 825                 830

Ser Trp Gly Met Met Gly Met Leu Ala Ser Gln Gln Asn Gln Ser Gly
```

```
            835                 840                 845

Pro Ser Gly Asn Asn Gln Asn Gln Gly Asn Met Gln Arg Glu Pro Asn
    850                 855                 860

Gln Ala Phe Gly Ser Gly Asn Asn Ser Tyr Ser Gly Ser Asn Ser Gly
865                 870                 875                 880

Ala Ala Ile Gly Trp Gly Ser Ala Ser Asn Ala Gly Ser Gly Ser Gly
                885                 890                 895

Phe Asn Gly Gly Phe Gly Ser Ser Met Asp Ser Lys Ser Ser Gly Trp
            900                 905                 910

Gly Met Trp Asp Pro Pro Val Ala Thr Met Val Ser Lys Gly Glu Glu
        915                 920                 925

Asp Asn Met Ala Ile Ile Lys Glu Phe Met Arg Phe Lys Val His Met
    930                 935                 940

Glu Gly Ser Val Asn Gly His Glu Phe Glu Ile Glu Gly Glu Gly Glu
945                 950                 955                 960

Gly Arg Pro Tyr Glu Gly Thr Gln Thr Ala Lys Leu Lys Val Thr Lys
                965                 970                 975

Gly Gly Pro Leu Pro Phe Ala Trp Asp Ile Leu Ser Pro Gln Phe Met
            980                 985                 990

Tyr Gly Ser Lys Ala Tyr Val Lys His Pro Ala Asp Ile Pro Asp Tyr
        995                1000                1005

Leu Lys Leu Ser Phe Pro Glu Gly Phe Lys Trp Glu Arg Val Met
   1010                1015                1020

Asn Phe Glu Asp Gly Gly Val Val Thr Val Thr Gln Asp Ser Ser
   1025                1030                1035

Leu Gln Asp Gly Glu Phe Ile Tyr Lys Val Lys Leu Arg Gly Thr
   1040                1045                1050

Asn Phe Pro Ser Asp Gly Pro Val Met Gln Lys Lys Thr Met Gly
   1055                1060                1065

Trp Glu Ala Ser Ser Glu Arg Met Tyr Pro Glu Asp Gly Ala Leu
   1070                1075                1080

Lys Gly Glu Ile Lys Gln Arg Leu Lys Leu Lys Asp Gly Gly His
   1085                1090                1095

Tyr Asp Ala Glu Val Lys Thr Thr Tyr Lys Ala Lys Lys Pro Val
   1100                1105                1110

Gln Leu Pro Gly Ala Tyr Asn Val Asn Ile Lys Leu Asp Ile Thr
   1115                1120                1125

Ser His Asn Glu Asp Tyr Thr Ile Val Glu Gln Tyr Glu Arg Ala
   1130                1135                1140

Glu Gly Arg His Ser Thr Gly Gly Met Asp Glu Leu Tyr Lys
   1145                1150                1155

<210> SEQ ID NO 86
<211> LENGTH: 829
<212> TYPE: PRT
<213> ORGANISM: Artificial Sequence
<220> FEATURE:
<223> OTHER INFORMATION: synthetic construct

<400> SEQUENCE: 86

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
```

```
                35                  40                  45
Gly Arg Ala Ser Arg Trp Trp Met Lys Gln Ser Leu Ala His Leu Ser
 50                  55                  60

Gln Ser Leu Lys Ala Leu Gly Ser Asp Leu Thr Leu Ile Lys Thr His
 65                  70                  75                  80

Asn Thr Ile Ser Ala Ile Leu Asp Cys Ile Arg Val Thr Gly Ala Thr
                     85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
                115                 120                 125

Tyr Asn Gly Asp Leu Leu Tyr Glu Pro Trp Glu Ile Tyr Cys Glu Lys
                130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
                195                 200                 205

Ala Trp Ser Pro Gly Trp Ser Asn Ala Asp Lys Leu Leu Asn Glu Phe
                210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Glu Ser Ala Asp Leu Phe Leu
                275                 280                 285

Arg Gly Ile Gly Leu Arg Glu Tyr Ser Arg Tyr Ile Cys Phe Asn Phe
                290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
                355                 360                 365

Phe Leu Leu Leu Pro Trp Lys Trp Gly Met Lys Tyr Phe Trp Asp Thr
                370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
                435                 440                 445

Trp Asp Ala Pro Leu Thr Val Leu Lys Ala Ser Gly Val Glu Leu Gly
450                 455                 460
```

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
            485                 490                 495

Ala Ala Ala Gln Asp Leu Ile Val Leu Gly Leu Pro Trp Lys Thr Thr
        500                 505                 510

Glu Gln Asp Leu Lys Glu Tyr Phe Ser Thr Phe Gly Glu Val Leu Met
    515                 520                 525

Val Gln Val Lys Lys Asp Leu Lys Thr Gly His Ser Lys Gly Phe Gly
530                 535                 540

Phe Val Arg Phe Thr Glu Tyr Glu Thr Gln Val Lys Val Met Ser Gln
545                 550                 555                 560

Arg His Met Ile Asp Gly Arg Trp Cys Asp Cys Lys Leu Pro Asn Ser
                565                 570                 575

Lys Gln Ser Gln Asp Glu Pro Leu Arg Ser Arg Asp Pro Pro Val Ala
            580                 585                 590

Thr Met Val Ser Lys Gly Glu Glu Asp Asn Met Ala Ile Ile Lys Glu
        595                 600                 605

Phe Met Arg Phe Lys Val His Met Glu Gly Ser Val Asn Gly His Glu
    610                 615                 620

Phe Glu Ile Glu Gly Glu Gly Glu Gly Arg Pro Tyr Glu Gly Thr Gln
625                 630                 635                 640

Thr Ala Lys Leu Lys Val Thr Lys Gly Gly Pro Leu Pro Phe Ala Trp
                645                 650                 655

Asp Ile Leu Ser Pro Gln Phe Met Tyr Gly Ser Lys Ala Tyr Val Lys
            660                 665                 670

His Pro Ala Asp Ile Pro Asp Tyr Leu Lys Leu Ser Phe Pro Glu Gly
        675                 680                 685

Phe Lys Trp Glu Arg Val Met Asn Phe Glu Asp Gly Gly Val Val Thr
    690                 695                 700

Val Thr Gln Asp Ser Ser Leu Gln Asp Gly Glu Phe Ile Tyr Lys Val
705                 710                 715                 720

Lys Leu Arg Gly Thr Asn Phe Pro Ser Asp Gly Pro Val Met Gln Lys
                725                 730                 735

Lys Thr Met Gly Trp Glu Ala Ser Ser Glu Arg Met Tyr Pro Glu Asp
            740                 745                 750

Gly Ala Leu Lys Gly Glu Ile Lys Gln Arg Leu Lys Leu Lys Asp Gly
        755                 760                 765

Gly His Tyr Asp Ala Glu Val Lys Thr Thr Tyr Lys Ala Lys Lys Pro
    770                 775                 780

Val Gln Leu Pro Gly Ala Tyr Asn Val Asn Ile Lys Leu Asp Ile Thr
785                 790                 795                 800

Ser His Asn Glu Asp Tyr Thr Ile Val Glu Gln Tyr Glu Arg Ala Glu
                805                 810                 815

Gly Arg His Ser Thr Gly Gly Met Asp Glu Leu Tyr Lys
            820                 825

<210> SEQ ID NO 87
<211> LENGTH: 815
<212> TYPE: PRT
<213> ORGANISM: Artificial Sequence
<220> FEATURE:
<223> OTHER INFORMATION: synthetic construct

<400> SEQUENCE: 87

-continued

```
Met Lys Met Asp Lys Lys Thr Ile Val Trp Phe Arg Arg Asp Leu Arg
1               5                   10                  15
Ile Glu Asp Asn Pro Ala Leu Ala Ala Ala His Glu Gly Ser Val
            20                  25                  30
Phe Pro Val Phe Ile Trp Cys Pro Glu Glu Gly Gln Phe Tyr Pro
        35                  40                  45
Gly Arg Ala Ser Arg Trp Trp Met Lys Gln Ser Leu Ala His Leu Ser
50                  55                  60
Gln Ser Leu Lys Ala Leu Gly Ser Asp Leu Thr Leu Ile Lys Thr His
65                  70                  75                  80
Asn Thr Ile Ser Ala Ile Leu Asp Cys Ile Arg Val Thr Gly Ala Thr
                85                  90                  95
Lys Val Val Phe Asn His Leu Tyr Asp Pro Val Ser Leu Val Arg Asp
            100                 105                 110
His Thr Val Lys Glu Lys Leu Val Glu Arg Gly Ile Ser Val Gln Ser
        115                 120                 125
Tyr Asn Gly Asp Leu Leu Tyr Glu Pro Trp Glu Ile Tyr Cys Glu Lys
130                 135                 140
Gly Lys Pro Phe Thr Ser Phe Asn Ser Tyr Trp Lys Lys Cys Leu Asp
145                 150                 155                 160
Met Ser Ile Glu Ser Val Met Leu Pro Pro Trp Arg Leu Met Pro
                165                 170                 175
Ile Thr Ala Ala Ala Glu Ala Ile Trp Ala Cys Ser Ile Glu Glu Leu
            180                 185                 190
Gly Leu Glu Asn Glu Ala Glu Lys Pro Ser Asn Ala Leu Leu Thr Arg
        195                 200                 205
Ala Trp Ser Pro Gly Trp Ser Asn Ala Asp Lys Leu Leu Asn Glu Phe
210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
            260                 265                 270
Ala Arg Asp Lys Asn Ser Glu Gly Glu Glu Ser Ala Asp Leu Phe Leu
        275                 280                 285
Arg Gly Ile Gly Leu Arg Glu Tyr Ser Arg Tyr Ile Cys Phe Asn Phe
290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
            340                 345                 350
Trp Met His Asn Arg Ile Arg Val Ile Val Ser Ser Phe Ala Val Lys
        355                 360                 365
Phe Leu Leu Leu Pro Trp Lys Trp Gly Met Lys Tyr Phe Trp Asp Thr
370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
```

```
Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
            485                 490                 495

Ala Ala Ala Gln Arg Lys Val Phe Val Gly Arg Cys Thr Glu Asp Met
        500                 505                 510

Thr Glu Asp Glu Leu Arg Glu Phe Phe Ser Gln Tyr Gly Asp Val Met
    515                 520                 525

Asp Val Phe Ile Pro Lys Pro Phe Arg Ala Phe Ala Phe Val Thr Phe
530                 535                 540

Ala Asp Asp Gln Ile Ala Gln Ser Leu Cys Gly Glu Asp Leu Ile Ile
545                 550                 555                 560

Lys Gly Ile Ser Val His Ile Ser Asn Ala Glu Pro Arg Asp Pro Pro
            565                 570                 575

Val Ala Thr Met Val Ser Lys Gly Glu Glu Asp Asn Met Ala Ile Ile
        580                 585                 590

Lys Glu Phe Met Arg Phe Lys Val His Met Glu Gly Ser Val Asn Gly
    595                 600                 605

His Glu Phe Glu Ile Glu Gly Glu Gly Glu Gly Arg Pro Tyr Glu Gly
610                 615                 620

Thr Gln Thr Ala Lys Leu Lys Val Thr Lys Gly Gly Pro Leu Pro Phe
625                 630                 635                 640

Ala Trp Asp Ile Leu Ser Pro Gln Phe Met Tyr Gly Ser Lys Ala Tyr
            645                 650                 655

Val Lys His Pro Ala Asp Ile Pro Asp Tyr Leu Lys Leu Ser Phe Pro
        660                 665                 670

Glu Gly Phe Lys Trp Glu Arg Val Met Asn Phe Glu Asp Gly Gly Val
    675                 680                 685

Val Thr Val Thr Gln Asp Ser Ser Leu Gln Asp Gly Glu Phe Ile Tyr
690                 695                 700

Lys Val Lys Leu Arg Gly Thr Asn Phe Pro Ser Asp Gly Pro Val Met
705                 710                 715                 720

Gln Lys Lys Thr Met Gly Trp Glu Ala Ser Ser Glu Arg Met Tyr Pro
            725                 730                 735

Glu Asp Gly Ala Leu Lys Gly Glu Ile Lys Gln Arg Leu Lys Leu Lys
        740                 745                 750

Asp Gly Gly His Tyr Asp Ala Glu Val Lys Thr Thr Tyr Lys Ala Lys
    755                 760                 765

Lys Pro Val Gln Leu Pro Gly Ala Tyr Asn Val Asn Ile Lys Leu Asp
770                 775                 780

Ile Thr Ser His Asn Glu Asp Tyr Thr Ile Val Glu Gln Tyr Glu Arg
785                 790                 795                 800

Ala Glu Gly Arg His Ser Thr Gly Gly Met Asp Glu Leu Tyr Lys
            805                 810                 815

<210> SEQ ID NO 88
<211> LENGTH: 901
<212> TYPE: PRT
```

<213> ORGANISM: Artificial Sequence
<220> FEATURE:
<223> OTHER INFORMATION: synthetic construct

<400> SEQUENCE: 88

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
        115                 120                 125

Tyr Asn Gly Asp Leu Leu Tyr Glu Pro Trp Glu Ile Tyr Cys Glu Lys
130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Glu Ser Ala Asp Leu Phe Leu
        275                 280                 285

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
        355                 360                 365

Phe Leu Leu Leu Pro Trp Lys Trp Gly Met Lys Tyr Phe Trp Asp Thr
    370                 375                 380

Leu Leu Asp Ala Asp Leu Glu Cys Asp Ile Leu Gly Trp Gln Tyr Ile

```
            385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
                420                 425                 430
Trp Leu Pro Glu Leu Ala Arg Leu Pro Thr Glu Trp Ile His His Pro
                435                 440                 445
Trp Asp Ala Pro Leu Thr Val Leu Lys Ala Ser Gly Val Glu Leu Gly
            450                 455                 460
Thr Asn Tyr Ala Lys Pro Ile Val Asp Ile Asp Thr Ala Arg Glu Leu
465                 470                 475                 480
Leu Ala Lys Ala Ile Ser Arg Thr Arg Gly Ala Gln Ile Met Ile Gly
                485                 490                 495
Ala Ala Ala Gln Asp Leu Ile Val Leu Gly Leu Pro Trp Lys Thr Thr
                500                 505                 510
Glu Gln Asp Leu Lys Glu Tyr Phe Ser Thr Phe Gly Glu Val Leu Met
                515                 520                 525
Val Gln Val Lys Lys Asp Leu Lys Thr Gly His Ser Lys Gly Phe Gly
            530                 535                 540
Phe Val Arg Phe Thr Glu Tyr Glu Thr Gln Val Lys Val Met Ser Gln
545                 550                 555                 560
Arg His Met Ile Asp Gly Arg Trp Cys Asp Cys Lys Leu Pro Asn Ser
                565                 570                 575
Lys Gln Ser Gln Asp Glu Pro Leu Arg Ser Arg Lys Val Phe Val Gly
                580                 585                 590
Arg Cys Thr Glu Asp Met Thr Glu Asp Glu Leu Arg Glu Phe Phe Ser
            595                 600                 605
Gln Tyr Gly Asp Val Met Asp Val Phe Ile Pro Lys Pro Phe Arg Ala
            610                 615                 620
Phe Ala Phe Val Thr Phe Ala Asp Asp Gln Ile Ala Gln Ser Leu Cys
625                 630                 635                 640
Gly Glu Asp Leu Ile Ile Lys Gly Ile Ser Val His Ile Ser Asn Ala
                645                 650                 655
Glu Pro Arg Asp Pro Pro Val Ala Thr Met Val Ser Lys Gly Glu Glu
                660                 665                 670
Asp Asn Met Ala Ile Ile Lys Glu Phe Met Arg Phe Lys Val His Met
            675                 680                 685
Glu Gly Ser Val Asn Gly His Glu Phe Glu Ile Glu Gly Glu Gly Glu
            690                 695                 700
Gly Arg Pro Tyr Glu Gly Thr Gln Thr Ala Lys Leu Lys Val Thr Lys
705                 710                 715                 720
Gly Gly Pro Leu Pro Phe Ala Trp Asp Ile Leu Ser Pro Gln Phe Met
                725                 730                 735
Tyr Gly Ser Lys Ala Tyr Val Lys His Pro Ala Asp Ile Pro Asp Tyr
            740                 745                 750
Leu Lys Leu Ser Phe Pro Glu Gly Phe Lys Trp Glu Arg Val Met Asn
            755                 760                 765
Phe Glu Asp Gly Gly Val Val Thr Val Thr Gln Asp Ser Ser Leu Gln
            770                 775                 780
Asp Gly Glu Phe Ile Tyr Lys Val Lys Leu Arg Gly Thr Asn Phe Pro
785                 790                 795                 800
Ser Asp Gly Pro Val Met Gln Lys Lys Thr Met Gly Trp Glu Ala Ser
                805                 810                 815
```

```
Ser Glu Arg Met Tyr Pro Glu Asp Gly Ala Leu Lys Gly Glu Ile Lys
            820                 825                 830

Gln Arg Leu Lys Leu Lys Asp Gly Gly His Tyr Asp Ala Glu Val Lys
            835                 840                 845

Thr Thr Tyr Lys Ala Lys Lys Pro Val Gln Leu Pro Gly Ala Tyr Asn
850                 855                 860

Val Asn Ile Lys Leu Asp Ile Thr Ser His Asn Glu Asp Tyr Thr Ile
865                 870                 875                 880

Val Glu Gln Tyr Glu Arg Ala Glu Gly Arg His Ser Thr Gly Met
                885                 890                 895

Asp Glu Leu Tyr Lys
            900

<210> SEQ ID NO 89
<211> LENGTH: 1016
<212> TYPE: PRT
<213> ORGANISM: Artificial Sequence
<220> FEATURE:
<223> OTHER INFORMATION: synthetic construct

<400> SEQUENCE: 89

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Glu Gly Gln Phe Tyr Pro
            35                  40                  45

Gly Arg Ala Ser Arg Trp Trp Met Lys Gln Ser Leu Ala His Leu Ser
50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
            85                  90                  95

Lys Val Val Phe Asn His Leu Tyr Asp Pro Val Ser Leu Val Arg Asp
            100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
            130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
            165                 170                 175

Ile Thr Ala Ala Ala Glu Ala Ile Trp Ala Cys Ser Ile Glu Glu Leu
            180                 185                 190

Gly Leu Glu Asn Glu Ala Glu Lys Pro Ser Asn Ala Leu Leu Thr Arg
            195                 200                 205

Ala Trp Ser Pro Gly Trp Ser Asn Ala Asp Lys Leu Leu Asn Glu Phe
            210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
            245                 250                 255

Ser Val Arg His Val Phe Gln Cys Ala Arg Met Lys Gln Ile Ile Trp
            260                 265                 270
```

```
Ala Arg Asp Lys Asn Ser Glu Gly Glu Ser Ala Asp Leu Phe Leu
            275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Met Ser Glu Tyr Ile Arg Val Thr Glu Asp Glu Asn
            500                 505                 510

Asp Glu Pro Ile Glu Ile Pro Ser Glu Asp Gly Thr Val Leu Leu
            515                 520                 525

Ser Thr Val Thr Ala Gln Phe Pro Gly Ala Cys Gly Leu Arg Tyr Arg
            530                 535                 540

Asn Pro Val Ser Gln Cys Met Arg Gly Val Arg Leu Val Glu Gly Ile
545                 550                 555                 560

Leu His Ala Pro Asp Ala Gly Trp Gly Asn Leu Val Tyr Val Val Asn
                565                 570                 575

Tyr Pro Lys Asp Asn Lys Arg Lys Met Asp Glu Thr Asp Ala Ser Ser
            580                 585                 590

Ala Val Lys Val Lys Arg Ala Val Gln Lys Thr Ser Asp Leu Ile Val
            595                 600                 605

Leu Gly Leu Pro Trp Lys Thr Thr Glu Gln Asp Leu Lys Glu Tyr Phe
610                 615                 620

Ser Thr Phe Gly Glu Val Leu Met Val Gln Val Lys Lys Asp Leu Lys
625                 630                 635                 640

Thr Gly His Ser Lys Gly Phe Gly Phe Val Arg Phe Thr Glu Tyr Glu
                645                 650                 655

Thr Gln Val Lys Val Met Ser Gln Arg His Met Ile Asp Gly Arg Trp
            660                 665                 670

Cys Asp Cys Lys Leu Pro Asn Ser Lys Gln Ser Gln Asp Glu Pro Leu
675                 680                 685
```

Arg Ser Arg Lys Val Phe Val Gly Arg Cys Thr Glu Asp Met Thr Glu
690                 695                 700

Asp Glu Leu Arg Glu Phe Phe Ser Gln Tyr Gly Asp Val Met Asp Val
705                 710                 715                 720

Phe Ile Pro Lys Pro Phe Arg Ala Phe Ala Phe Val Thr Phe Ala Asp
                725                 730                 735

Asp Gln Ile Ala Gln Ser Leu Cys Gly Glu Asp Leu Ile Ile Lys Gly
                740                 745                 750

Ile Ser Val His Ile Ser Asn Ala Glu Pro Lys His Asn Ser Asn Arg
            755                 760                 765

Gln Leu Glu Arg Ser Arg Asp Pro Pro Val Ala Thr Met Val Ser Lys
770                 775                 780

Gly Glu Glu Asp Asn Met Ala Ile Ile Lys Glu Phe Met Arg Phe Lys
785                 790                 795                 800

Val His Met Glu Gly Ser Val Asn Gly His Glu Phe Glu Ile Glu Gly
                805                 810                 815

Glu Gly Glu Gly Arg Pro Tyr Glu Gly Thr Gln Thr Ala Lys Leu Lys
                820                 825                 830

Val Thr Lys Gly Gly Pro Leu Pro Phe Ala Trp Asp Ile Leu Ser Pro
            835                 840                 845

Gln Phe Met Tyr Gly Ser Lys Ala Tyr Val Lys His Pro Ala Asp Ile
850                 855                 860

Pro Asp Tyr Leu Lys Leu Ser Phe Pro Glu Gly Phe Lys Trp Glu Arg
865                 870                 875                 880

Val Met Asn Phe Glu Asp Gly Gly Val Val Thr Val Thr Gln Asp Ser
                885                 890                 895

Ser Leu Gln Asp Gly Glu Phe Ile Tyr Lys Val Lys Leu Arg Gly Thr
                900                 905                 910

Asn Phe Pro Ser Asp Gly Pro Val Met Gln Lys Lys Thr Met Gly Trp
            915                 920                 925

Glu Ala Ser Ser Glu Arg Met Tyr Pro Glu Asp Gly Ala Leu Lys Gly
930                 935                 940

Glu Ile Lys Gln Arg Leu Lys Leu Lys Asp Gly Gly His Tyr Asp Ala
945                 950                 955                 960

Glu Val Lys Thr Thr Tyr Lys Ala Lys Lys Pro Val Gln Leu Pro Gly
                965                 970                 975

Ala Tyr Asn Val Asn Ile Lys Leu Asp Ile Thr Ser His Asn Glu Asp
                980                 985                 990

Tyr Thr Ile Val Glu Gln Tyr Glu Arg Ala Glu Gly Arg His Ser Thr
            995                 1000                1005

Gly Gly Met Asp Glu Leu Tyr Lys
    1010                1015

<210> SEQ ID NO 90
<211> LENGTH: 1040
<212> TYPE: PRT
<213> ORGANISM: Artificial Sequence
<220> FEATURE:
<223> OTHER INFORMATION: synthetic construct

<400> SEQUENCE: 90

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30

-continued

```
Phe Pro Val Phe Ile Trp Cys Pro Glu Glu Gly Gln Phe Tyr Pro
             35                  40                  45
Gly Arg Ala Ser Arg Trp Trp Met Lys Gln Ser Leu Ala His Leu Ser
 50                  55                  60
Gln Ser Leu Lys Ala Leu Gly Ser Asp Leu Thr Leu Ile Lys Thr His
 65                  70                  75                  80
Asn Thr Ile Ser Ala Ile Leu Asp Cys Ile Arg Val Thr Gly Ala Thr
                 85                  90                  95
Lys Val Val Phe Asn His Leu Tyr Asp Pro Val Ser Leu Val Arg Asp
                100                 105                 110
His Thr Val Lys Glu Lys Leu Val Glu Arg Gly Ile Ser Val Gln Ser
                115                 120                 125
Tyr Asn Gly Asp Leu Leu Tyr Glu Pro Trp Glu Ile Tyr Cys Glu Lys
130                 135                 140
Gly Lys Pro Phe Thr Ser Phe Asn Ser Tyr Trp Lys Lys Cys Leu Asp
145                 150                 155                 160
Met Ser Ile Glu Ser Val Met Leu Pro Pro Trp Arg Leu Met Pro
                165                 170                 175
Ile Thr Ala Ala Ala Glu Ala Ile Trp Ala Cys Ser Ile Glu Glu Leu
                180                 185                 190
Gly Leu Glu Asn Glu Ala Glu Lys Pro Ser Asn Ala Leu Leu Thr Arg
            195                 200                 205
Ala Trp Ser Pro Gly Trp Ser Asn Ala Asp Lys Leu Leu Asn Glu Phe
            210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
                260                 265                 270
Ala Arg Asp Lys Asn Ser Glu Gly Glu Ser Ala Asp Leu Phe Leu
            275                 280                 285
Arg Gly Ile Gly Leu Arg Glu Tyr Ser Arg Tyr Ile Cys Phe Asn Phe
290                 295                 300
Pro Phe Thr His Glu Gln Ser Leu Leu Ser His Leu Arg Phe Phe Pro
305                 310                 315                 320
Trp Asp Ala Asp Val Asp Lys Phe Lys Ala Trp Arg Gln Gly Arg Thr
                325                 330                 335
Gly Tyr Pro Leu Val Asp Ala Gly Met Arg Glu Leu Trp Ala Thr Gly
                340                 345                 350
Trp Met His Asn Arg Ile Arg Val Ile Val Ser Ser Phe Ala Val Lys
                355                 360                 365
Phe Leu Leu Leu Pro Trp Lys Trp Gly Met Lys Tyr Phe Trp Asp Thr
370                 375                 380
Leu Leu Asp Ala Asp Leu Glu Cys Asp Ile Leu Gly Trp Gln Tyr Ile
385                 390                 395                 400
Ser Gly Ser Ile Pro Asp Gly His Glu Leu Asp Arg Leu Asp Asn Pro
                405                 410                 415
Ala Leu Gln Gly Ala Lys Tyr Asp Pro Glu Gly Glu Tyr Ile Arg Gln
            420                 425                 430
Trp Leu Pro Glu Leu Ala Arg Leu Pro Thr Glu Trp Ile His His Pro
            435                 440                 445
Trp Asp Ala Pro Leu Thr Val Leu Lys Ala Ser Gly Val Glu Leu Gly
```

```
                    450             455             460
Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Cys Arg Ala Thr Met Tyr Pro Tyr Asp Val Pro Asp
            500                 505                 510

Tyr Ala Met Ala Ser Asn Asp Tyr Thr Gln Gln Ala Thr Gln Ser Tyr
                515                 520                 525

Gly Ala Tyr Pro Thr Gln Pro Gly Gln Gly Tyr Ser Gln Gln Ser Ser
530                 535                 540

Gln Pro Tyr Gly Gln Gln Ser Tyr Ser Gly Tyr Ser Gln Ser Thr Asp
545                 550                 555                 560

Thr Ser Gly Tyr Gly Gln Ser Ser Tyr Ser Tyr Gly Gln Ser Gln
                565                 570                 575

Asn Thr Gly Tyr Gly Thr Gln Ser Thr Pro Gln Gly Tyr Gly Ser Thr
                580                 585                 590

Gly Gly Tyr Gly Ser Ser Gln Ser Ser Gln Ser Ser Tyr Gly Gln Gln
                595                 600                 605

Ser Ser Tyr Pro Gly Tyr Gly Gln Gln Pro Ala Pro Ser Ser Thr Ser
610                 615                 620

Gly Ser Tyr Gly Ser Ser Gln Ser Ser Tyr Gly Gln Pro Gln
625                 630                 635                 640

Ser Gly Ser Tyr Ser Gln Gln Pro Ser Tyr Gly Gly Gln Gln Ser
                645                 650                 655

Tyr Gly Gln Gln Gln Ser Tyr Asn Pro Pro Gln Gly Tyr Gly Gln Gln
                660                 665                 670

Asn Gln Tyr Asn Ser Ser Gly Gly Gly Gly Gly Gly Gly Gly
                675                 680                 685

Gly Asn Tyr Gly Gln Asp Gln Ser Ser Met Ser Ser Gly Gly Gly Ser
                690                 695                 700

Gly Gly Gly Tyr Gly Asn Gln Asp Gln Ser Gly Gly Gly Gly Ser Gly
705                 710                 715                 720

Gly Tyr Gly Gln Gln Asp Arg Gly Gly Arg Gly Arg Gly Gly Ser Gly
                725                 730                 735

Gly Gly Gly Gly Gly Gly Gly Gly Tyr Asn Arg Ser Ser Gly Gly
                740                 745                 750

Tyr Glu Pro Arg Gly Arg Gly Gly Arg Gly Arg Gly Gly Met
                755                 760                 765

Gly Gly Ser Asp Arg Gly Gly Phe Asn Lys Phe Gly Gly Pro Arg Asp
770                 775                 780

Gln Gly Ser Arg His Asp Ser Glu Gln Asp Asn Ser Asp Asn Asn Thr
785                 790                 795                 800

Ile Phe Val Gln Gly Leu Gly Glu Asn Val Thr Ile Glu Ser Val Ala
                805                 810                 815

Asp Tyr Phe Lys Gln Ile Gly Ile Ile Lys Thr Asn Lys Thr Gly
                820                 825                 830

Gln Pro Met Ile Asn Leu Tyr Thr Asp Arg Glu Thr Gly Lys Leu Lys
                835                 840                 845

Gly Glu Ala Thr Val Ser Phe Asp Asp Pro Pro Ser Ala Lys Ala Ala
                850                 855                 860

Ile Asp Trp Phe Asp Gly Lys Glu Phe Ser Gly Asn Pro Ile Lys Val
865                 870                 875                 880
```

```
Ser Phe Ala Thr Arg Arg Ala Asp Phe Asn Arg Gly Gly Asn Gly
                885                 890                 895

Arg Gly Gly Arg Gly Arg Gly Gly Pro Met Gly Arg Gly Tyr Gly
            900                 905                 910

Gly Gly Gly Ser Gly Gly Gly Arg Gly Gly Phe Pro Ser Gly Gly
            915                 920                 925

Gly Gly Gly Gly Gly Gln Gln Arg Ala Gly Asp Trp Lys Cys Pro Asn
    930                 935                 940

Pro Thr Cys Glu Asn Met Asn Phe Ser Trp Arg Asn Glu Cys Asn Gln
945                 950                 955                 960

Cys Lys Ala Pro Lys Pro Asp Gly Pro Gly Gly Pro Gly Gly Ser
                965                 970                 975

His Met Gly Gly Asn Tyr Gly Asp Asp Arg Arg Gly Arg Gly Gly
            980                 985                 990

Tyr Asp Arg Gly Gly Tyr Arg Gly Arg Gly Gly Asp Arg Gly Gly Phe
                995                 1000                1005

Arg Gly  Gly Arg Gly Gly Gly  Asp Arg Gly Gly Phe  Gly Pro Gly
    1010             1015                  1020

Lys Met  Asp Ser Arg Gly Glu  His Arg Gln Asp Arg  Arg Glu Arg
    1025             1030                  1035

Pro Tyr
    1040

<210> SEQ ID NO 91
<211> LENGTH: 1283
<212> TYPE: PRT
<213> ORGANISM: Artificial Sequence
<220> FEATURE:
<223> OTHER INFORMATION: synthetic construct

<400> SEQUENCE: 91

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
            20                  25                  30

Phe Pro Val Phe Ile Trp Cys Pro Glu Glu Gly Gln Phe Tyr Pro
        35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
                180                 185                 190
```

```
Gly Leu Glu Asn Glu Ala Glu Lys Pro Ser Asn Ala Leu Leu Thr Arg
        195                 200                 205

Ala Trp Ser Pro Gly Trp Ser Asn Ala Asp Lys Leu Leu Asn Glu Phe
210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
            260                 265                 270

Ala Arg Asp Lys Asn Ser Glu Gly Glu Ser Ala Asp Leu Phe Leu
            275                 280                 285

Arg Gly Ile Gly Leu Arg Glu Tyr Ser Arg Tyr Ile Cys Phe Asn Phe
290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350

Trp Met His Asn Arg Ile Arg Val Ile Val Ser Ser Phe Ala Val Lys
                355                 360                 365

Phe Leu Leu Leu Pro Trp Lys Trp Gly Met Lys Tyr Phe Trp Asp Thr
                370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
                435                 440                 445

Trp Asp Ala Pro Leu Thr Val Leu Lys Ala Ser Gly Val Glu Leu Gly
                450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Gly Ala Gln Ile Met Ile Gly
                485                 490                 495

Ala Ala Ala Gln Cys Arg Ala Thr Met Tyr Pro Tyr Asp Val Pro Asp
                500                 505                 510

Tyr Ala Met Ala Ser Asn Asp Tyr Thr Gln Gln Ala Thr Gln Ser Tyr
                515                 520                 525

Gly Ala Tyr Pro Thr Gln Pro Gly Gln Gly Tyr Ser Gln Gln Ser Ser
                530                 535                 540

Gln Pro Tyr Gly Gln Gln Ser Tyr Ser Gly Tyr Ser Gln Ser Thr Asp
545                 550                 555                 560

Thr Ser Gly Tyr Gly Gln Ser Ser Tyr Ser Ser Tyr Gly Gln Ser Gln
                565                 570                 575

Asn Thr Gly Tyr Gly Thr Gln Ser Thr Pro Gln Gly Tyr Gly Ser Thr
                580                 585                 590

Gly Gly Tyr Gly Ser Ser Gln Ser Ser Gln Ser Ser Tyr Gly Gln Gln
                595                 600                 605
```

```
Ser Ser Tyr Pro Gly Tyr Gly Gln Gln Pro Ala Pro Ser Ser Thr Ser
    610             615             620

Gly Ser Tyr Gly Ser Ser Gln Ser Ser Tyr Gly Gln Pro Gln
625             630             635             640

Ser Gly Ser Tyr Ser Gln Gln Pro Ser Tyr Gly Gly Gln Gln Ser
            645             650             655

Tyr Gly Gln Gln Gln Ser Tyr Asn Pro Pro Gln Gly Tyr Gly Gln Gln
        660             665             670

Asn Gln Tyr Asn Ser Ser Gly Gly Gly Gly Gly Gly Gly Gly
        675             680             685

Gly Asn Tyr Gly Gln Asp Gln Ser Ser Met Ser Ser Gly Gly Gly Ser
    690             695             700

Gly Gly Gly Tyr Gly Asn Gln Asp Gln Ser Gly Gly Gly Ser Gly
705             710             715             720

Gly Tyr Gly Gln Gln Asp Arg Gly Gly Arg Gly Gly Ser Gly
            725             730             735

Gly Gly Gly Gly Gly Gly Gly Tyr Asn Arg Ser Ser Gly Gly
        740             745             750

Tyr Glu Pro Arg Gly Arg Gly Gly Arg Gly Arg Gly Gly Met
    755             760             765

Gly Gly Ser Asp Arg Gly Gly Phe Asn Lys Phe Gly Gly Pro Arg Asp
770             775             780

Gln Gly Ser Arg His Asp Ser Glu Gln Asp Asn Ser Asp Asn Asn Thr
785             790             795             800

Ile Phe Val Gln Gly Leu Gly Glu Asn Val Thr Ile Glu Ser Val Ala
            805             810             815

Asp Tyr Phe Lys Gln Ile Gly Ile Ile Lys Thr Asn Lys Lys Thr Gly
        820             825             830

Gln Pro Met Ile Asn Leu Tyr Thr Asp Arg Glu Thr Gly Lys Leu Lys
    835             840             845

Gly Glu Ala Thr Val Ser Phe Asp Asp Pro Pro Ser Ala Lys Ala Ala
    850             855             860

Ile Asp Trp Phe Asp Gly Lys Glu Phe Ser Gly Asn Pro Ile Lys Val
865             870             875             880

Ser Phe Ala Thr Arg Arg Ala Asp Phe Asn Arg Gly Gly Gly Asn Gly
            885             890             895

Arg Gly Gly Arg Gly Arg Gly Gly Pro Met Gly Arg Gly Gly Tyr Gly
            900             905             910

Gly Gly Gly Ser Gly Gly Gly Gly Arg Gly Gly Phe Pro Ser Gly Gly
            915             920             925

Gly Gly Gly Gly Gly Gln Gln Arg Ala Gly Asp Trp Lys Cys Pro Asn
930             935             940

Pro Thr Cys Glu Asn Met Asn Phe Ser Trp Arg Asn Glu Cys Asn Gln
945             950             955             960

Cys Lys Ala Pro Lys Pro Asp Gly Pro Gly Gly Pro Gly Gly Ser
            965             970             975

His Met Gly Gly Asn Tyr Gly Asp Asp Arg Arg Gly Gly Arg Gly Gly
            980             985             990

Tyr Asp Arg Gly Gly Tyr Arg Gly Arg Gly Gly Asp Arg Gly Gly Phe
        995             1000            1005

Arg Gly Gly Arg Gly Gly Gly Asp Arg Gly Gly Phe Gly Pro Gly
    1010            1015            1020

Lys Met Asp Ser Arg Gly Glu His Arg Gln Asp Arg Arg Glu Arg
```

```
                  1025                1030                1035

Pro Tyr Trp Asp Pro Val Ala Thr Met Val Ser Lys Gly Glu
         1040                1045                1050

Glu Asp Asn Met Ala Ile Ile Lys Glu Phe Met Arg Phe Lys Val
         1055                1060                1065

His Met Glu Gly Ser Val Asn Gly His Glu Phe Glu Ile Glu Gly
         1070                1075                1080

Glu Gly Glu Gly Arg Pro Tyr Glu Gly Thr Gln Thr Ala Lys Leu
         1085                1090                1095

Lys Val Thr Lys Gly Gly Pro Leu Pro Phe Ala Trp Asp Ile Leu
         1100                1105                1110

Ser Pro Gln Phe Met Tyr Gly Ser Lys Ala Tyr Val Lys His Pro
         1115                1120                1125

Ala Asp Ile Pro Asp Tyr Leu Lys Leu Ser Phe Pro Glu Gly Phe
         1130                1135                1140

Lys Trp Glu Arg Val Met Asn Phe Glu Asp Gly Gly Val Val Thr
         1145                1150                1155

Val Thr Gln Asp Ser Ser Leu Gln Asp Gly Glu Phe Ile Tyr Lys
         1160                1165                1170

Val Lys Leu Arg Gly Thr Asn Phe Pro Ser Asp Gly Pro Val Met
         1175                1180                1185

Gln Lys Lys Thr Met Gly Trp Glu Ala Ser Ser Glu Arg Met Tyr
         1190                1195                1200

Pro Glu Asp Gly Ala Leu Lys Gly Glu Ile Lys Gln Arg Leu Lys
         1205                1210                1215

Leu Lys Asp Gly Gly His Tyr Asp Ala Glu Val Lys Thr Thr Tyr
         1220                1225                1230

Lys Ala Lys Lys Pro Val Gln Leu Pro Gly Ala Tyr Asn Val Asn
         1235                1240                1245

Ile Lys Leu Asp Ile Thr Ser His Asn Glu Asp Tyr Thr Ile Val
         1250                1255                1260

Glu Gln Tyr Glu Arg Ala Glu Gly Arg His Ser Thr Gly Gly Met
         1265                1270                1275

Asp Glu Leu Tyr Lys
         1280

<210> SEQ ID NO 92
<211> LENGTH: 348
<212> TYPE: PRT
<213> ORGANISM: Artificial Sequence
<220> FEATURE:
<223> OTHER INFORMATION: synthetic construct

<400> SEQUENCE: 92

Met Asn Gly Leu Thr Pro Pro Leu Met Phe Cys Ser Arg Ser Asp
1               5                   10                  15

Pro Ser Thr Ser Asn Ile Asn Leu Asp Asp Val Phe Ala Asp Val
            20                  25                  30

Phe Phe Asn Ser Asn Gly Glu Leu Leu Asp Ile Asp Glu Ile Asp Asp
        35                  40                  45

Phe Gly Asp Asn Thr Cys Pro Lys Ser Ser Met Ser Val Asp Asp Asp
    50                  55                  60

Ala Ser Ser Gln Val Phe Gln Gly His Leu Phe Gly Asn Ala Leu Ser
65                  70                  75                  80

Ser Ile Ala Leu Ser Asp Ser Gly Asp Leu Ser Thr Gly Ile Tyr Glu
```

```
                85                  90                  95
Ser Gln Gly Asn Ala Ser Arg Gly Lys Ser Leu Arg Thr Lys Ser Ser
            100                 105                 110

Gly Ser Ile Ser Ser Glu Leu Thr Glu Ala Gln Lys Val Glu Arg Arg
            115                 120                 125

Glu Arg Asn Arg Glu His Ala Lys Arg Ser Arg Val Arg Lys Lys Phe
            130                 135                 140

Leu Leu Glu Ser Leu Gln Gln Ser Val Asn Glu Leu Asn His Glu Asn
145                 150                 155                 160

Asn Cys Leu Lys Glu Ser Ile Arg Glu His Leu Gly Pro Arg Gly Asp
                165                 170                 175

Ser Leu Ile Ala Gln Cys Ser Pro Glu Ala Asp Thr Leu Leu Thr Asp
                180                 185                 190

Asn Pro Ser Lys Ala Asn Arg Ile Leu Glu Asp Pro Asp Tyr Ser Leu
                195                 200                 205

Val Lys Ala Leu Gln Met Ala Gln Gln Asn Phe Val Ile Thr Asp Ala
            210                 215                 220

Ser Leu Pro Asp Asn Pro Ile Val Tyr Ala Ser Arg Gly Phe Leu Thr
225                 230                 235                 240

Leu Thr Gly Tyr Ser Leu Asp Gln Ile Leu Gly Arg Asn Cys Arg Phe
                245                 250                 255

Leu Gln Gly Pro Glu Thr Asp Pro Arg Ala Val Asp Lys Ile Arg Asn
            260                 265                 270

Ala Ile Thr Lys Gly Val Asp Thr Ser Val Cys Leu Leu Asn Tyr Arg
            275                 280                 285

Gln Asp Gly Thr Thr Phe Trp Asn Leu Phe Phe Val Ala Gly Leu Arg
            290                 295                 300

Asp Ser Lys Gly Asn Ile Val Asn Tyr Val Gly Val Gln Ser Lys Val
305                 310                 315                 320

Ser Glu Asp Tyr Ala Lys Leu Leu Val Asn Glu Gln Asn Ile Glu Tyr
                325                 330                 335

Lys Gly Val Arg Thr Ser Asn Met Leu Arg Arg Lys
            340                 345

<210> SEQ ID NO 93
<211> LENGTH: 145
<212> TYPE: PRT
<213> ORGANISM: Artificial Sequence
<220> FEATURE:
<223> OTHER INFORMATION: synthetic construct

<400> SEQUENCE: 93

Pro Asp Tyr Ser Leu Val Lys Ala Leu Gln Met Ala Gln Gln Asn Phe
1               5                   10                  15

Val Ile Thr Asp Ala Ser Leu Pro Asp Asn Pro Ile Val Tyr Ala Ser
            20                  25                  30

Arg Gly Phe Leu Thr Leu Thr Gly Tyr Ser Leu Asp Gln Ile Leu Gly
        35                  40                  45

Arg Asn Cys Arg Phe Leu Gln Gly Pro Glu Thr Asp Pro Arg Ala Val
    50                  55                  60

Asp Lys Ile Arg Asn Ala Ile Thr Lys Gly Val Asp Thr Ser Val Cys
65                  70                  75                  80

Leu Leu Asn Tyr Arg Gln Asp Gly Thr Thr Phe Trp Asn Leu Phe Phe
                85                  90                  95

Val Ala Gly Leu Arg Asp Ser Lys Gly Asn Ile Val Asn Tyr Val Gly
```

```
                  100                 105                 110
Val Gln Ser Lys Val Ser Glu Asp Tyr Ala Lys Leu Leu Val Asn Glu
            115                 120                 125

Gln Asn Ile Glu Tyr Lys Gly Val Arg Thr Ser Asn Met Leu Arg Arg
        130                 135                 140

Lys
145

<210> SEQ ID NO 94
<211> LENGTH: 435
<212> TYPE: DNA
<213> ORGANISM: Artificial Sequence
<220> FEATURE:
<223> OTHER INFORMATION: synthetic construct

<400> SEQUENCE: 94
cctgactaca gtctcgtgaa ggctctgcaa atggcacaac agaattttgt cattacagac      60
gcctccctcc cagacaaccc tatcgtctac gccagtagag ggtttctgac actgacaggc     120
tattctctcg accagatcct gggcaggaac tgcaggtttc tgcaagggcc agaaacagac     180
ccaagagctg tggataagat caggaatgcc atcaccaaag gcgttgatac cagtgtctgt     240
ctgctgaatt atagacagga tggcacaacc ttctggaatc tcttcttcgt ggctggactc     300
agagattcta aggcaatat tgtcaactac gtcggagtgc agtcaaaggt gagcgaagat      360
tatgccaagc tgctggtcaa cgagcagaac attgagtaca aggtgtgcg caccagtaac      420 atgctgcgca gaaag                                                      435

<210> SEQ ID NO 95
<211> LENGTH: 414
<212> TYPE: PRT
<213> ORGANISM: Artificial Sequence
<220> FEATURE:
<223> OTHER INFORMATION: synthetic construct

<400> SEQUENCE: 95

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175
```

```
Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Ser Gln Tyr Gly Asp Val Met Asp Val Phe Ile Pro Lys
    210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
            245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
            275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
            325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
            355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 96
<211> LENGTH: 311
<212> TYPE: PRT
<213> ORGANISM: Artificial Sequence
<220> FEATURE:
<223> OTHER INFORMATION: synthetic construct

<400> SEQUENCE: 96

Met Asp Leu Ile Val Leu Gly Leu Pro Trp Lys Thr Thr Glu Gln Asp
1               5                   10                  15

Leu Lys Glu Tyr Phe Ser Thr Phe Gly Glu Val Leu Met Val Gln Val
            20                  25                  30

Lys Lys Asp Leu Lys Thr Gly His Ser Lys Gly Phe Gly Phe Val Arg
        35                  40                  45

Phe Thr Glu Tyr Glu Thr Gln Val Lys Val Met Ser Gln Arg His Met
    50                  55                  60

Ile Asp Gly Arg Trp Cys Asp Cys Lys Leu Pro Asn Ser Lys Gln Ser
65                  70                  75                  80

Gln Asp Glu Pro Leu Arg Ser Lys Val Phe Val Gly Arg Cys Thr
            85                  90                  95

Glu Asp Met Thr Glu Asp Glu Leu Arg Glu Phe Phe Ser Gln Tyr Gly
            100                 105                 110

Asp Val Met Asp Val Phe Ile Pro Lys Pro Phe Arg Ala Phe Ala Phe
        115                 120                 125
```

-continued

```
Val Thr Phe Ala Asp Asp Gln Ile Ala Gln Ser Leu Cys Gly Glu Asp
            130                 135                 140

Leu Ile Ile Lys Gly Ile Ser Val His Ile Ser Asn Ala Glu Pro Lys
145                 150                 155                 160

His Asn Ser Asn Arg Gln Leu Glu Arg Ser Gly Arg Phe Gly Gly Asn
                165                 170                 175

Pro Gly Gly Phe Gly Asn Gln Gly Gly Phe Gly Asn Ser Arg Gly Gly
            180                 185                 190

Gly Ala Gly Leu Gly Asn Asn Gln Gly Ser Asn Met Gly Gly Gly Met
        195                 200                 205

Asn Phe Gly Ala Phe Ser Ile Asn Pro Ala Met Met Ala Ala Ala Gln
    210                 215                 220

Ala Ala Leu Gln Ser Ser Trp Gly Met Met Gly Met Leu Ala Ser Gln
225                 230                 235                 240

Gln Asn Gln Ser Gly Pro Ser Gly Asn Asn Gln Asn Gln Gly Asn Met
                245                 250                 255

Gln Arg Glu Pro Asn Gln Ala Phe Gly Ser Gly Asn Asn Ser Tyr Ser
            260                 265                 270

Gly Ser Asn Ser Gly Ala Ala Ile Gly Trp Gly Ser Ala Ser Asn Ala
        275                 280                 285

Gly Ser Gly Ser Gly Phe Asn Gly Gly Phe Gly Ser Ser Met Asp Ser
    290                 295                 300

Lys Ser Ser Gly Trp Gly Met
305                 310
```

<210> SEQ ID NO 97
<211> LENGTH: 225
<212> TYPE: PRT
<213> ORGANISM: Artificial Sequence
<220> FEATURE:
<223> OTHER INFORMATION: synthetic construct

<400> SEQUENCE: 97

```
Met Arg Lys Val Phe Val Gly Arg Cys Thr Glu Asp Met Thr Glu Asp
1               5                   10                  15

Glu Leu Arg Glu Phe Phe Ser Gln Tyr Gly Asp Val Met Asp Val Phe
            20                  25                  30

Ile Pro Lys Pro Phe Arg Ala Phe Ala Phe Val Thr Phe Ala Asp Asp
        35                  40                  45

Gln Ile Ala Gln Ser Leu Cys Gly Glu Asp Leu Ile Ile Lys Gly Ile
    50                  55                  60

Ser Val His Ile Ser Asn Ala Glu Pro Lys His Asn Ser Asn Arg Gln
65                  70                  75                  80

Leu Glu Arg Ser Gly Arg Phe Gly Gly Asn Pro Gly Gly Phe Gly Asn
                85                  90                  95

Gln Gly Gly Phe Gly Asn Ser Arg Gly Gly Ala Gly Leu Gly Asn
            100                 105                 110

Asn Gln Gly Ser Asn Met Gly Gly Gly Met Asn Phe Gly Ala Phe Ser
        115                 120                 125

Ile Asn Pro Ala Met Met Ala Ala Ala Gln Ala Ala Leu Gln Ser Ser
    130                 135                 140

Trp Gly Met Met Gly Met Leu Ala Ser Gln Gln Asn Gln Ser Gly Pro
145                 150                 155                 160

Ser Gly Asn Asn Gln Asn Gln Gly Asn Met Gln Arg Glu Pro Asn Gln
                165                 170                 175
```

```
Ala Phe Gly Ser Gly Asn Asn Ser Tyr Ser Gly Ser Asn Ser Gly Ala
            180                 185                 190

Ala Ile Gly Trp Gly Ser Ala Ser Asn Ala Gly Ser Gly Ser Gly Phe
            195                 200                 205

Asn Gly Gly Phe Gly Ser Ser Met Asp Ser Lys Ser Ser Gly Trp Gly
            210                 215                 220

Met
225

<210> SEQ ID NO 98
<211> LENGTH: 142
<212> TYPE: PRT
<213> ORGANISM: Artificial Sequence
<220> FEATURE:
<223> OTHER INFORMATION: synthetic construct

<400> SEQUENCE: 98

Met Gly Arg Phe Gly Gly Asn Pro Gly Gly Phe Gly Asn Gln Gly Gly
 1               5                  10                  15

Phe Gly Asn Ser Arg Gly Gly Gly Ala Gly Leu Gly Asn Asn Gln Gly
            20                  25                  30

Ser Asn Met Gly Gly Gly Met Asn Phe Gly Ala Phe Ser Ile Asn Pro
        35                  40                  45

Ala Met Met Ala Ala Ala Gln Ala Ala Leu Gln Ser Ser Trp Gly Met
    50                  55                  60

Met Gly Met Leu Ala Ser Gln Gln Asn Gln Ser Gly Pro Ser Gly Asn
65                  70                  75                  80

Asn Gln Asn Gln Gly Asn Met Gln Arg Glu Pro Asn Gln Ala Phe Gly
                85                  90                  95

Ser Gly Asn Asn Ser Tyr Ser Gly Ser Asn Ser Gly Ala Ala Ile Gly
            100                 105                 110

Trp Gly Ser Ala Ser Asn Ala Gly Ser Gly Ser Gly Phe Asn Gly Gly
        115                 120                 125

Phe Gly Ser Ser Met Asp Ser Lys Ser Ser Gly Trp Gly Met
    130                 135                 140

<210> SEQ ID NO 99
<211> LENGTH: 161
<212> TYPE: PRT
<213> ORGANISM: Artificial Sequence
<220> FEATURE:
<223> OTHER INFORMATION: synthetic construct

<400> SEQUENCE: 99

Gly Glu Phe Leu Ala Thr Thr Leu Glu Arg Ile Glu Lys Asn Phe Val
 1               5                  10                  15

Ile Thr Asp Pro Arg Leu Pro Asp Asn Pro Ile Ile Phe Ala Ser Asp
            20                  25                  30

Ser Phe Leu Gln Leu Thr Glu Tyr Ser Arg Glu Glu Ile Leu Gly Arg
        35                  40                  45

Asn Cys Arg Phe Leu Gln Gly Pro Glu Thr Asp Arg Ala Thr Val Arg
    50                  55                  60

Lys Ile Arg Asp Ala Ile Asp Asn Gln Thr Glu Val Thr Val Gln Leu
65                  70                  75                  80

Ile Asn Tyr Thr Lys Ser Gly Lys Lys Phe Trp Asn Leu Phe His Leu
                85                  90                  95

Gln Pro Met Arg Asp Gln Lys Gly Asp Val Gln Tyr Phe Ile Gly Val
```

```
              100                 105                 110
Gln Leu Asp Gly Thr Glu His Val Arg Asp Ala Ala Glu Arg Glu Gly
        115                 120                 125

Val Met Leu Ile Lys Lys Thr Ala Glu Asn Ile Asp Glu Ala Ala Lys
    130                 135                 140

Glu Leu Pro Asp Ala Asn Leu Arg Pro Glu Asp Leu Trp Ala Asn His
145                 150                 155                 160

Gly

<210> SEQ ID NO 100
<211> LENGTH: 225
<212> TYPE: PRT
<213> ORGANISM: Artificial Sequence
<220> FEATURE:
<223> OTHER INFORMATION: synthetic construct

<400> SEQUENCE: 100

Met Leu Asp Met Gly Gln Asp Arg Pro Ile Asp Gly Ser Gly Ala Pro
1               5                   10                  15

Gly Ala Asp Asp Thr Arg Val Glu Val Gln Pro Pro Ala Gln Trp Val
            20                  25                  30

Leu Asp Leu Ile Glu Ala Ser Pro Ile Ala Ser Val Ser Asp Pro
        35                  40                  45

Arg Leu Ala Asp Asn Pro Leu Ile Ala Ile Asn Gln Ala Phe Thr Asp
    50                  55                  60

Leu Thr Gly Tyr Ser Glu Glu Cys Val Gly Arg Asn Cys Arg Phe
65                  70                  75                  80

Leu Ala Gly Ser Gly Thr Glu Pro Trp Leu Thr Asp Lys Ile Arg Gln
                85                  90                  95

Gly Val Arg Glu His Lys Pro Val Leu Val Glu Ile Leu Asn Tyr Lys
            100                 105                 110

Lys Asp Gly Thr Pro Phe Arg Asn Ala Val Leu Val Ala Pro Ile Tyr
        115                 120                 125

Asp Asp Asp Asp Glu Leu Leu Tyr Phe Leu Gly Ser Gln Val Glu Val
    130                 135                 140

Asp Asp Asp Gln Pro Asn Met Gly Met Ala Arg Glu Arg Ala Ala
145                 150                 155                 160

Glu Met Leu Lys Thr Leu Ser Pro Arg Gln Leu Glu Val Thr Thr Leu
                165                 170                 175

Val Ala Ser Gly Leu Arg Asn Lys Glu Val Ala Ala Arg Leu Gly Leu
            180                 185                 190

Ser Glu Lys Thr Val Lys Met His Arg Gly Leu Val Met Glu Lys Leu
        195                 200                 205

Asn Leu Lys Thr Ser Ala Asp Leu Val Arg Ile Ala Val Glu Ala Gly
    210                 215                 220

Ile
225

<210> SEQ ID NO 101
<211> LENGTH: 261
<212> TYPE: PRT
<213> ORGANISM: Artificial Sequence
<220> FEATURE:
<223> OTHER INFORMATION: synthetic construct

<400> SEQUENCE: 101

Met Ala Ser Phe Gln Ser Phe Gly Ile Pro Gly Gln Leu Glu Val Ile
```

```
                1               5                      10                      15
            Lys Lys Ala Leu Asp His Val Arg Val Gly Val Val Ile Thr Asp Pro
                                20                      25                      30
            Ala Leu Glu Asp Asn Pro Ile Val Tyr Val Asn Gln Gly Phe Val Gln
                                35                      40                      45
            Met Thr Gly Tyr Glu Thr Glu Ile Leu Gly Lys Asn Cys Arg Phe
                 50                      55                      60
            Leu Gln Gly Lys His Thr Asp Pro Ala Glu Val Asp Asn Ile Arg Thr
             65                      70                      75                      80
            Ala Leu Gln Asn Lys Glu Pro Val Thr Val Gln Ile Gln Asn Tyr Lys
                                85                      90                      95
            Lys Asp Gly Thr Met Phe Trp Asn Glu Leu Asn Ile Asp Pro Met Glu
                               100                     105                     110
            Ile Glu Asp Lys Thr Tyr Phe Val Gly Ile Gln Asn Asp Ile Thr Lys
                               115                     120                     125
            Gln Lys Glu Tyr Glu Lys Leu Leu Glu Asp Ser Leu Thr Glu Ile Thr
                      130                     135                     140
            Ala Leu Ser Thr Pro Ile Val Pro Ile Arg Asn Gly Ile Ser Ala Leu
            145                     150                     155                     160
            Pro Leu Val Gly Asn Leu Thr Glu Glu Arg Phe Asn Ser Ile Val Cys
                               165                     170                     175
            Thr Leu Thr Asn Ile Leu Ser Thr Ser Lys Asp Asp Tyr Leu Ile Ile
                               180                     185                     190
            Asp Leu Ser Gly Leu Ala Gln Val Asn Glu Gln Thr Ala Asp Gln Ile
                      195                     200                     205
            Phe Lys Leu Ser His Leu Leu Lys Leu Thr Gly Thr Glu Leu Ile Ile
                 210                     215                     220
            Thr Gly Ile Lys Pro Glu Leu Ala Met Lys Met Asn Lys Leu Asp Ala
            225                     230                     235                     240
            Asn Phe Ser Ser Leu Lys Thr Tyr Ser Asn Val Lys Asp Ala Val Lys
                               245                     250                     255
            Val Leu Pro Ile Met
                      260

<210> SEQ ID NO 102
<211> LENGTH: 176
<212> TYPE: PRT
<213> ORGANISM: Artificial Sequence
<220> FEATURE:
<223> OTHER INFORMATION: synthetic construct

<400> SEQUENCE: 102

Met Asp Gln Lys Gln Phe Glu Lys Ile Arg Ala Val Phe Asp Arg Ser
             1               5                      10                      15
            Gly Val Ala Leu Thr Leu Val Asp Met Ser Leu Pro Glu Gln Pro Val
                                20                      25                      30
            Val Leu Ala Asn Pro Pro Phe Leu Arg Met Thr Gly Tyr Thr Glu Gly
                                35                      40                      45
            Gln Ile Leu Gly Phe Asn Cys Arg Phe Leu Gln Arg Gly Asp Glu Asn
                 50                      55                      60
            Ala Gln Ala Arg Ala Asp Ile Arg Asp Ala Leu Lys Leu Gly Arg Glu
             65                      70                      75                      80
            Leu Gln Val Val Leu Arg Asn Tyr Arg Ala Asn Asp Glu Pro Phe Asp
                                85                      90                      95
            Asn Leu Leu Phe Leu His Pro Val Gly Gly Arg Pro Asp Ala Pro Asp
```

```
                100                 105                 110
Tyr Phe Leu Gly Ser Gln Phe Glu Leu Gly Arg Ser Gly Asn Ser Glu
            115                 120                 125

Glu Ala Ala Ala Ala Gly His Ala Gly Ala Leu Thr Gly Glu Leu Ala
            130                 135                 140

Arg Ile Gly Thr Val Ala Ala Arg Leu Glu Met Asp Ser Arg Arg His
145                 150                 155                 160

Leu Ala Gln Ala Ala Ala Ala Leu Val Arg Ala Trp Glu Arg Arg Gly
            165                 170                 175
```